US008168201B2

(12) United States Patent
Hickle et al.

(10) Patent No.: US 8,168,201 B2
(45) Date of Patent: May 1, 2012

(54) VACCINES

(75) Inventors: Leslie Hickle, Chula Vista, CA (US); Abraham Anderson, Sherman Oaks, CA (US); Robert C. Brown, San Diego, CA (US); Paul Budworth, San Diego, CA (US); Gordana Djordjevic, La Jolla, CA (US); Scott Kroken, Tucson, AZ (US); Peter Luginbuhl, San Diego, CA (US); Toby Richardson, San Diego, CA (US); Genevieve Hansen, Rancho Sante Fe, CA (US)

(73) Assignee: Pfizer Canada Inc., Kirkland, Quebec (CA)

( * ) Notice: Subject to any disclaimer, the term of this patent is extended or adjusted under 35 U.S.C. 154(b) by 511 days.

(21) Appl. No.: 11/696,131

(22) Filed: Apr. 3, 2007

(65) Prior Publication Data

US 2007/0286871 A1 Dec. 13, 2007

Related U.S. Application Data

(63) Continuation of application No. PCT/US2005/035852, filed on Oct. 5, 2005.

(60) Provisional application No. 60/616,340, filed on Oct. 5, 2004, provisional application No. 60/678,359, filed on May 5, 2005, provisional application No. 60/699,720, filed on Jul. 15, 2005.

(51) Int. Cl.

| | |
|---|---|
| ***A61K 39/295*** | (2006.01) |
| ***A61K 48/00*** | (2006.01) |
| ***A61K 39/02*** | (2006.01) |
| ***C12N 15/117*** | (2010.01) |
| *A61K 38/00* | (2006.01) |

(52) U.S. Cl. ....................... 424/201.1; 514/44; 424/93.3

(58) Field of Classification Search ....................... None
See application file for complete search history.

(56) References Cited

U.S. PATENT DOCUMENTS

| | | | | |
|---|---|---|---|---|
| 5,843,464 | A | 12/1998 | Bakaletz et al. | |
| 6,713,301 | B1 * | 3/2004 | Wang | 435/328 |
| 6,936,256 | B2 * | 8/2005 | Vakharia | 424/204.1 |
| 7,135,282 | B1 * | 11/2006 | Hellendoorn et al. | 435/5 |
| 2002/0064515 | A1 * | 5/2002 | Krieg et al. | 424/85.1 |
| 2002/0115625 | A1 * | 8/2002 | Bot et al. | 514/44 |
| 2004/0086524 | A1 | 5/2004 | Kuzyk et al. | |
| 2005/0058658 | A1 | 3/2005 | Barnett | |

FOREIGN PATENT DOCUMENTS

| | | | |
|---|---|---|---|
| WO | WO00/04170 | A1 * | 1/2000 |
| WO | WO 01/08636 | | 2/2001 |
| WO | WO 01/08636 | A2 | 2/2001 |
| WO | WO 01/27282 | | 4/2001 |
| WO | WO 01/27282 | A1 | 4/2001 |

OTHER PUBLICATIONS

Labus et al. Fish & Shellfish Immunology, 2001, 11, 203-216.*
Lowenthal et al. Journal of Interferon and Cytokine Research, 1997, 17:551-558.*
Robinson et al. Proc. Natl. Acad. Sci. USA, 1998, vol. 95, pp. 5929-5934.*
Adams—J. Am Chem. Soc. (1983)—105—661-663.
Baldrick—Regul. Toxicol. Pharmacol. (2000)—32—210-9.
Beaucage—Tetr. Lett. (1981)—22—1859-1862.
Belousov—Nucleic Acids Res. (1997)—25—3440-3444.
Blommers—Biochemistry (1994)—33—7886-7896.
Brown—Meth. Enzymol. (1979)—68—109-151.
Brusic—Nucleic Acids Res. (1998)—26—368-71.
Caruthers—Nucleic Acids Res. Symp. Ser. (1980)—215-233.
Charman—J. Pharm. Sci. (2000)—89—967-78.
Dakappaggari—J Pept Res (2005)—65—189-199.
Demotz—J Immunology (1989)—15—3881-3886.
Dobeli—Protein Expr. Purif. (1998)—12—404-414.
Epstein—Proc. Natl. Acad. Sci. USA (1985)—82—3688-3692.
Frenkel—Free Radic. Biol. Med. (1995)—19—373-380.
Hayman—Immunol Cell Biol (2002)—80—178-87.
Horn—Nucleic Acids Res. Symp. Ser. (1980)—225-232.
Hwang—Proc. Natl. Acad. Sci. USA (1980)—77—4030-4034.
Kern—Biotechniques (1997)—23—120-124.
Kim—J Leukoc Biol (1999)—65—6-15.
Kirkely—Immunobiology (2001)—203—601-615.
Kroll—DNA Cell. Biol. (1993)—12—441-453.
Langer—J. Biomed Mater. Res. (1981)—15—167-277.
Langer—Chem. Tech. (1982)—12—98-105.
Lillehoj—Avian Dis (2000)—44—379-389.
Lillehoj—Vet Immunol Immunopathol (1989)—20—135-148.
Mackay—Curr Biol (1997)—1—384-386.
Mata—Toxicol. Appl. Pharmacol. (1997)—144—189-197.
McSparron—J Chem Inf Comput Sci (2003)—43—1276-1287.
Merrifield—Methods Enzymol (1997)—289—3-13.
Min—Vaccine (2001)—20—267-274, 2002.
Moser—Sci. Prog. (1998)—81—299-313.
Narang—Meth Enzymol (1979)—68—90-98.
Nelson—Curr Opin Immunol (1998)—10—265-270.
Panina-Bordignon—Eur J Immunol (1989)—19—2237-2242.
Partidos—J Gen Virol (1990)—71—2099-2105.
Pei—Virology (2003)—306—376-384.
Powell—PDA J Pharm Sci Technol (1998)—52—238-311.
Roberge—Science (1995)—269—202-204.
Rosenfeld—Nat Genet (1997)—15—333-335.
Samstag—Antisense Nucleic Acid Drug Dev. (1996)—6—153-156.
SEO—J Virol (1997)—71—7889-7894.
Sidman—Biopolymers (1983)—22—547-556.
Sneed—Viral Immunol (1989)—2—221-227.
Spatola—Peptides and Proteins (1983)—7—267-357.
Strauss-Soukup—Biochemistry (1997)—36—8692-8698.
Taub—Cytokine Growth Factor Rev.—(1996)—4—355-376.
Wang—Arch Virol (1995)—140—2201-2213.

(Continued)

*Primary Examiner* — Bao Li
(74) *Attorney, Agent, or Firm* — Joel Silver

(57) ABSTRACT

The present invention relates to compositions for inducing immune responses, including an antigen and a promiscuous T-cell epitope. Also provided are methods of inducing immune responses in hosts, comprising administering compositions comprising antigens and promiscuous T-cell epitopes to the host.

24 Claims, 32 Drawing Sheets

OTHER PUBLICATIONS

Wang—Int. J. Pharm. (2000)—1-60.
Ward—Immunity (1998)—9—1-11.
Williams—Biochemistry (1995)—34—1787-1797.
Williamson—Vaccine (1993)—11—1253-1258.
Wold—Academic Press (1983)—1-12.
Woon—Genomics (1998)—50—306-316.
Yusim—J Virol (2004)—78—2187-2200, Frahm.
GBIPO—Apr. 1, 2009—GB Exam Report—GB07087059.
Sundaram—Journal of Biological Chemistry (2004)—279—24141-24151.
O'Hern—Vaccine (1997)—16—1761-1766.
Allred, et. al. Molecular Basis for Surface Antigen Size Polymorphisms and Conservation of a Neutralization-Sensitive Epitope in Anaplasma Marginale. PNAS. 1990. vol. 87, pp. 3220-3224.
Breed, et. al., Vaccination Against *Eimeria tenella* Infection Using a Fraction of *E. tenella* Sporozites Selected by the Capacity to activate T Cells. Int'l Journal for Parasitology. 1999. vol. 29, pp. 1231-1240.
Bruggemann, et. al. The Genome Sequence of Clostridium Tetani, The Causative Agent of Tetanus Disease. PNAS. 2003. vol. 100, No. 3, pp. 1316-1321.
De La Fuente, et. al. Genetic Diversity and Molecular Phylogeny of Anaplasma Marginale Isolates from Minas Gerais, Brazil. Veterinary Parasitology. 2004. vol. 121, pp. 307-316.
Eisel, et. al., Tetanus Toxin: Primary Structure, Expression in *E. coli*, and Homology with Botulinum Toxins. Them EMBO Journal. 1986. vol. 5, No. 10, pp. 2495-2502.
Fairweather, et. al., Cloning, Nucleotide Sequencing, and Expression of Tetanus Toxin Fragments C in *Escherichia coli*. The Journal of Bacteriology. 1986. vol. 165, No. 1, pp. 21-27.
Lee, et. al., Tissue Distributio of Avian Infectious Bronchitis Virus Following in ovo inoculation of Chicken Embryos . . . J. Vet. Diagn. Invest. 2002. vol. 14, pp. 377-381.
Riley, et.al., Immunisation of Rainbow Trout Oncorhynchus Mykiss with a Multiple Antigen Peptide System (MAPS). Veterinary Immunology and Immunopathology. 1996. vol. 55, pp. 243-253.
Shella, et. al. Immune Response Against Salmonells Enterica Serovar Enteriditis. Clinical and Diagnostic Laboratory Immunology. 2003. vol. 10, No. 4, pp. 670-679, Sheela.
Tanabe, et. al. Stable SNPs in Malaria Antigen Genes in Isolated Populations. Science. 2004. vol. 303, p. 493.
GB0922611.9—Exam & Search Report—Jan. 11, 2010.
Sundaram et al. Journal of Biological Chemistry 2004 vol. 279, p. 24141-24145 "De Novo Design of Peptide Immunogenes that Mimic the Coiled Coil Region of Human T-cell Leukemia Virus Type-1 Glycoprotein 21 Transmembrane Subunit for Induction of Native Protein Reactive Neutralizing Antibodies".
O'Hern et al. Vaccine 1997 vol. 16 No. 15 p. 1761-1766 "Colinear Synthesis of an Antigen-Specific B-cell Epitope with a 'Promiscuous' Tetanus Toxin T-cell Epitope: a Synthetic Peptide Immunocontraceptive".

* cited by examiner

Weight Gain (kg) and Feed Conversion for 3-1E/PTCE compositions administered *in ovo*

*IN OVO* VACCINATION WITH *EIMERIA* 3-1E AND MIC-2 ANTIGENS WITH AND WITHOUT PTCEs

Weight Gain (kg) and Feed Conversion for Mic-2/PTCE compositions administered *in ovo*

PASK 5

BD17016 (pASK5 N'His + C'ToxA)

BD17018 (pASK5 N'His + C'ToxA + M)

BD17020 (pASK5 N'His + C'ToxA + T)

- tetA -35
- TetR binding site
- tetA -10
- +1 (tetA)
- TetR binding site
- putative RBS (tetA)
- mini-cistron (tetA)
- RBS
- N-his-tag
- protease cleavage site (XA)
- Cl.perfringens C'ToxA-T
- terminator BD17020
3647 bp tetR bla

BD17194 (pASK5 N'His + C'ToxA + GMGT)

- tetA -35
- TetR binding site
- tetA -10
- +1 (tetA)
- TetR binding site
- putative RBS (tetA)
- mini-cistron (tetA)
- RBS
- N-his-tag
- protease cleavage site (XA)
- Cl.perfringens C'ToxA-GMGT
- terminator BD17194
3647 bp tetR bla BD16978 (pASK5 N'His + C'ToxA + MGM)

- tetA -35
- TetR binding site
- tetA -10
- +1 (tetA)
- TetR binding site
- putative RBS (tetA)
- mini-cistron (tetA)
- RBS
- N-his-tag
- protease cleavage site (XA)
- Cl.perfringens C'ToxA-MGM
- terminator BD16978
3710 bp tetR bla BD16979 (pASK5 N'His + C'ToxA + MGMGM)

- tetA -35
- TetR binding site
- tetA -10
- +1 (tetA)
- TetR binding site
- putative RBS (tetA)
- mini-cistron (tetA)
- RBS
- N-his-tag
- protease cleavage site (XA)
- Cl.perfringens C'ToxA-MGMGM
- terminator BD16979
3785 bp tetR bla

BD16980 (pASK5 N'His + C'ToxA + TGT)

- tetA -35
- TetR binding site
- tetA -10
- +1 (tetA)
- TetR binding site
- putative RBS (tetA)
- mini-cistron (tetA)
- RBS
- N-his-tag
- protease cleavage site (XA)
- Cl.perfringens C'ToxA-TGT
- terminator BD1680
3725 bp tetR bla

**Performance, Days 0-13 of age of chicks administered *C. perfringens* C'ToxA/PTCE**

Graph 1. Summary of 0 - 13 day bird average weight and adjusted feed conversion.

| Treatment | Bird Average Weight (kg) | Adjusted Feed Conversion | Clostridia Challenge | Vaccine | Preparation or Feed Additive | Delivery | Volume/ Dose | Adjuvant |
|---|---|---|---|---|---|---|---|---|
| 1 | 0.257 | 1.216 | Yes | 1/1 | Pure Protein | In ovo | 0.1 ml | No |
| 2 | 0.259 | 1.196 | Yes | 1/2 | Pure Protein | SubQ | 0.2 ml | No |
| 3 | 0.266 | 1.222 | Yes | 1/3 | Crude Protein | In ovo | 0.1 ml | No |
| 4 | 0.260 | 1.196 | Yes | 1/4 | Crude Protein | SubQ | 0.2 ml | No |
| 5 | 0.262 | 1.203 | Yes | 1/5 | Crude Protein | SubQ | 0.2 ml | Yes |
| 6 | 0.259 | 1.206 | Yes | 2/1 | Pure Protein | In ovo | 0.1 ml | No |
| 7 | 0.256 | 1.214 | Yes | 2/2 | Pure Protein | SubQ | 0.2 ml | No |
| 8 | 0.266 | 1.208 | Yes | 2/3 | Crude Protein | In ovo | 0.1 ml | No |
| 9 | 0.260 | 1.212 | Yes | 2/4 | Crude Protein | SubQ | 0.2 ml | No |
| 10 | 0.263 | 1.213 | No | Control 1 | none | N/A | N/A | N/A |
| 11 | 0.261 | 1.188 | Yes | Control 2 | none | N/A | N/A | N/A |
| 12 | 0.252 | 1.208 | Yes | Control 3 | BMD | N/A | 25 g/ton | N/A |

*FIG. 10A*

**Performance, Days 13-21 of age of chicks administered *C. perfringens* C'ToxA/PTCE**

Graph 2. Summary of day 13 - 21 day bird average weight gain and adjusted feed conversion.

| Treatment | Bird Average Wt Gain (kg) | Adjusted Feed Conversion | Clostridia Challenge | Vaccine | Preparation or Feed Additive | Delivery | Volume/ Dose | Adjuvant |
|---|---|---|---|---|---|---|---|---|
| 1 | 0.257 | 1.430 | Yes | 1/1 | Pure Protein | In ovo | 0.1 ml | No |
| 2 | 0.266 | 1.423 | Yes | 1/2 | Pure Protein | SubQ | 0.2 ml | No |
| 3 | 0.248 | 1.437 | Yes | 1/3 | Crude Protein | In ovo | 0.1 ml | No |
| 4 | 0.261 | 1.423 | Yes | 1/4 | Crude Protein | SubQ | 0.2 ml | No |
| 5 | 0.267 | 1.414 | Yes | 1/5 | Crude Protein | SubQ | 0.2 ml | Yes |
| 6*** | 0.275 | 1.405 | Yes | 2/1 | Pure Protein | In ovo | 0.1 ml | No |
| 7 | 0.254 | 1.430 | Yes | 2/2 | Pure Protein | SubQ | 0.2 ml | No |
| 8 | 0.258 | 1.421 | Yes | 2/3 | Crude Protein | In ovo | 0.1 ml | No |
| 9 | 0.257 | 1.418 | Yes | 2/4 | Crude Protein | SubQ | 0.2 ml | No |
| 10 | 0.296 | 1.414 | No | Control 1 | none | N/A | N/A | N/A |
| 11 | 0.256 | 1.422 | Yes | Control 2 | none | N/A | N/A | N/A |
| 12 | 0.273 | 1.408 | Yes | Control 3 | BMD | N/A | 25 g/ton | N/A |

*FIG. 11A*

**Performance, Days 0-21 of age of chicks administered *C. perfringens* C'ToxA/PTCE**

Graph 3. Summary of 0 - 21 day bird average weight and adjusted feed conversion.

| Treatment | Bird Average Weight (kg) | Adjusted Feed Conversion | Clostridia Challenge | Vaccine | Preparation or Feed Additive | Delivery | Volume/ Dose | Adjuvant |
|---|---|---|---|---|---|---|---|---|
| 1 | 0.620 | 1.331 | Yes | 1/1 | Pure Protein | In ovo | 0.1 ml | No |
| 2 | 0.628 | 1.318 | Yes | 1/2 | Pure Protein | SubQ | 0.2 ml | No |
| 3 | 0.629 | 1.335 | Yes | 1/3 | Crude Protein | In ovo | 0.1 ml | No |
| 4 | 0.625 | 1.318 | Yes | 1/4 | Crude Protein | SubQ | 0.2 ml | No |
| 5 | 0.634 | 1.316 | Yes | 1/5 | Crude Protein | SubQ | 0.2 ml | Yes |
| 6 | 0.634 | 1.314 | Yes | 2/1 | Pure Protein | In ovo | 0.1 ml | No |
| 7 | 0.616 | 1.329 | Yes | 2/2 | Pure Protein | SubQ | 0.2 ml | No |
| 8*** | 0.643 | 1.321 | Yes | 2/3 | Crude Protein | In ovo | 0.1 ml | No |
| 9 | 0.628 | 1.322 | Yes | 2/4 | Crude Protein | SubQ | 0.2 ml | No |
| 10 | 0.663 | 1.323 | No | Control 1 | none | N/A | N/A | N/A |
| 11 | 0.629 | 1.312 | Yes | Control 2 | none | N/A | N/A | N/A |
| 12 | 0.625 | 1.317 | Yes | Control 3 | BMD | N/A | 25 g/ton | N/A |

*FIG. 12A*

**Lesion Scores of chicks administered *C. perfringens* C'ToxA/PTCE**

Graph 4. Summary of lesion scores done on study day 17

| Treatment | Average Lesion Score | Clostridia Challenge | Vaccine | Preparation or Feed Additive | Delivery | Volume/ Dose | Adjuvant |
|---|---|---|---|---|---|---|---|
| 1 | 1.08 | Yes | 1/1 | Pure Protein | In ovo | 0.1 ml | No |
| 2*** | 0.53 | Yes | 1/2 | Pure Protein | SubQ | 0.2 ml | No |
| 3 | 0.98 | Yes | 1/3 | Crude Protein | In ovo | 0.1 ml | No |
| 4*** | 0.65 | Yes | 1/4 | Crude Protein | SubQ | 0.2 ml | No |
| 5 | 0.98 | Yes | 1/5 | Crude Protein | SubQ | 0.2 ml | Yes |
| 6 | 1.08 | Yes | 2/1 | Pure Protein | In ovo | 0.1 ml | No |
| 7 | 1.00 | Yes | 2/2 | Pure Protein | SubQ | 0.2 ml | No |
| 8 | 1.00 | Yes | 2/3 | Crude Protein | In ovo | 0.1 ml | No |
| 9 | 0.93 | Yes | 2/4 | Crude Protein | SubQ | 0.2 ml | No |
| 10 | 0.13 | No | Control 1 | none | N/A | N/A | N/A |
| 11 | 1.80 | Yes | Control 2 | none | N/A | N/A | N/A |
| 12 | 0.43 | Yes | Control 3 | BMD | N/A | 25 g/ton | N/A |

*Infected with coccidia on day 7

*FIG. 13A*

Figure 14:
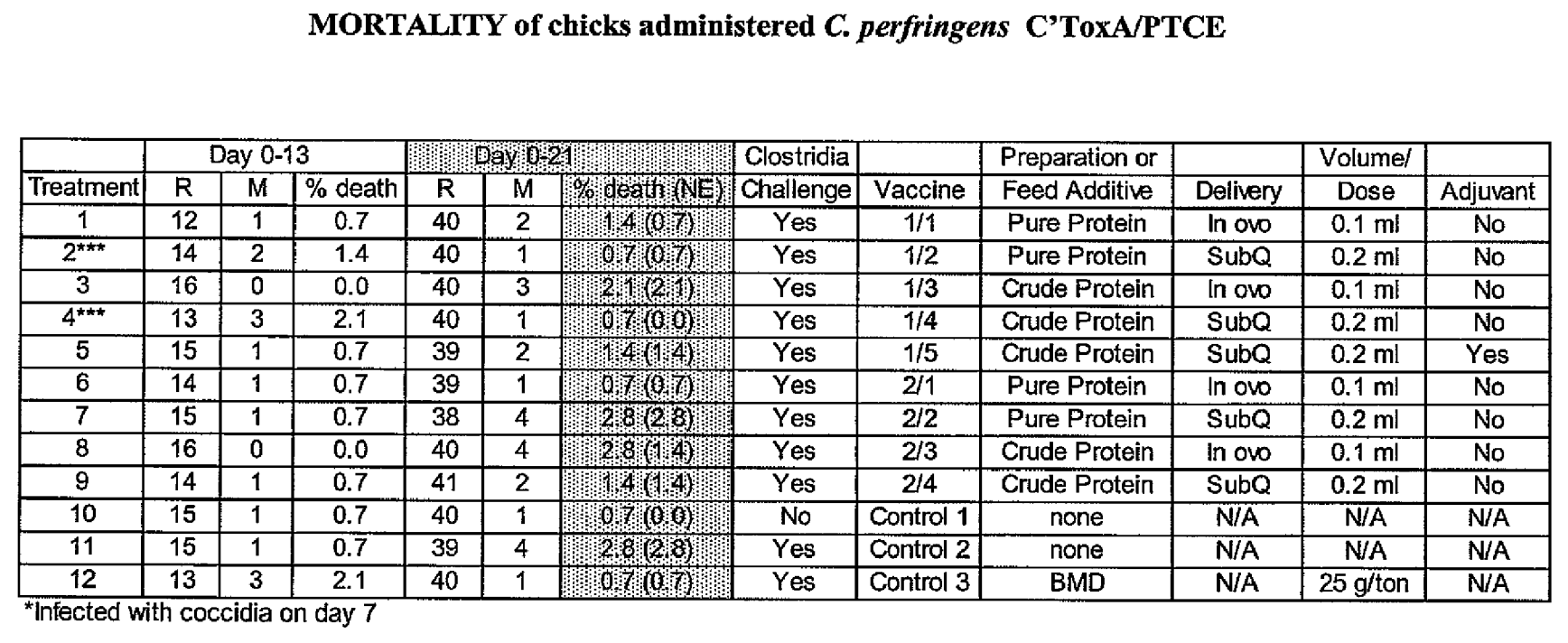

**MORTALITY of chicks administered *C. perfringens* C'ToxA/PTCE**

| | Day 0-13 | | | Day 0-21 | | | Clostridia | | Preparation or | | Volume/ | |
|---|---|---|---|---|---|---|---|---|---|---|---|---|
| Treatment | R | M | % death | R | M | % death (NE) | Challenge | Vaccine | Feed Additive | Delivery | Dose | Adjuvant |
| 1 | 12 | 1 | 0.7 | 40 | 2 | 1.4 (0.7) | Yes | 1/1 | Pure Protein | In ovo | 0.1 ml | No |
| 2*** | 14 | 2 | 1.4 | 40 | 1 | 0.7 (0.7) | Yes | 1/2 | Pure Protein | SubQ | 0.2 ml | No |
| 3 | 16 | 0 | 0.0 | 40 | 3 | 2.1 (2.1) | Yes | 1/3 | Crude Protein | In ovo | 0.1 ml | No |
| 4*** | 13 | 3 | 2.1 | 40 | 1 | 0.7 (0.0) | Yes | 1/4 | Crude Protein | SubQ | 0.2 ml | No |
| 5 | 15 | 1 | 0.7 | 39 | 2 | 1.4 (1.4) | Yes | 1/5 | Crude Protein | SubQ | 0.2 ml | Yes |
| 6 | 14 | 1 | 0.7 | 39 | 1 | 0.7 (0.7) | Yes | 2/1 | Pure Protein | In ovo | 0.1 ml | No |
| 7 | 15 | 1 | 0.7 | 38 | 4 | 2.8 (2.8) | Yes | 2/2 | Pure Protein | SubQ | 0.2 ml | No |
| 8 | 16 | 0 | 0.0 | 40 | 4 | 2.8 (1.4) | Yes | 2/3 | Crude Protein | In ovo | 0.1 ml | No |
| 9 | 14 | 1 | 0.7 | 41 | 2 | 1.4 (1.4) | Yes | 2/4 | Crude Protein | SubQ | 0.2 ml | No |
| 10 | 15 | 1 | 0.7 | 40 | 1 | 0.7 (0.0) | No | Control 1 | none | N/A | N/A | N/A |
| 11 | 15 | 1 | 0.7 | 39 | 4 | 2.8 (2.8) | Yes | Control 2 | none | N/A | N/A | N/A |
| 12 | 13 | 3 | 2.1 | 40 | 1 | 0.7 (0.7) | Yes | Control 3 | BMD | N/A | 25 g/ton | N/A |

*Infected with coccidia on day 7

*FIG. 14* pUCKTryp-GM-VP2-GT pUCKMuss-GM-VP2-T pUCKMussGMVP2GTcer+
4487bp

- cer
- P(BLA)
- KanR
- ORI
- P(LAC)
- Mussel Adhesive plaque protein
- G10
- Measles epitope
- IPN (VP2 truncated)
- Tetanus epitope pUCK AexT Tryp GM-VP2-T pUCK AexT SRS Tryp GM-VP2-GT

Labels around plasmid map:
- Tetanus epitope
- cer
- P(BLA)
- IPN (VP2 truncated)
- KanR
- Measles epitope
- G10
- pUCKAexTSRSTrypGMVP2GTcer+ 6221
- Trypsin protease
- ORI
- SRS
- AexT
- P(LAC)

pKLPR-CVP2eA1

BD17396 (pASK5 N'His + VP2)

- ApaLI (3790)
- tetA -35
- TetR binding site
- tetA -10
- +1 (tetA)
- TetR binding site
- putative RBS (tetA)
- mini-cistron (tetA)
- RBS
- NcoI (323)
- Bam HI (349)
- 257aaVP2_IBDV Del E
- ClaI (1064)
- Hind dIII (1141)
- terminator
- BD17396 3931 bp
- tetR
- bla
- ApaLI (1929)

BD17394 (pASK5 N'His + VP2 + GMGT)

BD17257 (pASK5 N'His + VP2 + M)

- ApaLI (3829)
- tetA -35
- TetR binding site
- tetA -10
- +1 (tetA)
- TetR binding site
- putative RBS (tetA)
- mini-cistron (tetA)
- RBS
- NcoI (323)
- 257aaVP2_IBDV DelE_M epitope
- ClaI (1058)
- Hind dIII (1180)
- terminator
- tetR
- bla
- ApaLI (1968)

BD17396
3931 bp

BD17246 (pASK5 N'His + VP2 + T)

- tetA -35
- TetR binding site
- tetA -10
- +1 (tetA)
- TetR binding site
- putative RBS (tetA)
- mini-cistron (tetA)
- RBS
- NcoI (323)
- BamHI (349)
- 257aaVP2_IBDV-DelE_T epitope
- ClaI (1064)
- AvaI (1179)
- HindIII (1195)
- terminator ApaLI (3844)
tetR
BD17246
3985 bp
bla
ApaLI (1983)

BD16040 (pASK5 N'His GMGT)

BD16042 (pASK5 N'His + VP2 + GMGT)

VACCINES

RELATED APPLICATIONS

The present application is a continuation of PCT/US2005/035852, filed Oct. 5, 2005, which designated the United States and was published in English, which claims priority under 35 U.S.C. §119(a)-(d) to U.S. Provisional Application No's 60/699,720, filed Jul. 15, 2005, 60/678,359, filed May 5, 2005, and 60/616,340, filed Oct. 5, 2004. The content of each of these applications is hereby incorporated by reference in its entirety.

REFERENCE TO SEQUENCE LISTING

The present application is being filed along with a Sequence Listing in electronic format. The Sequence Listing is provided as a file entitled DIVERSA.001C1.TXT, created Apr. 3, 2007, which is 233 KB in size. The information in the electronic format of the Sequence Listing is incorporated herein by reference in its entirety.

BACKGROUND OF THE INVENTION

The market for agents that benefit animal health includes feed enzymes, feed additives, nutraceuticals, small molecules, and protein therapeutics, such as vaccines, antibodies, enzymes, and peptides. Annually, over $13.4 billion is spent on agents to promote animal health, with more than half of that amount going to poultry, fish, and livestock e.g., cattle, swine, and sheep. Vaccines to protect against pathogens account for a large portion of the animal health market.

Eukaryotic (protozoan), viral, and bacterial pathogens afflict poultry, fish, and livestock, and can have devastating effects and impose significant economic problems on the poultry, fish and livestock industries. Accordingly, there is a need to develop compositions such as vaccines that are effective in protecting animals susceptible to pathogenic/disease-causing microorganisms.

Both humoral and cellular immunity are recognized as important in developing protection against several of the diseases derived from pathogenic microorganisms that afflict poultry, fish and livestock. Traditionally, vaccines have been based on live attenuated, or inactivated pathogens. However, these strategies are inefficient due to factors such as antigenic variability of pathogens such as viruses. Peptide vaccines that consist of antigenic peptides or peptide fragments of pathogens have been developed. Conserved peptide fragments are less likely to exhibit antigenic variability, and can overcome some of the problems associated with traditional peptides. Accordingly, subunit vaccines have been developed that target conserved regions of pathogens. However, synthetic peptide vaccines tend to be poorly immunogenic, and also tend to induce humoral antibody responses, but are less able to induce cell-mediated responses. Multivalent subunit vaccines, which contain both immunodominant B-cell and T-cell epitopes also address the above problems.

Effective vaccines generate effective memory responses for both humoral and cell-mediated immunity. This requires generation of a population of memory $T_h$ cells. By both directly contacting lymphokines and by secreting lymphokines such as IL2 and IL4, $T_h$ cells promote and support the expansion and differentiation of T and B cell precursors into effector cells.

$T_h$ cells, via T-cell receptors, recognize a complex formed between Class II MHC molecules and antigenic peptides (T-cell epitopes). Peptides containing epitopes recognized by $T_h$ cells are useful in inducing immune responses. Different class II MHC molecules are capable of binding to and presenting different peptides to $T_h$ cells. The genetic loci encoding MHC molecules are the most polymorphic known in higher vertebrates, resulting in a tremendous diversity of MHC proteins within a species. The differences between the different haplotypes (or unit of inheritance of MHC molecules) in turn influence the cells' ability to recognize a given peptide. Consequently, individuals differ in their ability to generate an immune response to any given pathogen. Accordingly, the identification of polypeptides that bind several MHC class II molecules is useful in the development of peptide vaccines that can induce an effective immune response in a wide variety of individuals.

Investigators have identified "promiscuous T-cell epitopes" ("PTCEs") in humans. See, U.S. Pat. No. 6,143,935; U.S. Pat. No. 6,143,517; U.S. Pat. No. 6,689,363. Promiscuous T-cell epitopes (or "PTC epitopes") are highly immunogenic peptides that can be characterized in part by their capacity to bind several isotypic and allotypic forms of human MHC class II molecules. By helping to bypass MHC restriction, they can induce T-cell and antibody responses in members of a genetically diverse population expressing diverse MHC haplotypes. The PTC epitopes can therefore be combined with antigens that, by themselves, are poorly immunogenic, to generate potent peptide immunogens.

The *Clostridium tetani* tetanus toxin P2 and measles virus fusion protein epitopes have been established as strong PTCEs that are highly immunogenic in human and murine models (Demotz, et al., (1989) *J Immunol.* 15; 143(12):3881-6; Panina-Bordignon, et al. (1989) *Eur J Immunol.;* 19(12): 2237-42; Partidos and Steward, (1990), *J Gen Virol.;* 71 (Pt 9):2099-105. U.S. Patent Publication No. 2004/0086524 describes fusion proteins between a tetanus toxin P2 PTCE or a measles virus PTCE and the OspA protein of the bacterium *Piscirickettsia salmonis*, a bacterial pathogen of salmonid species. The presence of the tetanus toxin PTCE or the measles virus PTCE augmented the antibody response to the OspA protein, and enhanced lymphocyte proliferation in response to the vaccine, and conferred protection against the pathogen.

To date, PTCEs that are effective in augmenting immune responses in poultry have not been identified. Further, the need exists to provide improved vaccines against protozoan pathogens. Finally, the discovery of novel PTCEs that are effective in augmenting immune responses in poultry, livestock and fish is desirable.

SUMMARY OF THE INVENTION

Aspects of the invention relate to compositions that include an antigen and a promiscuous T-cell epitope ("PTCE"). The PTCE can be a peptide, having the amino acid sequence of SEQ ID NOs: 1, 2, 3, 4, 5, 6 or 7. In some embodiments, the composition preferably includes a pharmaceutically acceptable carrier. In other embodiments, the composition preferably includes an adjuvant. The antigen in any of the above embodiments can be a viral antigen, a bacterial antigen, a protozoan antigen, or a fungal antigen. In still other embodiments, the composition can include an immunomodulator, such as cytokines or chemokines. For example, in some embodiments, the composition can include one or more of the following: human B cell-activating factor (BAFF), granulocyte colony-stimulating factor (G-CSF), granulocyte/macrophage colony-stimulating factor (GM-CSF), interferon-alpha (IFN-α), interferon-beta (IFN-β), interferon-gamma (IFN-γ), leukemia inhibitory factor (LIF), macrophage colony stimulating factor (M-CSF), macrophage inhibition factor (MIF), oncostatin M (OSM), stem cell factor (CSF), thrombopoietin (Tpo), transforming growth factor beta (TGF-β), tumor necrosis factor-alpha (TNF-α) and tumor necrosis factor-beta (TNF-β). In preferred embodiments, the cytokine can induce CD+4 helper cells, CD+8 helper cells. In more preferred embodiments, the composition can include a cytokine such as a chicken cytokine. In still more preferred embodiments, the composition can include chicken IFN-γ or chicken IL-12. The compositions above can, in certain embodiments, include more than one, i.e., a plurality, of PTCE's. The PTCE's can be linked to another PTCE through a linker. The PTCEs can also be linked to an antigen, peptide immunomodulator, or other peptide through a linker. In some embodiments, the linker can include one or more glycine amino acids. In one embodiment, the linker includes at least nine glycines. In another embodiment, the glycines are consecutive.

Other aspects relate to methods for inducing an immune response in a host, by administering to the host a composition including an antigen and a PTCE. In some embodiments, the host can be a mammal, a fish, or a bird. In some embodiments, the composition that is administered to the host can include a nucleic acid molecule that encodes the PTCE. The antigen can also be encoded by a nucleic acid molecule that is administered to the host, for example on the same nucleic acid molecule that encodes the PTCE. In other embodiments, the antigen can be a polypeptide that is administered to the host.

Yet other aspects relate to compositions including an antigen derived from a protozoan pathogen and a PTCE. In some embodiments, the composition can include a pharmaceutically acceptable carrier. In other embodiments, the composition preferably includes an adjuvant. In the embodiments above, the protozoan pathogen can be, for example *Eimeria, Trichomonas, Histomonas, Cryptosporidiosis, Toxoplasma, Neospora, Isoporoa, Crytosporidium, Babesia, Hammondia, Theileria*, and *Sarcocystis*. In further embodiments, the compositions can include a cytokine. In some embodiments, the PTCE can be a polypeptide that includes the amino acid sequence of SEQ ID NOs: 1, 2, 3, 4, 5, 6, or 7. The compositions above can, in certain embodiments, include more than one, i.e., a plurality, of PTCE's. The PTCE's can be linked to another PTCE through a linker. The PTCEs can also be linked to an antigen, peptide immunomodulator, or other peptide, such as through a linker. In some embodiments, the linker can include one or more glycine amino acids. In some embodiments, the linker includes at least nine glycines.

Other aspects relate to methods of inducing an immune response in a host, by administering any of the compositions embodied in paragraph [0013] to the host.

Other aspects relate to compositions including an antigen derived from a bird pathogen and a PTCE. In some embodiments, the bird pathogen can be a viral pathogen. For example, in some embodiments, the bird pathogen can be Infectious Bursal Disease (IBD) virus, Infectious bronchitis virus (IBV), Avian influenza, Fowl pox, Marek's disease virus, Newcastle disease virus, Chicken anemia virus, or Infectious Laryngotracheitis Virus (ILT). In preferred embodiments, the bird pathogen is IBD virus. In more preferred embodiments, the IBD viral antigen is derived from the polypeptide of SEQ ID NO: 154. In other embodiments, the bird pathogen can be a bacterial pathogen. For example, in some embodiments, the bird pathogen can be *Salmonella enterica, Chlamydia psitaci, Escherichia coli, Colibacillosis, Mycoplasma gallisepticum, Mycoplasma meleagridis, Mycoplasma synoviae, Pasteurella multocida, Clostridium colinum, Clostridium perfringens, Clostridium septicum, Salmonella pullorum, Salmonella gallinarum, Hemophilus gallinarum, Streptococcus, Staphylococcus, Proteus, Erysipelothrix insidios, Salmonella enteritidis, Bordetella avium, Actinobacillus salpingitidis, Chlamydophila psittaci, Mycoplasma iowae, Mycoplasma gallisepticum, Pasteurella multocida, Haemophilus paragallinarum, Ornithobacterium rhinotracheale*, and *Riemerella anatipestifer*. In preferred embodiments, the bird bacterial pathogen is *Clostridium* spp. In further embodiments that are more preferred, the antigen includes the C-terminal domain of the *Clostridium* toxin alpha. In yet other embodiments, the bird pathogen can be a protozoan pathogen. For example, in some embodiments, the bird protozoan pathogen is *Eimeria* spp., *Histomonas meleagridis, Hexamita meleagridis, Toxoplasma* or *Neospora*. In further embodiments of any of the above, the PTCE can include a peptide having the amino acid sequence of SEQ ID NOs: 1, 2, 3, 4, 5, 6, or 7. Any of the above embodiments can further include a cytokine.

Another aspect relates to a method for inducing an immune response in a bird against a pathogen, by administering any of the compositions embodied in paragraph [0014] to the bird. In some embodiments, the pathogen is a protozoan, while in other embodiments, the pathogen is a bacterium. In still other embodiments, the pathogen is a virus.

Still other aspects relate to compositions that include an antigen derived from a virus that infects fish, and a PTCE. In some embodiments, the fish can be a salmonid. In further embodiments, the virus can be infectious pancreatic necrosis virus (IPNV). In still further embodiments, the antigen can be a truncated antigen. For example, in some embodiments, the truncated antigen can include the amino acid sequence of SEQ ID NO: 146, encoding the N-terminal 257 amino acids of the IPNV VP2 protein.

Other aspects relate to a nucleic acid molecule that encodes an antigen from a pathogen, and also encodes a PTCE that includes the amino acid sequence of SEQ ID NOs: 1, 2, 3, 4, 5, 6, or 7. In some embodiments, the nucleic acid includes a vector. For example, in some embodiments, the vector can be an expression vector. In some embodiments, the nucleic acid can also encode a cytokine. In other embodiments, the antigen encoded by the nucleic acid is linked to the PTCE encoded by the nucleic acid though a linker. In some embodiments, the linker can be one or more glycine amino acids.

Still other aspects relate to compositions that include two or more PTCE's that are joined together by a linker. In some embodiments, the linker is a polyglycine linker.

Yet other aspects relate to methods of vaccinating an animal. An animal in need of vaccination against a pathogen can be selected, and an antigen derived from the pathogen can be administered to the animal with a PTCE in ovo.

Still another aspect relates to a method of vaccinating an animal. An animal in need of vaccination against a pathogen can be selected, and an antigen derived from the pathogen can be administered to the animal with a PTCE when said animal is pre-immunocompetent.

In any of the embodiments described above, the antigen can be a B-cell antigen.

Other aspects relate to compositions that include at least on B cell epitope derived from IBDV, and at least one T-cell epitope derived from infectious bronchitis virus (IBV). For example, some compositions include the B cell epitope of SEQ ID NO:179 (IBB239255) or SEQ ID NO:17 (IBB347372). Compositions can also include T-cell epitopes selected from the group consisting of SEQ ID NO:18 (IBT2735); SEQ ID NO:19 (IBT8593); SEQ ID NO:20 (IBT188196); SEQ ID NO:21 (IBT300308); SEQ ID NO:22 (IBT392400); SEQ ID NO:23 (IBT137145); SEQ ID NO:24

(IBT5159); SEQ ID NO:25 (IBT109117); SEQ ID NO:26 (IBT208219); SEQ ID NO:27 (IBT144152): SEQ ID NO:28 (IBT3644) and SEQ ID NO:29 (IBT329337).

BRIEF DESCRIPTION OF THE DRAWINGS

FIG. 14 is a chart depicting the mortality and removals of birds of various chicks from treatment groups described in Example 2. Various chicks to which different C'ToxA recombinant proteins (See FIGS. 3-6) were administered as described in Example 2 were assayed. Administration of the recombinant proteins was followed by a challenge with *C. perfringens.*

DETAILED DESCRIPTION OF THE PREFERRED EMBODIMENTS

Figure 1A:
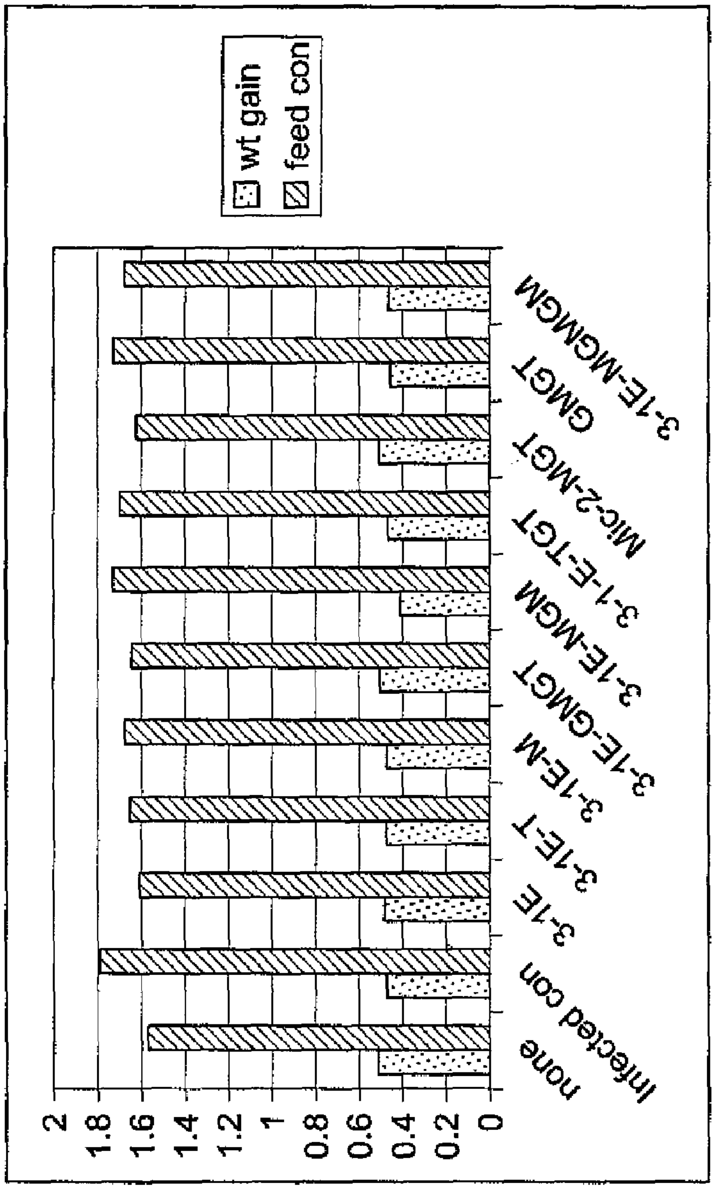
FIG. 1A is a bar graph showing weight gain and feed conversion of chicks vaccinated in ovo with *Eimeria* 3-1E and Mic2 antigens with and without PTCEs, followed by challenge with *Eimeria.*

Embodiments of the invention described herein relate to compositions for eliciting immune responses against a pathogenic agent in a host and to vaccines containing the compositions. Some embodiments relate to compositions that include an antigen and a promiscuous T-cell epitope having the amino acid sequence of SEQ ID NOs: 1, 2, 3, 4, 5, 6, or 7.

The compositions described herein can be administered to host animals that are susceptible to a pathogen and capable of responding to administration of a composition with an induced immune response. The terms pathogenic agent, pathogen, and pathogenic microorganism refer to agents of viral, bacterial or eukaryotic origin that cause disease in host. Examples of hosts and corresponding pathogenic agents contemplated in the embodiments described herein are discussed below.

DEFINITIONS

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (3rd ed., Cold Spring Harbor Laboratory Press, Cold Spring Harbor, N.Y. (2001)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

Hosts and Pathogens

Mammals

Examples of mammalian hosts include livestock animals and companion animals.

The term "livestock animals" as used herein refers to domesticated quadrupeds, which includes those being raised for meat and various byproducts, e.g., a bovine animal including cattle and other members of the genus *Bos*, a porcine animal including domestic swine and other members of the genus *Sus*, an ovine animal including sheep and other members of the genus *Ovis*, domestic goats and other members of the genus *Capra*; domesticated quadrupeds being raised for specialized tasks such as use as a beast of burden, e.g., an equine animal including domestic horses and other members of the family Equidae, genus *Equus*, or for searching and sentinel duty. Other livestock animals include those grown for their fur or other non-edible products.

The term "companion animals" includes mammals such as e.g., a canine animal including domestic dogs and other members of the genus *Canis*; and domesticated quadrupeds being raised primarily for recreational purposes, e.g., members of *Equus* and *Canis*, as well as a feline animal including domestic cats and other members of the family Felidae, genus *Felis*.

Non-limiting examples of mammalian pathogens include the following:

a. Viral

| Pathogen (disease) | Representative host species |
|---|---|
| Rabies | Mammals, raccoon, dog, human |
| Polio | Human |
| Smallpox | Human |
| West Nile virus, WNV | Horse |
| Avian influenza | Chicken, cats |
| Foot and Mouth Disease Virus | Cattle, swine, sheep, goats |
| Influenza B | Human |
| Feline leukemia virus | Cats |
| Rift Valley Fever virus | Ruminants, sheep, goats |
| Pox viruses | Human, goat, sheep (different pox viruses for different hosts) |
| African swine fever virus | Pigs |

-continued

| a. Viral | |
|---|---|
| Pathogen (disease) | Representative host species |
| Classical swine fever virus (hog cholera) | Pigs and wild boar |
| Arboviruses, which include Alphaviruses and Flaviviruses (Equine viral encephalitis) | Horses |
| Equine herpes virus (causes rhinopneumonitis) | Horses |
| Herpes B | Humans, macaque monkeys |
| Porcine reproductive and respiratory syndrome (PRRS) | Pigs |
| Post weaning multisystemic wasting syndrome (PWMS) | Pigs |
| Akabane virus | Calves |
| Lumpy skin disease (Pox virus) | Cattle |
| Rinderpest virus | Cattle |

| b. Bacterial | |
|---|---|
| Pathogen (disease) | Representative host species |
| *Mycobacterium ulcerans* | human |
| *Bacillus anthracis* (anthrax) | Human, wild animals |
| *Brucella* (brucellosis) | Cattle, sheep, goats, dogs, pigs |
| *Campylobacter* sp., e.g. fetus (Genital campylobacteriosis) | Human, farm animals, dogs |
| *Escherichia coli* O157:H7 | Human, cattle |
| *Leptospira* spp., e.g. *borgpetersenii* (leptospirosis, fevir) | Human, domestic and wild animals, cats and dogs |
| Lyme disease (*Borrelia burgdoferi*) | Human, dogs, horses |
| *Yersinia enterocolitica* | Human, pigs, cats, dogs, horses, cows, rodents, and rabbits |
| *Yersinia pestis* | Human, rodents, cats |
| Q fever (*Coxiella brunetti*) | Human, Cattle, sheep, and goats |
| *Mycobacterium tuberculosis* (TB) | Human |
| *Mycobacterium bovis* (tuberculosis) | cattle |
| *Francisella tularensis* (tularemia) | Human, rodents, rabbits |
| *Salmonella* spp. (salmonelosis) | Human, farm animals, cats, dogs, horses |
| *Chlamydia* | Human |
| *Bacillus anthracis* (anthrax) | Human/Cattle |
| *Clostridium botulinum* (botulism) | Human/Cattle |
| *Cowdria/Ehrlichia ruminatum* (Heartwater) | Cattle |
| *Mycobacterium avium* (Johnes) | Cattle |
| *Anaplasma marginale* (Anaplasmosis) | Cattle |
| *Mycobacterium bovis* (Tuberculosis) | Cattle |
| *Dermatophilus congolensis* (Dermatophilosis) | Cattle |
| *Streptococus uberis* (Mastitis) | Cattle |
| *Haemophilus somnus* (Abortion) | Cattle |
| *Brucella abortus* (Abortion) | Cattle |
| *Moraxella bovis* (Pinkeye) | Cattle |
| *Coxiella burnetti* (Q fever) | Multiple |
| *Mycoplasma mycoides* (bovine pleuropneumonia) | Multiple |
| *Borrelia hermsii* (Relapsing fever) | Multiple |
| *Mannheimia haemolytica* (Mastitis) | Multiple |
| *Clostridium difficile* (colitis) | Multiple |
| *Clostridium perfringens* (food poisoning) | Multiple |
| *Burkholderia mallei* (Glanders) | Horse |
| *Streptococcus zooepidericus* (inflammatory airway disease) | Horse |
| *Rhodococcus equi* (pneumonia) | Horse |
| *Streptococcus equi* (Strangles) | Horse |
| *Streptococcus suis* (Meningitis) | Pig |

-continued

| b. Bacterial | |
|---|---|
| Pathogen (disease) | Representative host species |
| *Erysipelothrix rhusiopathiae* (erysipelas) | Pig |
| *Brucella suis* (Abortion) | Pig |
| *Pasturella multocida* (rhinitis) | Pig |
| *Clostridium perfringens* (diarrhea, necrotic enteritis | Pig |
| *Clostridium septicum* (myonecrosis, gas gangrene, malignant edema) | guinea pigs, multiple animal species |
| *Actinobacillus pleuropneumoniae* (Severe respiratory disease) | Pig |
| *Lawsonia intracellularis* (proliferative enteropathy) | Pig |
| *Mycoplasma hypopneumoniae* (Pneumonia) | Pig |
| *Chlamydia abortus* (abortion) | Sheep/Goats |
| *Brucella ovis* (Abortion) | Sheep/Goats |
| *Corynebacterium pseudotuberculosis* (caseous lymphadentis) | Sheep/Goat |
| *Dichelobacter nodosus* (Footrot) | Sheep/Goat |
| *Bordetella Bronchiseptica* (kennel cough) | Dog |
| *Brucella canis* (Bordetellosis) | Dog |
| *Ehrlichia canis* (fever) | Dog |

Preferred embodiments relate to vaccines for bovine clostridial diseases, for example vaccines containing tox C and tox D proteins or antigens from *Clostridia sp.*

| c. Protozoan | |
|---|---|
| Pathogen (disease) | Representative host species |
| *Eimeria coccidiosis* | Poultry, turkey, cattle, swine, rodents |
| *Trichomonas* | Bovine, human |
| *Histomonas* | Turkey |
| Cryptosporidiosis | Cattle, sheep, goats, rabbits, swine, humans |
| *Toxoplasma gondii* | Feline, humans, cattle |
| *Neospora* | mammals |
| *Isoporoa* | mammals |
| *Pathogen* (disease) | Representative host species |
| *Crytosporidium parvum* (diarrhea) | Cattle/Goats/Sheep/Elk |
| *Toxoplasma gondii* | Multiple |
| *Babesia bigemina* (red water fever) | Cattle |
| *Babesia bovis* | Cattle |
| *Neospora caninum* | Cattle/Dogs |
| *Hammondia heydorni* | Dogs |
| *Theileria parva* (East coast fever) | Cattle |
| *Sarcocystis neurona* (neurological defects) | Horse |

Fish

Examples of fish hosts in the embodiments described herein include ornamental fish and fish that are commercially grown as food, such as salmon, catfish, trout, herring, codfish, mullet, mosquito fish, tench, eel, lampreys, round gobies, tilapia, zebrafish, medaka, carp, goldfish, loach, bass, and hybrid-stripped-bass (HBS).

Non-limiting examples of fish pathogens include the following:

| a. Viral | |
|---|---|
| Pathogen (disease) | Representative host species |
| infectious pancreatic necrosis virus (IPN) | Salmonids |
| infectious salmon anemia virus (ISA) | |

-continued

| a. Viral | |
|---|---|
| Pathogen (disease) | Representative host species |
| *Herpeviridae* (Herpes virus) | Catfish, turbot, trout, koi, carp and ornamental |
| *Iridoviridae* (Lymphocystis) | freshwater, saltwater, wild, cultured, warmwater, and coldwater |
| *Rhabdoviridae*: (infectious hematopoietic necrosis, IHN) | Salmonids |
| *Rhabdoviridae* (viral hemorrhagic septicemia, VHS) | Rainbow trout |
| Infectious hematopoietic necrosis virus (IHNV) | salmon |
| Heart and Skeletal muscle inflammation (HSMIV) | salmon |
| Salmon swimbladder sarcoma virus (SSSV) | Salmon |

Antigens from Infectious pancreatic necrosis virus (IPNV) are particularly useful in preferred embodiments. IPNV isolates (proteins and polyproteins) from Scotland, Chile or Norway are useful sources of antigens in embodiments described herein. For example, the VP2, VP3, VP4, or VP5, of IPNV isolates from Scotland, Chile or Norway or fragments or fusions thereof are useful antigens in embodiments described herein.

| b. Bacterial | |
|---|---|
| Pathogen (disease) | Representative host species |
| *Piscirickettsiae salmonis* (Septicemia) | Salmonid fish |
| *Mycobacterium tuberculosis* | Saltwater fish, Bass, HSB |
| *Rickettsiae* (chlamydia) | Epitheliocystis |
| *M. fortuitum*, piscine mycobacteriosis | Freshwater and saltwater fish |
| *Nocardia* | Salmonids, aquarium fish |
| *Renibacterium salmoninarum*, Corynebaqcteria (bacterial kidney disease) | Salmonids |
| *Clostridium botulinum* (e.g., type E) (botulism) | Cultured and wild fish, freshwater and saltwater |
| *Streptococcus iniae* | Yellowtail, Tilapia |
| *Staphylococcus* | Rainbow trout, tilapia, eel and yellowtail |
| *Flexibacter*; *Flexibacter columnaris* | Columnaris disease or saddleback |
| *Cytophaga psychrophilia* *Myxobacteria*, *Flavobacterium branchiophila* and *Flexibacter*; (bacterial gill disease) | Salmonids, coldwater |
| *Aeromonas* spp., e.g. *salmonicida* (Furunculosis) | freshwater fish and salmon |
| *Yersinia ruckeri* (Hagerman disease) | Salmonids, primarily rainbow trout |
| *Edwardsiella ictaluri* (Enteric septicemia) | Catfish, tilapia, eel |
| *Edwardsiell tarda* | Catfish, tilapia, eel |
| *Vibrio* sp., 7 species important, e.g. *salmonicida* | Marine, brackish, freshwater fish, e.g. Atlantic salmon |
| *Streptococcus agalactiae* (Pneumonia) | Fish |
| *Lactococcus garvieae* (Streptococcosis) | Tilapia |
| *Flavobacterium colmnare* (Columnaris) | catfish |
| *Perkinsus marinus* (Dermo) | oyster |

| c. Protozoan | |
|---|---|
| Pathogen (disease) | Representative host species |
| Ciliates, 13 genera; e.g. *Ichthyophthirius multifllis* or Ich in fresh water and *Cryptocaryon irritans* in salt water; *Uronema,Tetrahymena, Chilodenella Ambiphyra* (*Scyphidia*) and *Apiosoma*, *Trichodina, Trichodinella,* and *Tripartiella.* | Many species of fish |
| Flagellates: *Ichthyoboda* (Costia; fresh and salt water), *Amyloodinium* (saltwater species), *Crepidoodinium* (estuarine and marine) and *Piscinoodinium* (freshwater species), *Hexamita* (fresh and salt water) | |
| Suctorians; *Trichophyra* | Catfish |
| *Amoeba* | |
| Sporozoans: *Coccidia, Myxosporoa*, and *Microspora; Myxosoma cerebralis* is the *Myxosporidian* which causes whirling disease of salmonids; *Ceratomyxa Shasta* (PKD) | Salmonids |
| *Lepeophteirus salmonis* | salmon |
| *Kudoa thrysites* | salmon |

Birds

In other embodiments, the host can be any species bird. For example, the host can be commercial birds, such as poultry, including chickens, ducks, geese, turkeys, bantams, quails, or guinea fowl. Other commercial birds include ratites, such as ostriches, emus, and rheas.

Birds are not limited to commercial animals, but include companion animals, such as parrots, macaws, parakeets, budgies, and canaries.

Non-limiting examples of avian pathogens include:

| a. Viral | |
|---|---|
| Pathogen (disease) | Representative host species |
| Infectious Bursal Disease (IBD) virus | Chickens |
| Infectious bronchitis virus (IBV) | Poultry |
| Avian influenza | Chickens, ducks |
| Fowl pox | Chickens |
| Marek's disease virus | Poultry |
| Newcastle disease virus | Poultry |
| Chicken anemia virus | Chicken |
| Infectious Laryngotracheitis Virus (ILT) | Poultry |

Antigens from Infectious Bursal Disease Virus (IBDV) and Infectious bronchitis virus (IBV) are particularly useful in compositions described herein.

| b. Bacterial | |
|---|---|
| Pathogen (disease) | Representative host species |
| *Salmonella enterica* | poultry |
| *Chlamydia psitaci* (Psittacosis) | Pet birds, parrots |
| *Escherichia coli*; Colibacillosis (Coliform infections) | Chickens, turkeys |
| *Mycoplasma gallisepticum* (chronic respiratory disease (CRD)/air sac syndrome, infectious sinusitis) | Chickens, turkeys |
| *Mycoplasma meleagridis* (airsacculitis) | Turkeys |

-continued

| b. Bacterial | |
|---|---|
| Pathogen (disease) | Representative host species |
| *Mycoplasma synoviae* (synovitis, respiratory disease) | Chickens, turkeys |
| *Pasteurella multocida* (fowl cholera) | Chickens, turkeys, pheasants, pigeons, waterfowl, sparrows and other free-flying birds |
| *Clostridium colinum* (ulcerative enteritis; Quail disease) | Chickens, turkeys and other domestic fowl |
| *Clostridium perfringens* (necrotic enteritis), e.g. Types A and C | Chickens, turkeys and other poultry |
| *Clostridium septicum* (myonecrosis, gas gangrene, malignant edema) | Chickens, other poultry |
| *Salmonella pullorum*, pullorum disease | Primarily chickens and turkeys |
| *Salmonella gallinarum*, fowl typhoid | Chickens, turkeys, ducks, pigeons, pheasants |
| *Hemophilus gallinarum*, infectious coryza | Chickens |
| *Streptocossus, Staphylococcus, Proteus* (omphalitis) | |
| *Erysipelothrix insidios*, erysipelas | Chickens, ducks and geese, primary importance is the turkey (also human pathogen) |
| *Salmonella enteritidis* (Septicemia) | Poultry |
| *Bordetella avium* (Bordetellosis) | Poultry |
| *Actinobacillus salpingitidis* (oviduct inflammation) | Poultry |
| *Chlamydophila psittaci* (caviae) -Pneumonia | Poultry |
| *Mycoplasma iowae* (Respiratory disease) | Poultry |
| *Mycoplasma gallisepticum* (Respiratory disease) | Chicken |
| *Pasteurella multocida* (Fowl cholera) | Chicken |
| *Haemophilus paragallinarum* (Acute respiratory disease) | Chicken |
| *Ornithobacterium rhinotracheale* (Pneumonia) | Chicken |
| *Riemerella anatipestifer* (Septicamia) | Chicken |

Antigens from *Clostridum perfringens* are particularly useful in the compositions described herein.

| c. Protozoan | |
|---|---|
| Pathogen (disease) | Representative host species |
| *Eimeria* spp. (coccidiosis) | chicken, turkey |
| *Histomonas meleagridis* (blackhead) | turkey |
| *Hexamita meleagridis* (hexamitiasis) | turkey, quail, duck, partridges, pigeon |
| Toxoplasma | |
| Neospora | |

Antigens

Antigens are substances that elicit a specific immune response when introduced into an animal. An antigen may contain one or more antigenic determinants or epitopes. Antigens include polysaccharides, lipids, lipopolysaccharides, proteins, glycoproteins, lipoproteins, nucleoproteins, peptides, oligonucleotides and nucleic acids. Exogenous antigens are taken up by antigen presenting cells (APCs) such as dendritic cells, macrophages, B-lymphocytes and the like. Antigenic peptides are processed and presented on the APC surface in the context of a class II MHC molecule. The class II MHC/antigenic peptide complex is then recognized by $CD4^+$ T cells with T-cell receptors capable of recognizing the class II MHC/antigenic complex, referred to as the T-cell epitope. Alternatively, endogenous antigens are generated within a cell, and displayed at the cell surface in the context of a class I MHC molecule. The class I MHC/antigenic peptide complex is then recognized by $CD8^+$ T cells that have T-cell receptors capable of recognizing the class II MHC/antigenic complex, also referred to a T-cell epitope. Antibodies also recognize antigenic determinants (B cell epitopes).

Accordingly, as used herein, unless specified, the term "epitope" can refer to a T-cell epitope in the context of a class II MHC molecule, a T-cell epitope in the context of a class I MHC molecule, or a B cell epitope.

An antigen used in the embodiments disclosed herein is derived from a pathogen of a host. Specific pathogens and hosts are discussed above.

The antigen can be derived directly from complete or portions of naturally occurring proteins from pathogens or be expressed from naturally occurring nucleic acid sequences derived from the pathogen. Useful antigens can also be identified in related species as orthologs of known antigens from known pathogens.

The antigen can also be a variant of a naturally occurring polypeptide or be expressed from a variant of a naturally occurring nucleic acid sequence. Such variants can be obtained, for example, by (a) providing a template nucleic acid encoding an antigen from the pathogen; and (b) modifying, deleting or adding one or more nucleotides in the template sequence, or a combination thereof, to generate a variant of the template nucleic acid.

Several antigens useful in the present invention are discussed further below.

Promiscuous T-Cell Epitopes ("PTCs")

Promiscuous T-cell epitopes associated with either class II MHC or class I MHC molecules can be derived from naturally occurring immunogens derived from any pathogenic microorganism. Naturally occurring PTC epitopes can also be conservatively modified by single- or multiple-amino acid additions, deletions or substitutions (e.g. within classes of charged, hydrophilic/hydrophobic, steric amino acids) to obtain candidate sequences that can be screened for their ability to enhance immunogenicity.

Non-naturally occurring PTC epitopes can be artificially synthesized to obtain sequences that have comparable or better immunogenicity. Artificial PTC epitopes can range in size from about 7 to about 50 amino acid residues in length and can have structural features such as amphipathic helices, which are alpha-helical structures with hydrophobic amino acid residues dominating one face of the helix and charged or polar residues dominating the surrounding faces. The PTC epitopes may also contain additional primary amino acid patterns, such as a Gly or a charged residue followed by two to three hydrophobic residues, followed in turn by a charged or polar residue (a Rothbard sequence). In addition, PTC epitopes often obey the 1, 4, 5, 8 rule, where a positively charged residue is followed by hydrophobic residues at the fourth, fifth, and eighth positions after the charged residue.

These features may be incorporated into the designs of artificial PTC epitopes. Variable positions and preferred amino acids are available for MHC-binding motifs (Meister et al., Vaccine, 1995; 13:581-591). For example, the degenerate PTC epitope described in WO 95/11998 as SSAL1TH1 has the degenerate sequence (Asp/Glu)-(Leu/Ile/Val/Phe)-

Ser-(Asp/Gly)-(Leu/Ile/Val/Phe)-(Lys/Arg)-Gly-(Leu/Ile/Val/Phe)-(Leu/Ile/Val/Phe)-(Leu/Ile/Val/Phe)-His-(Lys/Arg)-Leu/Ile/Val/Phe)-(Asp/Glu)-Gly-(Leu/Ile/Val/Phe) (SEQ ID NO: 8).

Given this structural-functional guidance, it should be understood that many candidates for artificial PTC epitopes can be generated by conventional methods and screened for their ability to enhance the immune response of an associated antigen.

By way of example, particularly useful promiscuous T-cell epitopes useful in the embodiments disclosed herein include measles virus protein F LSEIKGVIVHRLEGV (SEQ ID NO:1); or tetanus sequence VDDALINSTKIYSYFPSV (SEQ ID NO:2). Other promiscuous T-cell epitopes useful in the embodiments disclosed herein include epitopes from tetanus toxoid (TT) (sequence 947-957 aa: Phe Asn Asn Phe Thr Val Ser Phe Trp Leu Arg Val Pro Lys Val Ser Ala Ser His Leu Glu; SEQ ID NO: 9). Yet other tetanus toxoid sequences include amino acid sequences 590-603, 615-629, 639-652, 830-843, and 947-967.

Still other useful PTC epitopes include Malaria *Plasmodium falciparum* CSP protein (sequence 378-398 aa, Asp Glu Lys Lys Ile Ala Lys Met Glu Lys Ala Ser Ser Val Phe Asn Val Val Asn Ser; SEQ ID NO: 10). Useful CMV CTL epitopes include $pp65_{13-24}$; $pp65_{417-426}$; $pp65_{265-275}$; $pp65_{363-373}$; $pp65_{369-379}$; $pp65_{188-195}$; $pp65_{186-196}$; $pp65_{367-379}$; and particularly NLVPMVATV ($pp65_{495-503}$; SEQ ID NO: 11).

Yet other promiscuous T-cell epitopes include hepatitis B surface and core antigen helper T-cell epitopes, pertussis toxin helper T-cell epitopes, *Chlamydia trachomatis* major outer membrane protein helper T-cell epitopes, diphtheria toxin helper T-cell epitopes, *Schistosoma mansoni* triose phosphate isomerase helper T-cell epitopes; *Escherichia coli* TraT helper T-cell epitopes; PADRE; and human immunodeficiency virus-1.

Various promiscuous T-cell epitopes are further described in U.S. Pat. No. 5,759,551, U.S. Pat. No. 6,107,021, and U.S. Pat. No. 6,783,761; and in U.S. Patent Publication No. 2004/0086524 A1, and references therein.

Non-limiting examples of promiscuous T-cell epitopes particularly useful in the embodiments described herein are listed below:

Examples of Promiscuous T-cell Epitopes

| Description | Amino acid sequence | SEQ ID NO: |
|---|---|---|
| measles 289-302 | LSEIKGVIVHRLEGV | 1 |
| tetanus toxin 582-599 | VDDALINSTKIYSYFPSV | 2 |
| tetanus toxin 830-844 | QYIKANSKFIGITEL | 3 |
| *Anaplasma marginale* | SSAGGQQQESS | 4 |
| circumsporozoite (CS) protein | ENDIEKKICKMEKCSSVFNV | 5 |
| influenza HA B epitope | SKAFSNCYPYDVPDYASL | 6 |
| PADRE | AKXVAAWTLKAAA | 7 |

Yet another useful immunogenic protein, although not strictly a PTC epitope, is cholera toxin B epitope (CTB).

In some embodiments, the composition described above is in association with a pharmaceutically acceptable carrier. Compositions disclosed herein can be administered intravenously or intramuscularly or through the nose or lung, preferably as a liquid or powder aerosol (lyophilized). The composition can also be administered subcutaneously, or in ovo, as described herein. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrans; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington: The Science and Practice of Pharmacy* ($20^{th}$ ed, Lippincott Williams & Wilkens Publishers (2003)). For example, dissolution or suspension of the active compound in a vehicle such as water or naturally occurring vegetable oil, like sesame, peanut, or cottonseed oil, or a synthetic fatty vehicle like ethyl oleate or the like, can be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res*., (1981) 15:167-277 and Langer, *Chem. Tech*., (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they can denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization can be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitoneally can produce a sustained release effect. Other compositions also include liposomally entrapped antibodies. Liposomes containing such antibodies are prepared by methods known per se: German Pat. No. DE 3,218,121; Epstein et al., *Proc. Natl. Acad. Sci. USA*, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

It will be appreciated that administration of compositions in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures can be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2):210-8 (2000), Wang W. "Lyophilization and development of solid protein pharmaceuticals." *Int. J. Pharm.* 203(1-2):1-60 (2000), Charman W N "Lipids, lipophilic drugs, and oral drug delivery-some emerging concepts." *J. Pharm. Sci.* 89(8):967-78 (2000), Powell et al. "Compendium of excipients for parenteral formulations" *PDA J. Pharm. Sci. Technol.* 52:238-311 (1998) and the citations therein for additional information related to formulations, excipients and carriers well known to pharmaceutical chemists.

In some embodiments, the compositions are associated with an adjuvant. Adjuvants are commonly combined with vaccines for the purpose of improving immune response. Suitable adjuvants include aluminum hydroxide, phosphate or oxide, amphigen, tocophenols, monophosphenyl lipid A, muramyl dipeptide, oil emulsions, glucans, carbomers, block copolymers, Montamide, saponins such as Quil A, and Simulsol 5100 (SEPIC). If aluminum hydroxide (alum) or aluminum phosphate is used, the amount used can generally be in the range 100-1000 μg, for example 250-750 μg, particularly about 500 μg per vaccine dose.

Some adjuvants are a mixture of oils and other molecules. Such adjuvants are thought to directly and indirectly stimulate the immune system. Without intending to be bound by any particular theory, one direct way in which oil-based adjuvants may stimulate the immune system may be through antigenic epitopes within the adjuvant. Alternatively, oil-based adjuvants may function indirectly as an antigen depot that increases the half-life of the vaccine, and as a means to increase the local concentration of antigen available to a given immune receptor.

In other embodiments, the composition can include a DNA or nucleic acid adjuvant. For example, CpG molecules can be used as an adjuvant in the compositions disclosed herein, having a motif of an unmethylated CpG dinucleotide flanked by two 5' purines and two 3' pyrimidines. Oligonucleotides containing CpG motifs have been shown to activate the immune system, thereby boosting an antigen-specific immune response. This effect can be used by mixing the CpG oligonucleotides with the DNA vaccine, or physically linking the CpG motifs to the plasmid. Other nucleic acid based adjuvants are known and contemplated in the embodiments described herein, including the use of plasmids that can express lipids as a dextrosome, thereby resulting in expression of a fully adjuvanted vaccine.

Antigenic peptides that do not result in a strong immune response can be presented to the immune system in alternate ways for the purpose of improving the immune response. Naturally these epitopes are part of a larger antigen molecule that is believed to be more "visible" to the immune system. Certain strong antigens have multiple copies of the same epitope.

Some of the benefits that complete antigens and adjuvants bring to vaccination can be reproduced by vaccine scaffolds. Antigenic epitopes can be linked to scaffold molecules, which may increase immunological "visibility." Increased visibility can be the result of an increase in the size of the antigenic or immunogenic unit or an increase in construct half-life. Scaffold molecules that agglomerate may also act to increase local concentration of the epitope. Kirkely et al. (2001) *Immunobiology;* 203(4):601-15 describes the benefits of linking synthetic peptides to immunogenic carrier proteins. The conjugates were more effective at generating a peptide specific immune response. Dakappaggari et al. (2005) *J Pept Res.;*65(2):189-99 mimicked the presentation of multiple CTL epitopes by tumors or virus infected cells by creating a multiepitope peptide vaccine and deliver it in a non-covalent complex with an amphipathic peptide carrier. Hayman (2002), *Immunol Cell Biol.,* 80(2):178-87 increased immunogenicity of a peptide vaccine by conjugating multiple copies of the epitope with oligomeric poly-lysine linkers, which form a lipid core that anchors the epitopes. These examples are not exhaustive, but illustrative of the diversity of engineered peptide vaccine carriers or scaffolds: coupled proteins, non-covalently linked carriers, and repeated linkers. The skilled artisan will readily appreciate one or a combination of antigenic epitopes and immunomodulatory domains such as T-cell epitopes, B-Cell epitopes, heat shock protein domains, and the like, is one method useful for increasing immunological "visibility," as discussed above. Using techniques readily available to those skilled in the art, homo- and heteropolymers of monomers containing one or more of the antigenic epitopes and immunomodulatory domains can be generated, using techniques known to the skilled artisan. Non-limiting examples of such are described in co-pending U.S. patent application Ser. No's: 09/997,807, 10/370,370, 60/250,426, 60/357,406, 60/556,393, 60/605,192; 11/046,203; and International Patent publications WO02/44336, WO03/70961, and International Patent Application No.: PCT/US05/09927.

In some embodiments, the antigen can be of viral origin. For example, the antigen may be derived from a virus that infects mammals, birds, or fish.

Non-limiting examples of viruses from which antigens useful in the present invention are derived are disclosed above. In some examples, the virus is infectious bronchitis virus (IBV) that infects poultry. For example, the composition may include a PTCE derived from the IBV nucleocapsid protein, and the antigen can be derived from the spike protein of IBV.

In other embodiments, the antigen can be derived from a bacterial pathogen. Antigens from any of the bacterial pathogens described above are useful in the present invention. As shown below, antigens derived from *C. perfringens*, a bacterium that afflicts mammalian (e.g., swine) and bird hosts, are useful in the present invention. For example, in preferred embodiments, the ToxA protein of *C. perfringens*, or a fragment thereof that includes approximately 120-125 amino acids of the ToxA protein the carboxy terminal end of the protein, referred to as C'ToxA, is useful in embodiments described herein.

In still other embodiments, the antigen can be derived from a protozoan pathogen. Antigens from certain protozoan pathogens are particularly useful in the invention, including but not limited to antigens from Eimeria, *Toxoplasma, Neospora, and Cryptosporida.*

Additional eukaryotic pathogens from which antigens in the embodiments described herein can be derived are from the phylum Arthropoda, including sea lice, mites, ice, ticks, fleas, and flies such as stable flies, horn flies, blow flies. Other eukaryotic pathogens from which antigens can be derived are from the phylum Nematoda including flatworms and Trematodes. These pathogens can affect avian, piscene, bovine, ovine, porcine, and equine species. They also affect man.

Several antigens of interest can be obtained from *Eimeria* oocysts, as well as from the surface of *Eimeria* sporozoites and merozoites, such as the antigen encoded by the 3-1E gene or Mic2 gene. Non-limiting examples of *Eimeria* antigens include:

SO7
SO255
SO52
TA4
EAMZ250
SO67
EASZ
GX3262
EASZ22
Eap30-47
cSZ1
cMZ-8
EAMZ92/100
p43
EtMIC1
EAMZ150
SZ18-120
pEM230
Ea1A
Et7B2
EMP100
EASZ 19
HSP70
EtMIC2
3-1E
HSP90 (SEQ ID NO:37)
HSP *Eimeria tenella* 200 to 280 amino acids 71AA (SEQ ID NO:38)
HSP *Eimeria maxima* (SEQ ID NO:40)

Non-limiting examples of antigens from *Toxoplasma* include:

23K calcium-binding major antigen precursor
24 kDa toxoplasma antigen
29 kD excretory dense granule protein
54-kda antigen
A Chain A
AH4_TOXGO ANTIGEN H4
antigen p28
apical membrane antigen 1 homolog
B Chain B
B10 protein
beta-tubulin
bradyzoite antigen glutathione-5-transfersase (GST) fusion protein (BAG-1)
bradyzoite surface antigen
bradyzoite surface antigen BSR4
cyst matrix protein
dense granule antigen
fructose-1,6-bisphosphate aldolase
GPI-anchored surface protein
GRA1_TOXGO Dense granule protein 1 precursor
GRA2_TOXGO Dense granule protein 2 precursor
GRA3_TOXGO Dense granule protein 3
GRA4_TOXGO Dense granule protein 4 precursor
GRA5_TOXGO Dense granule protein 5 precursor
GRA6_TOXGO Dense granule protein 6
GRA7_TOXGO Dense granule protein 7 precursor
granule antigen protein GRA6
H11 protein
H4 protein
major surface antigen p30
major surface antigen P30 precursor
major surface antigen precursor
major surface protein
MIC3 microneme protein
microneme protein 12
microneme protein 7
microneme protein 8
microneme protein 9
non-transmembrane antigen
p18 surface antigen
P28 antigen
p30 antigen
P30_TOXGO Major surface antigen p30 precursor
P35 surface antigen
proliferating cell nuclear antigen 1
proliferating cell nuclear antigen 2
putative bradyzoite-specific surface protein
putative GPI-anchored surface antigen SRS4
putative GPI-anchored surface BSR4-related antigen
rhomboid-like protease 5
rhoptry protein 2 precursor
ribosomal phosphoprotein P0
ROP2, ROP8
SAG1-related sequence 2
SAG1-related sequence 3
SAG1-related sequence 6
SAG1-related sequence 7
SAG1-related sequence 8
SAG2 related antigen SAG2B
SAG2 related antigen SAG2C
SAG2 related antigen SAG2D
SAG2-related antigen SAG2E
SAG5A
SAG5C
SAG5D
subtilisin-like protein
surface antigen 43
surface antigen 5A
surface antigen 5B
surface antigen 5C
surface antigen 5D
surface antigen P22
surface antigen P22 precursor
surface antigen SAG1 precursor
surface protein rhoptry ROP1 precursor
Tg34
TgMIC10 precursor
trypsin inhibitor Non-limiting examples of antigens from Neospora include:

14-3-3 PROTEIN HOMOLOG
alpha-tubulin
antigen N54
apical complex protein
Dense granule protein 1 precursor
Dense granule protein 2
dense granule protein 2; NCDG2
DNA dependent RNA polymerase beta subunit
Gra1
GRA2
MIC2-associated protein precursor
microneme protein NcMIC11 precursor
microneme protein Nc-P38
NcMIC10 precursor
NTPase
P20
p29 surface antigen
p36 protein
peptide recognized by serum from cattle that aborted due to neosporosis
putative dense granule protein 3
putative surface antigen protein
Rbj-like protein
SAG1 precursor
SAG1-related sequence 2
serine proteinase inhibitor PI-S
small heat shock protein
SRS2 surface antigen
subtilisin-like serine protease
SUL1
superoxide dismutase
surface antigen p35
surface antigen SAG1
surface protein Nc-p43
thrombospondin-related adhesive protein homolog Non-limiting examples of antigens from *Cryptosporida* include:

CP2
Cp17 antigen precursor
surface glycoprotein Cpgp40/15
surface glycoprotein 900 (GP900)
sporozoite surface antigen p23
S60 protein
Cp22.4.1 protein
immunodominant antigen Cp23
sporozoite antigen gp40/15
15 kDa glycoprotein gp15

In some embodiments, the composition further comprises a cytokine. Cytokines are a group of low-weight regulatory proteins or glycoproteins that are secreted by cells and that can mediate communication between cells. The immune response to an antigen can be enhanced by co-administration with cytokines, including recombinant cytokines and plasmids encoding cytokines, or their effective parts. (See Min et al., (2001) *Vaccine* 20:267-274).

As used herein, the term "cytokine" refers to a polypeptide comprising at least one subunit of a protein that can stimulate proliferation or differentiation of lymphocytes, macrophages, mast cells, natural killer cells, granulocytes; induce macrophages to secrete reactive nitrogen intermediates such as nitrite, nitrate, or nitric oxide; or induce such cells to secrete cytokines. The term includes peptides that have been chemically modified to extend its longevity or half-life, such as by adding a protecting group.

Particularly useful cytokine in compositions described herein are those that induce $CD4^+$ and $CD8^+$ T-helper cells to induce a strong immune response in the host. As such, compositions can include, for example, interferon gamma (IFN-γ) and interleukin-12 (IL-12).

Other cytokines that are used in certain embodiments include interleukins (IL)-1 through -25; human B cell-activating factor (BAFF); granulocyte colony-stimulating factor (G-CSF); granulocyte/macrophage colony-stimulating factor (GM-CSF); interferons (IFN)-alpha, -beta and -gamma; leukemia inhibitory factor (LIF), macrophage colony stimulating factor (M-CSF), macrophage inhibition factor (MIF), oncostatin M (OSM), stem cell factor (CSF), thrombopoietin (Tpo), transforming growth factor beta (TGF-β); and tumor necrosis factors -alpha and -beta (TNF-α, -β).

Many of these cytokines have been described in mammals, but homologous cytokines have been identified in other animals, such as in birds and especially chickens. While it can be desirable to select a cytokine from the same species as the intended host, cytokines can be selected from related or unrelated species, so long as the cytokine provides an enhanced immune response. For example, a chicken cytokine, such as chicken IFN-γ and/or IL-12. can be co-administered to a turkey or duck host. Other cytokines for species of interest can be obtained by standard procedures known to skilled artisans, such as by isolating corresponding nucleic acids using techniques familiar to those skilled in the art such as PCR or hybridization, followed by expression and screening.

Although any known cytokine can be used in the invention, particular cytokines can be selected from the following:

Examples Of Cytokines

IFN-γ
IFN-α
TGF-β4
IL-1b
IL-2
IL-8
IL-12
IL-15
IL-16
IL-17
IL-6
IFN-β
IL-18
IL-21
IL-5
IL-10

The usefulness of particular cytokines in the compositions will depend on factors appreciated by the skilled artisan, such as the antigen, the type of the immune response desired, and the intended host.

Chemokines are a family of small cytokines, that are released in response to infection together with other inflammatory cytokines (Mackay, C., (1997) *Curr Biol.,* 1; 7(6):R384-6. Their molecular masses range from 6-14 kDa (Ward, S. G., (1998) *Immunity,* 9(1):1-11, and they all have related amino acid sequences which are between 20 and 50% sequentially homologous. Chemokines are multiple mediators, but were first studied as inducers of chemotaxis of specific leukocytes (Nelson, P. I. & Krensky, E. M., (1998) *Curr Opin Immunol,* 10(3):265-70; Kim, C. H. et al., (1999) *J Leukoc Biol.,* 65(1):6-15; Moser B, (1998) *Sci Prog.,* 81 (Pt 4):299-313. Further studies have revealed that chemokines also stimulate lymphocyte development, angiogenesis, degranulation of granulocytes, respiratory bursts and the release of lysosomal enzymes in monocytes. Furthermore, chemokines were shown to reduce the threshold of responsiveness of immune cells to other inflammatory mediators. Taub, D. D., (1996), *Cytokine Growth Factor Rev.,* 7(4):355-76. Chemokines are contemplated in the embodiments described herein.

In some embodiments, the composition includes a plurality, or more than one PTCE. For example, in some embodiments, two measles PTCEs, e.g., amino acids 289-302 of the measles virus, can be present in the composition. The multiple PTCEs can be connected by a polylinker of 10 glycines. In some embodiments, the composition includes multiple PTCEs that are different, such as for example a measles PTCE and a tetanus toxin PTCE. Multiple PTCEs can be positioned so they flank the antigen, or they can be positioned on the same side (e.g., amino terminus or carboxy terminus) of the antigen.

The PTCE can be connected by direct covalent attachment to the N- or C-terminus of the antigen. The epitope can also be connected by a spacer to be near either terminus of the antigen, while providing a degree of separation in the three-dimensional folding of the PTCE and the antigen. The spacer can be a short spacer peptide (e.g. 4 to 8 amino acids), such as GPSL (SEQ ID NO: 12); SSGPSL (SEQ ID NO: 13); SSGPSLKL (SEQ ID NO: 14); and GLPG (SEQ ID NO: 15). In preferred embodiments, the linkers include either 9 or 10 consecutive glycine residues.

Thus, useful embodiments include 3 measles PTC epitopes connected with 2 Gly 10 spacers; 2 and 3 tetanus epitopes connected by Gly 10 or Gly 9 spacers, and mixed measles and tetanus epitopes connected with such Gly spacers.

The compositions described above can be peptides, nucleic acids encoding peptides, or a combination of peptides and nucleic acids. Accordingly, in one embodiment, the composition can contain one or more isolated or recombinant polypeptides composed of an amino acid sequence. Thus, the polypeptide can contain an antigen, a PTCE, and optionally the cytokine, as a single polypeptide, or they can be contained on two or more separate polypeptides. In other embodiments, the composition can contain one or more recombinant nucleic acids encoding an antigen, a PTCE and optionally a cytokine on a single nucleic acid, or on two or more separate nucleic acids. In yet other embodiments, any one of the components discussed above can be a recombinant polypeptide, whereas other components are recombinant nucleic acids.

The terms "amino acid" or "amino acid sequence" includes an oligopeptide, peptide, polypeptide, or protein sequence; or a fragment, portion, or subunit of any of these, and can refer to naturally occurring or synthetic molecules. The terms "polypeptide" and "protein" include amino acids joined to each other by peptide bonds or modified peptide bonds, and may contain modified amino acids other than the 20 gene-encoded amino acids. The term "polypeptide" also includes peptides and polypeptide fragments and motifs. The term also includes glycosylated polypeptides. The peptides and polypeptides of the invention also include all "mimetic" and "peptidomimetic" forms.

The term "isolated" includes material removed from its original environment, e.g., the natural environment if it is naturally occurring. For example, a polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment. As used herein, an isolated material or composition can also be a "purified" composition, i.e., it does not require absolute purity; rather, it is intended as a relative definition. Individual nucleic acids obtained from a library can be conventionally purified to electrophoretic homogeneity. In alternative aspects, the invention provides nucleic acids that have been purified from genomic DNA or from other sequences in a library or other environment, by at least one, two, three, four, five, or more orders of magnitude.

As used herein, the term "recombinant" can include nucleic acids adjacent to a "backbone" nucleic acid to which it is not adjacent in its natural environment. In one aspect, nucleic acids represent 5% or more of the number of nucleic acid inserts in a population of nucleic acid "backbone molecules." "Backbone molecules" according to the embodiments described herein include nucleic acids such as expression vectors, self-replicating nucleic acids, viruses, integrating nucleic acids, and other vectors or nucleic acids used to maintain or manipulate a nucleic acid insert of interest. In one aspect, the enriched nucleic acids represent 10%, 15%, 20%, 30%, 40%, 50%, 60%, 70%, 80%, 90%, 95%, 98% or more of the number of nucleic acid inserts in the population of recombinant backbone molecules. "Recombinant" polypeptides or proteins refer to polypeptides or proteins produced by recombinant DNA techniques; e.g. produced from cells transformed by an exogenous DNA construct encoding the desired polypeptide or protein. "Synthetic" polypeptides or protein are those prepared by chemical synthesis.

Peptides and polypeptides of the embodiments described herein can be made and isolated using any method known in the art. Polypeptide and peptides can also be synthesized, whole or in part, using chemical methods well known in the art. See, e.g., Caruthers, *Nucleic Acids Res. Symp. Ser.* 215-223 (1980); Horn, *Nucleic Acids Res. Symp. Ser.* 225-232 (1980); A. K. Banga, *Therapeutic Peptides and Proteins, Formulation, Processing and Delivery Systems* (1995). For example, peptide synthesis can be performed using various solid-phase techniques (see, e.g., Roberge, *Science* 269:202 (1995); Merrifield, *Methods Enzymol.* 289:3-13 (1997)), and automated synthesis may be achieved, e.g., using the ABI 431A Peptide Synthesizer (Perkin Elmer) in accordance with the manufacturer's instructions.

Peptides and polypeptides can also be glycosylated. The glycosylation can be added post-translationally either chemically or by cellular biosynthetic mechanisms, where the latter incorporates the use of known glycosylation motifs, which can be native to the sequence or can be added as a peptide or added in the nucleic acid coding sequence. The glycosylation can be O-linked or N-linked.

The terms peptides and polypeptides refer to all polymers comprising amino acids joined to each other by peptide bonds or modified peptide bonds (e.g. peptide isosteres) and may contain modified amino acids other than the 20 gene-encoded amino acids. Polypeptides may be modified by either natural processes, such as post-translational processing, or by chemical modification techniques that are well known in the art. Modifications can occur anywhere in the polypeptide, including the peptide backbone, the amino acid side-chains, and the amino or carboxyl termini. It will be appreciated that the same type of modification may be present in the same or varying degrees at several sites in a given polypeptide. Also a given polypeptide may have many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of a phosphytidylinositol, cross-linking cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation (see T. E. Creighton, *Proteins: Structure and Molecular Properties*, W.H. Freeman & Co., New York (2nd ed. 1993); B. C. Johnson, ed., *Posttranslational Covalent Modification of Proteins*, Academic Press, New York, pp. 1-12 (1983)).

Further, the terms peptide and polypeptide as used herein include all "mimetic" and "peptidomimetic" forms. The terms "mimetic" and "peptidomimetic" refer to a synthetic chemical compound that has substantially the same structural and/or functional characteristics of the polypeptides of the invention. The mimetic can be either entirely composed of synthetic, non-natural analogs of amino acids, or is a chimeric molecule of partly natural peptide amino acids and partly non-natural analogs of amino acids. The mimetic can also incorporate any amount of natural amino acid conservative substitutions, as long as such substitutions do not also substantially alter the mimetic's structure and/or activity. As with polypeptides of the invention that are conservative variants, routine experimentation will determine whether a mimetic is within the scope of the invention, i.e., that its structure and/or function is not substantially altered.

Polypeptide mimetics can contain any combination of non-natural structural components. In alternative aspect, mimetic compositions of the invention include one or all of the following three structural groups: (a) residue linkage groups other than the natural amide bond ("peptide bond") linkages; (b) non-natural residues in place of naturally occurring amino acid residues; or (c) residues that induce secondary structural mimicry, i.e., to induce or stabilize a secondary structure (e.g. a beta turn, gamma turn, beta sheet, or alpha helix conformation). For example, polypeptides can be characterized as a mimetic when all or some of its residues are joined by chemical means other than natural peptide bonds. Individual peptidomimetic residues can be joined by peptide bonds, other chemical bonds or coupling means, such as glutaraldehyde, N-hydroxysuccinimide esters, bifunctional maleimides, N,N'-dicyclohexylcarbodiimide (DCC), or N,N'-diisopropylcarbodiimide (DIC). Linking groups that can be an alternative to the traditional amide bond ("peptide bond") linkages include, ketomethylene (e.g. $-C(=O)-CH_2-$ for $-C(=O)-NH-$), aminomethylene ($CH_2-NH$), ethylene, olefin ($CH=CH$), ether ($CH_2-O$), thioether ($CH_2-S$), tetrazole ($CN_4-$), thiazole, retroamide, thioamide, or ester (see, e.g., Spatola in *Chemistry and Biochemistry of Amino Acids, Peptides and Proteins*, Vol. 7, pp 267-357, "Peptide Backbone Modifications," Marcell Dekker, NY (1983)).

Polypeptides can also be characterized as a mimetic by containing all or some non-natural residues in place of naturally occurring amino acid residues. Non-natural residues are well described in the scientific and patent literature; a few exemplary non-natural compositions useful as mimetics of natural amino acid residues and guidelines are described below. Mimetics of aromatic amino acids can be generated by replacing by, e.g., D- or L-naphylalanine; D- or L-phenylglycine; D- or L-2-thieneylalanine; D- or L-1, -2-, -3-, or -4-pyreneylalanine; D- or L-3-thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenylphenylalanine; D- or L-2-indole(alkyl)alanines; or D- or L-alkylamines, where alkyl can be substituted or unsubstituted methyl, ethyl, propyl, hexyl, butyl, pentyl, isopropyl, iso-butyl, sec-isotyl, iso-pentyl, or a non-acidic amino acid. Aromatic rings of a non-natural amino acid include thiazolyl, thiophenyl, pyrazolyl, benzimidazolyl, naphthyl, furanyl, pyrrolyl, and pyridyl aromatic rings.

Mimetics of acidic amino acids can be generated by substitution by non-carboxylate amino acids while maintaining a negative charge, e.g., (phosphono)alanine; sulfated threonine. Carboxyl side groups (e.g. aspartyl or glutamyl) can also be selectively modified by reaction with carbodiimides (R'—N—C—N—R') such as 1-cyclohexyl-3(2-morpholinyl-(4-ethyl)carbodiimide or 1-ethyl-3(4-azonia-4,4-dimetholpentyl)carbodiimide. Aspartyl or glutamyl can also be converted to asparaginyl and glutaminyl residues by reaction with ammonium ions. Mimetics of basic amino acids can be generated by substitution with (in addition to lysine and arginine) the amino acids ornithine, citrulline, (guanidino) acetic acid, or (guanidino)alkyl-acetic acid, where alkyl is defined above. Nitrile derivatives (e.g. containing the CN-moiety in place of COOH) can be substituted for asparagine or glutamine. Asparaginyl and glutaminyl residues can be deaminated to the corresponding aspartyl or glutamyl residues. Arginine residue mimetics can be generated by reacting arginyl with one or more conventional reagents, including phenylglyoxal, 2,3-butanedione, 1,2-cyclo-hexanedione, or ninhydrin, preferably under alkaline conditions. Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively. Cysteine residue mimetics can be generated by reacting cysteinyl residues with, e.g., alpha-haloacetates such as 2-chloroacetic acid or chloroacetamide and corresponding amines to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl)propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or chloro-7-nitrobenzo-oxa-1,3-diazole. Lysine mimetics can be generated (and amino terminal residues can be altered) by reacting lysinyl with succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitro-benzenesulfonic acid, O-methylisourea, 2,4,-pentanedione, and transamidase-catalyzed reactions with glyoxylate. Mimetics of methionine can be generated by reaction with methionine sulfoxide. Mimetics of proline include pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with diethylprocarbonate or para-bromophenacyl bromide. Other mimetics include those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A residue, e.g., an amino acid, of a polypeptide can also be replaced by an amino acid (or peptidomimetic residue) of the opposite chirality. Thus, any amino acid naturally occurring in the L-configuration (which can also be referred to as the R- or S-configuration, depending upon the structure of the chemical entity) can be replaced with the amino acid of the same chemical structural type or a peptidomimetic, but of the opposite chirality, referred to as the D-amino acid.

Modifications, additions or deletions can be introduced into the polypeptides described herein by known methods, such as error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, Gene Site Saturation Mutagenesis (GSSM™), synthetic ligation reassembly (SLR), or a combination thereof. In another aspect, the modifications, additions, or deletions can be introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and a combination thereof.

"Variant" includes polynucleotides or polypeptides of the invention modified at one or more base pairs, codons, introns, exons, or amino acid residues, yet still retain the immunogenic activity The term "saturation mutagenesis" or "GSSM" includes a method that uses degenerate oligonucleotide primers to introduce point mutations into a polynucleotide. GSSM is described more fully in U.S. Pat. Nos. 6,171,820, 6,562,594, and 6,764,835.

The term "optimized directed evolution system" or "optimized directed evolution" includes a method for reassembling fragments of related nucleic acid sequences, such as related genes.

The term "synthetic ligation reassembly" or "SLR" includes a method of ligating oligonucleotide fragments in a non-stochastic fashion. SLR is described more fully in U.S. Pat. Nos. 6,537,776 and 6,605,449.

The use of polypeptides of the invention as vaccines is described in greater detail below. Vaccine preparation is generally described in Voller et al., ed., *New Trends and Developments in Vaccines* (1978). Encapsulation within liposomes is described in U.S. Pat. No. 4,235,877. Conjugation of proteins to macromolecules is described in U.S. Pat. No. 4,372,945 and No. 4,474,757.

The amount of antigen in each vaccine dose is selected as an amount that induces an immune response without significant adverse side effects. The amount will vary, depending upon which specific antigen is used. Generally, an effective dose can comprise 1-1000 μg of protein, more particularly 50-500 μg, most particularly 100-300 μg.

In some embodiments, antigens, and/or PTCE's and/or cytokines are provided as fusion proteins. Accordingly, any polypeptide useful in the embodiments described herein can be fused to a heterologous peptide or polypeptide, such as N-terminal identification peptides that impart desired characteristics, such as increased stability or simplified purification, or fusions between antigens, linkers and one or more PTCEs. Peptides and polypeptides can also be synthesized and expressed as fusion proteins with one or more additional linked domains, such as for producing a more immunogenic peptide to more readily isolate a recombinantly synthesized peptide; or to identify and isolate antibodies and antibody-expressing B cells. Detection and purification facilitating domains include metal-chelating peptides such as polyhistidine tracts and histidine-tryptophan modules that allow purification on immobilized metals; protein A domains that allow purification on immobilized immunoglobulin; and the domain utilized in the FLAGS extension/affinity purification system (Immunex Corp., Seattle, Wash.). Other useful fusion proteins are based on the maltose binding protein (e.g., pMAL4).

Cleavable linker sequences such as Factor Xa or enterokinase (Invitrogen, San Diego, Calif.) can be included between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see, e.g., Williams, *Biochemistry* 34:1787-1797 (1995); Dobeli, *Protein Expr. Purif* 12:404-414 (1998)). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, e.g., Kroll, *DNA Cell. Biol.,* 12:441-53 (1993).

As discussed above, in some embodiments, compositions may include recombinant nucleic acid that encodes any polypeptide present in the embodiments described herein.

The phrases "nucleic acid" or "nucleic acid sequence" includes oligonucleotide, nucleotide, polynucleotide, or a fragment of any of these; including DNA or RNA (e.g. mRNA, rRNA, tRNA) of genomic or synthetic origin, which may be single-stranded or double-stranded and may represent a sense or antisense strand; peptide nucleic acid (PNA), or any DNA-like or RNA-like material, natural or synthetic in origin, including iRNA, ribonucleoproteins (e.g. iRNPs). The term encompasses nucleic acids, e.g., oligonucleotides, containing known analogs of natural nucleotides. The term also encompasses nucleic-acid-like structures with synthetic backbones. See Mata, *Toxicol. Appl. Pharmacol.* 144:189-197 (1997); Strauss-Soukup, *Biochemistry* 36:8692-8698 (1997); Samstag, *Antisense Nucleic Acid Drug Dev.* 6:153-156 (1996).

The nucleic acids of the invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. Any recombinant expression system can be used, including bacterial, mammalian, yeast, insect, or plant cell expression systems.

Alternatively, these nucleic acids can be synthesized in vitro by well-known chemical synthesis techniques. See, e.g., Adams, *J. Am. Chem. Soc.* 105:661 (1983); Belousov, *Nucleic Acids Res.* 25:3440-3444 (1997); Frenkel, *Free Radic. Biol. Med.* 19:373-380 (1995); Blommers, *Biochemistry* 33:7886-7896 (1994); Narang, *Meth. Enzymol.* 68:90 (1979); Brown, *Meth. Enzymol.* 68:109 (1979); Beaucage, *Tetra. Lett.* 22:1859 (1981); U.S. Pat. No. 4,458,066.

Techniques for manipulating nucleic acids, such as subcloning, labeling probes (e.g. random-primer labeling using Klenow polymerase, nick translation, and amplification), sequencing, hybridization, PCR agarose and PAGFE electrophoresis, end-labeling, and DNA purification are well described in the scientific and patent literature. See, e.g., Sambrook, ed., *Molecular Cloning: A Laboratory Manual*, Cold Spring Harbor Laboratory (3rd ed. 2000); Ausbel ed., *Current Protocols in Molecular Biology*, John Wiley & Sons, Inc., New York (1997); Tijssen ed., *Laboratory Techniques in Biochemistry and Molecular Biology: Hybridization with Nucleic Acid Probes, Part I. Theory and Nucleic Acid Preparation*, Elsevier, N.Y. (1993).

Another useful means of obtaining and manipulating nucleic acids useful in the embodiments described herein is to clone from genomic samples, and optionally screen and re-clone inserts isolated or amplified from genomic clones or cDNA clones. Sources of nucleic acid used in the methods of the invention include genomic or cDNA libraries contained in mammalian artificial chromosomes (MACs) (See, U.S. Pat. No. 5,721,118 and No. 6,025,155); human artificial chromosomes (Rosenfeld, *Nat. Genet.* 15:333-335 (1997)); yeast artificial chromosomes (YAC); bacterial artificial chromosomes (BAC); P1 artificial chromosomes (Woon, *Genomics* 50:306-316 (1998)); P1-derived vectors (PACs) (Kern, *Biotechniques* 23:120-124 (1997)); cosmids, recombinant viruses, phages, or plasmids.

Nucleic acid encoding polypeptides can be assembled in appropriate phase with a leader sequence capable of directing secretion of the translated polypeptide or fragment thereof.

In some embodiments, a composition that is a DNA vaccine is constructed by subcloning the nucleic acid encoding the components of the compositions described above into a eukaryotic plasmid vector such as pcDNA3, pCI, VR1012, and VR1020. Preferably, the nucleic acid composition is inserted in the correct orientation in order for the genes to be expressed under the control of a eukaryotic promoter.

Other aspects relate to vectors that include nucleic acids described herein. The term "vector" includes a nucleic acid that can infect, transfect, transiently, or permanently transduce a cell. It will be recognized that a vector can be a naked nucleic acid, or a nucleic acid complexed with protein or lipid. The vector optionally includes viral or bacterial nucleic acids and/or proteins, and/or membranes (e.g., a cell membrane, or a viral lipid envelope). Vectors can include replicons (e.g. RNA replicons, bacteriophages) to which fragments of DNA may be attached and become replicated. Vectors thus include RNA, autonomous self-replicating circular or linear DNA or RNA (e.g., plasmids, viruses, see U.S. Pat. No. 5,217,879); and include both the expression and non-expression plasmids. Where a recombinant microorganism or cell culture is described as hosting an "expression vector", this includes both extra-chromosomal circular and linear DNA and DNA that has been incorporated into the host chromosome(s). Where a vector is being maintained by a host cell, the vector may either be stably replicated by the cells during mitosis as an autonomous structure, or be incorporated within the host's genome.

Some embodiments provide expression vectors and/or cloning vehicles comprising nucleic acids of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus*, and yeast). Vectors of the invention can include chromosomal, non-chromosomal and synthetic DNA sequences. Large numbers of suitable vectors are known to those of skill in the art, and are commercially available. Bacterial vectors include pQE vectors (Qiagen), pBluescript plasmids, pNH vectors, lambda-ZAP vectors (Stratagene), ptrc99a, pKK223-3, pDR540, and pRIT2T (Pharmacia). Eukaryotic vectors include pXT1, pSG5 (Stratagene), pSVK3, pBPV, pMSG, and pSVLSV40 (Pharmacia). However, any other plasmid or other vector may be used so long as they are replicable and viable in the host. Low copy number or high copy number vectors may be used Expression vectors can include a promoter, a ribosome binding site for translation initiation, and a transcription terminator. The vector may also include appropriate sequences for amplifying expression. Mammalian expression vectors can comprise an origin of replication, any necessary ribosome binding sites, a polyadenylation site, splice donor and acceptor sites, transcriptional termination sequences, and 5' flanking non-transcribed sequences. In some embodiments, DNA sequences derived from the SV40 splice and polyadenylation sites can be used to provide the required non-transcribed genetic elements. In some embodiments, the expression vectors contain one or more selectable marker genes to permit selection of host cells containing the vector. Non-limiting examples of selectable markers include genes encoding dihydrofolate reductase or genes conferring neomycin resistance for eukaryotic cell culture, genes conferring tetracycline, kanamycin or ampicillin resistance in *E. coli*, and the *S. cerevisiae* TRP1 gene. Promoter regions can be selected from any desired gene using chloramphenicol transferase (CAT) vectors or other vectors with selectable markers.

Vectors for expressing the polypeptide or fragment thereof in eukaryotic cells can also contain enhancers to increase expression levels. Enhancers are cis-acting elements of DNA, usually from about 10 to about 300 bp in length, that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

A nucleic acid sequence can be inserted into a vector by a variety of procedures well known to those skilled in the art. In general, the sequence is ligated to the desired position in the vector following digestion of the insert and the vector with appropriate restriction endonucleases. Alternatively, blunt ends in both the insert and the vector may be ligated. A variety of cloning techniques are known in the art, e.g., as described in Ausubel and Sambrook, supra. Such procedures and others are within the scope of those skilled in the art.

The vector can be in the form of a plasmid, a viral particle, or a phage. Other vectors include chromosomal, non-chromosomal and synthetic DNA sequences, derivatives of SV40; bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic host cells are known in the art.

Particular bacterial vectors that can be used include the commercially available plasmids comprising genetic elements of the well known cloning vector pBR322 (ATCC 37017), pKK223-3 (Pharmacia Fine Chemicals, Uppsala, Sweden), GEM1 (Promega Biotec, Madison, Wis.) pQE70, pQE60, pQE-9 (Qiagen), pD10, psiX174 pBluescript II KS, pNH8A, pNH16a, pNH18A, pNH46A (Stratagene), ptrc99a, pKK223-3, pKY233-3, DR540, pRIT5 (Pharmacia), pKK232-8, pcDNA3.1 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and viable in the host cell.

As used herein, the term "promoter" includes all sequences capable of driving transcription of a coding sequence in a cell. Thus, promoters used in the constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence. These cis-acting sequences typically interact with proteins or other biomolecules to carry out (turn on/off, regulate, modulate, etc.) transcription. "Constitutive" promoters are those that drive expression continuously under most environmental conditions and states of development or cell differentiation. "Inducible" or "regulatable" promoters direct expression of the nucleic acid of the invention under the influence of environmental conditions or developmental conditions. Examples of environmental conditions that may affect transcription by inducible promoters include anaerobic conditions, elevated temperature, drought, or the presence of light.

Useful eukaryotic promoters include cytomegalovirus (CMV) immediate early promoter, human tissue plasminogen activator (t-PA) gene, and the promoter/enhancer region of the human elongation factor alpha. Orientation can be identified by PCR, restriction endonuclease digestion, and DNA sequencing. Some embodiments relate to an expression vector comprising the nucleic acids described herein.

Other aspects relate to host cells transformed with the expression vectors and/or cloning vectors described herein. Transformed host cells may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera, *Streptomyces*, and *Staphylococcus*. Exemplary insect cells include *Drosophila* S2 and *Spodoptera* S19. Exemplary animal cells include CHO, COS or Bowes melanoma or any mouse or human cell line. The selection of an appropriate host cell is within the abilities of those skilled in the art. Vectors can be introduced into the host cells using any of a variety of techniques, including transformation, transfection, transduction, viral infection, gene guns, or Ti-mediated gene transfer. Particular methods include calcium phosphate transfection, DEAE-dextran mediated transfection, lipofection, or electroporation (Davis et al., *Basic Methods in Molecular Biology* (1986)).

In certain embodiments, the nucleic acids or vectors of the invention are introduced into the cells for screening for subsequent expression of the polypeptides encoded on the nucleic acid. The method of introduction is largely dictated by is the targeted cell type. Exemplary methods include $CaPO_4$ precipitation, liposome fusion, lipofection (e.g. using lipofectin), electroporation, and viral infection. Nucleic acids may stably integrate into the genome of the host cell (for example, with retroviral introduction) or may exist either transiently or stably in the cytoplasm (i.e. through the use of traditional plasmids, utilizing standard regulatory sequences, selection markers). As many pharmaceutically important polypeptides require human or model mammalian cell targets, retroviral vectors capable of transfecting such targets are useful.

Where appropriate, the engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g. temperature shift or chemical induction) and the cells may be cultured for an additional period to allow them to produce the desired polypeptide or its fragment.

Cells can be harvested by centrifugation, disrupted by physical or chemical means, and the resulting crude extract can be retained for further purification. Microbial cells used for expression of proteins can be disrupted by any convenient method, including freeze-thaw cycling, sonication, mechanical disruption, or use of cell lysing agents. The expressed polypeptide or fragment thereof can be recovered and purified from recombinant cell cultures by methods including affinity chromatography, ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Protein refolding steps can be used, as necessary, in completing configuration of the polypeptide. High performance liquid chromatography (HPLC) can be used for final purification steps.

Various mammalian cell culture systems can also be used to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Expressed polypeptides of the invention may or may not also include an initial methionine residue.

Cell-free translation systems can also be used to produce a polypeptide of the invention. Cell-free translation systems can use mRNAs transcribed from a DNA construct comprising a promoter operably linked to a nucleic acid encoding the polypeptide or fragment. In some aspects, the DNA construct may be linearized before conducting an transcription reaction in vitro. The transcribed mRNA is then incubated with an appropriate cell-free translation extract, such as a rabbit reticulocyte extract, to produce the desired polypeptide or fragment.

The expression vectors can contain one or more selectable marker genes to provide a phenotypic trait for selection of transformed host cells, such as dihydrofolate reductase or neomycin resistance for eukaryotic cell culture, or such as tetracycline, kanamycin or ampicillin resistance in *E. coli.*

Recombinant polypeptides useful in the embodiments described herein can be made by: (a) providing a nucleic acid operably linked to a promoter, wherein the nucleic acid comprises a nucleic acid of the invention; and (b) expressing the nucleic acid of step (a) under conditions that allow expression of the polypeptide, thereby producing a recombinant polypeptide.

"Operably linked" as used herein refers to a functional relationship between two or more nucleic acid (e.g. DNA) segments. Typically, it refers to the functional relationship of transcriptional regulatory sequence to a transcribed sequence. For example, a promoter is operably linked to a coding sequence, such as a nucleic acid of the invention, if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

In one aspect, the method can further comprise transforming a host cell with the nucleic acid of step (a) followed by expressing the nucleic acid of step (a), thereby producing a recombinant polypeptide in a transformed cell. The composition can be overexpressed using a vector with a strong promoter. Vectors for use in this technique include pREST (Invitrogen Inc., Calif.), pKK233-3 (Pharmacia, Calif.), and the pET system (Promega, Wis.), although any vector with a strong promoter can be used.

Other aspects of the invention relate to methods of inducing an immune response in a host, by administering the compositions described above to the host. Induction of an immune response includes enhancing the immune response that would have occurred to the antigen had the composition not been administered. It can also result in acquisition of long-lasting immunity. Here, "immune response" means any specific or nonspecific, humoral, cell-mediated or innate, response to an antigen. The immune response can be "induced" by initiation of a response or stimulation of the type or extent of an inadequate, ineffective or absent immune response.

Induction of the immune response can result in treating a current pathology in the host or prevent disease that would result by further exposure to the pathogen. More specifically, the immune response can cause the host to inhibit infection or the progression of a disease state, resulting in reduced symptoms, such as weight loss, tumor growth, morbidity, mortality, or pathogen load.

In addition to enhancing an immune response, administering the composition can also provide a variety of other useful effects, including enhancing the growth of the host, enhancing proliferation, activation, or differentiation of cells, such as bone marrow cells, B cells, T cells, macrophages, or monocytes.

In embodiments of the methods above, the composition can be administered by a number of routes, including, oral, enteral, buccal, nasal, intranasal, topical, rectal, vaginal, aerosol, transmucosal, epidermal, transdermal, ophthalmic, pulmonary, and/or parenteral administration. A parenteral administration refers to an administration route that typically relates to injection, including intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal, and/or intrasternal injection and/or infusion.

In embodiments of the methods above, the host can be a mammal, a fish, or a bird.

In some embodiments of the methods above, administering the compositions described above includes administering a DNA molecule to the host, wherein the DNA molecules encodes the PTCE. In other embodiments of the methods above, administering the compositions described above includes administering a DNA molecule to the host, wherein the DNA molecules encodes the antigen. In further embodiments, the DNA molecule can encode both the PTCE and the antigen.

Particular routes for DNA delivery include intramuscular, intradermal, intravenous, intranasal and epidermal injections. A gene gun can also be used to transport DNA-coated gold beads into cells. When injected directly into the muscle of the host, the muscle cells can take up the plasmid and express the encoded vaccine, leading to both a humoral antibody and a cell-mediated response. DNA compositions can also cause prolonged expression of the antigen, which can generate significant immunological memory.

Other embodiments relate to compositions that include an antigen derived from a protozoan pathogen and a PTCE. Examples of antigens derived from protozoan pathogens and PTCE's suitable for the embodiments described herein are discussed above. In further embodiments, the compositions include a pharmaceutically acceptable carrier, such as those described above. In still other embodiments, the compositions include an adjuvant, such as those described above.

Non-limiting examples of protozoan pathogens are *Eimeria, Trichomonas, Histomonas, Cryptosporidiosis, Toxoplasma, Neospora, Isoporoa, Crytosporidium, Babesia, Babesia, Hammondia, Theileria*, and *Sarcocystis*.

Compositions including antigens from protozoan pathogens can further include cytokines, such as chemokines. In further embodiments, these compositions can include more than one PTCE. For example, in some embodiments, the compositions include more than one PTCE linked to one another through a linker, such a plurality of glycine amino acids.

Embodiments provide inducing an immune response in a host, by administering the compositions including antigens derived from protozoan pathogens to a host, such as a mammal, a bird, or a fish.

Other aspects relate to compositions including an antigen derived from a bird pathogen and a PTCE. In some embodiments, the bird pathogen can be a viral pathogen. For example, in some embodiments, the bird pathogen can be Infectious Bursal Disease (IBD) virus, Infectious Bronchitis Virus (IBV), Avian influenza, Fowl pox, Marek's disease virus, Newcastle disease virus, Chicken anemia virus, or Infectious Laryngotracheitis Virus (ILT). In preferred embodiments, the bird pathogen is IBD virus. In more preferred embodiments, the IBD viral antigen is derived from the polypeptide of SEQ ID NO: 154. In other embodiments, the bird pathogen can be a bacterial pathogen. For example, in some embodiments, the bird pathogen can be *Salmonella enterica, Chlamydia psitaci, Escherichia coli, Colibacillosis, Mycoplasma gallisepticum, Mycoplasma meleagridis, Mycoplasma synoviae, Pasteurella multocida, Clostridium colinum, Clostridium perfringens, Clostridium septicum, Salmonella pullorum, Salmonella gallinarum, Hemophilus gallinarum, Streptocossus, Staphylococcus, Proteus, Erysipelothrix insidios, Salmonella enteritidis, Bordetella avium, Actinobacillus salpingitidis, Chlamydophila psittaci, Mycoplasma iowae, Mycoplasma gallisepticum, Pasteurella multocida, Haemophilus paragallinarum, Ornithobacterium rhinotracheale, and Riemerella anatipestifer*. In preferred embodiments, the bird bacterial pathogen is *Clostridium* spp. In further embodiments that are more preferred, the antigen includes the C-terminal domain of the *Clostridium toxin* alpha (ToxA). In yet other embodiments, the bird pathogen can be a protozoan pathogen. For example, in some embodiments, the bird protozoan pathogen is *Eimeria* spp., *Histomonas meleagridis, Hexamita meleagridis, Toxoplasma* or *Neospora*. In further embodiments of any of the above, the PTCE can include a peptide having the amino acid sequence of SEQ ID NOs: 1, 2, 3, 4, 5, 6, or 7. Any of the above embodiments can further include a cytokine.

Another aspect relates to a method for inducing an immune response in a bird against a pathogen, by administering any of the compositions described above to the bird. In some embodiments, the pathogen is a protozoan, while in other embodiments, the pathogen is a bacterium. In still other embodiments, the pathogen is a virus.

Still other aspects relate to compositions that include an antigen derived from a virus that infects fish, and a PTCE. In some embodiments, the fish can be a salmonid. In further embodiments, the virus can be IPNV. In still further embodiments, the antigen can be a truncated antigen. For example, in some embodiments, the truncated antigen can include the amino acid sequence of SEQ ID NO: 146 (carboxy terminal 257 amino acids of IPNV VP2 protein).

Other aspects relate to a nucleic acid that encodes an antigen from a pathogen, and also encodes a PTCE that includes the amino aid sequence of SEQ ID NOs: 1, 2, 3, 4, 5, 6, or 7. In some embodiments, the nucleic acid includes a vector. For example, in some embodiments, the vector can be an expression vector. In some embodiments, the nucleic acid can also encode a cytokine. In other embodiments, the antigen encoded by the nucleic acid is linked to the PTCE encoded by the nucleic acid though a linker. In some embodiments, the linker can be one or more glycine amino acids.

Still other aspects relate to compositions that include two or more PTCE's that are joined together by a linker. In some embodiments, the linker is a polyglycine linker.

Yet other aspects relate to methods of vaccinating an animal. An animal in need of vaccination against a pathogen can be selected, and an antigen derived from the pathogen can be administered to the animal with a PTCE in ovo.

Still another aspect relates to a method of vaccinating an animal. An animal in need of vaccination against a pathogen can be selected, and an antigen derived from the pathogen can be administered to the animal with a PTCE when said animal is pre-immunocompetent. As used herein, the phrase pre-immunocompetent refers to hosts that have not fully developed an immune system.

Chickens do not appear to have fully functional immune system until Day 4-5 of age, some authors believe until day 7 of age. During that time native, and perhaps cellular, immune systems are thought to help cope with infection.

In any of the embodiments described above, the antigen can be a B-cell antigen.

EXAMPLES

Example 1

In Ovo Protection Against *Eimeria* Protozoan Pathogens in Chickens Using Protein-Based Vaccines Coccidiosis in chickens is caused by *Eimeria* sp. protozoans. *Eimeria* sp. live and multiply in the intestinal tract and cause tissue damage as evinced by lesions, which can interfere with the food digestion and nutrient absorption. Affected birds do not eat. The 3-1E and Mic2 proteins are native surface antigens in *Eimeria* sp. These antigens were tested for their ability alone or fused to PTCE epitopes (measles and/or tetanus toxin) to immunize chickens against coccidiosis in ovo, as measured by weight gain, feed conversion (discussed below) and lesion scoring.

Expression Vectors for Chimeric *Eimeria* Antigens and PTCEs

Expression vectors were constructed to produce in-frame fusion proteins of at least one PTCE and native or evolved surface antigens obtained from *Eimeria*.

The PTCEs used in these experiments were the measles sequence LSEIKGVIVHRLEGV (SEQ ID NO:1)("M") or the tetanus sequence VDDALINSTKIYSYFPSV (SEQ ID NO:2)("T") or both. Multiple PTCEs were joined to each other by a polylinker of 10 glycines ("G") between the two or three PTCEs.

The nucleic acid encoding *Eimeria acervulnia* 3-1E (SEQ ID NO:30) was cloned into the pMAL-C2x vector (New England Biolabs, Ipswich, Mass.) for expression of the 3-1E-MBP protein. The same strategy was used to generate vectors for the expression of variant 3-1E fusion proteins, with C-terminal fusions to tetanus toxin PTCE ("3-1E-T"); measles virus PTCE ("3-1E-M"); glycine linker-measles PTCE-glycine linker-tetanus PTCE ("3-1E-GMGT"); measles PTCE-glycine linker-measles PTCE ("3-1E-MGM"); and tetanus PTCE-glycine linker-tetanus PTCE ("3-1E TGT"). Similarly, the cDNA encoding *Eimeria acervulnia* Mic2 (SEQ ID NO32) was cloned into the pMAL-C2x vector (New England Biolabs, Ipswich, Mass.) for expression of the Mic2 protein. The same strategy was used to generate vectors for the expression of the following variant Mic2 fusion proteins, with C-terminal fusions to PTCEs: Mic2-T; Mic2-TGT; Mic2-M; Mic2-MGM; Mic2-MGMGM; and Mic-2-GMGT. Likewise, the nucleic acid encoding the first 257 amino acids of Infectious Bronchitis Virus VP2 protein (SEQ ID NO: 154), and the sequence for the glycine linker-PTCE GMGT were cloned into the pMAL-C2x vector. The ins were expressed and purified using affinity chromatography with amylase resin (New and Biolabs, Ipswich, Mass.), according to the manufacturer's instructions.

Animals, Vaccination and *Eimeria* Challenge

Treatment groups consisted of the following:

| Group # | Vaccination |
|---|---|
| 1 | neg. control (no challenge) |
| 2 | infected control (no vaccine) |
| 3 | 3-1E |
| 4 | 3-1E-T |
| 5 | 3-1E-M |
| 6 | 3-1E-GMGT |
| 7 | 3-1E-MGM |
| 8 | 3-1E-TGT |
| 9 | Mic2-MGT |
| 10 | GMGT |
| 11 | 3-1E-MGMGM |
| 12 | Mic-2 |
| 13 | Mic-2-T |
| 14 | Mic-2-TGT |
| 15 | Mic-2-M |
| 16 | Mic-2-MGM |
| 17 | 3-1E-MBP |
| 18 | VP2-GMGT |
| 19 | Mic-2-MGMGM |
| 20 | Mic-2-GMGT |

Fertile eggs were selected by candling. At day 19 of incubation, 100R1 of the composition with 100 μg or 300 μg of the protein was administered. Compositions were administered below the shell (aircell) membrane and chorioallantoic membrane. A 22 gauge needle attached to a syringe was used to pierce a hole in the shell at the large end of the egg. The egg was subsequently sealed with wax. The vaccinated embryonated eggs were transferred to an incubator to hatch.

Once hatched, the chicks were placed in separate cages based upon their treatment group. The chicks for treatments groups 2-20 were challenged with a mixed coccidial inoculum containing approximately 25,000 oocysts of *E. acervulina* per bird and 5,000 oocysts each of *E. maxima* and *E. tenella* oocysts at 2 weeks of age according to the protocol of Lillehoj et al., (1989) *Vet Immunol Immunopathol.*;20(2): 135-48 and Lillehoj et al. (2000) *Avian Dis.*;44(2):379-89.

Feed Conversion, Weight Gain, and Lesion Scoring

All birds were weighed by cage on Day 20 after hatching. Feed was weighed on Day 0 and remaining feed was weighed on Day 20. Means for cage weight gain, feed consumption, feed conversion and lesion scores (discussed below) were calculated. Feed conversion is calculated as feed consumed/(final weight−initial weight)+removed weight.

On Day 20, three birds from each treatment group were sacrificed and examined for the degree of lesions in the upper intestine, mid intestine, or ceca. The scoring was based on a 0 to 4 scale, with 0 being normal and 4 being the most severe.

Figure 1B:
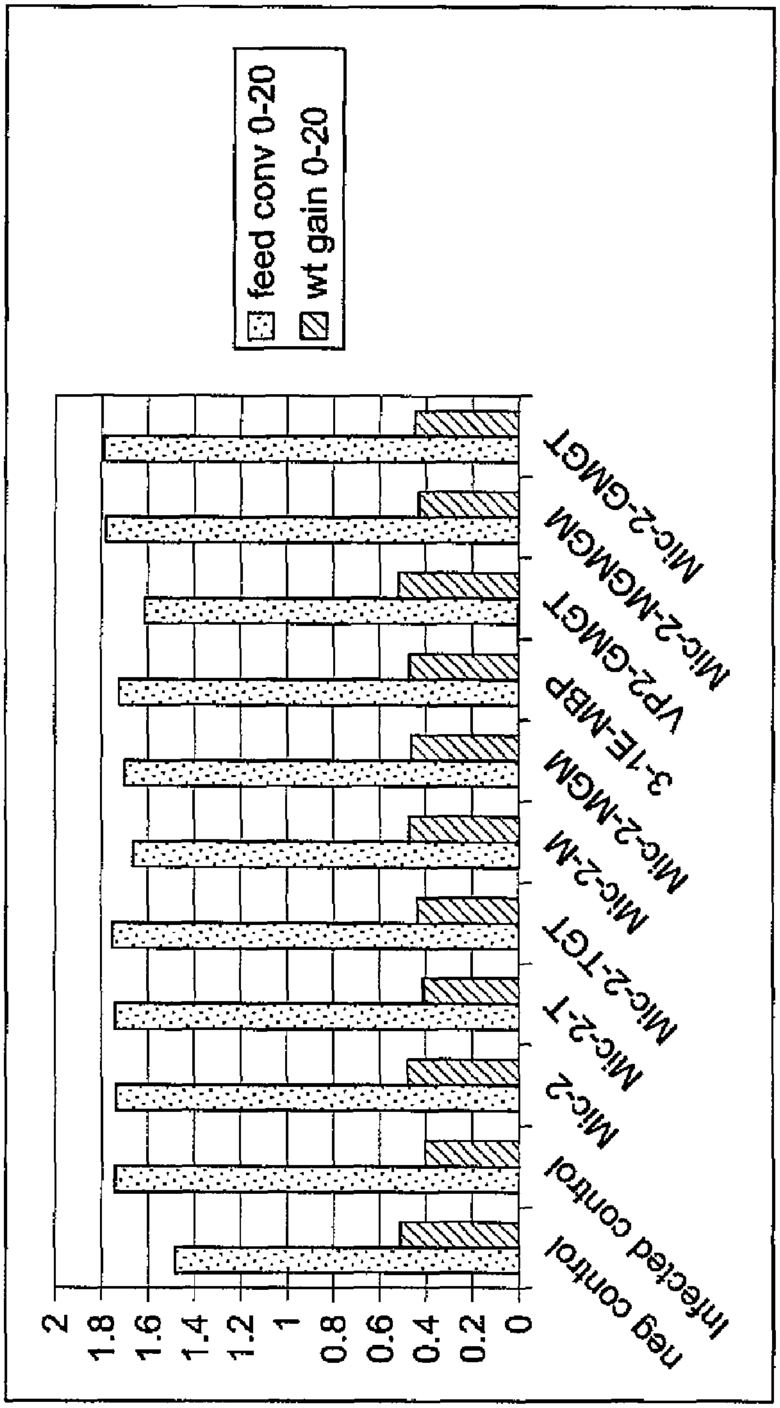
FIG. 1B is a bar graph showing weight gain and feed conversion of chicks vaccinated in ovo with *Eimeria* Mic2 antigens with and without PTCEs, followed by challenge with *Eimeria.*
Figure 1C:
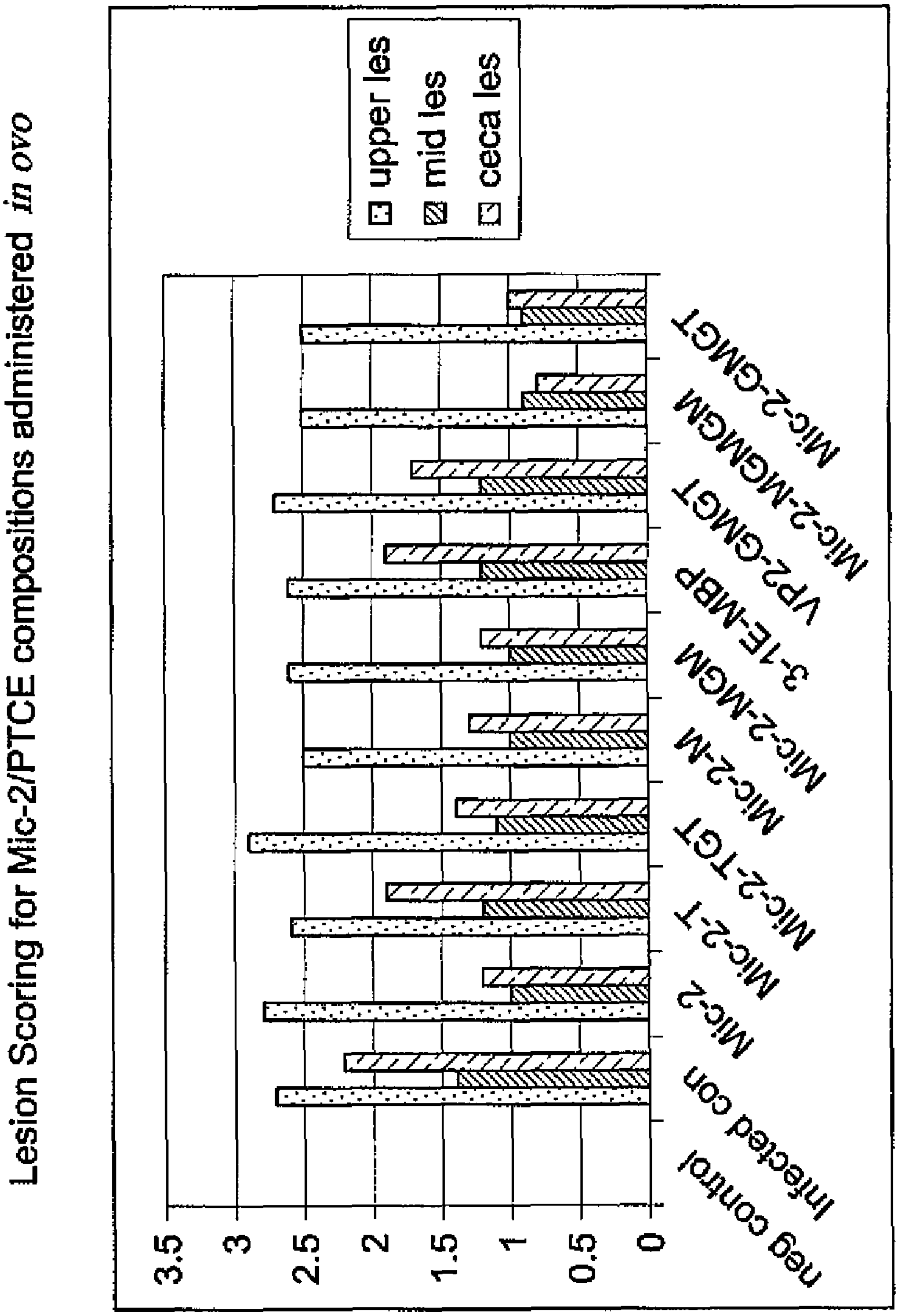
FIG. 1C is a bar graph showing lesion scoring (upper intestine, middle intestine, ceca) ofr chicks vaccinated in ovo with *Eimeria* Mic2, 3-1E, and VP2 antigens.

Results:

The results are shown in FIGS. 1A-1C. As indicated in FIG. 1C, chicks vaccinated in ovo with Mic-2 antigens showed improved lesion scores.

Example 2

Improved Vaccines Derived from Bacterial Pathogens and PTCEs Delivered Subcutaneously on Broiler Chicken Provide Protection 1N Necrotic Enteritis Challenge Model The following examples demonstrates that DNA vaccines encoding fusion proteins of antigens derived from bacterial pathogens and PTCEs are effective in protecting against necrotic enteritis in chickens.

Necrotic enteritis is an enterotoxemia caused by types A and C of the enteric bacterium *Clostridium perfringens. C. perfringens* is present in the guts of healthy chickens, but under certain conditions, caused by factors such as coccidial infection, or wheat in the chicken's diet, the bacterium produces various types of toxins (α, β and β2) that result in necrotic enteritis. Symptoms of necrotic enteritis include depression and reduced feed intake, intestinal lesions, and mortality in the most severe cases.

Antibiotics are still the major current treatment for *C. perfringens*, but are often ineffective, and in some countries prohibited. The C' terminal 112 amino acids of the *C. perfringens* Toxin a (C'ToxA) is a B-cell antigen. See, Williamson et al. (1993), *Vaccine,* 11:1253-1258. The following study was conducted to determine the ability of C'ToxA alone when or fused to PTCE epitopes (measles and/or tetanus toxin) to immunize chickens against necrotic enteritis, as measured by weight gain, feed conversion (discussed below) and lesion scoring Materials and Methods:

One-day-old male broiler chicks were purchased from Cobb-Vantress hatchery, Cleveland, Ga. on Feb. 17, 2005. The strain was Cobb X Cobb. Breeder flock identification number was 2849 and was 43 weeks old at time of lay. At the hatchery, the birds were sexed and received routine vaccinations. Only healthy appearing chicks were used in the study.

Procedures:

A. Vaccine Preparations

Figure 2:
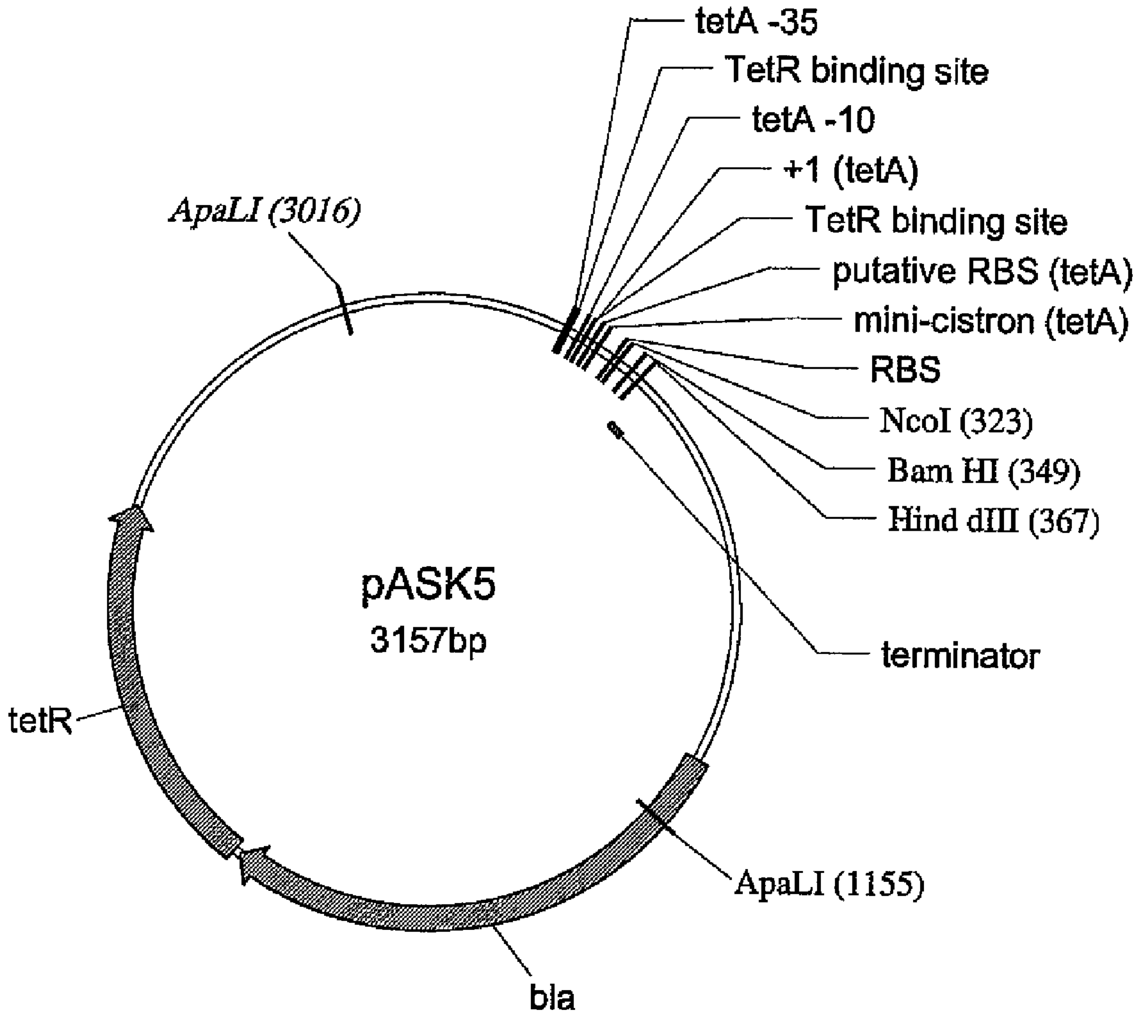
FIG. 2 is a vector map showing the features of the pASK5 vector. The pASK5 vector was modified to engineer N-terminal $His_6$ ("N'His") fusion proteins. The pASK5 vector facilitates overexpression and subsequent recovery of recombinant proteins by virtue of the control elements, such as the tetracycline regulatable promoter (TetR).
Figure 4:
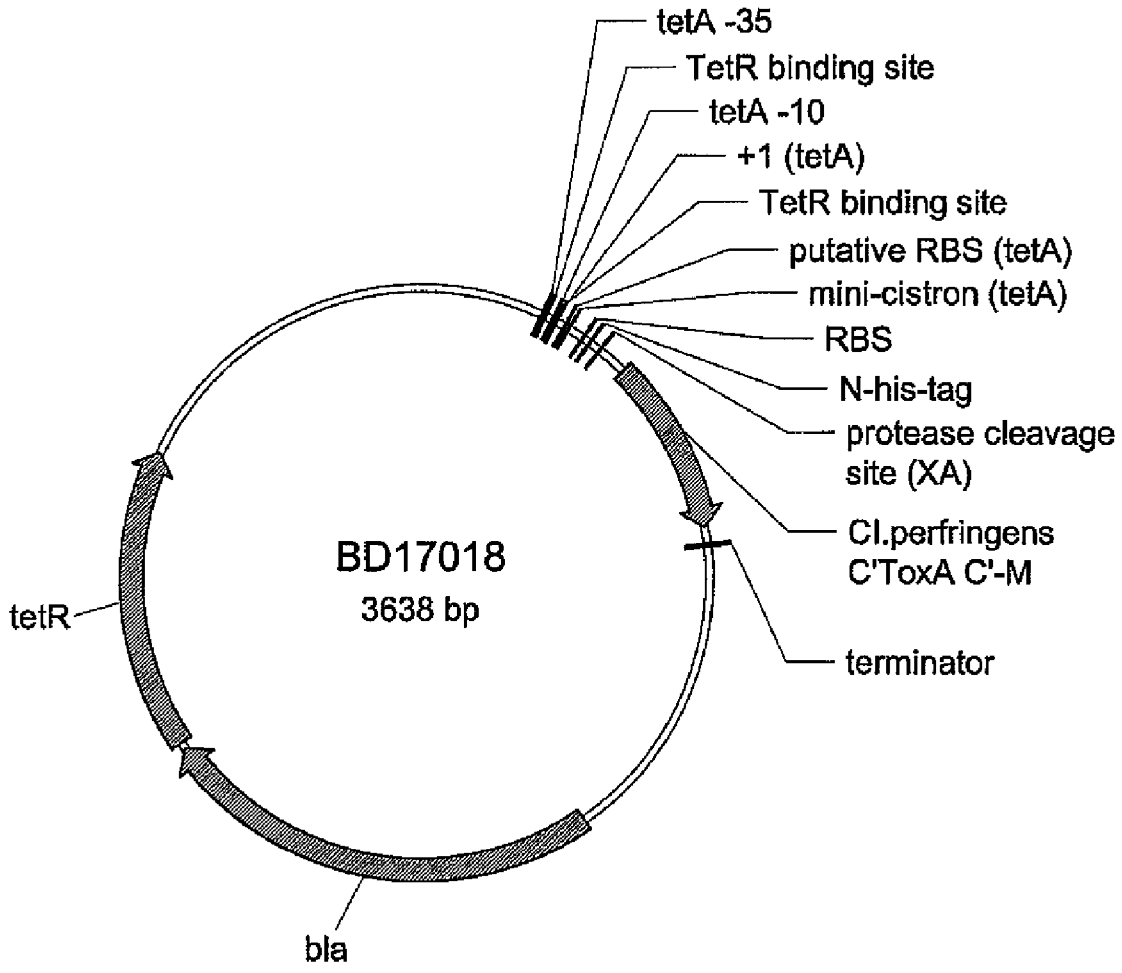
FIG. 4 is a vector map showing the features of pASK5 N'His C'ToxA+M. The plasmid was used to generate the BD17018 vaccine, and is designed to express an in-frame fusion protein of the *C. perfringens* C'ToxA B cell epitope with a glycine linker, and a measles virus PTCE at the C' terminal end of the protein. The recombinant fusion protein was administered to chicks, which were subsequently challenged with *C. perfringens* as described in Example 2.
Figure 5:
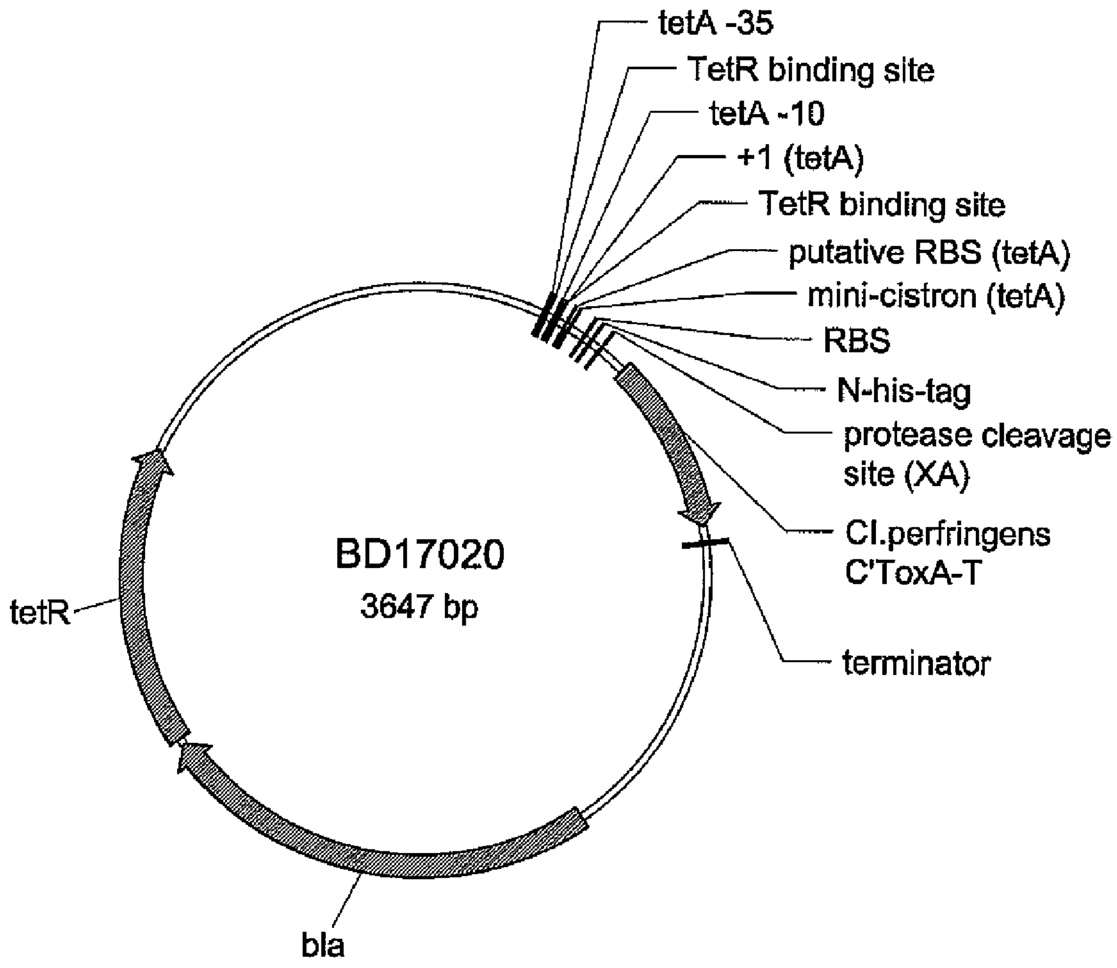
FIG. 5 is a map of the vector used to generate the BD17020 vaccine. The vector is designed to express an in-frame fusion protein of the *C. perfringens* C'ToxA B cell epitope with a glycine linker, and a tetanus virus PTCE at the C' terminal end of the protein. The recombinant fusion protein was administered to chicks, which were subsequently challenged with *C. perfringens* as described in Example 2.
Figure 6:
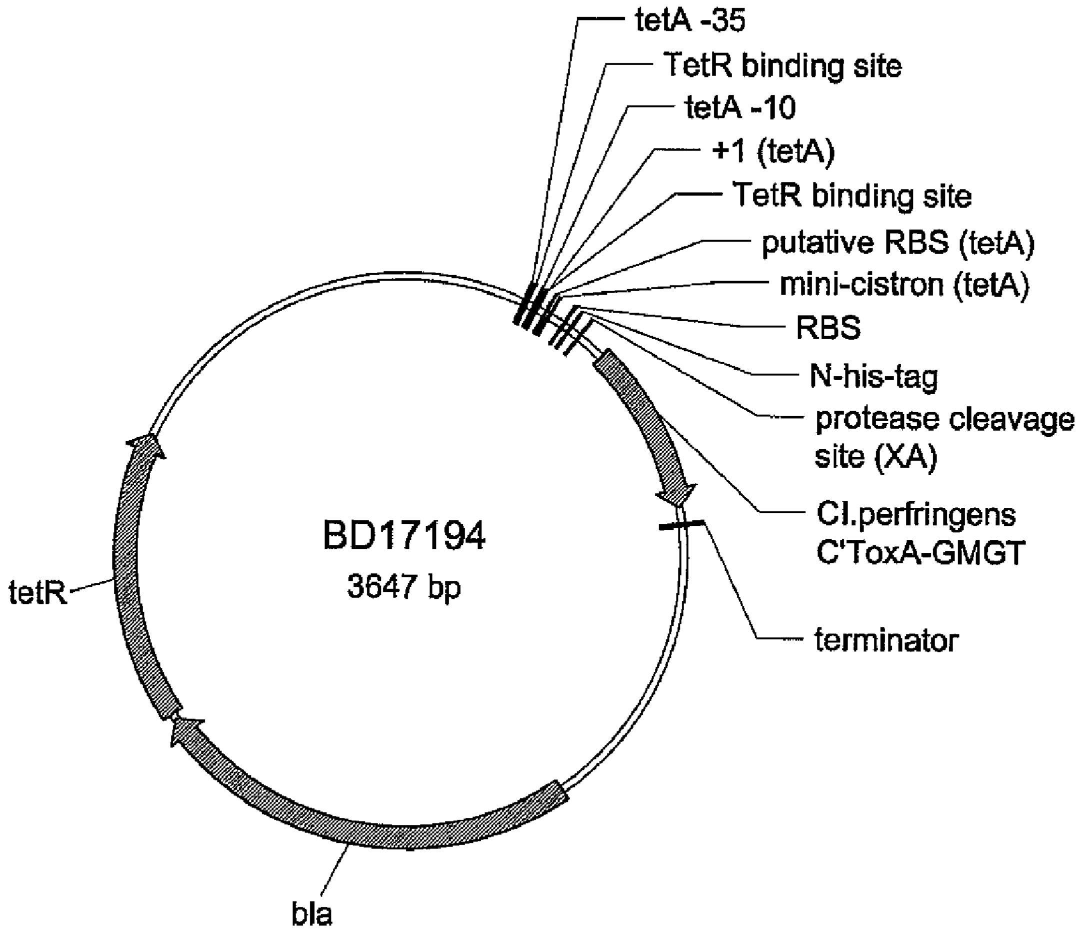
FIG. 6 is a map of the vector used to generate the BD17194 vaccine. The vector is designed to express an in-frame fusion protein of the *C. perfringens* C'ToxA B cell epitope with a glycine linker, a measles virus PTCE, another glycine linker and a tetanus toxin PTCE at the C' terminal end of the protein. The recombinant fusion protein was administered to chicks, which were subsequently challenged with *C. perfringens* as described in Example 2.
Figure 7:
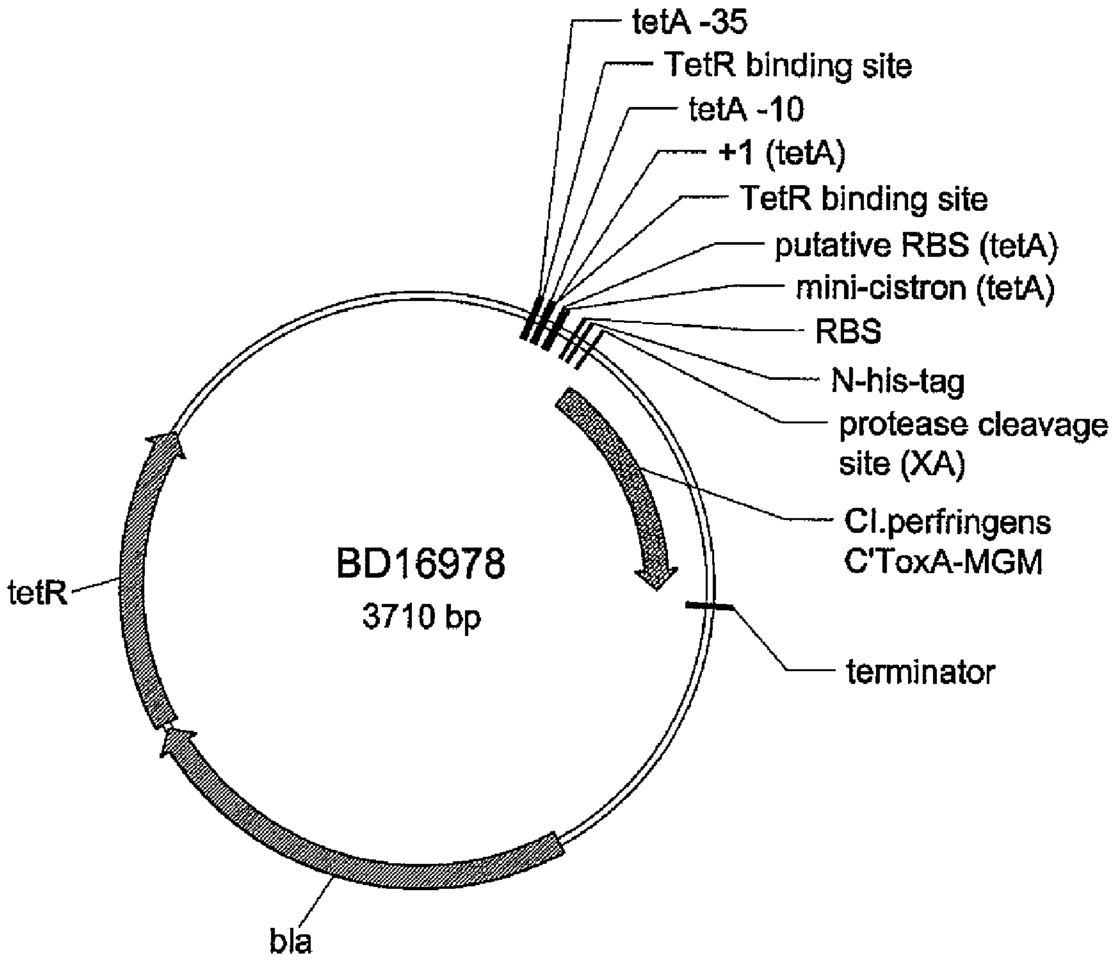
FIG. 7 is a map of the vector used to generate the BD16978 vaccine. The vector is designed to express an in-frame fusion protein of the *C. perfringens* C'ToxA B cell epitope with a measles PTCE, glycine linker, and second measles PTCE.
Figure 8:
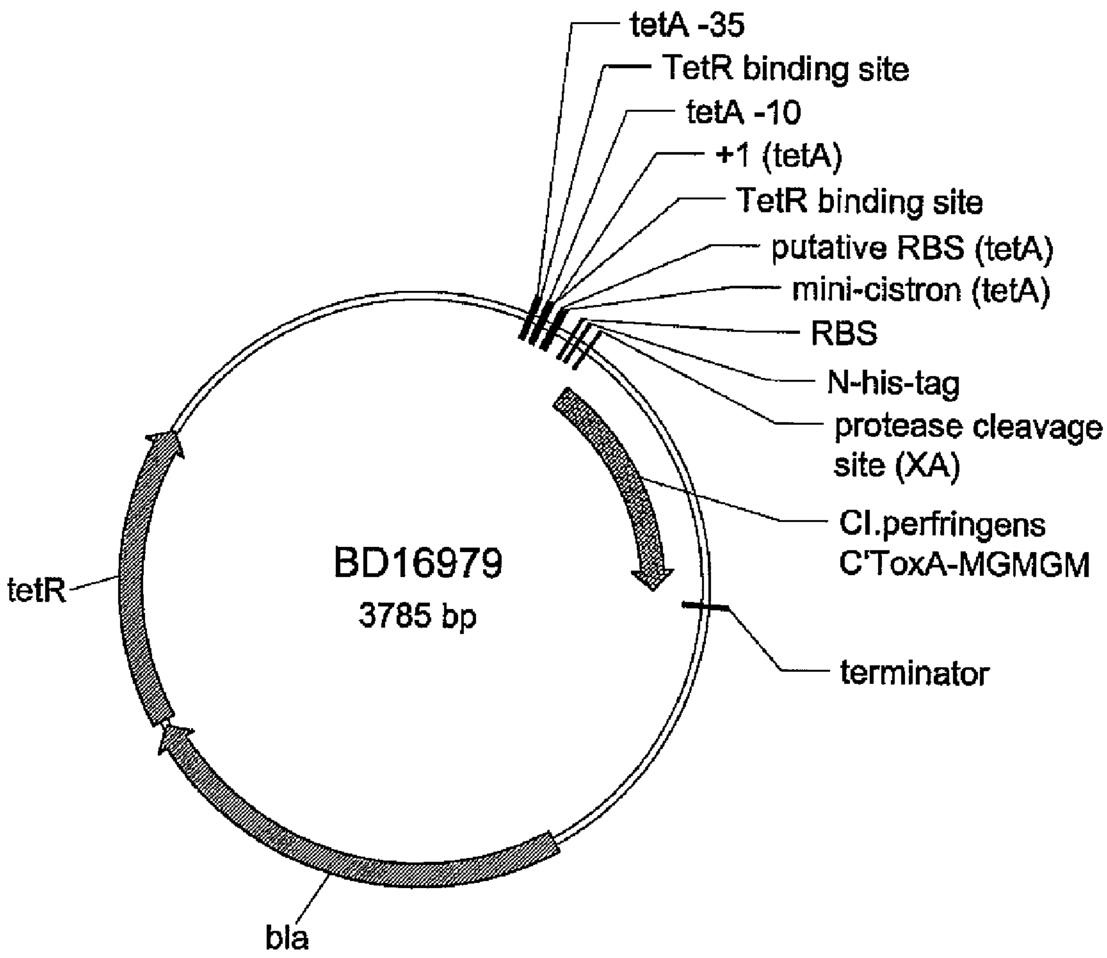
FIG. 8 is a map of the vector used to generate the BD16979 vaccine. The vector is designed to express an in-frame fusion protein of the *C. perfringens* C'ToxA with three measles PTCEs, through two glycine linkers.
Figure 9:
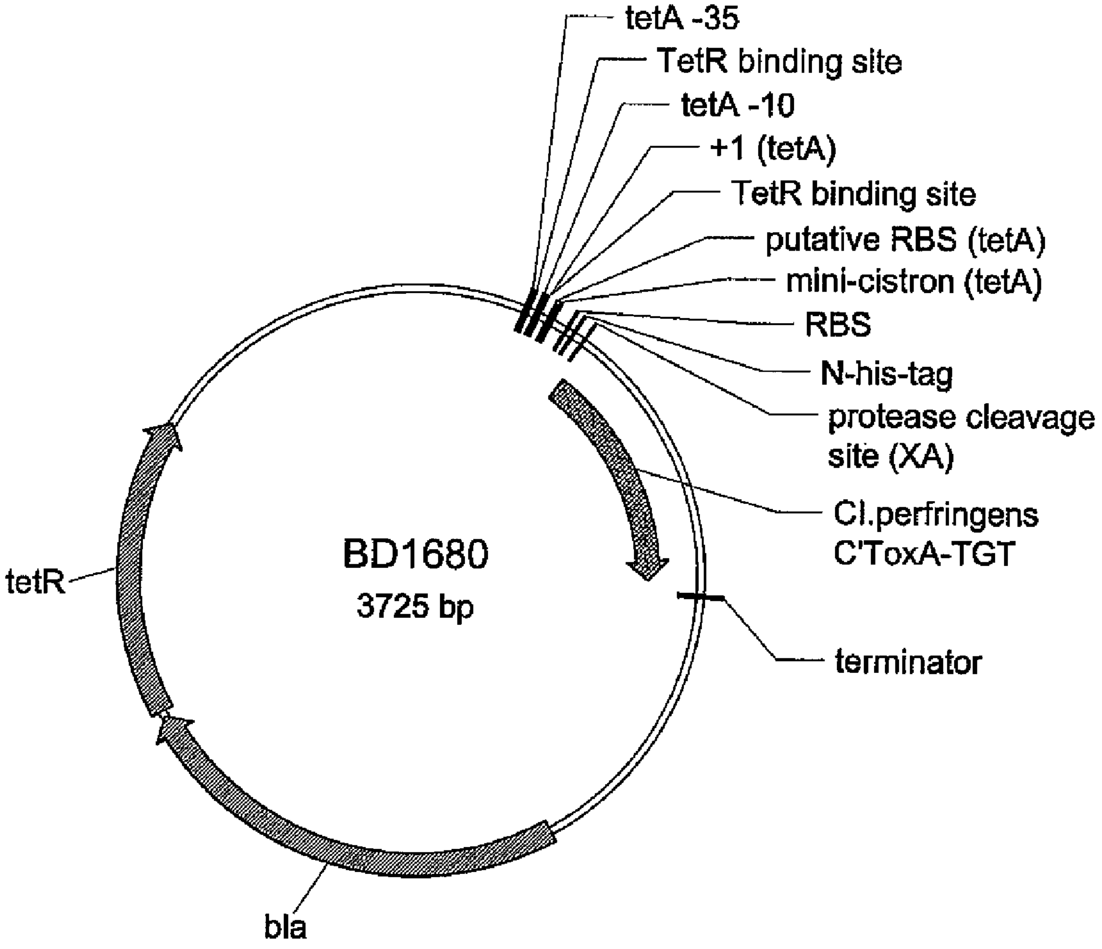
FIG. 9 is a map of the vector used to generate the BD16980 vaccine. The vector is designed to express an in-frame fusion protein of the *C. perfringens* C'ToxA antigen, with two tetanus toxin PTCE's linked by a glycine linker.
Figure 10B:
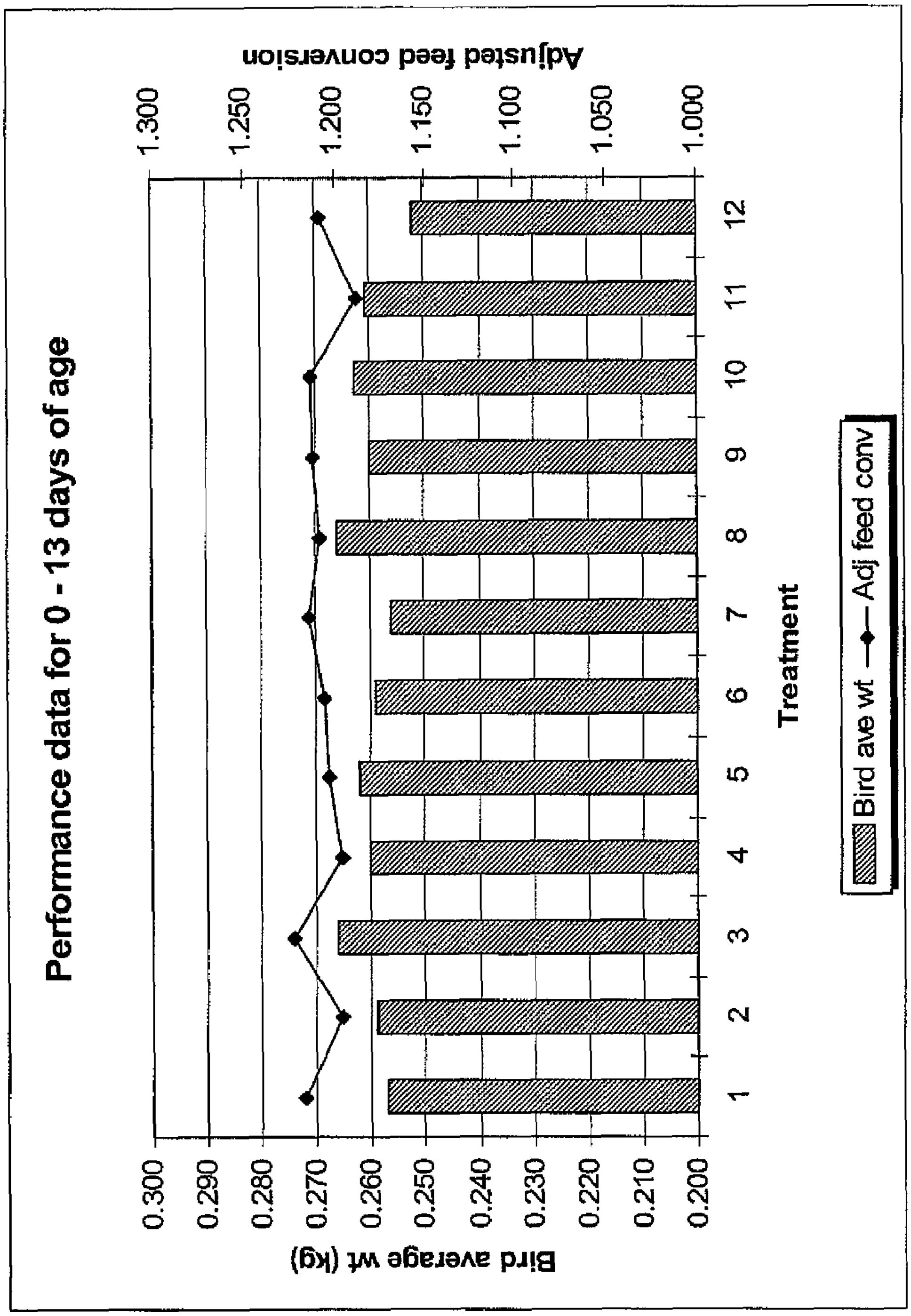
FIG. 10(A-B) depicts the bird average weights (bar graph) and feed conversions (data points) from days 0-13 of various chicks to which various C'ToxA recombinant proteins (See FIGS. 5-8) were administered as described in Example 2. Administration of the recombinant proteins was followed by a challenge with *C. perfringens.*
Figure 11B:
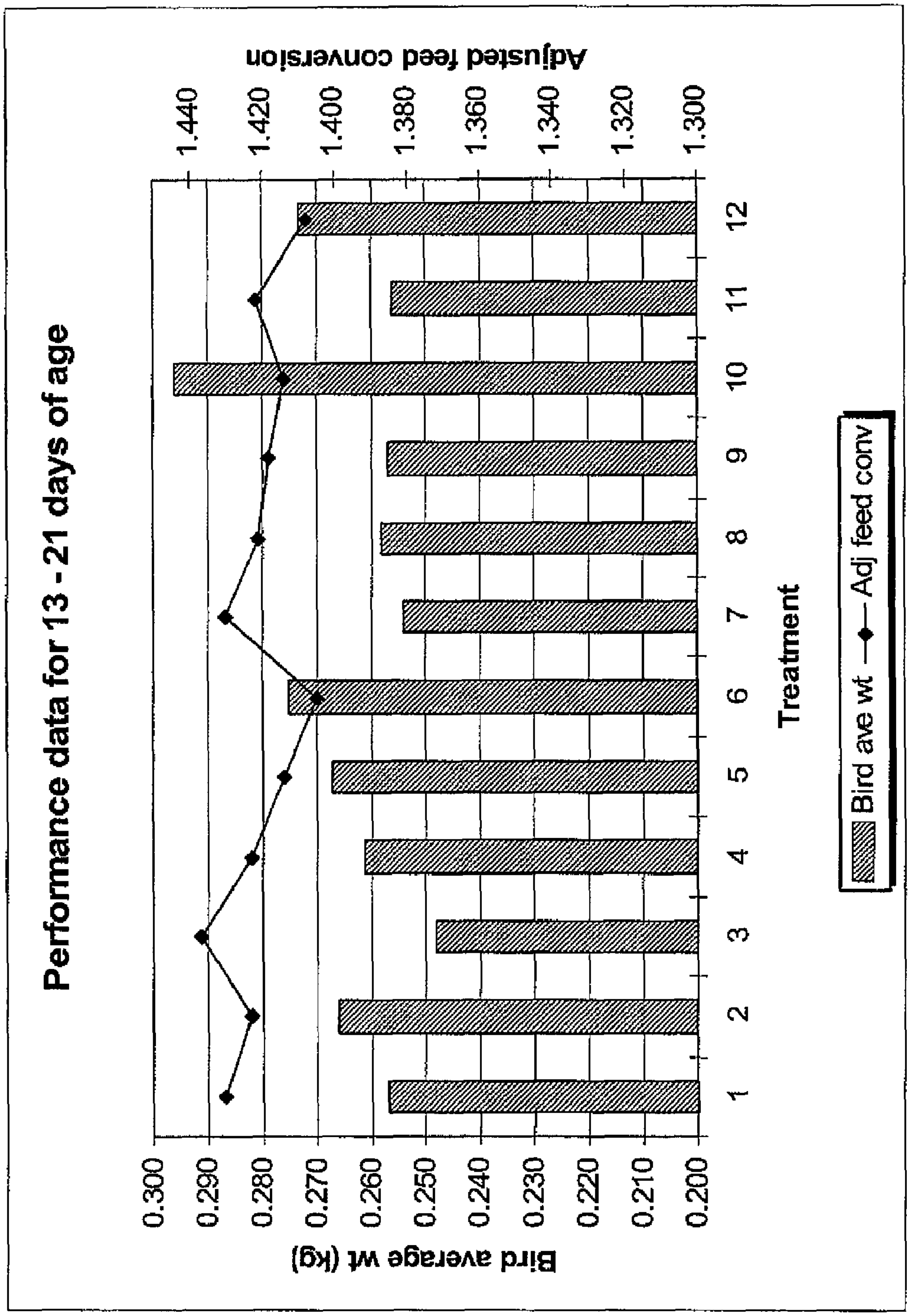
FIG. 11 depicts the bird average weights (bar graph) and feed conversions (data points) from days 13-21 of various chicks to which different C'ToxA recombinant proteins (See FIGS. 3-6) were administered as described in Example 2 Administration of the recombinant proteins was followed by a challenge with *C. perfringens.*
Figure 12B:
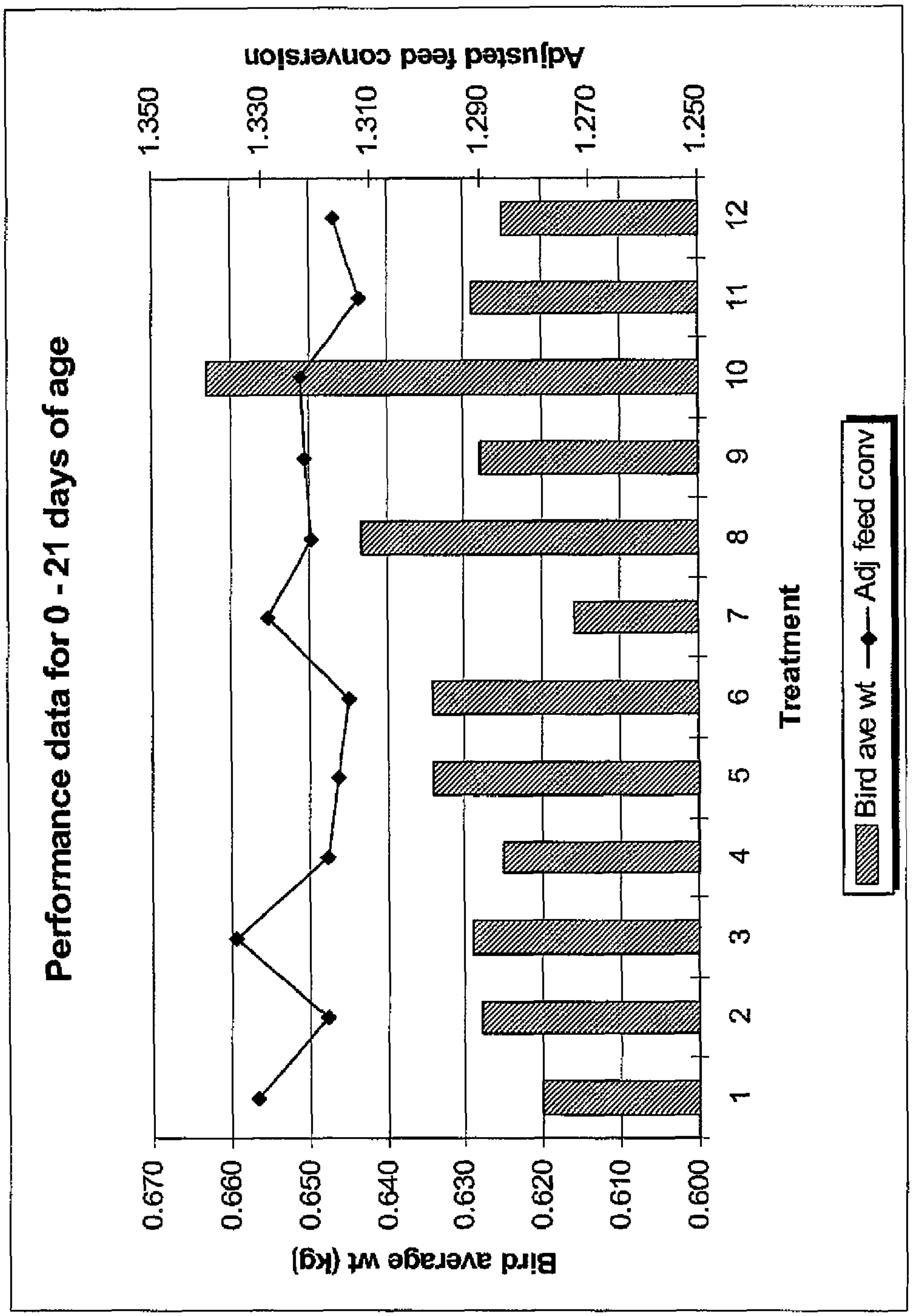
FIG. 12 depicts the bird average weights (bar graph) and feed conversions (data points) from days 0-21 of various chicks to which different C'ToxA recombinant proteins (See FIGS. 3-6) were administered as described in Example 2. Administration of the recombinant proteins was followed by a challenge with *C. perfringens.*
Figure 13B:
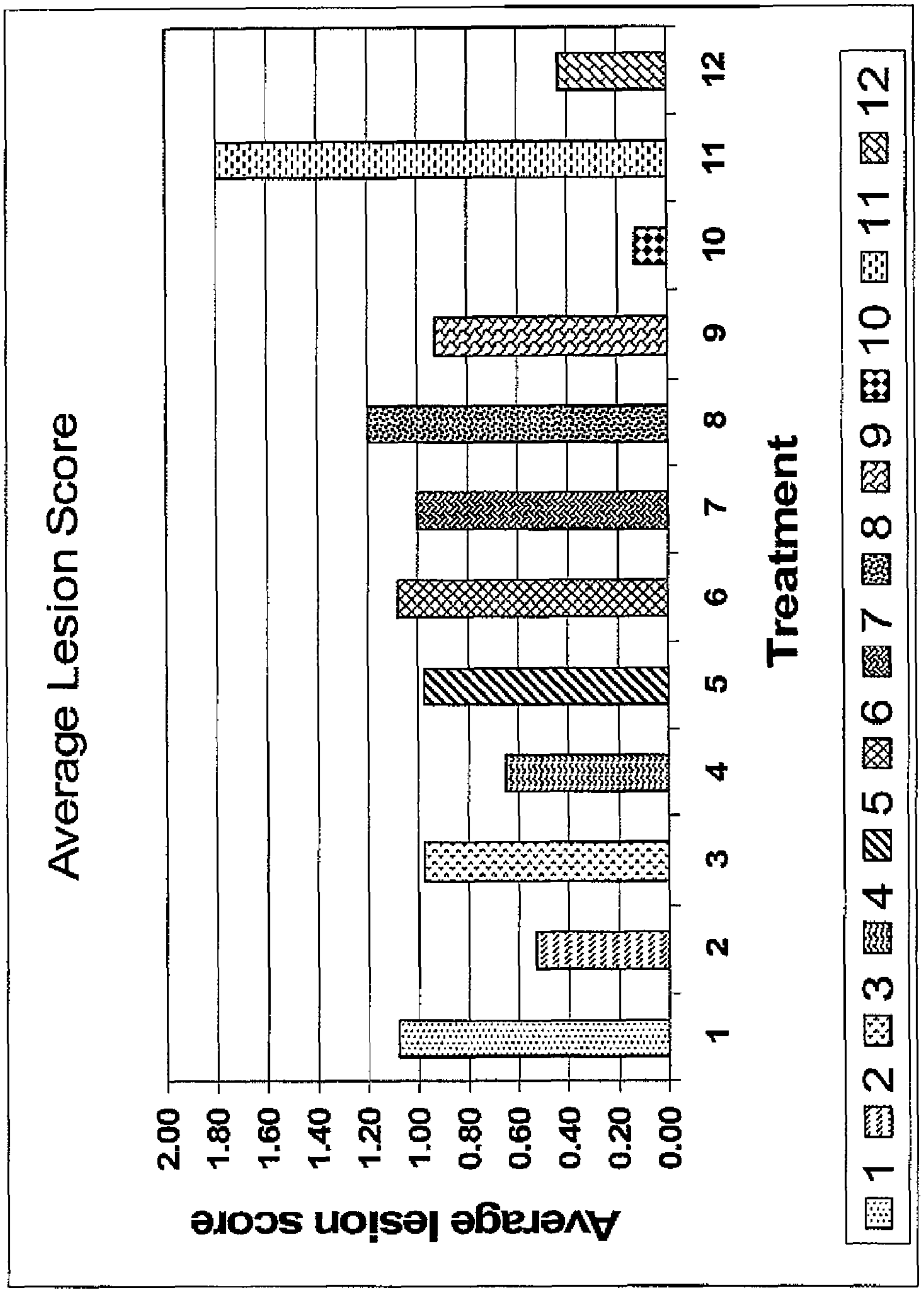
FIG. 13(A-B) is a bar chart and table depicting the average necrotic enteritis lesion scores of various chicks from treatment groups described in Example 2 were assayed. Various chicks to which different C'ToxA recombinant proteins (See FIGS. 3-6) were administered as described in Example 2. Administration of the recombinant proteins was followed by a challenge with *C. perfringens.*
Figure 15:
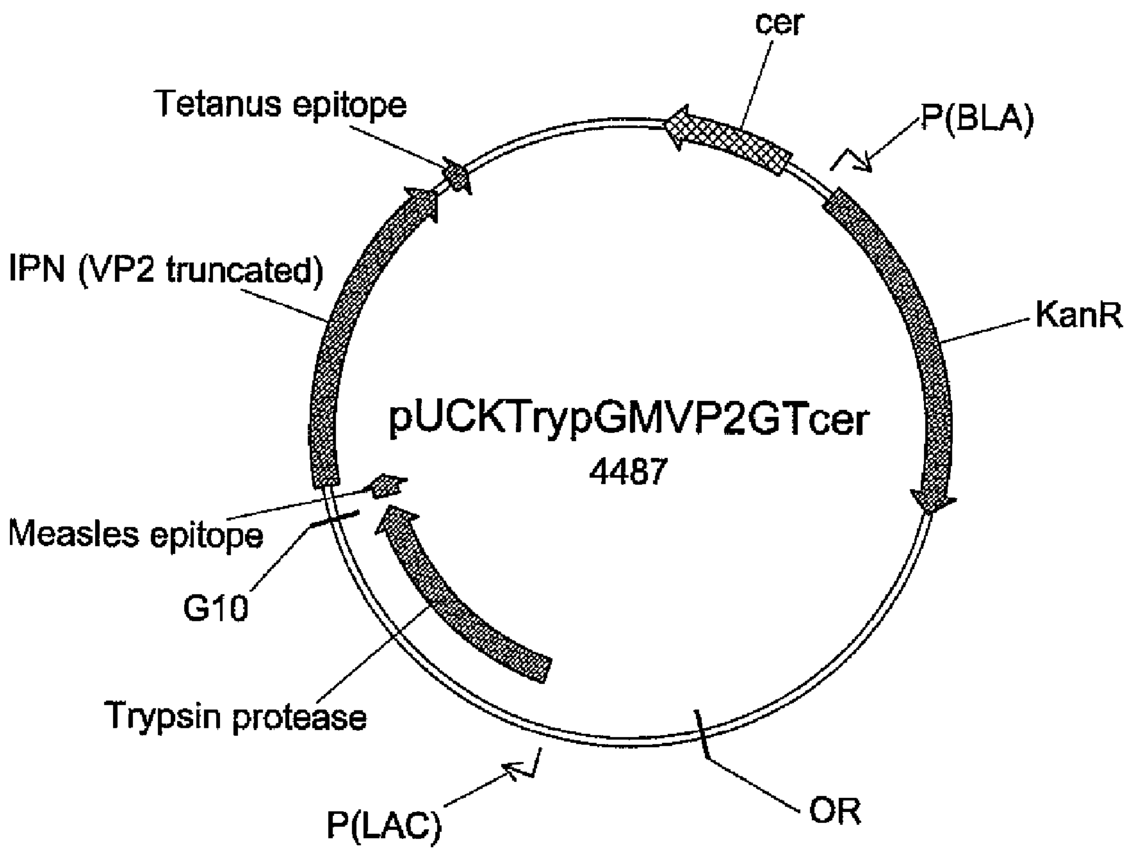
FIG. 15 is a map of the pUCKTrypGMVP2GTcer+ plasmid, which encodes an in-frame fusion between the protozoan *Lepeophteirus salmonis* (sea lice) trypsin protease antigen, a 10 glycine linker, the measles PTCE, the carboxy terminal 257 amino acids from the IPNV VP2 protein, another 10 glycine linker, followed by the tetanus PTCE. The cer element is a stability element from the wild type ColE1 plasmid.

The pASK5 vector shown in FIG. 2 (IBA, GmbH, Göttingen, Germany) was engineered to facilitate expression of recombinant proteins with N' $His_6$ tags, (pASK5 N'His). The pASK5 N'His derivative was used to engineer the expression vectors shown in FIGS. 4-9, which contain various versions of a *C. perfringens* antigen fused to PTCEs. BD 17016 (FIG. 4) encodes the C-terminal 112 amino acids of the *C. perfringens* ToxA protein ("C'ToxA") (SEQ ID NO: 162). BD17018 (FIG. 5), BD17020 (FIG. 6), and BD17194 (FIG. 7) were used to express C-terminal fusion proteins of the C'ToxA protein with the measles PTCE ("M") of SEQ ID NO: 164, the tetanus toxin PTCE ("T") of SEQ ID NO:166, or a glycine linker-M-glycine linker-T ("GMGT") PTCE, of SEQ ID NO:168, respectively. Other constructs made included BD16978 (FIG. 7), which expresses a C'ToxA-MGM fusion protein; BD16979 (FIG. 8), which expresses a C'ToxA-MG-MGM fusion protein; and BD16980, which expresses a C'ToxA TGT fusion protein.

*E. coli* BL21DE3(pLysE) colonies harboring the expression vectors BD17016, BD17018, BD17020, and BD17194 were cultured to over-express the recombinant proteins. Recombinant proteins were recovered either as inclusion bodies (See, Sambrook, supra), or were purified from the cells using Nickel nitrilotriacetic acid (Ni-NTA) resin (Qiagen, Valencia, Calif.). Proteins were quantified using standard techniques (See, Sambrook, supra).

B. Bird Allocation and Cage Randomization:

The study began when the birds were placed (day of hatch) (DOT 0) at which time they were allocated to the experimental cages based on treatment group (see below). On DOT 0, group body weights were recorded by cage. No birds were replaced during the course of the experiment.

| TREATMENT | | Coccidial Challenge | *Clostridium perfringens* | Pens/Trt |
|---|---|---|---|---|
| T1 | Nonmedicated, Noninfected | DOT 14 | No | 8 |
| T2 | Nonmedicated, Infected | DOT 14 | DOT 19, 20, and 21 | 8 |
| T7 | NE Vaccine 1 BD17016 | DOT 14 | DOT 19, 20, and 21 | 8 |
| T8 | NE Vaccine 2 BD17018 | DOT 14 | DOT 19, 20, and 21 | 8 |
| T9 | NE Vaccine 3 BD17020 | DOT 14 | DOT 19, 20, and 21 | 8 |
| T10 | NE Vaccine 4 BD17194 | DOT 14 | DOT 19, 20, and 21 | 8 |
| T11 | Virginiamycin 15 g/t | DOT 14 | DOT 19, 20, and 21 | 8 |

C. Vaccination:

On Day of hatch, all treatments 7, 8, 9, and 10 chicks were injected subcutaneously in the neck region with the appropriate NE vaccine. For each treatment, 300 μg of protein was administered in 0.2 mL volume.

D. Disease Induction:

On DOT 14, all birds were orally inoculated with a mixed coccidial inoculum containing approximately 25,000 oocysts of *E. acervulina* per bird and 5,000 oocysts of *E. maxima* per bird. Starting on DOT 19, all birds, except Treatment 1, were given a broth culture of *C. perfringens* $10^8$ cfu/ml. The birds were administered a fresh broth culture once daily for 3 days (on DOTs 19, 20, and 21).

| Date | Dosage |
|---|---|
| DOT 19: | $4.0 \times 10^8$ |
| DOT 20: | $1.8 \times 10^8$ |
| DOT 21: | $1.0 \times 10^8$ |

E. DOT 0, 14 and 28 Weights:

All birds were weighed by cage on DOT 0, 14, and 28. Feed was weighed in on DOT 0 and remaining feed was weighed on DOT 14 and 28. The experiment was terminated on DOT 28.

F. Necrotic Enteritis Intestinal Lesion Scoring:

On DOT 22, three birds from each cage were selected, sacrificed, weighed, and examined for the degree of presence of Necrotic Enteritis lesions. The scoring was based on a 0 to 3 score, with 0 being normal and 3 being the most severe.

Upon mortality, birds were removed from cages, the cage number, date, weight of the bird, sex, and probable cause of death were recorded. Means for cage weight gain, feed consumption, feed conversion, lesion scores, and mortality were calculated and are shown below. Weights are given in kilograms. Feed conversion is calculated as feed consumed/(final weight−initial weight)+removed weight.

Results:

| | Feed Consumption | | Feed Conversion | | Weight Gain | | | |
|---|---|---|---|---|---|---|---|---|
| Treatment | Day 0-28 | Day 14-28 | Day 0-28 | Day 14-28 | Day 0-28 | Day 14-28 | Lesion score | Mortality |
| no infection | 9.45 | 6.83 | 1.37 | 1.67 | 0.79 | 0.52 | 0.3 | 0 |
| none | 8.64 | 6.03 | 1.53 | 2.08 | 0.72 | 0.45 | 1.9 | 17 |
| C'toxA | 9.06 | 6.40 | 1.35 | 1.74 | 0.79 | 0.50 | 0.8 | 7 |
| C'toxA/M | 8.24 | 6.01 | 1.42 | 1.79 | 0.69 | 0.44 | 1.9 | 3 |
| C'toxA/T | 8.70 | 6.32 | 1.47 | 1.99 | 0.71 | 0.44 | .6 | 3 |
| C'toxA/GMGT | 8.47 | 5.95 | 1.36 | 1.73 | 0.73 | 0.46 | 1.8 | 4 |
| Virginiamycin | 9.70 | 6.98 | 1.31 | 1.61 | 0.84 | 0.55 | 0.5 | 0 |

Significant reduction in mortality and lesion scores and improved feed conversion were observed. The presence of PTCE in addition to the antigen augmented the reduction in mortality.

Example 3

Vaccines with Fusion Proteins of Antigens Derived from Bacterial Pathogens and PTCEs Protect Chickens when Administered Subcutaneously in a Necrotic Enteritis Challenge Model

Figure 3:
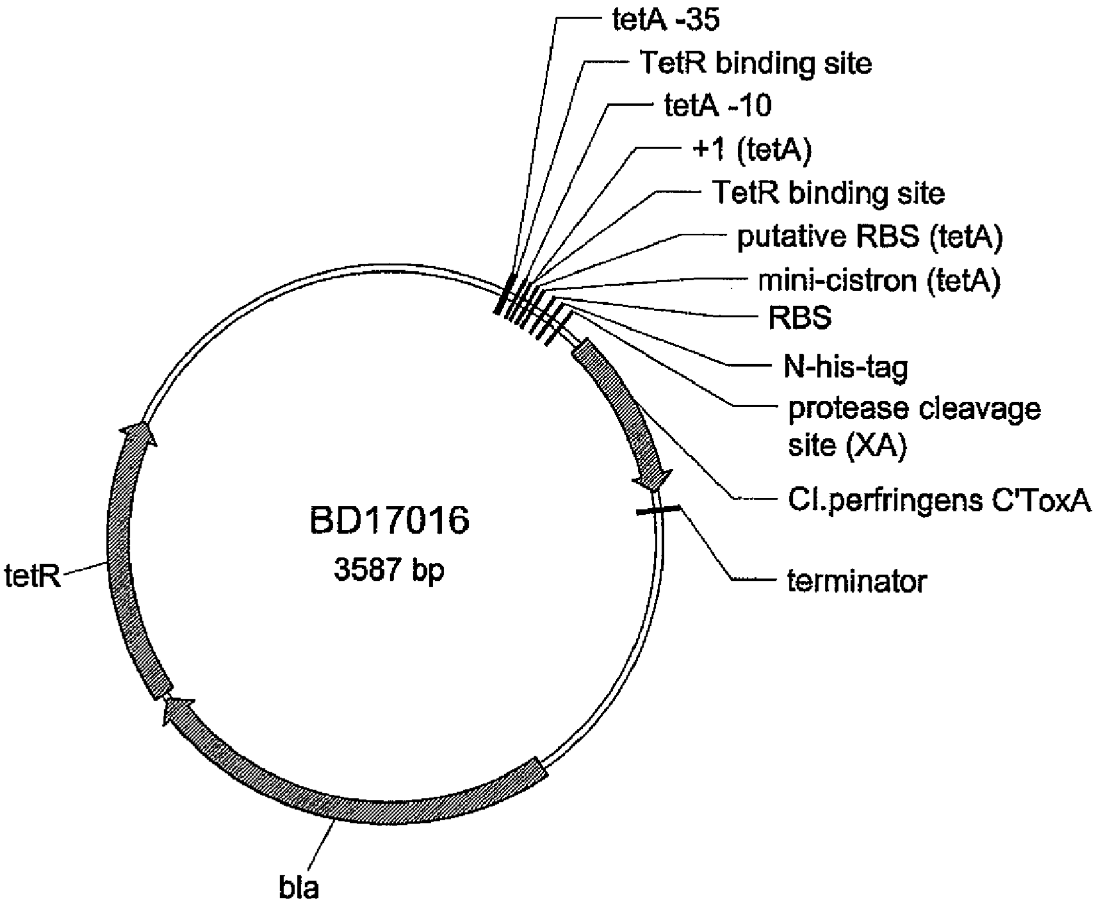
FIG. 3 is a vector map showing the features of pASK5 N'His+C'ToxA. The plasmid was used to generate the BD17016 vaccine, and encodes the recombinant *C. perfringens* C'ToxA B cell epitope. Chicks were vaccinated with the C'ToxA recombinant protein, and subsequently challenged with *C. perfringens* as described in Example 2.

*Clostridium perfringens* is the causative agent of necrotic enteritis in chickens. Recombinant C'ToxA antigen with or without PTCEs from BD17016, FIG. 3/SEQ ID NO: 162 and from BD 17194, FIG. 6/SEQ ID NO:168, described in Example 2 were purified and delivered subcutaneously to chickens. The birds were subsequently challenged with *C. perfringens* and the effects of the vaccinations on growth, feed conversion, mortality, and necrotic enteritis lesion scores were measured.

Materials and Methods

Three different types of treatments were used in the following study.

Treatment 1/Vaccine 1: C' ToxA from *C. perfringens* (BD17016) Pure protein, crude prep, with or without adjuvant. 100 μL of a 2 mg/mL solution was used for in ovo administration, and 200 μL of a 1 mg/mL solution was used for subcutaneous administration.

Treatment 2/Vaccine 2: C' ToxA from *C. perfringens* Gly linker-Measles Virus PTCE-Gly linker—Tetanus toxin PTCE (BD17194); Pure protein, crude preparation, without adjuvant 100 μL of a 2 mg/mL solution was used for in ovo administration, and 200 μL of a 1 mg/mL solution was used for subcutaneous administration.

Treatment 3/Bacitracin MD (BMD): Bacitracin MD in the form of a feed additive from Alpharma, Inc. (Fort Lee, N.J.) at a concentration of 50 g/lb was administered from days 0-21 in complete feed.

Diets: The standard starter diet contained fishmeal and wheat. The basal diet was manufactured at Agland, Inc. (Eaton, Colo.). Treatment diet mixing was carried out at Colorado Quality Research (Wellington, Colo.) using a 500 lb capacity vertical mixer. The control compositions were added to the basal diet as discussed below.

Animals: 1728 Ross 308 Broiler Chickens were assigned to 96 different pens (20 birds/pen). The test facility was divided into 8 bocks of 12 pens. Each pen was assigned to a different treatment (12 total), such that for each treatment listed, 144 birds received the treatment. Specific treatment groups were as follows:

Experimental Design

In ovo vaccination was carried out at Welp Hatchery (Bancroft, 2 mg/mL, according to the treatment number. Each hatching tray was marked with the treatment IA) at day 19. Eggs vaccinated in ovo received a 100 μL dose of either Pure or Crude protein at number. Chicks receiving the Pure or Crude Protein treatments subcutaneously were inoculated with 200 μL of a 1 mg/mL solution at the day of hatch.

The chicks were transferred to assigned pens as described above, based on their treatment groups. Feed was provided ad libitum throughout the study via one hanging, ~17 inch diameter tube feeder per pen. A chick feeder tray was placed in each pen for approximately the first 4 days. Birds were then placed on their respective treatment diets upon receipt according to the treatment groups. Feed added and removed from pens from study day 0 to the end of the study was weighed and recorded.

Starting on study day 0, any bird that was found dead was weighed and necropsied. Birds that are unable to reach feed or water were sacrificed, weighed and documented. The weight and probable cause of death and necroscopy findings were recorded on the pen mortality record.

Birds were weighed, by pen, on days 13 and 21 of the study. The feed remaining in each pen was weighed and recorded at each body weight measurement. The feed intakes during days 0-13 and 0-21 were calculated.

Average bird weight, on a pen basis, on each weigh day was summarized. The average feed conversion was calculated for each measurement period (i.e. days 0-13, 0-21) using the total feed consumption for the pen divided by the total weight of the surviving birds. Adjusted feed conversion was calculated using the total feed consumption in a pen divided by the total weight of surviving birds and weight of birds that died or were removed from that pen.

Method of Administration

Administration of the coccidiosis and Clostridia perfringens (Type A, α and β2 toxins) cultures in the study were administered via the feed. Feed from each pen's feeder was used to mix with the culture. Prior to placing the cultures in the pens the treatment feed was removed form the birds for approximately 4-6 hours. Birds that are not challenged with *C. perfringens* also had the feed removed during the same time period as the challenged groups.

An extra pen of challenged birds (non-study) was used to monitor the course of the infection to achieve a target of 5%-10% mortality due to necrotic enteritis. Birds from this pen were removed and necropsied periodically during the challenge phase to determine if the challenge was sufficient as well as the optimum day for scoring lesions.

Clostridia Challenge

Approximately five days prior to administering the *C. perfringens* culture, birds in the challenged groups received multiple doses of a coccidiosis vaccine via the feed.

The *C. perfringens* culture was grown for approximately 24 hours at 37° C. in fluid BBL Thioglycollate broth (Krackeler Scientific Inc., Albany, N.Y.). A fresh broth culture was prepared and used each day. For each pen of birds, a fixed amount of the overnight broth culture was mixed with a fixed amount of basal feed in the feeder tray. The amount of feed used was documented and all pens were treated the same. The birds received the *C. perfringens* culture for one to three consecutive days.

Necrotic Enteritis Lesion Scoring

The day following the last *C. perfringens* administration, five birds were randomly selected from each pen and sacrificed. Intestinal lesions were scored for necrotic enteritis as follows:

0=normal: no NE lesions, intestine has normal elasticity (rolls back on itself after being opened)

1=mild: thin and flaccid intestinal wall (intestine remains flat when opened and doesn't roll back into normal positions); thickened mucous covering mucous membrane.

2=moderate: noticeable reddening and swelling of the intestinal wall; minor ulceration and necrosis of the intestine membrane; excess mucous.

3=severe: extensive area of necrosis and ulceration of the small intestine membrane; significant hemorrhage, layer of fibrin and necrotic debris on the mucous membrane (Turkish towel appearance).

4=dead or moribund bird (bird that would likely die within 24 hours) with NE gross lesions scored 2 or more.

Results

Results of the study are shown in FIGS. 10-14. Significant reduction in mortality and lesion scores and improved feed conversion were observed following treatment as shown. The presence of PTCE in addition to the C'ToxA antigen augmented the reduction in mortality.

Example 4

Vaccines with Fusion Proteins of Antigens Derived from Viral Pathogens and PTCEs Protect Fish in a Infectious Pancreatic Necrosis Virus (IPNV) Challenge Model Infectious pancreatic necrosis virus (prototype *Birnavirus*) ("IPNV") is the causative agent of infectious pancreatic necrosis in fish. IPNV displays a high degree of antigenic variability. The IPNV genome consists of a 3.1 kb region, "Segment A," that encodes a 100 kDa polyprotein which is subsequently cleaved to produce the VP2, VP4, and VP3 proteins. VP2 is the major structural and antigenic protein. The amino and carboxy terminus of the VP2 protein are highly conserved, whereas the internal segment is comprised of three hypervariable regions.

To test the ability of the amino terminus of the IPNV VP2 in conjunction with a PTCE to immunize against IPNV, fusion proteins with the first 257 amino acids of the IPNV VP2 protein and a measles virus PTCE and a tetanus PTCE were used to vaccinate Atlantic Salmon. The fish were subsequently challenged with IPNV and the effects of the vaccinations on mortality were measured. The following example demonstrates that a recombinant vaccine comprising antigenic viral pathogen proteins in combination with PTCEs protect Chilean Atlantic Salmon against subsequent viral challenge.

A. Vaccine Preparations

Figure 19:
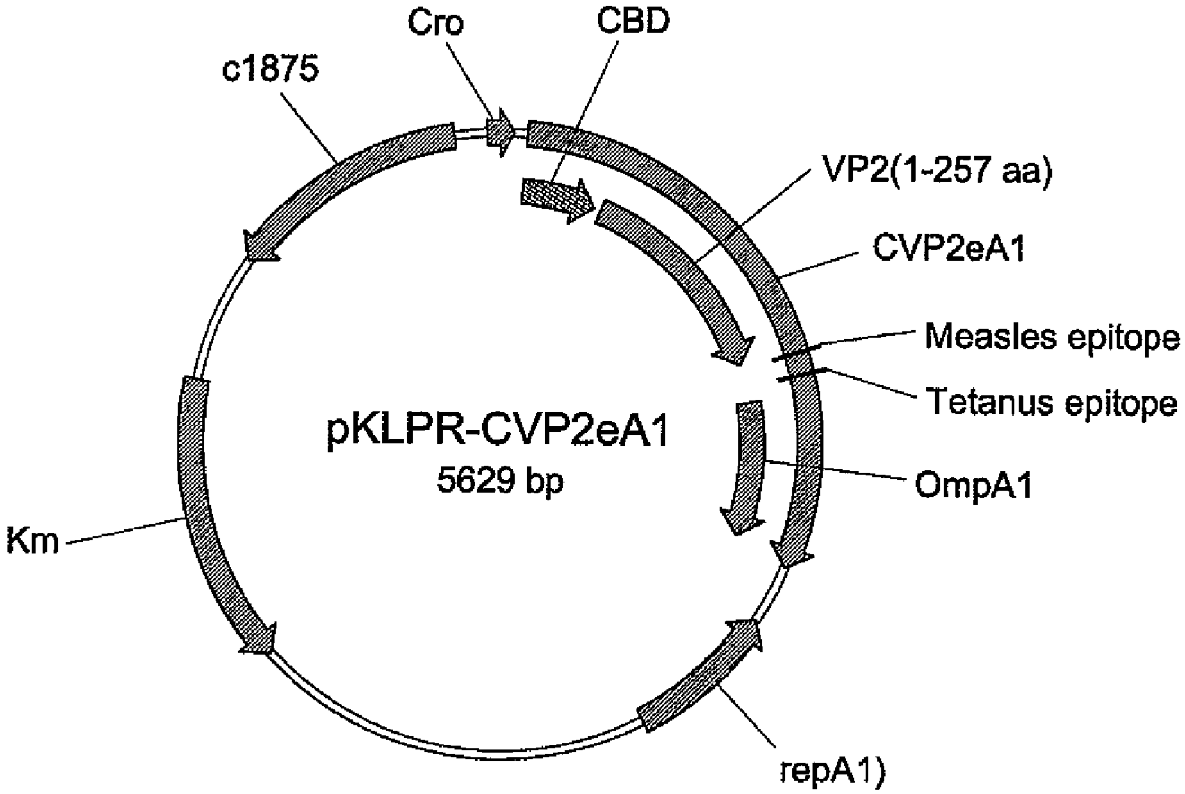
FIG. 19 is a map of the pKLPR-CVP2eA1 vector used to generate an IPNV vaccine as described in Example 4. The vector is designed to express an in-frame fusion protein of the first 257 amino acids of the IPNV VP2 protein with a measles virus PTCE and a tetanus virus PTCE at the C' terminal end of the protein. Fish to which the protein was administered were subsequently challenged with IPNV as described in Example 4.

The expression vector shown in FIG. 19, described in U.S. Patent Application Publication 2004/0086524, expresses the N-terminal 257 amino acids of the VP2 protein from IPNV ("truncated VP2 antigen") (SEQ ID NO: 148), as well as the measles PTCE (SEQ ID NO:1) and the tetanus toxin 830-844 PTCE (SEQ ID NO:3).

An isolated *E. coli* host cell was used for over-expression and recovery of the recombinant protein. Recombinant protein accumulated inside cells as insoluble aggregates of protein. The insoluble recombinant protein was recovered by methods known to those skilled in the art. (See, Sambrook, supra). The protein was diluted to a final concentration of 250 mg/L.

B. Vaccination Protocol:

Four groups of 80 randomly assigned Atlantic Salmon (*Salmo salar*) were vaccinated with the indicated doses of recombinant IPNV vaccine formulations (250 mg/L) in 0.2 mL volume. One group was injected with PBS. Each group was held in a separate tank.

At approximately 700 degree days (degree days=° C., multiplied by the number of days in holding), post vaccination, 50 fish from each group were selected for injection (0.1 cc) challenge with a field isolate of IPNV serotype SP. 0.2 ml of 1×10e8 pfu/ml of live IPNV was administered by i.p. injection.

Results:

| Group | # of challenged fish | % Cumulative mortality due to IPNV challenge (CPE+) | Relative Percent Survival |
|---|---|---|---|
| Control | 50 | 92.0% | — |
| 1 | 38 | 2.6% | 97.1% |
| 2 | 50 | 4.0% | 95.7% |
| 3 | 50 | 10.0% | 89.1% |
| 4 | 50 | 22.0% | 76.1% |

Significant reduction in mortality was observed in fish that received IPNV vaccines.

Example 4A

Novel Vaccines Against IPNV

To provide improved vaccines against IPNV, the vectors shown in FIGS. 15-18 were constructed, which contain different antigens and PTCE's in combination with the IPNV VP2 fusion protein discussed in Example 4. The vectors were derived from pUCK19, which is a derivative of pUC19 (New England Biolabs, Ipswich, Mass.). The ribosome binding site of pUC19 was modified from the nucleotide sequence cacacaggaaacagct (SEQ ID NO: 180) to caagaggagtatatct (SEQ ID NO: 181). The cer element from ColE1 was inserted at the AatII site. The bla gene of pUC19 for ampicillin resistance was replaced a kanR gene for kanamycin resistance.

The pUCKTryp-GMVP2GTcer+ plasmid (FIG. 15) was derived from pUCK19 above, to express an in-frame fusion between the protozoan *Lepeophteirus salmonis* (sea lice) trypsin protease antigen, a 10 glycine linker, the measles PTCE, the carboxy terminal 257 amino acids from the IPNV VP2 protein (source: pKLPRCVP2eA1), another 10 glycine linker, followed by the tetanus PTCE of SEQ ID NO:2., which includes amino acids 582-599 of the tetanus toxoid protein.

Figure 16:
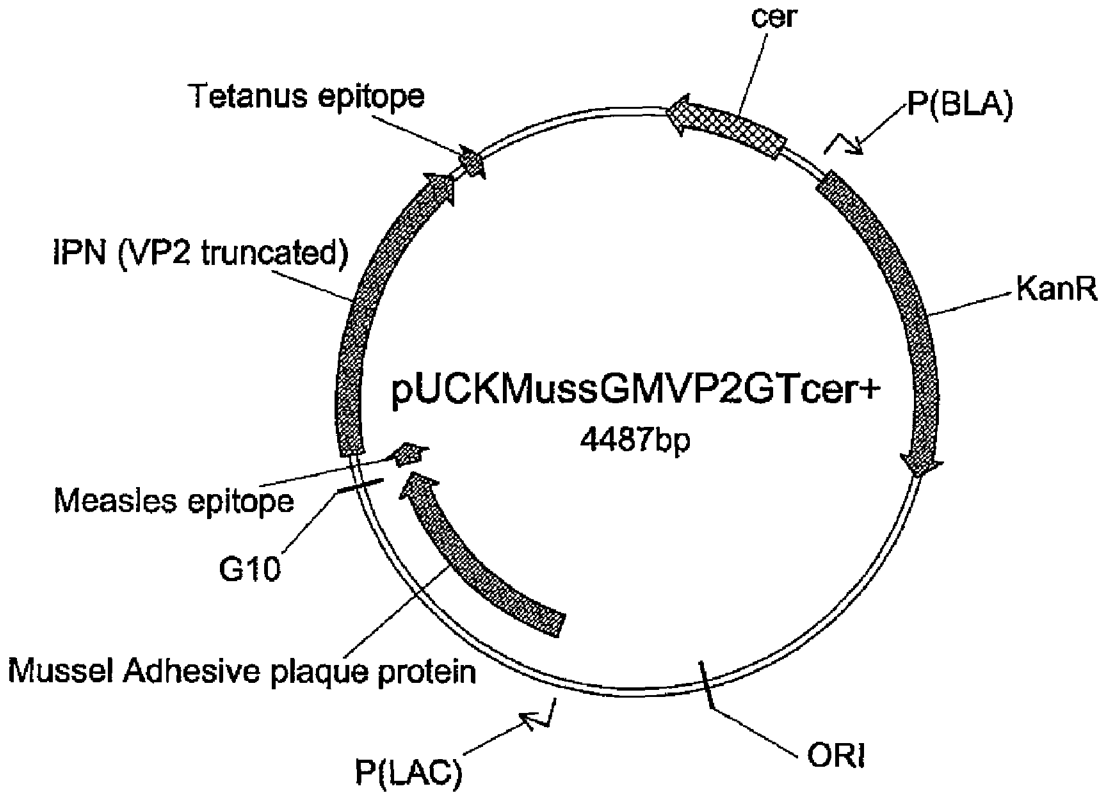
FIG. 16 is a map of the pUCKMussGMVP2GTcer+ plasmid. This plasmid encodes and in-frame fusion between *Lepeophteirus salmonis* (sea lice) mussel adhesive plaque protein, followed by a 10 glycine linker, the measles PTCE, the carboxy terminal 257 amino acids from the IPNV VP2 protein, and the tetanus epitope.
Figure 17:
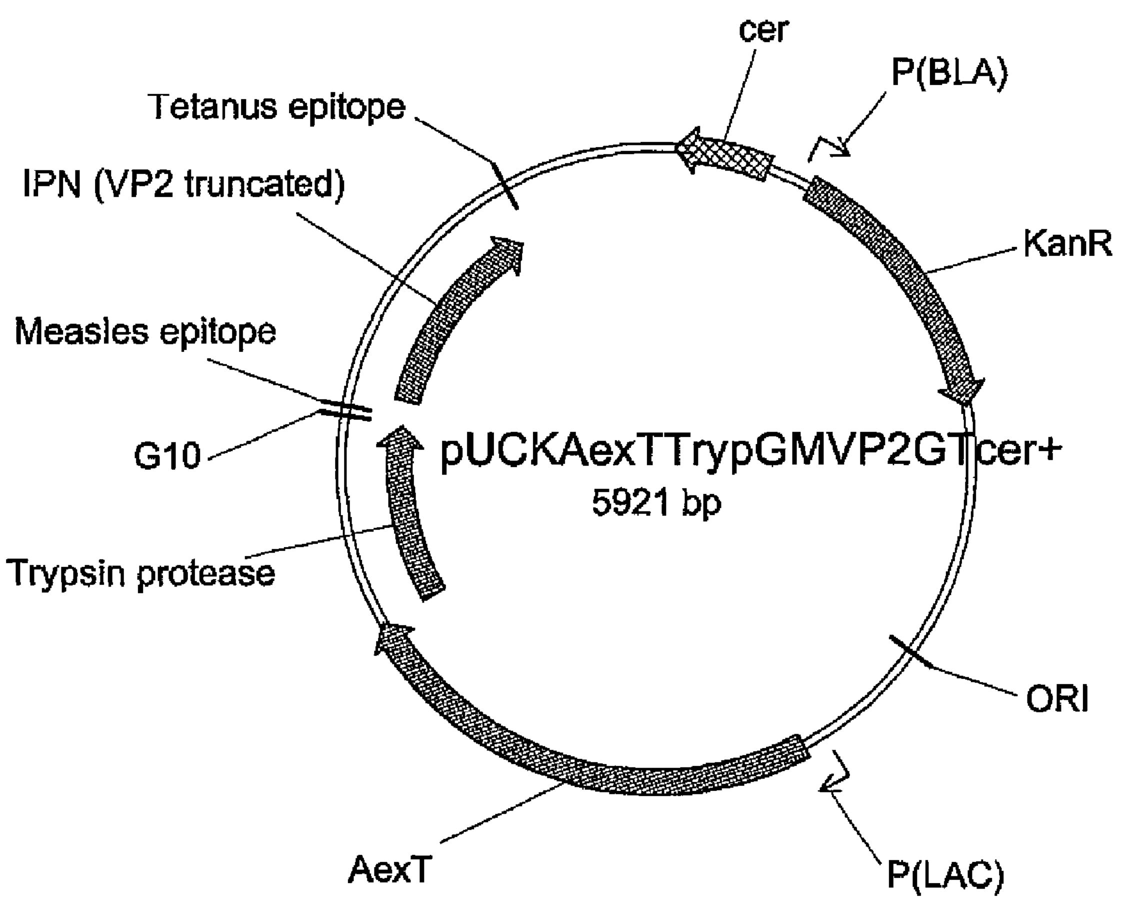
FIG. 17 is a map of the pUCKAexTTrypGMVP2GTcer+ plasmid, designed to generate a vaccine against IPNV, such as those described in Example 4. This plasmid encodes a fusion protein between the AexT *Aeromonas salmonicida* exoenzyme T (AexT) antigen, the *Lepeophteirus salmonis* (sea lice) trypsin protease antigen, a glycine linker, a measles PTCE, the carboxy terminal 257 amino acids from the IPNV VP2 protein, and the tetanus toxin PTCE.

FIG. 16 illustrates the features of the pUCKMussGMVP2GTcer+ plasmid. This plasmid encodes and in-frame fusion between *Lepeophteirus salmonis* (sea lice) mussel adhesive plaque protein, followed by a 10 glycine linker, the measles PTCE, the carboxy terminal 257 amino acids from the IPNV VP2 protein, and the tetanus epitope of SEQ ID NO:3. FIG. 17 shows features of the pUCKAexTTrypGMVP2GTcer+ plasmid. This plasmid encodes a fusion protein between the AexT *Aeromonas salmonicida* exoenzyme T (AexT) antigen, the *Lepeophteirus salmonis* (sea lice) trypsin protease antigen, a glycine linker, a measles PTCE, the carboxy terminal 257 amino acids from the IPNV VP2 protein, followed by the tetanus toxin PTCE (SEQ ID NO:2).

Figure 18:
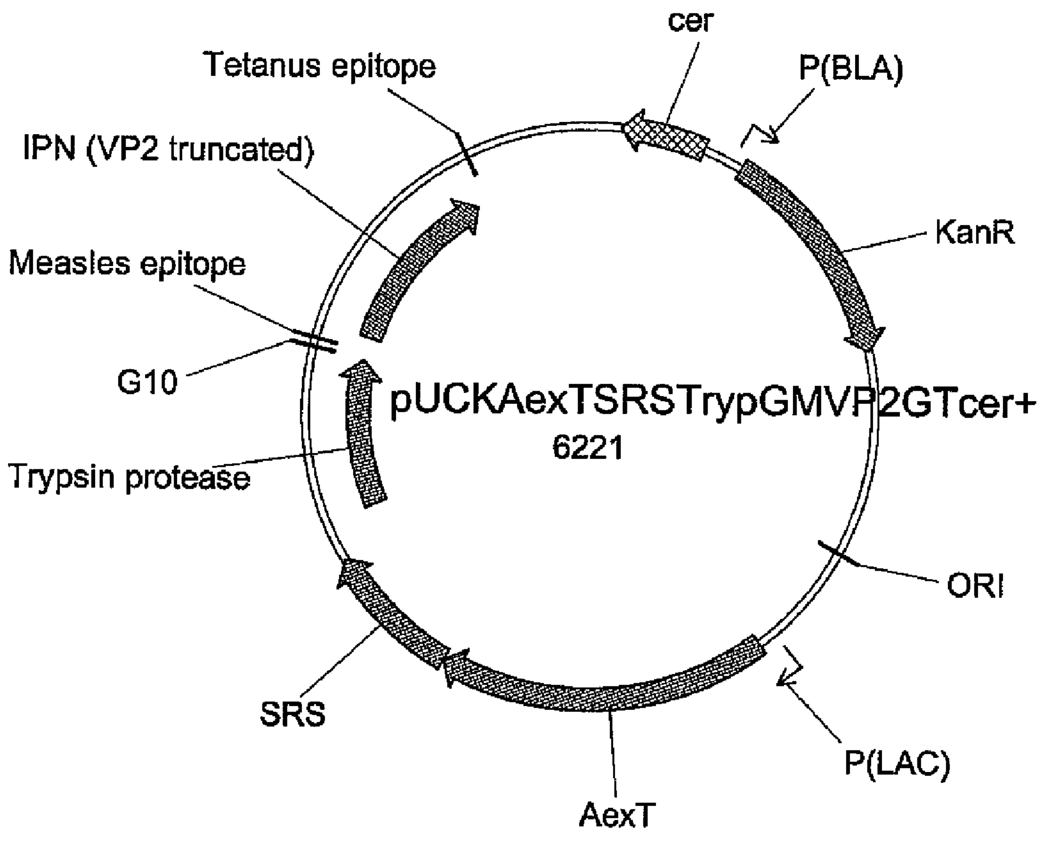
FIG. 18 is a map of the pUCKAexTSRSTrypGMVP2GTcer+ plasmid. This plasmid encodes a fusion protein between the AexT *Aeromonas salmonicida* exoenzyme T (AexT) antigen, the *Lepeophteirus salmonis* (sea lice) trypsin protease antigen, a glycine linker, a measles PTCE, the carboxy terminal 257 amino acids from the IPNV VP2 protein, followed by the tetanus toxin PTCE.

Finally, FIG. 18 shows the features of the pUCKAexTSRSTrypGMVP2GTcer+ plasmid. This plasmid encodes a fusion protein between the AexT *Aeromonas salmonicida* exoenzyme T (AexT) antigen, the *Lepeophteirus salmonis* (sea lice) trypsin protease antigen, a glycine linker, a measles PTCE, the carboxy terminal 257 amino acids from the IPNV VP2 protein, followed by the tetanus toxin PTCE (SEQ ID NO:2)

Host cells harboring the recombinant plasmids are cultured under conditions that lead to overexpression of the recombinant proteins. The proteins are recovered from the cells using methods known to those skilled in the art.

Fish are allocated into different treatment groups. Treatment groups include controls (no vaccination/treatment; no infection), and groups to which each of the above fusion proteins are administered. Administration of the treatments, followed by the IPNV challenge is as described in Example 4. Mortality rates in the different treatment groups are compared as in Example 4.

A significant reduction in mortality is seen in fish that receive the IPNV VP2 vaccines described herein.

Example 5

Novel B and T-Cell Epitopes Derived from Infectious Bursal Disease Virus (IBDV) Useful in Compostions to Protect Against IBDV Infectious bursal disease (IBD) is a highly contagious disease in chickens 3 weeks of age and older, resulting in high mortality and immune suppression. Although not related, both IPNV (described above) and IBDV are *Birnaviruses*. IBD has a similar genetic organization as IPNV described in Example 4.

Clinical signs of IBDV infection include bursal inflammation, hemorrhage, lymphocytolysis, atrophy, depression, and liver necrosis. The Delaware E variant strain of IBDV is particularly virulent. The following study was conducted to determine: (1) if the IPNV VP2 fusion protein described in Example 4 (FIG. 19, comprising SEQ ID NOs:148, 1 and 3) could cross-protect chickens from the IBDV; (2) if novel truncated B cell epitopes from IBDV Del-E and various T-cell epitopes are effective in protecting against IBD; and (3) the role of various PTCEs in protecting against IBDV.

A. Vaccine Preparations

Figure 24:
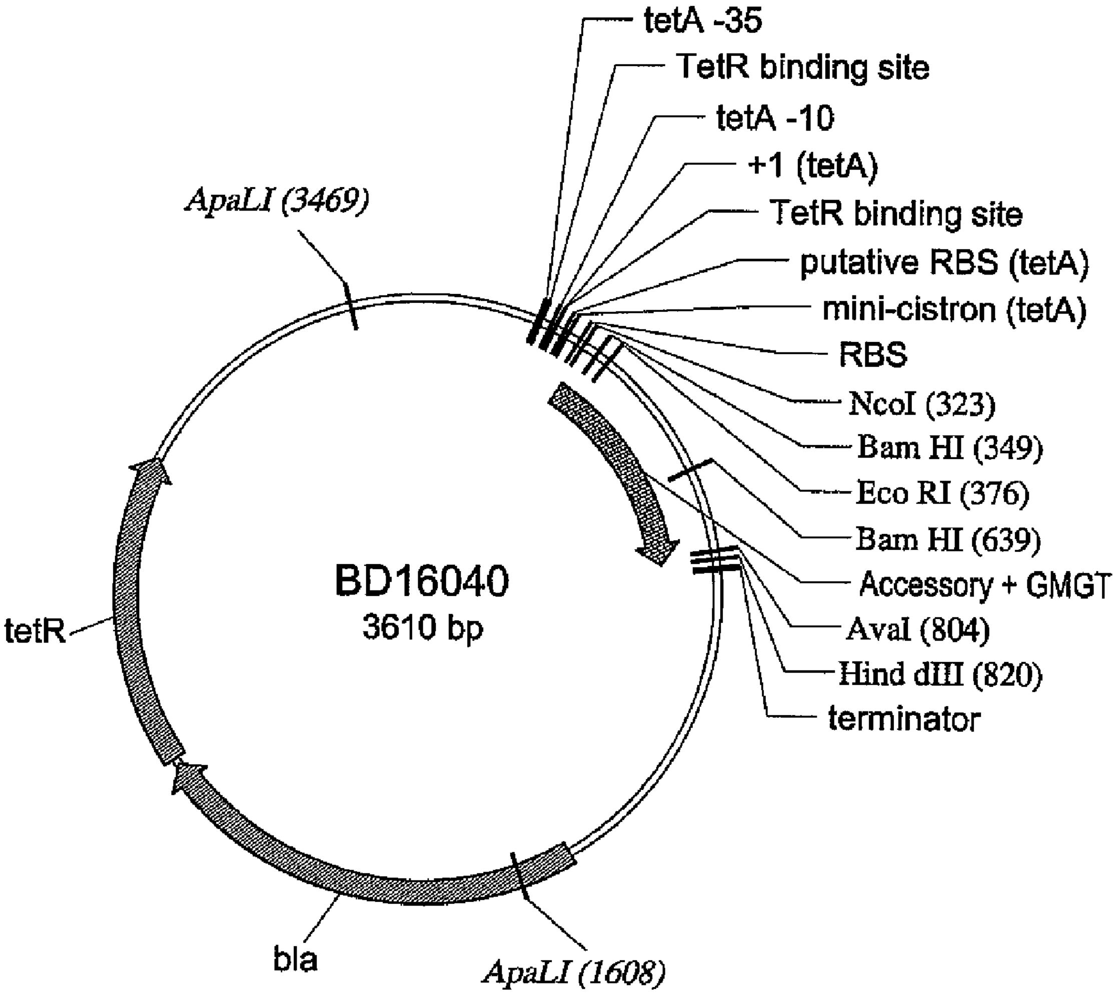
FIG. 24 is a map of the vector used to generate the BD1640 vaccine. This vector is designed to produce the GMGT PTCE/glycine linker polypeptide.

The pKLPR-CVP2eA1 vector (FIG. 19), described above, is used to express the N-terminal 257 amino acids of the VP2 protein from IPNV ("truncated VP2 antigen") (SEQ ID NO:148), as well as the measles PTCE (SEQ ID NO:1) and the tetanus toxin 830-844 PTCE (SEQ ID NO:3). To generate BD16040 (FIG. 24), an expression vector containing a GMGT epitope/linker with the tetanus toxin PTCE of SEQ ID NO:2, the pKLPR-CVP2eA1vector was digested with NdeI and NheI. The insert including the VP2eA1(257 amino acids of the VP2 protein IPNV), as well as the measles and tetanus epitopes, and A1 (155 amino acids of membrane protein OmpA1 form *Aeromonas salmonicida*). The GMGT epitope cassette was cloned as NdeI/NheI fragment into the backbone of pKLPR-CVP2eA1. The GMGT cassette encodes 10 Glycines (Gly), followed by 1 copy of measles (M) epitope, spacer of 10 Gly and one copy of tetanus epitope (T; Gly-M-Gly-T). The cassette was generated by annealing oligos encoding Gly-M and Gly-T. The Gly-M and Gly-T fragments used as a template for an additional PCR reaction, with primers that contain NdeI and NheI sites. The PCR fragment was digested with NdeI/NheI and cloned into vector backbone described above. The GMGT fragment of the resulting vector was cloned into pASK5 N'His, described above, to create BD16040.

Figure 25:
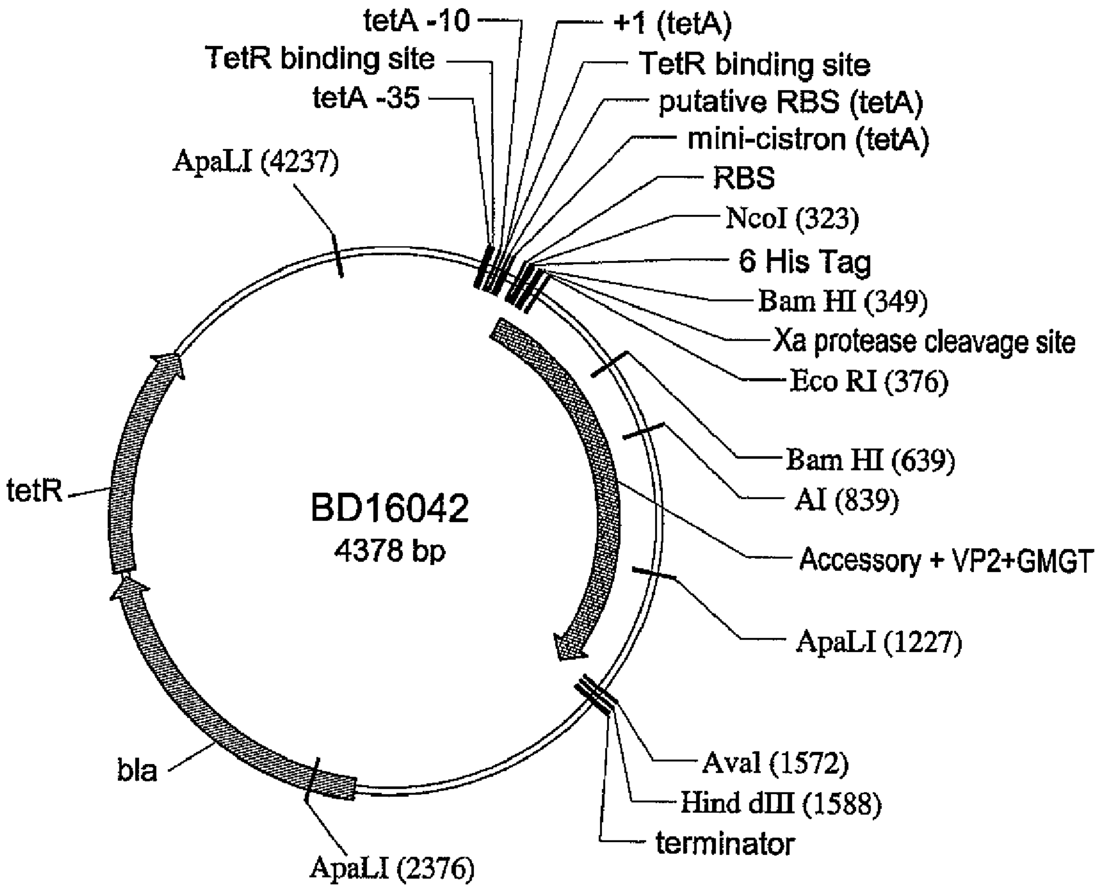
FIG. 25 is a map of the vector used to generate the BD16042 vaccine. This vector is designed to produce a fusion protein between amino acids 1-257 of the IPNV VP2 polypeptide and the GMGT PTCE/glycine linker polypeptide.

BD16042 (FIG. 25) encodes the GMGT epitope/linker from pKLPR-CVP2eA1, described above, as well as the truncated VP2 antigen of IPNV (SEQ ID NO: 148) +OmpA from pKLPR-CVP2eA1, cloned into the pASK5 N'His vector.

Figure 20:
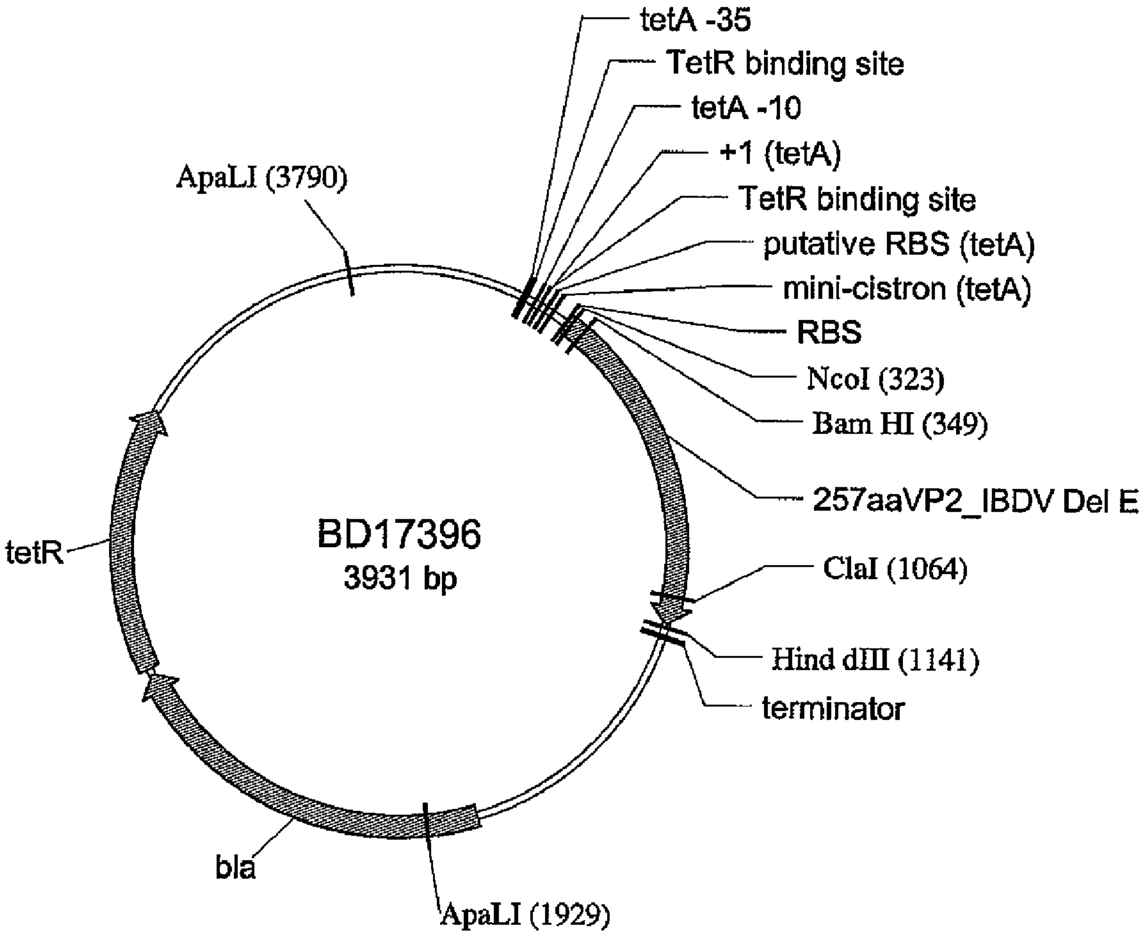
FIG. 20 is a map of the pASK5 N'His +VP2 vector used to generate the BD17396 vaccine. The 17396 vaccine includes a polypeptide of the first 257 amino acids from the IBDV VP2 protein, from the Delaware E strain.
Figure 21:
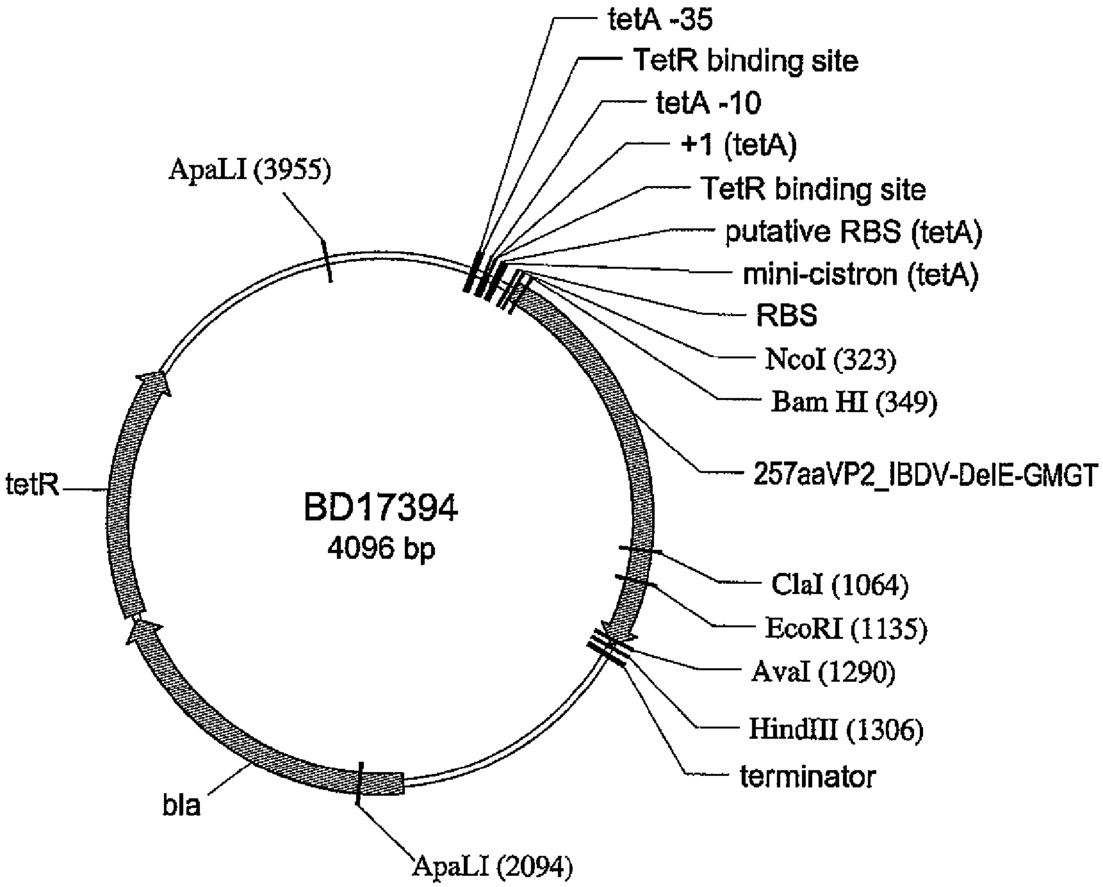
FIG. 21 is a map of the pASK5 N'His +VP2 +GMGT vector used to generate the BD17394 vaccine as described in Example 5. The vector is designed to produce a fusion protein of the first 257 amino acids of the IBDV Del E VP2 protein with a glycine linker, followed by a measles virus PTCE, followed by another glycine linker, and the tetanus toxin PTCE. Chickens to which the protein was administered were subsequently challenged with IBDV as described in Example 5.
Figure 22:
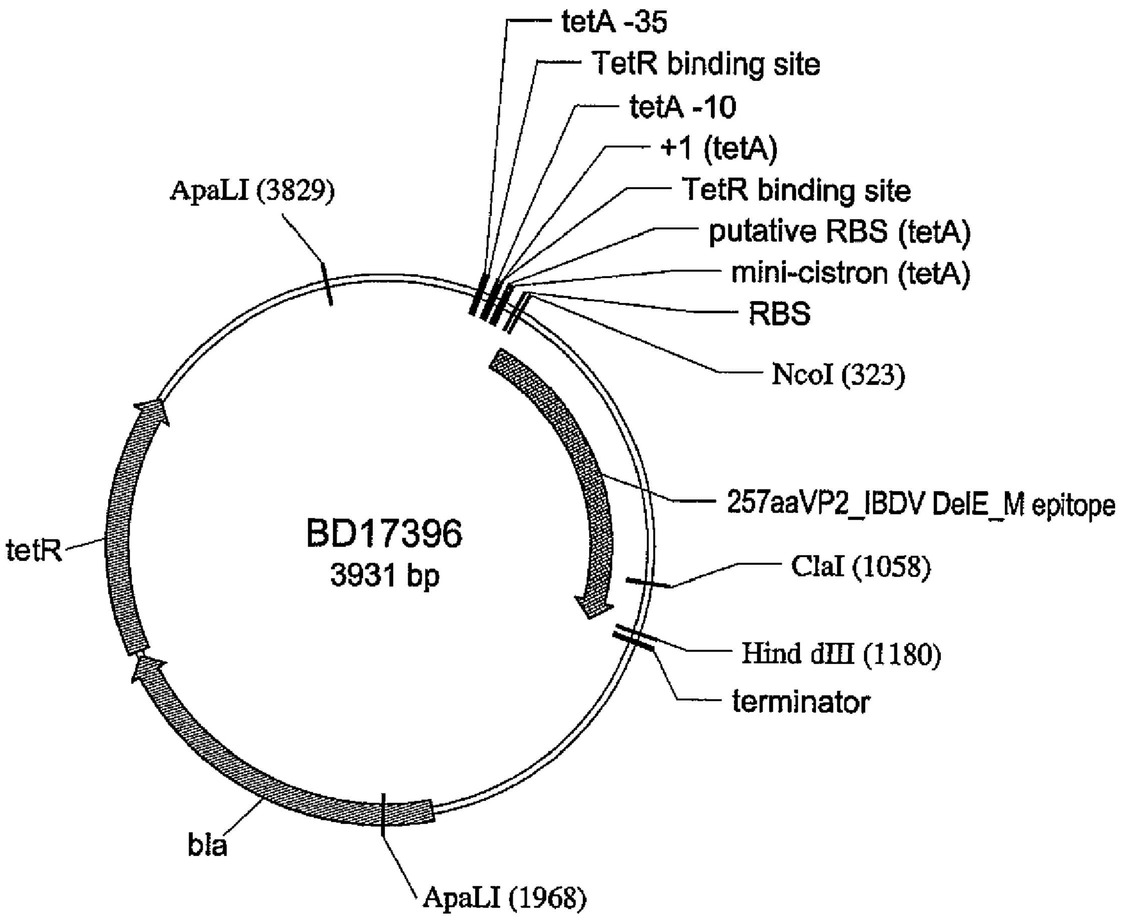
FIG. 22 is a map illustrating the vector used to generate the BD17257 vaccine as described in Example 5. The vector is designed to produce a fusion protein of the first 257 amino acids of the IBDV Del-E VP2 protein with a measles virus PTCE as described in Example 5. Chickens to which the protein was administered were subsequently challenged with IBDV as described in Example 5.
Figure 23:
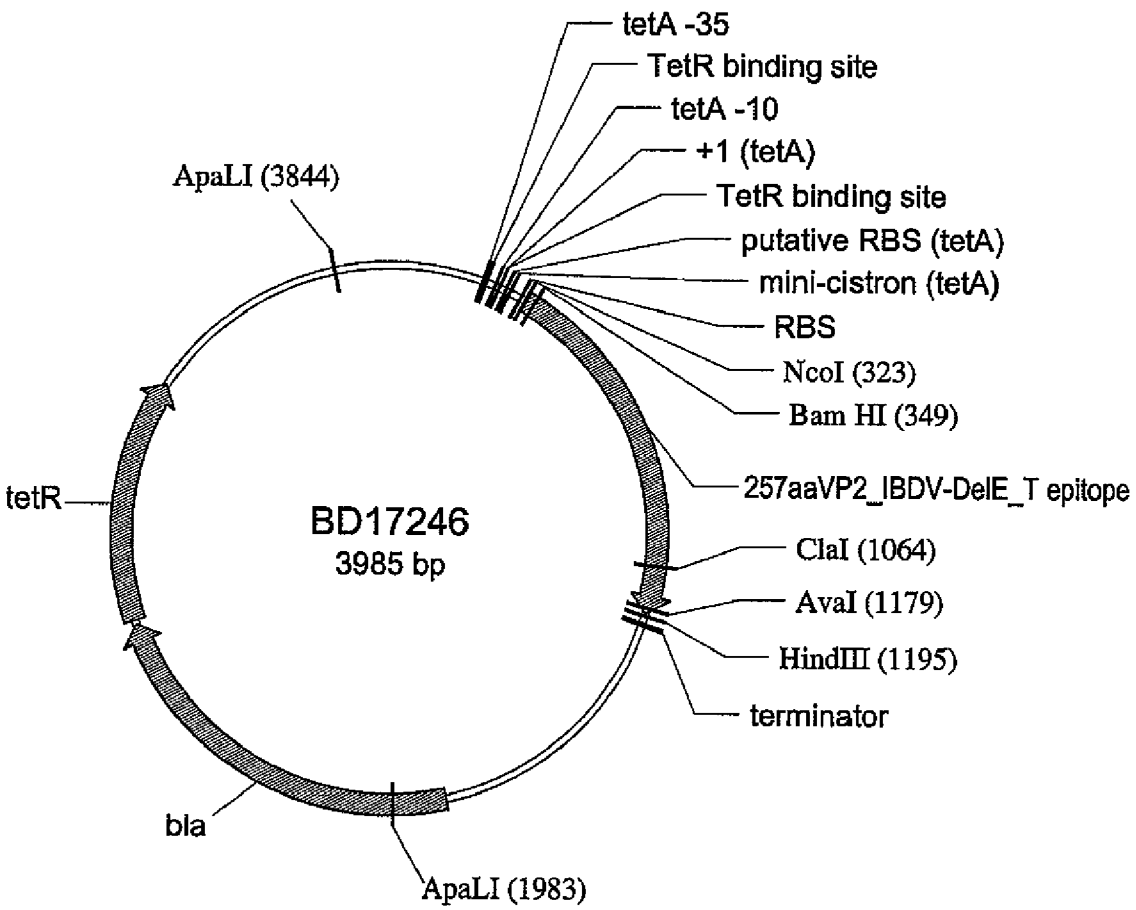
FIG. 23 is a map illustrating the vector used to generate the BD17246 vaccine as described in Example 5. The vector is designed to produce a fusion protein of the first 257 amino acids of the IBDV Del-E VP2 protein with a tetanus toxin PTCE as described in Example 5. Chickens to which the protein was administered were subsequently challenged with IBDV as described in Example 5.

The pASK5 N'His vector, described in Example 2, was also used to construct the following expression vectors. BD17936 (FIG. 20) is a vector for the expression of a recombinant polypeptide of the amino terminal 257 amino acids of the VP2 protein from the virulent IBDV strain ("VP2_IBDV-DelE"). BD17394 (FIG. 21) is a vector for the expression of a fusion protein between VP2_IBDV-DelE and the GMGT multiple PTCE/linker polypeptide (SEQ ID NO:160), with the tetanus toxin PTCE "T" sequence of SEQ ID NO:2, which spans amino acids 582-599 of the tetanus toxin. BD17257 (FIG. 22) is a vector for the expression of a fusion protein between VP2_IBDV-DelE and the measles PTCE (SEQ ID NO:155). BD17246 (FIG. 23) is a vector for the expression of a fusion protein between VP2_IBDV-DelE and the tetanus PTCE of SEQ ID NO:2 (SEQ ID NO: 158).

Animals 250 broiler chicks are used in the study, which consists of 10 treatments, including three controls. 25 birds will receive each treatment.

Administration

The treatments consists of two intramuscular injections at Days 7 and 21 post hatch. 100 μg of each antigen is administered in 100 μL volume, in PBS.

IBDV Challenge and Scoring

On day 28, birds from each treatment group are challenged with Delaware-E IBDV ($10^3$ $EID_{50}$). 5 birds from each treatment group are removed necropsied at day 0, 4, 7, 10 and 14 post-challenge. The birds are weighed and examined for signs of IBDV infection as measured by bursal lesions. Bursa/body weights and antibody responses are measured and compared to controls.

Birds that are treated with the IPNV VP2, and IBDV VP2 vaccines show improved weight and feed conversion, as well and antibody responses, to IBDV challenge. Vaccines that include PTCEs show enhanced protection to IBDV challenge compared to the vaccines that do not include PTCEs.

Fermentation

The following protocol is used to produce and recover IPNV VP2 fusion proteins. An isolated *E. coli* colony harboring the expression vector is used to inoculate TB media (Ausubel et al., supra) containing TB (4 g/L glycerol) with 20 μg/mL kanamycin ("kan"). The culture is grown at 30° C. until it reaches an $OD_{600}$ of 5-10. Another IL of TB media with glycerol and kan is added to the culture. The culture is incubated at 42° C., shaking, for 3-8 hours. The cells are harvested by centrifugation. The cells were lysed by adding 50% thymol in EtOH to a final concentration of 0.1%, and 0.5 M EDTA to a final concentration of 1 mM. The lysates is inactivated by adding 10% BEI solution. BEI solution is prepared by adding 2-bromoethylamine-HBr (BEA, 20 g/L) to 0.175 M NaOH and waiting 60 minutes at 37° C. with pH dropping from 12.5 to 8.5. The solution is diluted to a final concentration of 0.5 mM EDTA 0.05% thymol.

Example 6

Novel Vaccines Against Infectious Bronchitis Virus (IBV) in Poultry

Infectious bronchitis virus is an enveloped RNA virus (a member of the *Coronavirus* family), and is the causative agent of infectious bronchitis, which is characterized by a highly contagious respiratory, enteric and reproductive disease in poultry, especially young birds. Several strains of IBV are also known to cause nephrophathogenesis (kidney lesions).

Traditionally, vaccines based on live attenuated viruses, or inactivated viruses, have been used to protect against IBV. However, due to the high antigenic variability of IBV, the lack of replication, short duration of immunity, recombinant peptide/subunit vaccines provide an attractive alternative to address the problems above.

Identification of Novel IBV-Derived B and T-Cell Epitopes

Both humoral and cellular immunity are important in developing protection against IBV infection and clinical disease. Many antigenic determinants of IBV have been identified on the spike protein (S1), including several B cell epitopes (Sneed et al. (1989), *Viral Immunol.,* 2(3):221-7). A synthetic peptide comprising amino acids 240-255 of IBV S1 has been shown to react with polyclonal antisera raised against several different IBV strains (Wang et al., (1995) *Arch Virol.* 1995; 140(12):2201-13). Based on its cross-reactivity and functional immunogenicity, the antigenic determinant was identified as a potential candidate to develop cross-reactive subunit vaccines, but has not been exploited for this purpose to date.

Seo et al. (1997) *J. Virol.;* 71(10):7889-94. reported a specific cytotoxic T-lymphocyte response (CTL, CD8+) to the IBV nucleocapsid protein (NP). Novel B and T-cell epitopes, as well as novel combinations of IBV B and T-cell epitopes are discussed below.

Potential B cell epitopes in the IBDV sequences were predicted based on secondary structure and solvent accessibility using the software program ProfPHD (B. Rost (2005), submitted).

T-cell receptor recognition of ligands with immunogenic epitopes requires MHC binding of the epitope. Accordingly, peptides that can be presented by the MHC receptor were prioritized as potential T-cell epitopes. Three different methods were used to make predictions of T-cell epitopes: homology search, Hidden Markov Model (HMM) search, and sequence pattern matching. The sequences of immunogenic peptides were aligned with the protein sequence, and alignments of at least 60% identity were recorded as potential epitopes. Sequences were collected from immunoinformatics databases: MHCPEP (Brusic et al., (1998) *Nucleic Acids Res.;*26(1):368-71), and AntiJen (McSparron et al. (2003) *J Chem Inf Comput Sci.;* 43(4):1276-87). A HMM is a statistical model which calculates the probability of observing a sequence of residues given a training set of sequences. HMMs, modeling the epitopes of different MHC alleles, were used to search for peptides with a high probability of being an epitope. Potential epitopes were further prioritized by the predictive power of the model used to identify them. Sequence motifs, which describe the essential residues (anchor residues) responsible for ligand binding to MHC receptors, were used to prioritize the predictions from homology and HMM methods. Anchor residue motifs and their sources are described in (Yusim et al. (2004) *J. Virol.;*78(5):2187-200. Promiscuous epitopes were identified by having multiple epitope motifs, or being identified by HMMs for different alleles. Predictions that were longer than the expected length of an immunogenic peptide were treated with a set of methods comprising: division into smaller overlapping subsequences, and reduction to a hypothetically essential subsequence with the aid of anchor residue motifs.

Based on the above, the following epitopes were identified.

TABLE 1

| Putative epitope | Designation | Amino acid sequence | MHC bias | Seq ID No: |
|---|---|---|---|---|
| B-cell | IBB239255 | CQYNTGNFSDGFYPFT | N/A | 179 |
| B-cell | IBB347372 | SDFMYGSYHPHCSFRPETL NNG | N/A | 17 |
| T-cell | IBT2735 | VGSSGNASW | Class I | 18 |
| T-cell | IBT8593 | KPVPDAWYF | Class I | 19 |
| T-cell | IBT188196 | RRSGSEDDL | Class I | 20 |
| T-cell | IBT300308 | FEFTTVVPR | Class I | 21 |
| T-cell | IBT392400 | DEPKVINWG | Class II | 22 |
| T-cell | IBT137145 | FDQYPLRFS | Class II | 23 |
| T-cell | IBT5159 | FEGSGVPDN | Class II | 24 |
| T-cell | IBT109117 | SQDGIVWVA | Class II | 25 |
| T-cell | IBT208219 | QKKGSRITKAKA | Class II | 26 |
| T-cell | IBT144152 | FSDGGPDGN | Class I + II | 27 |
| T-cell | IBT3644 | FQAIKAKKL | Class I + II | 28 |
| T-cell | IBT329337 | TRPKDDEPR | Class I + II | 29 |

The above B and T-cell epitopes are confirmed using a variety of techniques known to those skilled in the art, including ELISA assays, Virus neutralization assays (See, Sneed et al. (1989), *Viral Immunol.,* 2(3):221-7; Tissue culture CTL assays (Seo et al. (1997) *J. Virol.;*71(10):7889-94; Pei et. al., (2003), *Virology;* 306(2):376-84.; and virus isolation and titration from infected tissues Seo et al. (1997) *J. Virol.;*71 (10):7889-94.

Evaluation of B and T-cell Epitopes as Vaccine Components

Peptides listed in Table 1 are synthesized by Sigma-Genosys and formulated with Montamide ISA763A adjuvant as described in the Tables shown below. Putative B-cell epitopes are conjugated to a protein carrier (keyhole limpet hemocyanin) by the peptide manufacturer. Two overlapping studies are conducted. Each study comprises eight treatments (groups), including controls, with 12 birds per treatment. Specific pathogen-free chicks will be used and two vaccinations will be administered. The first vaccination will occur on day 6 post-hatch and the second (boost) on day 16 post-hatch. For vaccinated birds, 100 micrograms of peptide formulated with adjuvant will be injected intramuscularly at each time. Treatment groups are shown in Table 2. Control groups include non-vaccinated non-infected (Group 1), non-vaccinated infected (Group 2), and birds which are given adjuvant without peptides (Group 3). Groups 2 and 3 are challenged on day 21 post hatch with $10^7$ $ID_{50}$ of IBV Gray strain. The field trial will continue for 20-25 days post challenge. During that time, birds are scored for clinical illness (coughing, sneezing, discharge, etc.) and tissue samples (lung and kidney) are collected for viral isolation and determination of virus titer (by RT-PCR). Determining virus titer in infected tissues indirectly measures the CTL response (e.g. if T-cell epitopes included in vaccine formulations will induce CTL, virus titer will decline or virus will be eliminated). The CTL response is directly measured by assays discussed above. Blood samples are collected at Days 0, 9 and 20 post challenge and antibody titer will be determined by ELISA (see above). A viral neutralization assay is done to determine if neutralizing antibodies are generated.

Clinical illness scores will reflect overall efficacy of B- and T-cell epitope mixtures administered as peptide vaccines.

TABLE 2

Treatment groups for the first proof of concept study.

| Group # | Adjuvant | B Peptides | T Peptides | Virus Challenge |
|---|---|---|---|---|
| 1 | None | None | None | None |
| 2 | None | None | None | $10^7$ $EID_{50}$ Gray |
| 3 | Montanide ISA763A | IBB347372 | None | $10^7$ $EID_{50}$ Gray |
| 4 | Montanide ISA763A | IBB239255 | None | $10^7$ $EID_{50}$ Gray |
| 5 | Montanide ISA763A | IBB239255 | IBT188196 + 2735 | $10^7$ $EID_{50}$ Gray |
| 6 | Montanide ISA763A | IBB239255 | IBT137145 + 5159 | $10^7$ $EID_{50}$ Gray |
| 7 | Montanide ISA763A | IBB239255 | IBT109117 + 208219 | $10^7$ $EID_{50}$ Gray |
| 8 | Montanide ISA763A | IBB239255 | IBT144152 + 3644 | $10^7$ $EID_{50}$ Gray |

Example 7

In ovo Protection Against *Eimeria* Protozoan Pathogens in Chickens Using Protein-Based Vaccines The 3-1E and or Mic2 genes are native surface antigens in *Eimeria*. The *Eimeria* heat shock protein (HSP90) and transhydrogenase protein (TH) are also antigenic. These antigens were used to test the measure the contribution of antigen, PTCE epitope (measles and/or tetanus toxin), and cytokines in immunizing chickens against coccidiosis in ovo.

Expression Vectors for PTCE/Antigen Fusions

Nucleic acids encoding the following were cloned into the pASK5 N'His expression vector described in Example 1: the GMGT polypeptide of SEQ ID NO: 144; a 71 amino acid fragment of the HSP90 polypeptide of *E. tenella* (SEQ ID NO:39)("HSP"); a fusion protein the nucleic acid encoding a polypeptide fragment from the C-terminal portion of the transhydogenase peptide of *E. tenella* (SEQ ID NO: 175)("TH") and the nucleic acid encoding the GMT polypeptide (SEQ ID NO:144) ("TH-GMGT"); a fusion protein encoded by the nucleic acid encoding TH and the Mic2 antigen of *E. acervi-luna* (SEQ ID NO: 32)("TH-Mic2"); and a fusion protein encoded ny the nucleic acid encoding TH and the 3-1E antigen of *E. acerviluna* (SEQ ID NO: 30)("TH-3-1E").

The PTCEs used in these experiments were the measles sequence LSEIKGVIVHRLEGV (SEQ ID NO:1) or the tetanus sequence VDDALINSTKIYSYFPSV (SEQ ID NO:2) or both. Multiple PTCEs were joined to each other by a polylinker of 10 glycines is present between the two or three PTCEs. The following vectors were also constructed to express fusion proteins between an antigen and the corresponding PTCEs, in place of the "Gly-ME-Gly-Tet" PTCE above:

| | |
|---|---|
| pKLPR-C-MGMGM | ME-Gly-ME-Gly-ME |
| pKLPR-C-MGM | ME-Gly-ME |
| pKLPR-C-M | ME |
| pKLPR-C-TGTGT | Tet-Gly-Tet-Gly-Tet |
| pKLPR-C-TGT | Tet-Gly-Tet |
| pKLPR-C-T | Tet |
| pKLPR-C-MGT | ME-Gly-Tet |

Expression and Isolation of *Eimeria* Fusion Proteins

An isolated *E. coli* host cell was used for over-expression and recovery of the recombinant proteins. Recombinant proteins accumulated inside cells as insoluble aggregates of protein. The insoluble recombinant protein was recovered by methods known to those skilled in the art. (See, Sambrook, supra).

Vaccination and *Eimeria* Challenge

Fertile eggs were selected by candling. At day 18 of incubation, 100 μg or 300 μg, as indicated, of the proteins were administered in a 100 μl volume below the shell (aircell) membrane and chorioallantoic membrane of the egg. A 22 gauge needle attached to a syringe was used to pierce a hole in the shell at the large end of the egg. The egg was subsequently sealed with wax.

The vaccinated embryonated eggs were transferred to an incubator to hatch.

Once hatched, the chicks were challenged with *Eimeria* oocysts at 2 weeks of age as described in Example 1. At 4 weeks of age, the number of oocysts shedding in the feces was determined according to the protocol of Min et al. (2001) *Vaccine* 20:267-274) to evaluate the immunogenicity of the composition.

Figure 26:
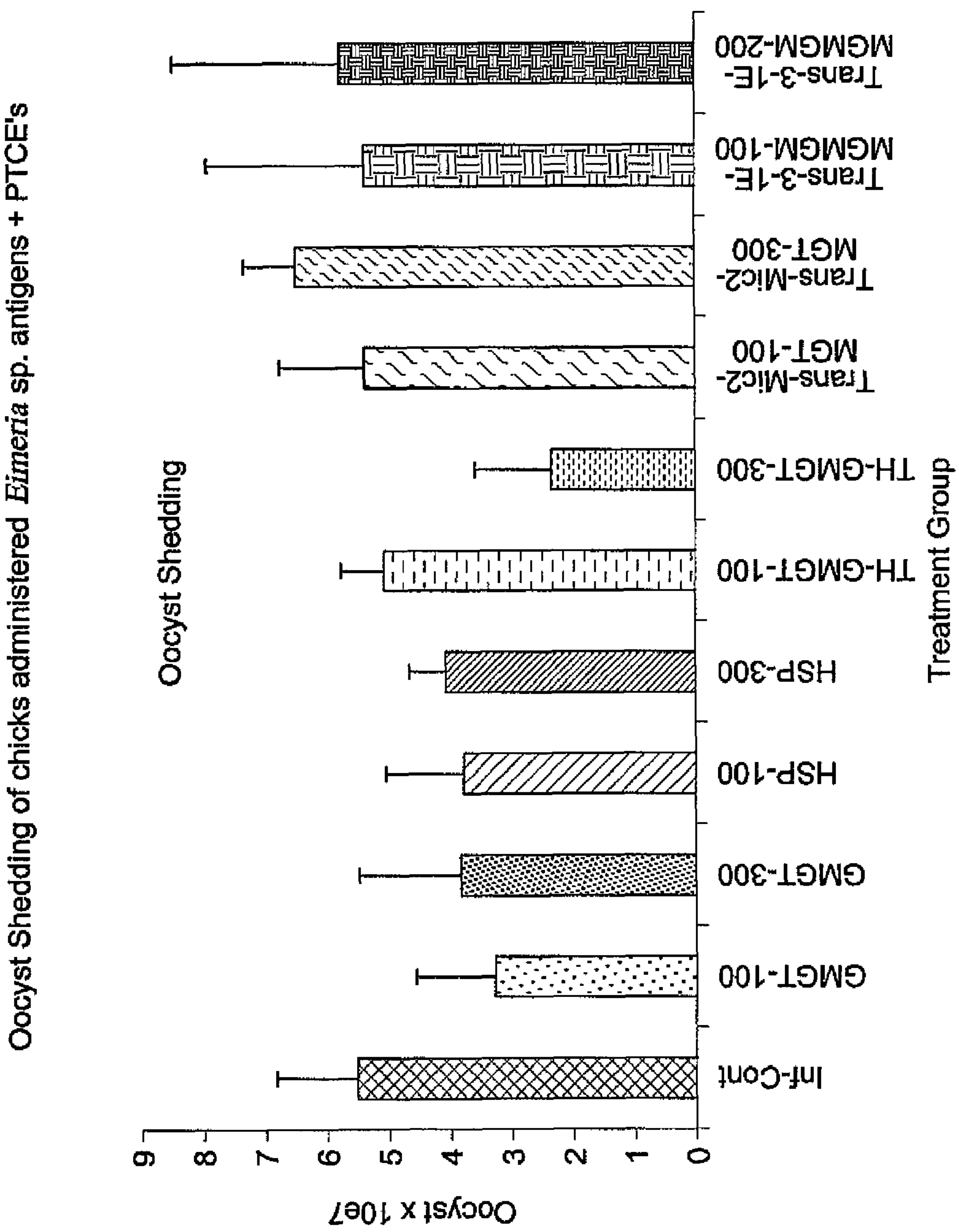
FIG. 26 shows data of oocyst shedding in chicks to which indicated amounts of various compositions [PTCE's, *E. tenella* heat shock protein 90 (HSP90), the C'terminal region of *E. tenella* transhydrogenase +PCTE, the *E. tenella* Mic2 antigen +PTCE, and the *E. tenella* 3-1E antigen +PTCE] were administered to chicks in ovo, followed by a challenge with *Eimeria*, as described in Example 1.

Results:

The results are shown in FIG. 26. The amount of oocyst shedding was significantly reduced in chicks that received IFNγ+the Transhydrogenase antigen/GMGT fusion protein in ovo, when compared to chicks that received only IFNγ, or PTCE alone, indicating that the PTCE/antigen vaccines protect chicks against subsequent challenges with protozoans when administered in ovo, prior to the development of any immune system.

The following combinations of 3-1E antigen, Mic2 antigen, PTCE's and optionally cytokines are also tested for their ability to immunize against IBDV as described above:

| Gene | protein kd | PTC epitope | Cytokine |
|---|---|---|---|
| 3-1E | 19 | Measles | |
| 3-1E | 19 | measles (2 epitopes in a row) | |
| 3-1E | 19 | measles (3 epitopes in a row) | |
| 3-1E | 19 | Tetanus | |
| 3-1E | 19 | measles and tetanus epitopes in a row | |
| 3-1E | 19 | | IFN-γ |
| 3-1E | 19 | | |
| 3-1E | 19 | | IL-12 |
| 3-1E | 19 | Measles | IFN-γ |
| 3-1E | 19 | Tetanus | IFN-γ |
| 3-1E | 19 | Measles | IL-12 |
| N-terminal 3-1E | 9.5 | Measles | IFN-γ |

-continued

| Gene | protein kd | PTC epitope | Cytokine |
|---|---|---|---|
| C-terminal 3-1E | 9.5 | Measles | IFN-γ |
| 3-1E + Mic2 | 19 + 32 | | |
| 3-1E + Mic2 | 19 + 32 | Measles | |
| 3-1E + Mic2 | 19 + 32 | Measles | IFN-γ |
| 3-1E + Mic2 | 19 + 32 | Tetanus | IFN-γ |
| Mic2 | 32 | | |

EQUIVALENTS

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention can be practiced in many ways and the invention should be construed in accordance with the appended claims and any equivalents thereof.

What is claimed is:

1. A composition comprising:

(a) a truncated VP2 antigen of infectious pancreatic necrosis virus (IPNV), wherein said truncated VP2 antigen is selected from the group consisting of SEQ ID NO: 146 SEQ ID NO: 148, SEQ ID NO: 150 and SEQ ID NO: 152; and (b) optionally including a promiscuous T-cell epitope comprising a peptide having the amino acid sequence of selected from group consisting of SEQ ID NO: 1, 2, 3, 4, 5, 6, 7, or a combination thereof.

2. The composition of claim 1, further comprising a pharmaceutically acceptable carrier.

3. The composition of claim 1, further comprising an adjuvant.

4. The composition of claim 1, wherein said composition further comprises a cytokine.

5. The composition of claim 4, wherein said cytokine is selected from the group consisting of: interleukins (IL)-1 through -25, human B cell-activating factor (BAFF), granulocyte colony-stimulating factor (G-CSF), granulocyte/macrophage colony-stimulating factor (GM-CSF), interferon-alpha, interferon-beta, interferon-gamma, leukemia inhibitory factor (LIF), macrophage Colony stimulating factor (M-CSF), macrophage inhibition factor (MIF), oncostatin M (OSM), stem cell factor (CSF), thrombopoietin (Tpo), transforming growth factor beta (TGF-β) tumor necrosis factor-alpha (TNF-α) and tumor necrosis factor-beta (TNF-β).

6. The composition of claim 4, wherein the cytokine induces CD4+ T helper cells or CD8+ T helper cells.

7. The composition of claim 4, wherein the cytokine is a chicken cytokine.

8. The composition of claim 7, wherein the chicken cytokine is chicken IFN-γ or chicken IL-12.

9. The composition of claim 1, wherein said composition comprises a plurality of promiscuous T-cell epitopes.

10. The composition of claim 1, wherein said antigen comprises SEQ ID NO: 148.

11. The composition of claim 1, wherein said antigen comprises SEQ ID NO: 146.

12. The composition of claim 1, further comprising a membrane protein OmpA1 from *Aeromonas salmonicida*, or a fragment thereof.

13. The composition of claim 12, wherein the membrane protein OmpA1 comprises or consists of a 155 amino acid fragment of a membrane protein OmpA1.

14. The composition of claim 1, wherein the promiscuous epitope is connected to the antigen by a spacer.

15. The composition of claim 1, wherein at least one T-cell epitope is linked to another T-cell epitope by a linker comprising at least one glycine.

16. The composition of claim 1, wherein the composition comprises the promiscuous T-cell, epitope.

17. A method for inducing an immune response in a host, comprising administering the composition of claim 1 to a fish.

18. A composition comprising a DNA molecule encoding a polypeptide, wherein the polypeptide comprises: (i) a truncated VP2 antigen of infectious pancreatic necrosis virus (IPNV) and (ii) optionally encoding a promiscuous T-cell epitope having the amino acid sequence selected from group consisting of SEQ ID NO: 1, 2, 3, 4, 5, 6, 7 or a combination thereof, wherein said DNA molecule encoding the truncated VP2 antigen of IPNV comprises the nucleotide sequence of SEQ ID NO: 145 or SEQ ID NOI: 147.

19. The composition of claim 18, wherein said antigen comprises SEQ ID NO: 148.

20. The composition of claim 18, wherein the DNA molecule further comprises a nucleic acid sequence encoding a linker comprising at least one glycine, wherein the linker joins at least one T-cell epitope to another T-cell epitope.

21. The DNA molecule of claim 18, further encoding a membrane protein OmpA1 from *Aeromonas salmonicida*, or a fragment thereof.

22. The DNA molecule of claim 21, wherein the membrane protein OmpA1 comprises or consists of a 155 amino acid fragment of a membrane protein OmpA1.

23. A method for inducing an immune response comprises administering a composition of claim 18 into a host, wherein said composition comprises the DNA molecule encoding the truncated VP2 antigen of IPNV and the promiscuous T-cell epitope.

24. A method for inducing an immune response comprises administering a composition of claim 18 into a host, wherein said composition comprises the DNA molecule encoding the truncated VP2 antigen of IPNV.

* * * * *

SEQUENCE LISTING

```
<160> NUMBER OF SEQ ID NOS: 181

<210> SEQ ID NO 1
<211> LENGTH: 15
<212> TYPE: PRT
<213> ORGANISM: Morbillivirus measles virus

<400> SEQUENCE: 1

Leu Ser Glu Ile Lys Gly Val Ile Val His Arg Leu Glu Gly Val
 1               5                  10                  15


<210> SEQ ID NO 2
<211> LENGTH: 18
<212> TYPE: PRT
<213> ORGANISM: Clostridium tetani tetanus

<400> SEQUENCE: 2

Val Asp Asp Ala Leu Ile Asn Ser Thr Lys Ile Tyr Ser Tyr Phe Pro
 1               5                  10                  15

Ser Val


<210> SEQ ID NO 3
<211> LENGTH: 15
<212> TYPE: PRT
<213> ORGANISM: Clostridium tetani tetanus

<400> SEQUENCE: 3

Gln Tyr Ile Lys Ala Asn Ser Lys Phe Ile Gly Ile Thr Glu Leu
 1               5                  10                  15


<210> SEQ ID NO 4
<211> LENGTH: 11
<212> TYPE: PRT
<213> ORGANISM: Anaplasma marginale

<400> SEQUENCE: 4

Ser Ser Ala Gly Gly Gln Gln Gln Glu Ser Ser
 1               5                  10


<210> SEQ ID NO 5
<211> LENGTH: 20
```

-continued

<212> TYPE: PRT
<213> ORGANISM: Plasmodium falciparum

<400> SEQUENCE: 5

Glu Asn Asp Ile Glu Lys Lys Ile Cys Lys Met Glu Lys Cys Ser Ser
 1               5                   10                  15

Val Phe Asn Val
            20

<210> SEQ ID NO 6
<211> LENGTH: 18
<212> TYPE: PRT
<213> ORGANISM: Influenzavirus

<400> SEQUENCE: 6

Ser Lys Ala Phe Ser Asn Cys Tyr Pro Tyr Asp Val Pro Asp Tyr Ala
 1               5                   10                  15

Ser Leu

<210> SEQ ID NO 7
<211> LENGTH: 13
<212> TYPE: PRT
<213> ORGANISM: Artificial Sequence
<220> FEATURE:
<221> NAME/KEY: VARIANT
<222> LOCATION: 3
<223> OTHER INFORMATION: Xaa = Any Amino Acid
<220> FEATURE:
<223> OTHER INFORMATION: Synthetically prepared amino acid sequence

<400> SEQUENCE: 7

Ala Lys Xaa Val Ala Ala Trp Thr Leu Lys Ala Ala Ala
 1               5                   10

<210> SEQ ID NO 8
<211> LENGTH: 15
<212> TYPE: PRT
<213> ORGANISM: Artificial Sequence
<220> FEATURE:
<223> OTHER INFORMATION: Synthetically prepared amino acid sequence
<220> FEATURE:
<221> NAME/KEY: VARIANT
<222> LOCATION: 1, 13
<223> OTHER INFORMATION: Xaa =Asp or Glu
<220> FEATURE:
<221> NAME/KEY: VARIANT
<222> LOCATION: 6, 11
<223> OTHER INFORMATION: Xaa =Lys or Arg
<220> FEATURE:
<221> NAME/KEY: VARIANT
<222> LOCATION: 4
<223> OTHER INFORMATION: Xaa =Asp or Gly
<220> FEATURE:
<221> NAME/KEY: VARIANT
<222> LOCATION: 2, 5, 7, 8, 9, 12, 15
<223> OTHER INFORMATION: Xaa = Leu, Ile, Val, or Phe

<400> SEQUENCE: 8

Xaa Xaa Ser Xaa Xaa Xaa Xaa Xaa Xaa His Xaa Xaa Xaa Gly Xaa
 1               5                   10                  15

<210> SEQ ID NO 9
<211> LENGTH: 21
<212> TYPE: PRT
<213> ORGANISM: Clostridium tetani tetanus

<400> SEQUENCE: 9

Phe Asn Asn Phe Thr Val Ser Phe Trp Leu Arg Val Pro Lys Val Ser
 1               5                   10                  15

```
Ala Ser His Leu Glu
            20


<210> SEQ ID NO 10
<211> LENGTH: 20
<212> TYPE: PRT
<213> ORGANISM: Plasmodium falciparum

<400> SEQUENCE: 10

Asp Glu Lys Lys Ile Ala Lys Met Glu Lys Ala Ser Ser Val Phe Asn
 1               5                  10                  15

Val Val Asn Ser
            20


<210> SEQ ID NO 11
<211> LENGTH: 9
<212> TYPE: PRT
<213> ORGANISM: Cytomegalovirus

<400> SEQUENCE: 11

Asn Leu Val Pro Met Val Ala Thr Val
 1               5


<210> SEQ ID NO 12
<211> LENGTH: 4
<212> TYPE: PRT
<213> ORGANISM: Artificial Sequence
<220> FEATURE:
<223> OTHER INFORMATION: Synthetic linker peptide sequence

<400> SEQUENCE: 12

Gly Pro Ser Leu
 1


<210> SEQ ID NO 13
<211> LENGTH: 6
<212> TYPE: PRT
<213> ORGANISM: Artificial Sequence
<220> FEATURE:
<223> OTHER INFORMATION: Synthetic linker peptide sequence

<400> SEQUENCE: 13

Ser Ser Gly Pro Ser Leu
 1               5


<210> SEQ ID NO 14
<211> LENGTH: 8
<212> TYPE: PRT
<213> ORGANISM: Artificial Sequence
<220> FEATURE:
<223> OTHER INFORMATION: Synthetic linker peptide sequence

<400> SEQUENCE: 14

Ser Ser Gly Pro Ser Leu Lys Leu
 1               5


<210> SEQ ID NO 15
<211> LENGTH: 4
<212> TYPE: PRT
<213> ORGANISM: Artificial Sequence
<220> FEATURE:
<223> OTHER INFORMATION: Synthetic linker peptide sequence

<400> SEQUENCE: 15

Gly Leu Pro Gly
 1
```

<210> SEQ ID NO 16
<211> LENGTH: 174
<212> TYPE: DNA
<213> ORGANISM: Artificial Sequence
<220> FEATURE:
<223> OTHER INFORMATION: Synthetic chimeric nucleic acid sequence encoding T-cell epitopes from morbillivirus measles virus, clostridium tetani tetanus toxin, and glycine linkers (GMGT)

<400> SEQUENCE: 16
catatgggyg gyggyggygg yggyggyggy ggyggyctgt ctgaaatcaa aggtgttatc 60
gttcaccgtc tggaaggtgt tggyggyggy ggyggyggyg gyggyggygg ygtggatgat 120
gcgctgatca acagcaccaa aatttacagc tacttcccga gcgtgtaagc tagc 174

<210> SEQ ID NO 17
<211> LENGTH: 22
<212> TYPE: PRT
<213> ORGANISM: Aquabirnavirus infect. pancreatic necrosis virus

<400> SEQUENCE: 17

Ser Asp Phe Met Tyr Gly Ser Tyr His Pro His Cys Ser Phe Arg Pro
1 5 10 15

Glu Thr Leu Asn Asn Gly
20

<210> SEQ ID NO 18
<211> LENGTH: 9
<212> TYPE: PRT
<213> ORGANISM: Coronavirus avian infectious bronchitis virus

<400> SEQUENCE: 18

Val Gly Ser Ser Gly Asn Ala Ser Trp
1 5

<210> SEQ ID NO 19
<211> LENGTH: 9
<212> TYPE: PRT
<213> ORGANISM: Coronavirus avian infectious bronchitis virus

<400> SEQUENCE: 19

Lys Pro Val Pro Asp Ala Trp Tyr Phe
1 5

<210> SEQ ID NO 20
<211> LENGTH: 9
<212> TYPE: PRT
<213> ORGANISM: Coronavirus avian infectious bronchitis virus

<400> SEQUENCE: 20

Arg Arg Ser Gly Ser Glu Asp Asp Leu
1 5

<210> SEQ ID NO 21
<211> LENGTH: 9
<212> TYPE: PRT
<213> ORGANISM: Coronavirus avian infectious bronchitis virus

<400> SEQUENCE: 21

Phe Glu Phe Thr Thr Val Val Pro Arg
1 5

<210> SEQ ID NO 22

<211> LENGTH: 9
<212> TYPE: PRT
<213> ORGANISM: Coronavirus avian infectious bronchitis virus

<400> SEQUENCE: 22

Asp Glu Pro Lys Val Ile Asn Trp Gly
1               5

<210> SEQ ID NO 23
<211> LENGTH: 9
<212> TYPE: PRT
<213> ORGANISM: Coronavirus avian infectious bronchitis virus

<400> SEQUENCE: 23

Phe Asp Gln Tyr Pro Leu Arg Phe Ser
1               5

<210> SEQ ID NO 24
<211> LENGTH: 9
<212> TYPE: PRT
<213> ORGANISM: Coronavirus avian infectious bronchitis virus

<400> SEQUENCE: 24

Phe Glu Gly Ser Gly Val Pro Asp Asn
1               5

<210> SEQ ID NO 25
<211> LENGTH: 9
<212> TYPE: PRT
<213> ORGANISM: Coronavirus avian infectious bronchitis virus

<400> SEQUENCE: 25

Ser Gln Asp Gly Ile Val Trp Val Ala
1               5

<210> SEQ ID NO 26
<211> LENGTH: 12
<212> TYPE: PRT
<213> ORGANISM: Coronavirus avian infectious bronchitis virus

<400> SEQUENCE: 26

Gln Lys Lys Gly Ser Arg Ile Thr Lys Ala Lys Ala
1               5                   10

<210> SEQ ID NO 27
<211> LENGTH: 9
<212> TYPE: PRT
<213> ORGANISM: Coronavirus avian infectious bronchitis virus

<400> SEQUENCE: 27

Phe Ser Asp Gly Gly Pro Asp Gly Asn
1               5

<210> SEQ ID NO 28
<211> LENGTH: 9
<212> TYPE: PRT
<213> ORGANISM: Coronavirus avian infectious bronchitis virus

<400> SEQUENCE: 28

Phe Gln Ala Ile Lys Ala Lys Lys Leu
1               5

<210> SEQ ID NO 29
<211> LENGTH: 9
<212> TYPE: PRT
<213> ORGANISM: Coronavirus avian infectious bronchitis virus

<400> SEQUENCE: 29

Thr Arg Pro Lys Asp Asp Glu Pro Arg
1 5

<210> SEQ ID NO 30
<211> LENGTH: 510
<212> TYPE: DNA
<213> ORGANISM: Eimeria acervulnia

<400> SEQUENCE: 30
atgggtgaag aggctgatac tcaggcgtgg gatacctcag tgaaggaatg gctcgtggat 60
acggggaagg tatacgccgg cggcattgct agcattgcag atgggtgccg cctgtttggc 120
gctgcaatag acaatgggga ggatgcgtgg agtcagttgg tgaagacagg atatcagatt 180
gaagtgcttc aagaggacgg ctcttcaact caagaggact gcgatgaagc ggaaaccctg 240
cggcaagcaa ttgttgacgg ccgtgcccca aacggtgttt atattggagg aattaaatat 300
aaactcgcag aagttaaacg tgatttcacc tataacgacc agaactacga cgtggcgatt 360
ttggggaaga acaagggtgg cggtttcctg attaagactc cgaacgacaa tgtggtgatt 420
gctctttatg acgaggagaa agagcagaac aaagcagatg cgctgacaac ggcacttgcc 480
ttcgctgagt acctgtacca gggcggcttc 510

<210> SEQ ID NO 31
<211> LENGTH: 170
<212> TYPE: PRT
<213> ORGANISM: Eimeria acervulnia

<400> SEQUENCE: 31

Met Gly Glu Glu Ala Asp Thr Gln Ala Trp Asp Thr Ser Val Lys Glu
1 5 10 15

Trp Leu Val Asp Thr Gly Lys Val Tyr Ala Gly Gly Ile Ala Ser Ile
20 25 30

Ala Asp Gly Cys Arg Leu Phe Gly Ala Ala Ile Asp Asn Gly Glu Asp
35 40 45

Ala Trp Ser Gln Leu Val Lys Thr Gly Tyr Gln Ile Glu Val Leu Gln
50 55 60

Glu Asp Gly Ser Ser Thr Gln Glu Asp Cys Asp Glu Ala Glu Thr Leu
65 70 75 80

Arg Gln Ala Ile Val Asp Gly Arg Ala Pro Asn Gly Val Tyr Ile Gly
85 90 95

Gly Ile Lys Tyr Lys Leu Ala Glu Val Lys Arg Asp Phe Thr Tyr Asn
100 105 110

Asp Gln Asn Tyr Asp Val Ala Ile Leu Gly Lys Asn Lys Gly Gly Gly
115 120 125

Phe Leu Ile Lys Thr Pro Asn Asp Asn Val Val Ile Ala Leu Tyr Asp
130 135 140

Glu Glu Lys Glu Gln Asn Lys Ala Asp Ala Leu Thr Thr Ala Leu Ala
145 150 155 160

Phe Ala Glu Tyr Leu Tyr Gln Gly Gly Phe
165 170

<210> SEQ ID NO 32
<211> LENGTH: 1029
<212> TYPE: DNA
<213> ORGANISM: Eimeria acervulnia

<400> SEQUENCE: 32

```
atggctcgag cgttgtcgct ggtcgctttg ggcttgcttt tttcccttcc tccaagctca     60

gccgttagga cgagagtccc aggcgaagat agcttctctc ctgaatctgg cgttctcagt    120

gggacagatg cgccggaacg acgtcccatc gtgcctggac tagttgaagg taactgcggc    180

aggctgacgg ttcgtaacgg cctgagcgtg gatgagacca tcaaagtgac cagcgctgga    240

tggacgaaga gcgaacggga cttcattgtc tcccttgttg ccgacgaaac gcgcaaagtt    300

gttcagctga gagaatcaga aggtgcatcc ggcgccagtg gccctggacc cgcgccagct    360

gaaaagcctc caagtggcca aggaagcgct gaggaggctc ctaaagggga aggtggacag    420

gagaagccgt ctgtaccctt gattgctgtt cgcatccatg gatctggcgg cgacaaaggg    480

gagagcgctc cgcagtcggc tgttctgctt tacggaaatg atgaaagcga gcctacggag    540

gttcccctag aaacagcagc tggaccgacc acgccactca tggtactcat tacgcagcag    600

aacccaaagg aagtggaagt ccgtgttctt gcttggatat ctacggacgc tacaactgga    660

aagggctctt ggaaagaaaa ttccgtggtc gttggcagct ccttgagcgg gcgcgacctt    720

accgtgaact tgagcgactg tggaccaagc tccctcaggg tttatggctc ggcatcagct    780

gaccttgtaa ctgtcaagga gggcatgtgt gaggcagacg acccagagtt gatcgcgctg    840

actcggcctc atacatcggc agcttctccg ctgcctgcag aggaaggaga cgtagcgcag    900

gacgcccagc agagcgcagg agcccagcag gaagcagaag cccaggaggt tggagaaccc    960

cagcaggaag cagttgctgc agagcaagga agcagcgctg cagagagtga cactcaacag   1020

tcatcctga                                                           1029
```

<210> SEQ ID NO 33
<211> LENGTH: 800
<212> TYPE: DNA
<213> ORGANISM: Gallus gallus

<400> SEQUENCE: 33

```
ggcacgagtt tgaataccag catacagata actgggacac tgccatgatg tgcaaagtac     60

tgatctttgg ctgtatttcg gtagcaatgc taatgactac agcttatgga gcatctctat    120

catcagcaaa aaggaaacct cttcaaacat taataaagga tttagaaata ttggaaaata    180

tcaagaacaa gattcatctc gagctctaca caccaactga gacccaggag tgcacccagc    240

aaactctgca gtgttacctg ggagaagtgg ttactctgaa gaaagaaact gaagatgaca    300

ctgaaattaa agaagaattt gtaactgcta ttcaaaatat cgaaaagaac ctcaagagtc    360

ttacgggtct aaatcacacc ggaagtgaat gcaagatctg tgaagctaac aacaagaaaa    420

aatttcctga ttttctccat gaactgacca actttgtgag atatctgcaa aaataagcaa    480

ctaatcattt ttattttact gctatgttat ttatttaatt atttaattac agataattta    540

tatattttat cccgtggcta actaatctgc tgtccattct gggaccactg tatgctctta    600

gtctgggtga tatgacgtct gttctaagat catatttgat cctttctgta agccctacgg    660

gctcaaaatg tacgttggaa aactgattga ttctcacttt gtcggtaaag tgatatgtgt    720

ttactgaaag aatttttaaa agtcacttct agatgacatt taataaattt cagtaatata    780

tgaaaaaaaa aaaaaaaaaa                                                800
```

<210> SEQ ID NO 34
<211> LENGTH: 840
<212> TYPE: DNA
<213> ORGANISM: Gallus gallus
<220> FEATURE:
<221> NAME/KEY: misc_feature -continued
<222> LOCATION: 828
<223> OTHER INFORMATION: n = A,T,C or G

<400> SEQUENCE: 34

```
tgaccagtgc aaatttatcg tagttccgta ccaacttgtc cataggtttc cgaggcttgt     60
accgcaatgt atattcccga tccagattct gttcttctgt tctgagtgat gttacagtta    120
acaagatgct ggggatggca cagccaacac aaaactctgc cggagcacgg agaaggccgg    180
agagtcagaa aacacatgtg aaaagtattt gtctccagta ccaactgtat ctacttttga    240
acagccattt cttttgcctt ttaaagaata agactggact aaccatcttc ttcctatgtg    300
cttatgtacc aaagacagaa gcaaatcact gtaagtggtc agacgttctg aaagatttgg    360
agctgatcaa gacatctgaa gacattgatg tcagtttata tactgcaaac acatacgagg    420
atatagaatg ccaggaacct gtaatgagat gttttttttt agagatgaaa gtgattcttc    480
acgaatgtga tatcaaaaaa tgtagtagga agcatgatgt acggaacata tggaaaaatg    540
gaaatgcaag atttgcaact taccagttga attccacaac agcaaaaaaa tgcaaagaat    600
gtgaagagta tgaagaaaaa aattttacag aatttataca gagttttgta aaggttatac    660
agagggaatg caaaaaatac gctaactaaa atacgcaagc tgggaacagt gacttttcaa    720
gaaacatacc tcagataaat tagattgtca ataacattga actaaaaaga acttcacttc    780
tagtcctatt tgcacagaat aaaaaaataa agaataataa aatctccnaa aaaaaaaaaa    840
```

<210> SEQ ID NO 35
<211> LENGTH: 1330
<212> TYPE: DNA
<213> ORGANISM: Gallus gallus

<400> SEQUENCE: 35

```
cggcacgaga gaagacataa ctattagaag ctgaagctca ctgagcttat atctgacatc     60
tcccagaagc tatctgagca tttgaactga gccatcacca agaagatgac ttgccagact    120
tacaacttgt ttgttctgtc tgtcatcatg atttattatg gacatactgc aagtagtcta    180
aatcttgttc aacttcaaga tgatatagac aaactgaaag ctgactttaa ctcaagtcat    240
tcagatgtag ctgacggtgg acctattatt gtagagaaac tgaagaactg gacagagaga    300
aatgagaaaa ggatcatact gagccagatt gtttcgatgt acttggaaat gcttgaaaac    360
actgacaagt caaagccgca catcaaacac atatctgagg agctctatac tctgaaaaac    420
aaccttcctg atggcgtgaa gaaggtgaaa gatatcatgg acctggccaa gctcccgatg    480
aacgacttga gaatccagcg caaagccgcg aatgaactct tcagcatctt acagaagctg    540
gtggatcctc cgagtttcaa aaggaaaagg agccagtctc agaggagatg caattgctaa    600
tggcatctta tgacctcctg tgctcaacta ttttaaattt tacaatgcac aatttttatg    660
ttttgatttt ttaactgagt ttttatacat ttatttatta atatttaagt attttaaata    720
attatttata ttaaaaaaaa aaccaggcaa acaatgaaag tatttatacc tcctactgct    780
gtgtaagaaa cgattttgtc ttaaaatact gtctatctgt tgtatgtttg ttgacctgaa    840
aataccgaat gaggtgatgt ttaccgagtt tctgtgtgga aatactgaat tgacgttgat    900
actgtactca ggaaaaccca ctcatacctg ctcagctcta agcatatcta aatccaaatc    960
aaggaagtag acttgcttta aggtgagaaa atgctgaagc acttttctga actgggatct   1020
gagagattta ttactgatag ttattgttat gcactgaagc aactgagagg ccaggcaact   1080
tggcagctcc aggaaatgtg acactctatt gcactgactt aacttcaact catttactat   1140
gaacgtctct gtacttcttt gtattgaatc atctaagtgt gtctgacatc agtttattta   1200
```

tttggaagta gcagtatgga agattttatc ttaaggactg tatttttgta cttgaatatt 1260
atttaaaact ttggatttta caatgaaggt ttcttaaaat ttggatatga aataaagaaa 1320
agaataaatt 1330

<210> SEQ ID NO 36
<211> LENGTH: 375
<212> TYPE: DNA
<213> ORGANISM: Vibrio cholerae

<400> SEQUENCE: 36
atgattaaat taaaatttgg tgtttttttt acagttttac tatcttcagc atatgcacat 60
ggaacacctc aaaatattac tgatttgtgt gcagaatacc acaacacaca aatacatacg 120
ctaaatgata agatattttc gtatacagaa tctctagctg gaaaaagaga gatggctatc 180
attactttta agaatggtgc aacttttcaa gtagaagtac caggtagtca acatatagat 240
tcacaaaaaa aagcgattga aaggatgaag gataccctga ggattgcata tcttactgaa 300
gctaaagtcg aaaagttatg tgtatggaat aataaaacgc ctcatgcgat tgccgcaatt 360
agtatggcaa attaa 375

<210> SEQ ID NO 37
<211> LENGTH: 712
<212> TYPE: PRT
<213> ORGANISM: Eimeria tenella

<400> SEQUENCE: 37

Met Glu Asn Lys Glu Thr Phe Ala Phe Asn Ala Asp Ile Gln Gln Leu
1 5 10 15

Met Ser Leu Ile Ile Asn Thr Phe Tyr Ser Asn Lys Glu Ile Phe Leu
20 25 30

Arg Glu Leu Ile Ser Asn Ala Ser Asp Ala Leu Asp Lys Ile Arg Tyr
35 40 45

Glu Ala Ile Thr Asp Pro Glu Lys Leu Lys Thr Lys Pro Glu Leu Phe
50 55 60

Ile Arg Leu Ile Pro Asp Lys Ala Asn Asn Thr Leu Thr Ile Glu Asp
65 70 75 80

Ser Gly Ile Gly Met Thr Lys Ala Glu Leu Val Asn Asn Leu Gly Thr
85 90 95

Ile Ala Arg Ser Gly Thr Lys Ala Phe Met Glu Ala Leu Gln Ala Gly
100 105 110

Gly Asp Ile Ser Met Ile Gly Gln Phe Gly Val Gly Phe Tyr Ser Ala
115 120 125

Tyr Leu Val Ala Asp Ser Val Thr Val Val Ser Lys His Asn Asp Asp
130 135 140

Glu Gln Tyr Val Trp Glu Ser Ala Ala Gly Gly Ser Phe Thr Val Gln
145 150 155 160

Lys Asp Asp Lys Tyr Glu Pro Leu Gly Arg Gly Thr Arg Ile Ile Leu
165 170 175

His Leu Lys Glu Asp Gln Gly Glu Tyr Leu Glu Glu Arg Arg Leu Lys
180 185 190

Asp Leu Val Lys Lys His Ser Glu Phe Ile Ser Phe Pro Ile Glu Leu
195 200 205

Ala Val Glu Lys Thr His Glu Arg Glu Val Thr Glu Ser Glu Glu Glu
210 215 220

Glu Lys Lys Ala Asp Glu Lys Ala Glu Glu Lys Glu Gly Glu Lys Ala

-continued

```
225                 230                 235                 240

Glu Glu Gly Glu Glu Lys Lys Glu Gly Glu Glu Glu Lys Lys Glu Lys
                245                 250                 255

Thr Lys Lys Thr Lys Lys Val Lys Glu Val Thr Arg Glu Trp Glu Gln
            260                 265                 270

Leu Asn Lys Gln Lys Pro Leu Trp Met Arg Lys Pro Glu Glu Val Thr
        275                 280                 285

Glu Glu Glu Tyr Ala Ser Phe Tyr Lys Ser Leu Ser Asn Asp Trp Glu
    290                 295                 300

Glu His Leu Ala Val Lys His Phe Ser Val Glu Gly Gln Leu Glu Phe
305                 310                 315                 320

Lys Ala Leu Leu Phe Val Pro Lys Arg Ala Pro Phe Asp Leu Phe Glu
                325                 330                 335

Thr Arg Lys Lys Arg Asn Asn Ile Lys Leu Tyr Val Arg Arg Val Phe
            340                 345                 350

Ile Met Asp Asp Cys Glu Asp Ile Ile Pro Glu Trp Leu Asn Phe Val
        355                 360                 365

Lys Gly Val Val Asp Ser Glu Asp Leu Pro Leu Asn Ile Ser Arg Glu
    370                 375                 380

Ser Leu Gln Gln Asn Lys Ile Leu Lys Val Ile Arg Lys Asn Leu Val
385                 390                 395                 400

Lys Lys Cys Leu Glu Met Phe Ala Glu Ile Glu Glu Lys Lys Glu Asn
                405                 410                 415

Tyr Thr Lys Phe Tyr Glu Gln Phe Ser Lys Asn Leu Lys Leu Gly Ile
            420                 425                 430

His Glu Asp Ser Ala Asn Arg Ala Lys Ile Ala Glu Leu Leu Arg Phe
        435                 440                 445

His Ser Ser Lys Ser Gly Glu Asp Met Val Ser Phe Lys Glu Tyr Val
    450                 455                 460

Asp Arg Met Lys Glu Gly Gln Lys Asp Ile Tyr Tyr Ile Thr Gly Glu
465                 470                 475                 480

Ser Arg Gln Thr Val Ala Asn Ser Pro Phe Leu Glu Lys Leu Thr Lys
                485                 490                 495

Lys Gly Tyr Glu Val Leu Tyr Met Thr Asp Pro Ile Asp Glu Tyr Ala
            500                 505                 510

Val Gln Gln Leu Lys Glu Phe Asp Asn His Lys Leu Arg Cys Cys Thr
        515                 520                 525

Lys Glu Gly Leu Glu Ile Asp Glu Thr Glu Glu Glu Lys Lys Lys Phe
    530                 535                 540

Glu Glu Leu Lys Ala Glu Phe Glu Pro Leu Leu Lys Leu Ile Lys Glu
545                 550                 555                 560

Val Leu His Asp Lys Val Asp Lys Val Val Leu Ser Asn Arg Ile Thr
                565                 570                 575

Asp Ser Pro Cys Val Leu Val Thr Thr Glu Phe Gly Trp Ser Ala Asn
            580                 585                 590

Met Glu Arg Ile Met Lys Ala Gln Ala Leu Arg Asp Asn Ser Met Thr
        595                 600                 605

Ser Tyr Met Val Ser Lys Lys Thr Met Glu Val Asn Gly His His Ser
    610                 615                 620

Ile Met Val Glu Ile Lys Asn Lys Ala Ala Val Asp Lys Ser Asp Lys
625                 630                 635                 640

Thr Val Lys Asp Leu Ile Trp Leu Leu Tyr Asp Thr Ala Leu Leu Thr
                645                 650                 655
```

-continued

```
Ser Gly Phe Ser Leu Glu Glu Pro Thr Gln Phe Ala Ala Arg Ile His
            660                 665                 670

Arg Met Ile Lys Leu Gly Leu Ser Ile Asp Asp Asp Glu Glu Ala Lys
        675                 680                 685

Glu Asp Asp Leu Pro Pro Leu Glu Glu Val Glu Gly Ala Ala Asp Glu
    690                 695                 700

Ala Ser Lys Met Glu Glu Val Asp
705                 710


<210> SEQ ID NO 38
<211> LENGTH: 70
<212> TYPE: PRT
<213> ORGANISM: Eimeria tenella

<400> SEQUENCE: 38

Leu Glu Glu Arg Arg Leu Lys Asp Leu Val Lys Lys His Ser Glu Phe
 1               5                  10                  15

Ile Ser Phe Pro Ile Glu Leu Ala Val Glu Lys Thr His Glu Arg Glu
            20                  25                  30

Val Thr Glu Ser Glu Glu Glu Glu Lys Lys Ala Asp Glu Lys Ala Glu
        35                  40                  45

Glu Lys Glu Gly Glu Lys Ala Glu Glu Gly Glu Glu Lys Lys Glu Gly
    50                  55                  60

Glu Glu Glu Lys Lys Glu
65                  70


<210> SEQ ID NO 39
<211> LENGTH: 84
<212> TYPE: PRT
<213> ORGANISM: Eimeria maxima

<400> SEQUENCE: 39

Ile Leu His Leu Lys Glu Asp Gln Gly Glu Tyr Leu Glu Glu Arg Arg
 1               5                  10                  15

Leu Lys Asp Leu Val Lys Lys His Ser Glu Phe Ile Ser Phe Pro Ile
            20                  25                  30

Glu Leu Ala Val Glu Lys Thr His Glu Arg Glu Val Thr Glu Ser Glu
        35                  40                  45

Asp Glu Glu Glu Lys Glu Ala Asp Glu Lys Ala Glu Glu Lys Lys Glu
    50                  55                  60

Gly Glu Lys Glu Gly Glu Glu Ala Glu Glu Lys Lys Glu Gly Glu Glu
65                  70                  75                  80

Glu Lys Lys Glu


<210> SEQ ID NO 40
<211> LENGTH: 255
<212> TYPE: DNA
<213> ORGANISM: Eimeria maxima

<400> SEQUENCE: 40

attttgcacc ttaaagaaga ccaggggaa tatctggaag aacgccgtct caaagatctg      60

gttaaaaagc atagcgaatt catcagcttt ccgattgagt tagcggtgga aaaaacgcat    120

gagcgcgagg tcaccgaaag cgaagatgag gaagagaagg aagcagatga gaaggctgag    180

gaaaaaaaag agggcgaaaa agagggcgaa gaagccgaag aaaaaaaaga aggtgaggaa    240

gaaaagaaag aatag                                                     255


<210> SEQ ID NO 41
```

-continued

<211> LENGTH: 2811
<212> TYPE: DNA
<213> ORGANISM: Aquabirnavirus infect. pancreatic necrosis virus

<400> SEQUENCE: 41

```
atgaacacaa acaaggcaac cgcaacttac ttgaaatcca ttatgcttcc agagactgga      60

ccagcaagca tcccggacga cataacggag agacacatct taaaacaaga gacctcgtca     120

tacaacttag aggtctccga ctcaggaagt ggcattcttg tttgtttccc tggggcacca     180

ggctcacgga tcggcgcaca ctacagatgg aatgcgaacc agacggggct ggagttcgac     240

cagtggctgg agacgtcgca ggacctgaag aaagccttca actacgggag gctgatctca     300

aggaaatacg acattcaaag ctccacacta ccggccggtc tctatgctct gaacgggacg     360

ctcaacgccg ccaccttcga aggcagtctg tctgaggtgg agagcctgac ctacaacagc     420

ctgatgtccc taacaacgaa cccccaggac aaagtcaaca accagctggt gaccaaagga     480

gtcacagtcc tgaatctacc aacagggttc gacaagccat acgtccgcct agaggacgag     540

acaccccagg gtctccagtc aatgaacggg gccaagatga ggtgcacagc tgcaattgca     600

ccacggaggt acgagatcga cctcccatcc caacgcctac cccccgttcc tgcgacagga     660

gccctcacca ctctctacga gggaaacgcc gacatcgtca actcaacaac agtgacggga     720

gacataaact tcagtctggc agaacaaccc gcaatcgaga ccaagttcga cttccagctg     780

gacttcatgg gccttgacaa tgacgtccca gtggtcacag tggtcagctc cgtgctggcc     840

acaaacgaca actacagagg agtctcagcc aagatgaccc agtccatccc gaccgagaac     900

atcaccaagc cgatcaccag ggtcaagctg tcatacaagc tcaaccaaca gacagcaatc     960

ggcaatgtcg ccaccctggg cacaatgggt ccagcatccg tctccttctc atcggggaac    1020

ggaaacgtcc ccggcgtgct cagaccaatc acactggtgg cctatgagaa gatgacaccg    1080

ctgtccatcc tgaccgtagc tggagtgtcc aactacgagc tgatcccaaa cccagaactc    1140

ctcaagaaca tggtgacacg ctatggcaag tacgaccccg agggtctcaa ctatgccaag    1200

atgatcctgt cccacaggga agagctggac atcaggacag tgtggaggac agaggagtac    1260

aaggagagga ccagagtctt caacgaaatc acggacttct ccagtgacct gcccacgtca    1320

aaggcatggg gctggagaga catagtcaga ggaattcgga aagtcgcagc tcctgtactg    1380

tccacgctgt ttccaatggc agcaccactc ataggaatgg cagaccaatt cattggagat    1440

ctcaccaaga ccaacgcagc aggcggaagg taccactcca tggccgcagg agggcgctac    1500

aaagacgtgc tcgagtcctg ggcaagcgga gggcccgatg gaaaattctc ccgagccctc    1560

aagaacaggc tggagtccgc caactacgag gaagtcgagc ttccaccccc ctcaaaagga    1620

gtcatcgtcc ctgtggtgca cacagtcaag agtgcaccag gcgaggcatt cgggtccctg    1680

gcaatcataa ttccagggga gtaccccgag cttctagatg ccaaccagca ggtcctatcc    1740

cacttcgcaa acgacaccgg gagcgtgtgg ggcataggag aggacatacc cttcgaggga    1800

gacaacatgt gctacactgc actcccactc aaggagatca agagaaacgg gaacatagta    1860

gtcgagaaga tctttgctgg gccaatcatg ggtccctctg ctcaactagg actgtcccta    1920

cttgtgaacg acatcgagga cggagttcca aggatggtat tcaccggcga aatcgccgat    1980

gacgaggaga caatcatacc aatctgcgga gtagacatca aagccatcgc agcccatgaa    2040

caagggctgc cactcatcgg caaccaacca ggagtggacg aggaggtgcg aaacacatcc    2100

ctggccgcgc acctgatcca gaccggaacc ctgcccgtac aacgcgcaaa gggctccaac    2160

aagaggatca agtacctggg agagctgatg gcatcaaatg catccgggat ggacgaggaa    2220
```

-continued

```
ctgcaacgcc tcctgaacgc cacaatggca cgggccaaag aagtccagga cgccgagatc   2280

tacaaacttc tcaagctcat ggcatggacc agaaagaacg acctcaccga ccacatgtac   2340

gagtggtcga aagaggaccc cgatgcacta aagttcggaa agctcatcag cacgccacca   2400

aagcaccctg agaagcccaa aggaccagac caacaccacg cccaagaggc gagagccacc   2460

cgcatatcac tggacgccgt gagagccggg gcggacttcg ccacgccgga gtgggtcgcg   2520

ctgaacaact accgcggccc atctcccggg cagttcaagt actacctgat caccggacga   2580

gaaccagaac caggtgacga gtacgaggac tacataaaac aacccatcgt gaaaccgacc   2640

gatatgaaca aaatcagacg tctagccaac agtgtgtacg gcctcccaca ccaggaacca   2700

gcaccagagg agttctacga tgcagttgca gctgtattcg cacagaacgg aggcagaggt   2760

cccgaccagg accaaatgca agacctcagg gagctagcaa gacagatgaa a            2811
```

<210> SEQ ID NO 42
<211> LENGTH: 402
<212> TYPE: DNA
<213> ORGANISM: Aquabirnavirus infect. pancreatic necrosis virus

<400> SEQUENCE: 42

```
atgcaagatg aacacaaaca aggcaaccgc aacttacttg aaatccatta tgcttccaga     60

gactggacca gcaagcatcc cggacgacat aacggagaga cacatcttaa aacaagagac    120

ctcgtcatac aacttagagg tctccgactc aggaagtggc attcttgttt gtttccctgg    180

ggcaccaggc tcacggatcg gcgcacacta cagatggaat gcgaaccaga cggggctgga    240

gttcgaccag tggctggaga cgtcgcagga cctgaagaaa gccttcaact acgggaggct    300

gatctcaagg aaatacgaca ttcaaagctc cacactaccg gccggtctct atgctctgaa    360

cgggacgctc aacgccgcca ccttcgaagg cagtctgtct ga                       402
```

<210> SEQ ID NO 43
<211> LENGTH: 1359
<212> TYPE: DNA
<213> ORGANISM: Aquabirnavirus infect. pancreatic necrosis virus

<400> SEQUENCE: 43

```
atgaacacaa acaaggcaac cgcaacttac ttgaaatcca ttatgcttcc agagactgga     60

ccagcaagca tcccggacga cataacggag agacacatct taaaacaaga gacctcgtca    120

tacaacttag aggtctccga ctcaggaagt ggcattcttg tttgtttccc tggggcacca    180

ggctcacgga tcggcgcaca ctacagatgg aatgcgaacc agacggggct ggagttcgac    240

cagtggctgg agacgtcgca ggacctgaag aaagccttca actacgggag gctgatctca    300

aggaaatacg acattcaaag ctccacacta ccggccggtc tctatgctct gaacgggacg    360

ctcaacgccg ccaccttcga aggcagtctg tctgaggtgg agagcctgac ctacaacagc    420

ctgatgtccc taacaacgaa cccccaggac aaagtcaaca accagctggt gaccaaagga    480

gtcacagtcc tgaatctacc aacagggttc gacaagccat acgtccgcct agaggacgag    540

acaccccagg gtctccagtc aatgaacggg gccaagatga ggtgcacagc tgcaattgca    600

ccacggaggt acgagatcga cctcccatcc caacgcctac cccccgttcc tgcgacagga    660

gccctcacca ctctctacga gggaaacgcc gacatcgtca actcaacaac agtgacggga    720

gacataaact tcagtctggc agaacaaccc gcaatcgaga ccaagttcga cttccagctg    780

gacttcatgg gccttgacaa tgacgtccca gtggtcacag tggtcagctc cgtgctggcc    840

acaaacgaca actacagagg agtctcagcc aagatgaccc agtccatccc gaccgagaac    900
```

-continued atcaccaagc cgatcaccag ggtcaagctg tcatacaagc tcaaccaaca gacagcaatc 960
ggcaatgtcg ccaccctggg cacaatgggt ccagcatccg tctccttctc atcggggaac 1020
ggaaacgtcc ccggcgtgct cagaccaatc acactggtgg cctatgagaa gatgacaccg 1080
ctgtccatcc tgaccgtagc tggagtgtcc aactacgagc tgatcccaaa cccagaactc 1140
ctcaagaaca tggtgacacg ctatggcaag tacgaccccg agggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgg 1359

<210> SEQ ID NO 44
<211> LENGTH: 756
<212> TYPE: DNA
<213> ORGANISM: Aquabirnavirus infect. pancreatic necrosis virus

<400> SEQUENCE: 44
gtcgcagctc ctgtactgtc cacgctgttt ccaatggcag caccactcat aggaatggca 60
gaccaattca ttggagatct caccaagacc aacgcagcag gcggaaggta ccactccatg 120
gccgcaggag ggcgctacaa agacgtgctc gagtcctggg caagcggagg gcccgatgga 180
aaattctccc gagccctcaa gaacaggctg gagtccgcca actacgagga agtcgagctt 240
ccacccccct caaaaggagt catcgtccct gtggtgcaca cagtcaagag tgcaccaggc 300
gaggcattcg ggtccctggc aatcataatt ccaggggagt accccgagct tctagatgcc 360
aaccagcagg tcctatccca cttcgcaaac gacaccggga gcgtgtgggg cataggagag 420
gacataccct tcgagggaga caacatgtgc tacactgcac tcccactcaa ggagatcaag 480
agaaacggga acatagtagt cgagaagatc tttgctgggc caatcatggg tccctctgct 540
caactaggac tgtccctact tgtgaacgac atcgaggacg gagttccaag gatggtattc 600
accggcgaaa tcgccgatga cgaggagaca atcataccaa tctgcggagt agacatcaaa 660
gccatcgcag cccatgaaca agggctgcca ctcatcggca accaaccagg agtggacgag 720
gaggtgcgaa acacatccct ggccgcgcac ctgatc 756

<210> SEQ ID NO 45
<211> LENGTH: 645
<212> TYPE: DNA
<213> ORGANISM: Aquabirnavirus infect. pancreatic necrosis virus

<400> SEQUENCE: 45
atcaagtacc tgggagagct gatggcatca aatgcatccg ggatggacga ggaactgcaa 60
cgcctcctga acgccacaat ggcacgggcc aaagaagtcc aggacgccga gatctacaaa 120
cttctcaagc tcatggcatg gaccagaaag aacgacctca ccgaccacat gtacgagtgg 180
tcgaaagagg accccgatgc actaaagttc ggaaagctca tcagcacgcc accaaagcac 240
cctgagaagc ccaaaggacc agaccaacac cacgcccaag aggcgagagc cacccgcata 300
tcactggacg ccgtgagagc cggggcggac ttcgccacgc cggagtgggt cgcgctgaac 360
aactaccgcg gcccatctcc cgggcagttc aagtactacc tgatcaccgg acgagaacca 420
gaaccaggtg acgagtacga ggactacata aaacaaccca tcgtgaaacc gaccgatatg 480
aacaaaatca gacgtctagc caacagtgtg tacggcctcc cacaccagga accagcacca 540
gaggagttct acgatgcagt tgcagctgta ttcgcacaga acggaggcag aggtcccgac 600
caggaccaaa tgcaagacct cagggagcta gcaagacaga tgaaa 645

-continued

<210> SEQ ID NO 46
<211> LENGTH: 2811
<212> TYPE: DNA
<213> ORGANISM: Aquabirnavirus infect. pancreatic necrosis virus

<400> SEQUENCE: 46
atgaacacaa acaaggcaac cgcaacttac ttgaaatcca ttatgcttcc agagactgga 60
ccagcaagca tcccggacga cataacggag agacacatct taaaacaaga gacctcgtca 120
tacaacttag aggtctccga atcaggaagt ggcattcttg tttgtttccc tggggcacca 180
ggctcacgga tcggcgcaca ctacagatgg aatgcgaacc agacggggct ggagttcgac 240
cagtggctgg agacgtcgca ggacctgaag aaagccttca actacgggag gctgatctca 300
aggaaatacg acattcaaag ctccacacta ccggccggtc tctatgctct gaacgggacg 360
ctcaacgccg ccaccttcga aggcagtctg tctgaggtgg agagcctgac ctacaacagc 420
ctgatgtccc taacaacgaa cccccaggac aaagtcaaca accagctggt gaccaaagga 480
gtcacagtcc tgaatctacc aacagggttc gacaagccat acgtccgcct agaggacgag 540
acaccccagg gtctccagtc aatgaacggg gccaagatga ggtgcacagc tgcaattgca 600
ccacggaggt acgagatcga cctcccatcc caacgcctac cccccgttcc tgcgacagga 660
gccctcacca ctctctacga gggaaacgcc gacatcgtca actcaacaac agtgacggga 720
gacataaact tcagtctggc agaacaaccc gcagtcgaga ccaagttcga cttccagctg 780
gacttcatgg gccttgacaa tgacgtccca gtggtcacag tggtcagctc cgtgctggcc 840
acaaacgaca actacagagg agtctcagcc aagatgaccc agtccatccc gaccgagaac 900
atcaccaagc cgatcaccag ggtcaagctg tcatacaaga tcaaccaaca gacagcaatc 960
ggcaacgtcg ccaccctggg cacaatgggt ccagcatccg tctccttctc atcggggaac 1020
ggaaacgtcc ccggcgtgct cagaccaatc acactggtgg cctatgagaa gatgacaccg 1080
ctgtccatcc tgaccgtagc tggagtgtcc aactacgagc tgatcccaaa cccagaactc 1140
ctcaagaaca tggtgacacg ctatggcaag tatgaccccg agggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgga aagtcgcagc tcctgtactg 1380
tccacgctgt ttccaatggc agcaccactc ataggaatgg cagaccaatt cattggagat 1440
ctcaccaaga ccaacgcagc aggcggaagg taccactcca tggccgcagg agggcgctac 1500
aaagacgtgc tcgagtcctg ggcaagcgga gggcccgatg gaaaattctc ccgagccctc 1560
aagaacaggc tggagtccgc caactacgag gaagtcgagc ttccaccccc ctcaaaagga 1620
gtcatcgtcc ctgtggtgca cacagtcaag agtgcaccag gcgaggcatt cgggtccctg 1680
gcaatcataa ttccagggga gtaccccgag cttctagatg ccaaccagca ggtcctatcc 1740
cacttcgcaa acgacaccgg gagcgtgtgg ggcataggag aggacatacc cttcgaggga 1800
gacaacatgt gctacactgc actcccactc aaggagatca agagaaacgg gaacatagta 1860
gtcgagaaga tctttgctgg gccaatcatg ggtccctctg ctcaactagg actgtcccta 1920
cttgtgaacg acatcgagga cggagttcca aggatggtat tcaccggcga aatcgccgat 1980
gacgaggaga caatcatacc aatctgcgga gtagacatca aagccatcgc agcccatgaa 2040
caagggctgc cactcatcgg caaccaacca ggagtggacg aggaggtgcg aaacacatcc 2100
ctggccgcgc acctgatcca gaccggaacc ctgcccgtac aacgcgcaaa gggctccaac 2160

-continued

```
aagaggatca agtacctggg agagctgatg gcatcaaatg catccgggat ggacgaggaa   2220

ctgcaacgcc tcctgaatgc cacaatggca cgggccaaag aagtccagga cgccgagatc   2280

tacaaacttc tcaagctcat ggcatggacc agaaagaacg acctcaccga ccacatgtac   2340

gagtggtcga aagaggaccc cgatgcacta aagttcggaa agctcatcag cacgccacca   2400

aagcaccctg agaagcccaa aggaccagac caacaccacg cccaagaggc gagagccacc   2460

cgcatatcac tggacgccgt gagagccggg gcggacttcg ccacgccgga gtgggtcgcg   2520

ctgaacaact accgcggccc atctcccggg cagttcagta ctacctgatc accggacgag   2580

aaccagaacc aggtgacgag tacgaggact acataaaaca acccatcgtg aaaccgaccg   2640

atatgaacaa aatcagacgt ctagccaaca gtgtgtacgg cctcccacac caggaaccag   2700

caccagagga gttctacgat gcagttgcag ctgtattcgc acagaacgga ggcagaggtc   2760

ccgaccagga ccaaatgcaa gacctcaggg agctagcaag acagatgaaa c            2811
```

<210> SEQ ID NO 47
<211> LENGTH: 402
<212> TYPE: DNA
<213> ORGANISM: Aquabirnavirus infect. pancreatic necrosis virus

<400> SEQUENCE: 47

```
atgcaagatg aacacaaaca aggcaaccgc aacttacttg aaatccatta tgcttccaga     60

gactggacca gcaagcatcc cggacgacat aacggagaga cacatcttaa aacaagagac    120

ctcgtcatac aacttagagg tctccgaatc aggaagtggc attcttgttt gtttccctgg    180

ggcaccaggc tcacggatcg gcgcacacta cagatggaat gcgaaccaga cggggctgga    240

gttcgaccag tggctggaga cgtcgcagga cctgaagaaa gccttcaact acgggaggct    300

gatctcaagg aaatacgaca ttcaaagctc cacactaccg gccggtctct atgctctgaa    360

cgggacgctc aacgccgcca ccttcgaagg cagtctgtct ga                       402
```

<210> SEQ ID NO 48
<211> LENGTH: 1359
<212> TYPE: DNA
<213> ORGANISM: Aquabirnavirus infect. pancreatic necrosis virus

<400> SEQUENCE: 48

```
atgaacacaa acaaggcaac cgcaacttac ttgaaatcca ttatgcttcc agagactgga     60

ccagcaagca tcccggacga cataacggag agacacatct taaaacaaga gacctcgtca    120

tacaacttag aggtctccga atcaggaagt ggcattcttg tttgtttccc tggggcacca    180

ggctcacgga tcggcgcaca ctacagatgg aatgcgaacc agacggggct ggagttcgac    240

cagtggctgg agacgtcgca ggacctgaag aaagccttca actacgggag gctgatctca    300

aggaaatacg acattcaaag ctccacacta ccggccggtc tctatgctct gaacgggacg    360

ctcaacgccg ccaccttcga aggcagtctg tctgaggtgg agagcctgac ctacaacagc    420

ctgatgtccc taacaacgaa cccccaggac aaagtcaaca accagctggt gaccaaagga    480

gtcacagtcc tgaatctacc aacagggttc gacaagccat acgtccgcct agaggacgag    540

acaccccagg gtctccagtc aatgaacggg gccaagatga ggtgcacagc tgcaattgca    600

ccacggaggt acgagatcga cctcccatcc caacgcctac cccccgttcc tgcgacagga    660

gccctcacca ctctctacga gggaaacgcc gacatcgtca actcaacaac agtgacggga    720

gacataaact tcagtctggc agaacaaccc gcagtcgaga ccaagttcga cttccagctg    780

gacttcatgg gccttgacaa tgacgtccca gtggtcacag tggtcagctc cgtgctggcc    840
```

acaaacgaca actacagagg agtctcagcc aagatgaccc agtccatccc gaccgagaac 900
atcaccaagc cgatcaccag ggtcaagctg tcatacaaga tcaaccaaca gacagcaatc 960
ggcaacgtcg ccaccctggg cacaatgggt ccagcatccg tctccttctc atcggggaac 1020
ggaaacgtcc ccggcgtgct cagaccaatc acactggtgg cctatgagaa gatgacaccg 1080
ctgtccatcc tgaccgtagc tggagtgtcc aactacgagc tgatcccaaa cccagaactc 1140
ctcaagaaca tggtgacacg ctatggcaag tatgaccccg agggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgg 1359

<210> SEQ ID NO 49
<211> LENGTH: 756
<212> TYPE: DNA
<213> ORGANISM: Aquabirnavirus infect. pancreatic necrosis virus

<400> SEQUENCE: 49
gtcgcagctc ctgtactgtc cacgctgttt ccaatggcag caccactcat aggaatggca 60
gaccaattca ttggagatct caccaagacc aacgcagcag gcggaaggta ccactccatg 120
gccgcaggag ggcgctacaa agacgtgctc gagtcctggg caagcggagg gcccgatgga 180
aaattctccc gagccctcaa gaacaggctg gagtccgcca actacgagga agtcgagctt 240 ccaccccccct caaaaggagt catcgtccct gtggtgcaca cagtcaagag tgcaccaggc 300
gaggcattcg ggtccctggc aatcataatt ccaggggagt accccgagct tctagatgcc 360
aaccagcagg tcctatccca cttcgcaaac gacaccggga gcgtgtgggg cataggagag 420
gacataccct tcgagggaga caacatgtgc tacactgcac tcccactcaa ggagatcaag 480
agaaacggga acatagtagt cgagaagatc tttgctgggc caatcatggg tccctctgct 540
caactaggac tgtccctact tgtgaacgac atcgaggacg gagttccaag gatggtattc 600
accggcgaaa tcgccgatga cgaggagaca atcataccaa tctgcggagt agacatcaaa 660
gccatcgcag cccatgaaca agggctgcca ctcatcggca accaaccagg agtggacgag 720
gaggtgcgaa acacatccct ggccgcgcac ctgatc 756

<210> SEQ ID NO 50
<211> LENGTH: 645
<212> TYPE: DNA
<213> ORGANISM: Aquabirnavirus infect. pancreatic necrosis virus

<400> SEQUENCE: 50
atcaagtacc tgggagagct gatggcatca aatgcatccg ggatggacga ggaactgcaa 60
cgcctcctga atgccacaat ggcacgggcc aaagaagtcc aggacgccga gatctacaaa 120
cttctcaagc tcatggcatg gaccagaaag aacgacctca ccgaccacat gtacgagtgg 180
tcgaaagagg accccgatgc actaaagttc ggaaagctca tcagcacgcc accaaagcac 240
cctgagaagc ccaaaggacc agaccaacac cacgcccaag aggcgagagc cacccgcata 300
tcactggacg ccgtgagagc cggggcggac ttcgccacgc cggagtgggt cgcgctgaac 360
aactaccgcg gcccatctcc cgggcagttc agtactacct gatcaccgga cgagaaccag 420
aaccaggtga cgagtacgag gactacataa aacaacccat cgtgaaaccg accgatatga 480
acaaaatcag acgtctagcc aacagtgtgt acggcctccc acaccaggaa ccagcaccag 540
aggagttcta cgatgcagtt gcagctgtat tcgcacagaa cggaggcaga ggtcccgacc 600

-continued aggaccaaat gcaagacctc agggagctag caagacagat gaaac 645

<210> SEQ ID NO 51
<211> LENGTH: 2811
<212> TYPE: DNA
<213> ORGANISM: Aquabirnavirus infect. pancreatic necrosis virus

<400> SEQUENCE: 51
atgaacacaa acaaggcaac cgcaacttac ttgaaatcca ttatgcttcc agagactgga 60
ccagcaagca tcccggacga cataacggag agacacatct taaaacaaga gacctcgtca 120
tacaacttag aggtctccga atcaggaagt ggcattcttg tttgtttccc tggggcacca 180
ggctcacgga tcggcgcaca ctacagatgg aatgcgaacc agacggggct ggagttcgac 240
cagtggctgg agacgtcgca ggacttgaag aaagccttca actacgggag gctgatctca 300
aggaaatacg acattcaaag ctccacacta ccggccggtc tctatgctct gaacgggacg 360
ctcaacgccg ccaccttcga aggcagtctg tctgaggtgg agagcctgac ctacaacagc 420
ctgatgtccc taacaacgaa cccccaggac aaagtcaaca accagctggt gaccaaagga 480
gtcacagtcc tgaatctacc aacagggttc gacaagccat acgtccgcct agaggacgag 540
acaccccagg gtctccagtc aatgaacggg gccaagatga ggtgcacagc tgcaattgca 600
ccacggaggt acgagatcga cctcccatcc caacgcctac cccccgttcc tgcgacagga 660
gccctcacca ctctctacga gggaaacgcc gacatcgtca actcaacaac agtgacggga 720
gacataaact tcagtctggc agaacaaccc gcagtcgaga ccaagttcga cttccagctg 780
gacttcatgg gccttgacaa tgacgtccca gtggtcacag tggtcagctc cgtgctggct 840
acaaacgaca actacagagg agtctcagcc aagatgaccc agtccatccc gaccgagaac 900
atcaccaagc cgatcaccag ggtcaagctg tcatacaaga tcaaccaaca gacagcaatc 960
ggcaacgtcg ccaccctggg cacaatgggt ccagcatccg tctccttctc atcggggaac 1020
ggaaacgtcc ccggcgtgct cagaccaatc acactggtgg cctatgagaa gatgacaccg 1080
ctgtccatcc tgaccgtagc tggagtgtcc aactacgagc tgatcccaaa cccagaactc 1140
ctcaagaaca tggtgacacg ctatggcaag tatgaccccg agggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgga aagtcgcagc tcctgtactg 1380
tccacgctgt ttccaatggc agcaccactc ataggaatgg cagaccaatt cattggagat 1440
ctcaccaaga ccaacgcagc aggcggaagg taccactcca tggccgcagg agggcgctac 1500
aaagacgtgc tcgagtcctg ggcaagcgga gggcccgatg gaaaattctc ccgagccctc 1560
aagaacaggc tggagtccgc caactacgag gaagtcgagc ttccaccccc ctcaaaagga 1620
gtcatcgtcc ctgtggtgca cacagtcaag agtgcaccag gcgaggcatt cgggtccctg 1680
gcaatcataa ttccagggga gtaccccgag cttctagatg ccaaccagca ggtcctatcc 1740
cacttcgcaa acgacaccgg gagcgtgtgg ggcataggag aggacatacc cttcgaggga 1800
gacaacatgt gctacactgc actcccactc aaggagatca agagaaacgg gaacatagta 1860
gtcgagaaga tctttgctgg gccaatcatg ggtccctctg ctcaactagg actgtcccta 1920
cttgtgaacg acatcgagga cggagttcca aggatggtat tcaccggcga aatcgccgat 1980
gacgaggaga caatcatacc aatctgcgga gtagacatca aagccatcgc agcccatgaa 2040
caagggctgc cactcatcgg caaccaacca ggagtggacg aggaggtgcg aaacacatcc 2100

-continued

```
ctggccgcgc acctgatcca gaccggaacc ctgcccgtac aacgcgcaaa gggctccaac   2160

aagaggatca agtacctggg agagctgatg gcatcaaatg catccgggat ggacgaggaa   2220

ctgcaacgcc tcctgaacgc cacaatggca cgggccaaag aagtccagga cgccgagatc   2280

tacaaacttc tcaagctcat ggcatggacc agaaagaacg acctcaccga ccacatgtac   2340

gagtggtcga aagaggaccc cgatgcacta aagttcggaa agctcatcag cacgccacca   2400

aagcaccctg agaagcccaa aggaccagac caacaccacg cccaagaggc gagagccacc   2460

cgcatatcac tggacgccgt gagagccggg gcggacttcg ccacgccgga gtgggtcgcg   2520

ctgaacaact accgcggccc atctcccggg cagttcaagt actacctgat caccggacga   2580

gaaccagaac caggtgacga gtacgaggac tacataaaac aacccatcgt gaaaccgacc   2640

gatatgaaca aaatcagacg tctagccaac agtgtgtacg gcctcccaca ccaggaacca   2700

gcaccagagg agttctacga tgcagttgca gctgtattcg cacagaacgg aggcagaggt   2760

cccgaccagg accaaatgca agacctcagg gagctagcaa gacagatgaa a            2811
```

<210> SEQ ID NO 52
<211> LENGTH: 402
<212> TYPE: DNA
<213> ORGANISM: Aquabirnavirus infect. pancreatic necrosis virus

<400> SEQUENCE: 52

```
atgcaagatg aacacaaaca aggcaaccgc aacttacttg aaatccatta tgcttccaga     60

gactggacca gcaagcatcc cggacgacat aacggagaga cacatcttaa aacaagagac    120

ctcgtcatac aacttagagg tctccgaatc aggaagtggc attcttgttt gtttccctgg    180

ggcaccaggc tcacggatcg gcgcacacta cagatggaat gcgaaccaga cggggctgga    240

gttcgaccag tggctggaga cgtcgcagga cttgaagaaa gccttcaact acgggaggct    300

gatctcaagg aaatacgaca ttcaaagctc cacactaccg gccggtctct atgctctgaa    360

cgggacgctc aacgccgcca ccttcgaagg cagtctgtct ga                       402
```

<210> SEQ ID NO 53
<211> LENGTH: 1359
<212> TYPE: DNA
<213> ORGANISM: Aquabirnavirus infect. pancreatic necrosis virus

<400> SEQUENCE: 53

```
atgaacacaa acaaggcaac cgcaacttac ttgaaatcca ttatgcttcc agagactgga     60

ccagcaagca tcccggacga cataacggag agacacatct taaaacaaga gacctcgtca    120

tacaacttag aggtctccga atcaggaagt ggcattcttg tttgtttccc tggggcacca    180

ggctcacgga tcggcgcaca ctacagatgg aatgcgaacc agacggggct ggagttcgac    240

cagtggctgg agacgtcgca ggacttgaag aaagccttca actacgggag gctgatctca    300

aggaaatacg acattcaaag ctccacacta ccggccggtc tctatgctct gaacgggacg    360

ctcaacgccg ccaccttcga aggcagtctg tctgaggtgg agagcctgac ctacaacagc    420

ctgatgtccc taacaacgaa cccccaggac aaagtcaaca accagctggt gaccaaagga    480

gtcacagtcc tgaatctacc aacagggttc gacaagccat acgtccgcct agaggacgag    540

acaccccagg gtctccagtc aatgaacggg gccaagatga ggtgcacagc tgcaattgca    600

ccacggaggt acgagatcga cctcccatcc caacgcctac cccccgttcc tgcgacagga    660

gccctcacca ctctctacga gggaaacgcc gacatcgtca actcaacaac agtgacggga    720

gacataaact tcagtctggc agaacaaccc gcagtcgaga ccaagttcga cttccagctg    780
```

-continued gacttcatgg gccttgacaa tgacgtccca gtggtcacag tggtcagctc cgtgctggct 840
acaaacgaca actacagagg agtctcagcc aagatgaccc agtccatccc gaccgagaac 900
atcaccaagc cgatcaccag ggtcaagctg tcatacaaga tcaaccaaca gacagcaatc 960
ggcaacgtcg ccaccctggg cacaatgggt ccagcatccg tctccttctc atcggggaac 1020
ggaaacgtcc ccggcgtgct cagaccaatc acactggtgg cctatgagaa gatgacaccg 1080
ctgtccatcc tgaccgtagc tggagtgtcc aactacgagc tgatcccaaa cccagaactc 1140
ctcaagaaca tggtgacacg ctatggcaag tatgaccccg agggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgg 1359

<210> SEQ ID NO 54
<211> LENGTH: 756
<212> TYPE: DNA
<213> ORGANISM: Aquabirnavirus infect. pancreatic necrosis virus

<400> SEQUENCE: 54
gtcgcagctc ctgtactgtc cacgctgttt ccaatggcag caccactcat aggaatggca 60
gaccaattca ttggagatct caccaagacc aacgcagcag gcggaaggta ccactccatg 120
gccgcaggag ggcgctacaa agacgtgctc gagtcctggg caagcggagg gcccgatgga 180
aaattctccc gagccctcaa gaacaggctg gagtccgcca actacgagga agtcgagctt 240 ccaccccccct caaaaggagt catcgtccct gtggtgcaca cagtcaagag tgcaccaggc 300
gaggcattcg ggtccctggc aatcataatt ccaggggagt accccgagct tctagatgcc 360
aaccagcagg tcctatccca cttcgcaaac gacaccggga gcgtgtgggg cataggagag 420
gacataccct tcgagggaga caacatgtgc tacactgcac tcccactcaa ggagatcaag 480
agaaacggga acatagtagt cgagaagatc tttgctgggc caatcatggg tccctctgct 540
caactaggac tgtccctact tgtgaacgac atcgaggacg gagttccaag gatggtattc 600
accggcgaaa tcgccgatga cgaggagaca atcataccaa tctgcggagt agacatcaaa 660
gccatcgcag cccatgaaca agggctgcca ctcatcggca accaaccagg agtggacgag 720
gaggtgcgaa acacatccct ggccgcgcac ctgatc 756

<210> SEQ ID NO 55
<211> LENGTH: 645
<212> TYPE: DNA
<213> ORGANISM: Aquabirnavirus infect. pancreatic necrosis virus

<400> SEQUENCE: 55
atcaagtacc tgggagagct gatggcatca aatgcatccg ggatggacga ggaactgcaa 60
cgcctcctga acgccacaat ggcacgggcc aaagaagtcc aggacgccga gatctacaaa 120
cttctcaagc tcatggcatg gaccagaaag aacgacctca ccgaccacat gtacgagtgg 180
tcgaaagagg accccgatgc actaaagttc ggaaagctca tcagcacgcc accaaagcac 240
cctgagaagc ccaaaggacc agaccaacac cacgcccaag aggcgagagc cacccgcata 300
tcactggacg ccgtgagagc cggggcggac ttcgccacgc cggagtgggt cgcgctgaac 360
aactaccgcg gcccatctcc cgggcagttc aagtactacc tgatcaccgg acgagaacca 420
gaaccaggtg acgagtacga ggactacata aaacaaccca tcgtgaaacc gaccgatatg 480
aacaaaatca gacgtctagc caacagtgtg tacggcctcc cacaccagga accagcacca 540

-continued gaggagttct acgatgcagt tgcagctgta ttcgcacaga acggaggcag aggtcccgac 600
caggaccaaa tgcaagacct cagggagcta gcaagacaga tgaaa 645

<210> SEQ ID NO 56
<211> LENGTH: 2818
<212> TYPE: DNA
<213> ORGANISM: Aquabirnavirus infect. pancreatic necrosis virus

<400> SEQUENCE: 56
atgcaagatg aacacaaaca aggcaaccgc aacttacctg aaatccatta tgcttccaga 60
gactggacca gcaagcatcc cggacgacat aacggagaga cacatcttaa aacaagagac 120
ctcgtcatac aacttagagg tctccgaatc aggaagtggc attcttgttt gtttccctgg 180
ggcaccaggc tcacggatcg gcgcacacta cagatggaat gcgaaccaga cggggctgga 240
gttcgaccag tggctggaga cgtcgcagga cctgaagaaa gccttcaact acgggaggct 300
gatctcaagg aaatacgaca ttcaaagctc cacactaccg gccggtctct atgctctgaa 360
cgggacgctc aatgccgcca ccttcgaagg cagtctgtct gaggtggaga gcctgaccta 420
caacagcctg atgtccctaa caacgaaccc ccaggacaaa gtcaacaacc agctggtgac 480
caaaggagtc acagtcctga atctaccaac agggttcgac aagccatacg tccgcctaga 540
ggacgagaca ccccagggtc tccagtcaat gaacggggcc aagatgaggt gcacagctgc 600
aattgcacca cggaggtacg agatcgacct cccatcccaa cgcctacccc ccgttcctgc 660
gacaggaacc ctcaccactc tctacgaggg aaacgccgac atcgtcaact caacaacagt 720
gacgggagac ataaacttca gtctggcaga acaacccgca gtcgagacca agttcgactt 780
ccagctggac ttcatgggcc ttgacaatga cgtcccagtg gtcacagtgg tcagctccgt 840
gctggccaca aacgacaact acagaggagt ctcagccaag atgacccagt ccatcccgac 900
cgagaacatc accaagccga tcaccagggt caagctgtca tacaaggtca accaacagac 960
agcaatcggc aatgtcgcca ccctgggcac aatgggtcca gcatccgtct ccttctcatc 1020
ggggaacgga aacgtccccg gcgtgctcag accaatcaca ctggtggcct atgagaagat 1080
gacaccgctg tccatcctga ccgtagctgg agtgtccaac tacgagctga tcccaaaccc 1140
agaactcctc aagaacatgg tgacacgcta tggcaagtac gaccccgagg gtctcaacta 1200
tgccaagatg atcctgtccc acagggaaga gctggacatc aggacagtgt ggaggacaga 1260
ggagtacaag gagaggacca gagtcttcaa cgaaatcacg gacttctcca gtgacctgcc 1320
cacgtcaaag gcatggggct ggagagacat agtcagagga attcggaaag tcgcagctcc 1380
tgtactgtcc acgctgtttc caatggcagc accactcata ggaatggcag accaattcat 1440
tggagatctc accaagacca acgcagcagg cggaaggtac cactccatgg ccgcaggagg 1500
gcgctacaaa gacgtgctcg agtcctgggc aagcggaggg cccgatggaa aattctcccg 1560
agccctcaag aacaggctgg agtccgccaa ctacgaggaa gtcgagcttc cacccccctc 1620
aaaaggagtc atcgtccctg tggtgcacac agtcaagagt gcaccaggcg aggcattcgg 1680
gtccctggca atcataattc caggggagta ccccgagctt ctagatgcca accagcaggt 1740
cctatcccac ttcgcaaacg acaccgggag cgtgtggggc ataggagagg acatacccct 1800
cgagggagac aacatgtgct acactgcact cccactcaag gagatcaaga gaaacgggaa 1860
catagtagtc gagaagatct ttgctgggcc aatcatgggt ccctctgctc aactaggact 1920
gtccctactt gtgaacgaca tcgaggacgg agttccaagg atggtattca ccggcgaaat 1980
cgccgatgac gaggagacaa tcataccaat ctgcggagta gacatcaaag ccatcgcagc 2040

-continued

```
ccatgaacaa gggctgccac tcatcggcaa ccaaccagga gtggacgagg aggtgcgaaa   2100

cacatccctg gccgcgcacc tgatccagac cggaaccctg cccgtacaac gcgcaaaggg   2160

ctccaacaag aggatcaagt acctgggaga gctgatggca tcaaatgcat ccgggatgga   2220

cgaggaactg caacgcctcc tgaacgccac aatggcacgg gccaaagaag tccaggacgc   2280

cgagatctac aaacttctta agctcatggc atggaccaga aagaacgacc tcaccgacca   2340

catgtacgag tggtcgaaag aggaccccga tgcactaaag ttcggaaagc tcatcagcac   2400

gccaccaaag caacctgaga agcccaaagg accagaccaa caccacgccc aagaggcgag   2460

agccacccgc atatcactgg acgccgtgag agccggggcg gacttcgcca cgccggagtg   2520

ggtcgcgctg aacaactacc gcggcccatc tcccgggcag ttcaagtact acctgatcac   2580

cggacgagaa ccagaaccag gtgacgagta cgaggactac ataaaacaac ccatcgtgaa   2640

accgaccgac atgaacaaaa tcagacgtct agccaacagt gtgtacggcc tcccacacca   2700

ggaaccagca ccagaggagt tctacgatgc agttgcagct gtattcgcac agaacggagg   2760

cagaggtccc gaccaggacc aaatgcaaga cctcagggag ctagcaagac agatgaaa     2818
```

```
<210> SEQ ID NO 57
<211> LENGTH: 402
<212> TYPE: DNA
<213> ORGANISM: Aquabirnavirus infect. pancreatic necrosis virus

<400> SEQUENCE: 57

atgcaagatg aacacaaaca aggcaaccgc aacttacctg aaatccatta tgcttccaga     60

gactggacca gcaagcatcc cggacgacat aacggagaga cacatcttaa aacaagagac    120

ctcgtcatac aacttagagg tctccgaatc aggaagtggc attcttgttt gtttccctgg    180

ggcaccaggc tcacggatcg gcgcacacta cagatggaat gcgaaccaga cggggctgga    240

gttcgaccag tggctggaga cgtcgcagga cctgaagaaa gccttcaact acgggaggct    300

gatctcaagg aaatacgaca ttcaaagctc cacactaccg gccggtctct atgctctgaa    360

cgggacgctc aatgccgcca ccttcgaagg cagtctgtct ga                       402
```

```
<210> SEQ ID NO 58
<211> LENGTH: 1359
<212> TYPE: DNA
<213> ORGANISM: Aquabirnavirus infect. pancreatic necrosis virus

<400> SEQUENCE: 58

atgaacacaa acaaggcaac cgcaacttac ctgaaatcca ttatgcttcc agagactgga     60

ccagcaagca tcccggacga cataacggag agacacatct taaaacaaga gacctcgtca    120

tacaacttag aggtctccga atcaggaagt ggcattcttg tttgtttccc tggggcacca    180

ggctcacgga tcggcgcaca ctacagatgg aatgcgaacc agacggggct ggagttcgac    240

cagtggctgg agacgtcgca ggacctgaag aaagccttca actacgggag gctgatctca    300

aggaaatacg acattcaaag ctccacacta ccggccggtc tctatgctct gaacgggacg    360

ctcaatgccg ccaccttcga aggcagtctg tctgaggtgg agagcctgac ctacaacagc    420

ctgatgtccc taacaacgaa cccccaggac aaagtcaaca accagctggt gaccaaagga    480

gtcacagtcc tgaatctacc aacagggttc gacaagccat acgtccgcct agaggacgag    540

acaccccagg gtctccagtc aatgaacggg gccaagatga ggtgcacagc tgcaattgca    600

ccacggaggt acgagatcga cctcccatcc caacgcctac cccccgttcc tgcgacagga    660

accctcacca ctctctacga gggaaacgcc gacatcgtca actcaacaac agtgacggga    720
```

-continued

```
gacataaact tcagtctggc agaacaaccc gcagtcgaga ccaagttcga cttccagctg    780

gacttcatgg gccttgacaa tgacgtccca gtggtcacag tggtcagctc cgtgctggcc    840

acaaacgaca actacagagg agtctcagcc aagatgaccc agtccatccc gaccgagaac    900

atcaccaagc cgatcaccag ggtcaagctg tcatacaagg tcaaccaaca gacagcaatc    960

ggcaatgtcg ccaccctggg cacaatgggt ccagcatccg tctccttctc atcggggaac   1020

ggaaacgtcc ccggcgtgct cagaccaatc acactggtgg cctatgagaa gatgacaccg   1080

ctgtccatcc tgaccgtagc tggagtgtcc aactacgagc tgatcccaaa cccagaactc   1140

ctcaagaaca tggtgacacg ctatggcaag tacgaccccg agggtctcaa ctatgccaag   1200

atgatcctgt cccacaggga agagctggac atcaggacag tgtggaggac agaggagtac   1260

aaggagagga ccagagtctt caacgaaatc acggacttct ccagtgacct gcccacgtca   1320

aaggcatggg gctggagaga catagtcaga ggaattcgg                          1359
```

```
<210> SEQ ID NO 59
<211> LENGTH: 756
<212> TYPE: DNA
<213> ORGANISM: Aquabirnavirus infect. pancreatic necrosis virus

<400> SEQUENCE: 59

gtcgcagctc ctgtactgtc cacgctgttt ccaatggcag caccactcat aggaatggca     60

gaccaattca ttggagatct caccaagacc aacgcagcag gcggaaggta ccactccatg    120

gccgcaggag ggcgctacaa agacgtgctc gagtcctggg caagcggagg gcccgatgga    180

aaattctccc gagccctcaa gaacaggctg gagtccgcca actacgagga agtcgagctt    240

ccaccccccct caaaaggagt catcgtccct gtggtgcaca cagtcaagag tgcaccaggc    300

gaggcattcg ggtccctggc aatcataatt ccaggggagt accccgagct tctagatgcc    360

aaccagcagg tcctatccca cttcgcaaac gacaccggga gcgtgtgggg catagggagag    420

gacataccct tcgagggaga caacatgtgc tacactgcac tcccactcaa ggagatcaag    480

agaaacggga acatagtagt cgagaagatc tttgctgggc caatcatggg tccctctgct    540

caactaggac tgtccctact tgtgaacgac atcgaggacg gagttccaag gatggtattc    600

accggcgaaa tcgccgatga cgaggagaca atcataccaa tctgcggagt agacatcaaa    660

gccatcgcag cccatgaaca agggctgcca ctcatcggca accaaccagg agtggacgag    720

gaggtgcgaa acacatccct ggccgcgcac ctgatc                              756
```

```
<210> SEQ ID NO 60
<211> LENGTH: 645
<212> TYPE: DNA
<213> ORGANISM: Aquabirnavirus infect. pancreatic necrosis virus

<400> SEQUENCE: 60

atcaagtacc tgggagagct gatggcatca aatgcatccg ggatggacga ggaactgcaa     60

cgcctcctga acgccacaat ggcacgggcc aaagaagtcc aggacgccga gatctacaaa    120

cttcttaagc tcatggcatg gaccagaaag aacgacctca ccgaccacat gtacgagtgg    180

tcgaaagagg accccgatgc actaaagttc ggaaagctca tcagcacgcc accaaagcaa    240

cctgagaagc ccaaaggacc agaccaacac cacgcccaag aggcgagagc cacccgcata    300

tcactggacg ccgtgagagc cggggcggac ttcgccacgc cggagtgggt cgcgctgaac    360

aactaccgcg gcccatctcc cgggcagttc aagtactacc tgatcaccgg acgagaacca    420

gaaccaggtg acgagtacga ggactacata aaacaaccca tcgtgaaacc gaccgacatg    480
```

-continued

```
aacaaaatca gacgtctagc caacagtgtg tacggcctcc cacaccagga accagcacca    540

gaggagttct acgatgcagt tgcagctgta ttcgcacaga acggaggcag aggtcccgac    600

caggaccaaa tgcaagacct cagggagcta gcaagacaga tgaaa                    645


<210> SEQ ID NO 61
<211> LENGTH: 2818
<212> TYPE: DNA
<213> ORGANISM: Aquabirnavirus infect. pancreatic necrosis virus

<400> SEQUENCE: 61

atgcaagatg aacacaaaca aggcaaccgc aacttacttg aaatccatta tgcttccaga     60

gactggacca gcaagcatcc cggacgacat aacggagaga cacatcttaa aacaagagac    120

ctcgtcatac aacctagagg tctccgaatc aggaagtggc attcttgttt gtttccctgg    180

ggcaccaggc tcacggatcg gcgcacacta cagatggaat gcgaaccaga cggggctgga    240

gttcgaccag tggctggaga cgtcgcagga cctgaagaaa gccttcaact acgggaggct    300

gatctcaagg aaatacgaca ttcaaagctc cacactaccg gccggtctct atgctctgaa    360

cgggacgctc aacgccgcca ccttcgaagg cagtctgtct gaggtggaga gcctgaccta    420

caacagcctg atgtccctaa caacgaaccc ccaggacaaa gtcaacaacc agctggtgac    480

caaaggagtc acagtcctga atctaccaac agggttcgac aagccatacg tccgcctaga    540

ggacgagaca ccccagggtc tccagtcaat gaatggggcc aagatgaggt gcacagctgc    600

aattgcacca cggaggtacg agatcgacct cccatcccaa cgcctacccc ccgttcctgc    660

gacaggaacc ctcaccactc tctacgaggg aaacgccgac atcgtcaact caacaacagt    720

gacgggagac ataaacttca gtctggcaga acaacccgca gtcgagacca agttcgactt    780

ccagctggac ttcatgggcc ttgacaatga cgtcccagtg gtcacagtgg tcagctccgt    840

gctggccaca aacgacaact acagaggagt ctcagccaag atgacccagt ccatcccgac    900

cgagaacatc accaagccga tcaccagggt caagctgtca tacaaggtca accaacagac    960

agcaatcggc aatgtcgcca ccctgggcac aatgggtcca gcatccgtct ccttctcatc   1020

ggggaacgga aacgtccccg gcgtgctcag accaatcaca ctggtggcct atgagaagat   1080

gacaccgctg tccatcctga ccgtagctgg agtgtccaac tacgagctga tcccaaaccc   1140

agaactcctc aagaacatgg tgacacgcta tggcaagtac gaccccgagg gtctcaacta   1200

tgccaagatg atcctgtccc acagggaaga gctggacatc aggacagtgt ggaggacaga   1260

ggagtacaag gagaggacca gagtcttcaa cgaaatcacg gacttctcca gtgacctgcc   1320

cacgtcaaag gcatggggct ggagagacat agtcagagga attcggaaag tcgcagctcc   1380

tgtactgtcc acgctgtttc caatggcagc accactcata ggaatggcag accaattcat   1440

tggagatctc accaagacca acgcagcagg cggaaggtac cactccatgg ccgcaggagg   1500

gcgctacaaa gacgtgctcg agtcctgggc aagcggaggg cccgatggaa aattctcccg   1560

agccctcaag aacaggctgg agtccgccaa ctacgaggaa gtcgagcttc caccccccctc   1620

aaaaggagtc atcgtccctg tggtgcacac agtcaagagt gcaccaggcg aggcattcgg   1680

gtccctggca atcataattc caggggagta ccccgagctt ctagatgcca accagcaggt   1740

cctatcccac ttcgcaaacg acaccgggag cgtgtggggc ataggagagg acatacccctt   1800

cgagggagac aacatgtgct acactgcact cccactcaag gagatcaaga gaaacgggaa   1860

catagtagtc gagaagatct ttgctgggcc aatcatgggt ccctctgctc aactaggact   1920

gtccctactt gtgaacgaca tcgaggacgg agttccaagg atggtattca ccggcgaaat   1980
```

-continued

```
cgccgatgac gaggagacaa tcataccaat ctgcggagta gacatcaaag ccatcgcagc   2040

ccatgaacaa gggctgccac tcatcggcaa ccaaccagga gtggacgagg aggtgcgaaa   2100

cacatccctg gccgcgcacc tgatccagac cggaaccctg cccgtacaac gcgcaaaggg   2160

ctccaacaag aggatcaagt acctgggaga gctgatggca tcaaatgcat ccgggatgga   2220

cgaggaactg caacgcctcc tgaacgccac aatggcacgg gccaaagaag tccaggacgc   2280

cgagatctac aaacttctta agctcatggc atggaccaga aagaacgacc tcaccgacca   2340

catgtacgag tggtcgaaag aggaccccga tgcactaaag ttcggaaagc tcatcagcac   2400

gccaccaaag caccccgaga agcccaaagg accagaccaa caccacgccc aagaggcgag   2460

agccacccgc atatcactgg acgccgtgag agccggggcg gacttcgcca cgccggagtg   2520

ggtcgcgctg aacaactacc gcggcccatc tcccgggcag ttcaagtact acctgatcac   2580

cggacgagaa ccagaaccag gtgacgagta cgaggactac ataaaacaac ccatcgtgaa   2640

accgaccgac atgaacaaaa tcagacgtct agccaacagt gtgtacggcc tcccacacca   2700

ggaaccagca ccagaggagt tctacgatgc agttgcagct gtattcgcac agaacggagg   2760

cagaggtccc gaccaggacc aaatgcaaga cctcagggag ctagcaagac agatgaaa     2818
```

```
<210> SEQ ID NO 62
<211> LENGTH: 402
<212> TYPE: DNA
<213> ORGANISM: Aquabirnavirus infect. pancreatic necrosis virus

<400> SEQUENCE: 62

atgcaagatg aacacaaaca aggcaaccgc aacttacttg aaatccatta tgcttccaga     60

gactggacca gcaagcatcc cggacgacat aacggagaga cacatcttaa aacaagagac    120

ctcgtcatac aacctagagg tctccgaatc aggaagtggc attcttgttt gtttccctgg    180

ggcaccaggc tcacggatcg gcgcacacta cagatggaat gcgaaccaga cggggctgga    240

gttcgaccag tggctggaga cgtcgcagga cctgaagaaa gccttcaact acgggaggct    300

gatctcaagg aaatacgaca ttcaaagctc cacactaccg gccggtctct atgctctgaa    360

cgggacgctc aacgccgcca ccttcgaagg cagtctgtct ga                       402
```

```
<210> SEQ ID NO 63
<211> LENGTH: 1359
<212> TYPE: DNA
<213> ORGANISM: Aquabirnavirus infect. pancreatic necrosis virus

<400> SEQUENCE: 63

atgaacacaa acaaggcaac cgcaacttac ttgaaatcca ttatgcttcc agagactgga     60

ccagcaagca tcccggacga cataacggag agacacatct taaaacaaga gacctcgtca    120

tacaacctag aggtctccga atcaggaagt ggcattcttg tttgtttccc tggggcacca    180

ggctcacgga tcggcgcaca ctacagatgg aatgcgaacc agacggggct ggagttcgac    240

cagtggctgg agacgtcgca ggacctgaag aaagccttca actacgggag gctgatctca    300

aggaaatacg acattcaaag ctccacacta ccggccggtc tctatgctct gaacgggacg    360

ctcaacgccg ccaccttcga aggcagtctg tctgaggtgg agagcctgac ctacaacagc    420

ctgatgtccc taacaacgaa cccccaggac aaagtcaaca accagctggt gaccaaagga    480

gtcacagtcc tgaatctacc aacagggttc gacaagccat acgtccgcct agaggacgag    540

acaccccagg gtctccagtc aatgaatggg gccaagatga ggtgcacagc tgcaattgca    600

ccacggaggt acgagatcga cctcccatcc caacgcctac cccccgttcc tgcgacagga    660
```

```
acccteacca ctctctacga gggaaacgcc gacatcgtca actcaacaac agtgacggga    720

gacataaact tcagtctggc agaacaaccc gcagtcgaga ccaagttcga cttccagctg    780

gacttcatgg gccttgacaa tgacgtccca gtggtcacag tggtcagctc cgtgctggcc    840

acaaacgaca actacagagg agtctcagcc aagatgaccc agtccatccc gaccgagaac    900

atcaccaagc cgatcaccag ggtcaagctg tcatacaagg tcaaccaaca gacagcaatc    960

ggcaatgtcg ccaccctggg cacaatgggt ccagcatccg tctccttctc atcggggaac   1020

ggaaacgtcc ccggcgtgct cagaccaatc acactggtgg cctatgagaa gatgacaccg   1080

ctgtccatcc tgaccgtagc tggagtgtcc aactacgagc tgatcccaaa cccagaactc   1140

ctcaagaaca tggtgacacg ctatggcaag tacgaccccg agggtctcaa ctatgccaag   1200

atgatcctgt cccacaggga agagctggac atcaggacag tgtggaggac agaggagtac   1260

aaggagagga ccagagtctt caacgaaatc acggacttct ccagtgacct gcccacgtca   1320

aaggcatggg gctggagaga catagtcaga ggaattcgg                          1359
```

<210> SEQ ID NO 64
<211> LENGTH: 756
<212> TYPE: DNA
<213> ORGANISM: Aquabirnavirus infect. pancreatic necrosis virus

<400> SEQUENCE: 64

```
gtcgcagctc ctgtactgtc cacgctgttt ccaatggcag caccactcat aggaatggca     60

gaccaattca ttggagatct caccaagacc aacgcagcag gcggaaggta ccactccatg    120

gccgcaggag ggcgctacaa agacgtgctc gagtcctggg caagcggagg gcccgatgga    180

aaattctccc gagccctcaa gaacaggctg gagtccgcca actacgagga agtcgagctt    240

ccacccccct caaaaggagt catcgtccct gtggtgcaca cagtcaagag tgcaccaggc    300

gaggcattcg ggtccctggc aatcataatt ccaggggagt accccgagct tctagatgcc    360

aaccagcagg tcctatccca cttcgcaaac gacaccggga gcgtgtgggg cataggagag    420

gacataccct tcgagggaga caacatgtgc tacactgcac tcccactcaa ggagatcaag    480

agaaacggga acatagtagt cgagaagatc tttgctgggc caatcatggg tccctctgct    540

caactaggac tgtccctact tgtgaacgac atcgaggacg gagttccaag gatggtattc    600

accggcgaaa tcgccgatga cgaggagaca atcataccaa tctgcggagt agacatcaaa    660

gccatcgcag cccatgaaca agggctgcca ctcatcggca accaaccagg agtggacgag    720

gaggtgcgaa acacatccct ggccgcgcac ctgatc                             756
```

<210> SEQ ID NO 65
<211> LENGTH: 645
<212> TYPE: DNA
<213> ORGANISM: Aquabirnavirus infect. pancreatic necrosis virus

<400> SEQUENCE: 65

```
atcaagtacc tgggagagct gatggcatca aatgcatccg ggatggacga ggaactgcaa     60

cgcctcctga acgccacaat ggcacgggcc aaagaagtcc aggacgccga gatctacaaa    120

cttcttaagc tcatggcatg gaccagaaag aacgacctca ccgaccacat gtacgagtgg    180

tcgaaagagg accccgatgc actaaagttc ggaaagctca tcagcacgcc accaaagcac    240

cccgagaagc ccaaaggacc agaccaacac cacgcccaag aggcgagagc cacccgcata    300

tcactggacg ccgtgagagc cggggcggac ttcgccacgc cggagtgggt cgcgctgaac    360

aactaccgcg gcccatctcc cgggcagttc aagtactacc tgatcaccgg acgagaacca    420
```

```
gaaccaggtg acgagtacga ggactacata aaacaaccca tcgtgaaacc gaccgacatg    480

aacaaaatca gacgtctagc caacagtgtg tacggcctcc cacaccagga accagcacca    540

gaggagttct acgatgcagt tgcagctgta ttcgcacaga acggaggcag aggtcccgac    600

caggaccaaa tgcaagacct cagggagcta gcaagacaga tgaaa                    645
```

<210> SEQ ID NO 66
<211> LENGTH: 2819
<212> TYPE: DNA
<213> ORGANISM: Aquabirnavirus infect. pancreatic necrosis virus

<400> SEQUENCE: 66

```
aatgcaagat gaacacaaac aaggcaaccg caacttacct gaaatccatt atgcttccag     60

agactggacc agcaagcatc ccggacgaca taacggagag acacatctta aaacaagaga    120

cctcgtcata caacttagag gtctccgaat caggaagtgg cattcttgtt tgtttccctg    180

gggcaccagg ctcacggatc ggcgcacact acagatggaa tgcgaaccag acggggctgg    240

agttcgacca gtggctggag acgtcgcagg acctgaagaa agccttcaac tacgggaggc    300

tgatctcaag gaaatacgac attcaaagct ccacactacc ggccggtctc tatgctctga    360

acgggacgct caacgccgcc accttcgaag gcagtctgtc tgaggtggag agcctgacct    420

acaacagcct gatgtcccta acaacgaacc cccaggacaa agtcaacaac cagctggtga    480

ccaaaggagt cacagtcctg aatctaccaa cagggttcga caagccatac gtccgcctag    540

aggacgagac accccagggt ctccagtcaa tgaacggggc caagatgagg tgcacagctg    600

caattgcacc acggaggtac gagatcgacc tcccatccca acgcctaccc cccgttcctg    660

cgacaggagc cctcaccact ctctacgagg gaaacgccga catcgtcaac tcaacaacag    720

tgacgggaga cataaacttc agtctggcag aacaacccgc agtcgagacc aagttcgact    780

tccagctgga cttcatgggc cttgacaatg acgtcccagt ggtcacagtg gtcagctccg    840

tgctggccac aaacgacaac tacagaggag tctcagccaa gatgacccag tccatcccga    900

ccgagaacat caccaagccg atcaccaggg tcaagctgtc gtacaagatc aaccaacaga    960

cagcaatcgg caatgtcgcc accctgggca caatgggtcc agcatccgtc tccttctcat   1020

cggggaacgg aaacgtcccc ggcgtgctca gaccgatcac actggtggcc tatgagaaga   1080

tgacaccgct gtccatcctg accgtagctg gagtgtccaa ctacgagctg atcccaaacc   1140

cagaactcct caagaacatg gtgacacgct atggcaagta cgaccccgag ggtctcaact   1200

atgccaagat gatcctgtcc cacagggaag agctggacat caggacagtg tggaggacag   1260

aggagtacaa ggagaggacc agagtcttca acgaaatcac ggacttctcc agtgacctgc   1320

ccacgtcaaa ggcatggggc tggagagaca tagtcagagg aattcggaaa gtcgcagctc   1380

ctgtactgtc cacgctgttt ccaatggcag caccactcat aggaatggca gaccaattca   1440

ttggagatct caccaagagc aacgcagcag gcggaaggta ccactccatg gccgcaggag   1500

ggcgctacaa agacgtgctc gagtcctggg caagcggagg gcccgatgga aaattctccc   1560

gagccctcaa gaacaggctg gagtccgcca actacgagga agtcgagctt ccacccccct   1620

caaaaggagt catcgtccct gtggtgcaca cagtcaagag tgcaccaggc gaggcattcg   1680

ggtccctggc aatcataatt ccaggggagt accccgagct tctagatgcc aaccagcagg   1740

tcctatccca cttcgcaaac gacaccggga gcgtgtgggg cataggagag gacataccct   1800

tcgagggaga caacatgtgc tacactgcac tcccactcaa ggagatcaag agaaacggga   1860

acatagtagt cgagaagatc tttgctgggc caatcatggg tccctctgct caactaggac   1920
```

-continued

```
tgtccctact tgtgaacgac atcgaggacg gagttccaag gatggtattc accggcgaaa   1980

tcgccgatga cgaggagaca atcataccaa tctgcggagt agacatcaaa gccatcgcag   2040

cccatgaaca agggctgcca ctcatcggca accaaccagg agtggacgag gaggtgcgaa   2100

acacatccct ggccgcgcac ctgatccaga ccggaaccct gcccgtacaa cgcgcaaagg   2160

gctccaacaa gaggatcaag tacctgggag agctgatggc atcaaatgca tccgggatgg   2220

acgaggaact gcaacgcctc ctgaacgcca caatggcacg ggccaaagaa gtccaggacg   2280

ccgagatcta caaacttctt aagctcatgg catggaccag aaagaacgac ctcaccgacc   2340

acatgtacga gtggtcgaaa gaggaccccg atgcactaaa gttcggaaag ctcatcagca   2400

cgccaccaaa gcaccctgag aagcccaaag gaccagacca acaccacgcc caagaggcga   2460

gagccacccg catatcactg gacgccgtga gagccggggc ggacttcgcc acgccggagt   2520

gggtcgcgct gaacaactac cgcggcccat ctcccgggca gttcaagtac tacctgatca   2580

ccggacgaga accagaacca ggtgacgagt acgaggacta cataaaacaa cccatcgtga   2640

aaccgaccga tatgaacaaa atcagacgtc tagccaacag tgtgtacggc ctcccacacc   2700

aggaaccagc accagaggag ttctacgatg cagttgcagc tgtattcgca cagaacggag   2760

gcagaggtcc cgaccaggac caaatgcaag acctcaggga gctagcaaga cagatgaaa    2819
```

```
<210> SEQ ID NO 67
<211> LENGTH: 402
<212> TYPE: DNA
<213> ORGANISM: Aquabirnavirus infect. pancreatic necrosis virus

<400> SEQUENCE: 67

atgcaagatg aacacaaaca aggcaaccgc aacttacctg aaatccatta tgcttccaga     60

gactggacca gcaagcatcc cggacgacat aacggagaga cacatcttaa aacaagagac    120

ctcgtcatac aacttagagg tctccgaatc aggaagtggc attcttgttt gtttccctgg    180

ggcaccaggc tcacggatcg gcgcacacta cagatggaat gcgaaccaga cggggctgga    240

gttcgaccag tggctggaga cgtcgcagga cctgaagaaa gccttcaact acgggaggct    300

gatctcaagg aaatacgaca ttcaaagctc cacactaccg gccggtctct atgctctgaa    360

cgggacgctc aacgccgcca ccttcgaagg cagtctgtct ga                       402
```

```
<210> SEQ ID NO 68
<211> LENGTH: 1359
<212> TYPE: DNA
<213> ORGANISM: Aquabirnavirus infect. pancreatic necrosis virus

<400> SEQUENCE: 68

atgaacacaa acaaggcaac cgcaacttac ctgaaatcca ttatgcttcc agagactgga     60

ccagcaagca tcccggacga cataacggag agacacatct taaaacaaga gacctcgtca    120

tacaacttag aggtctccga atcaggaagt ggcattcttg tttgtttccc tggggcacca    180

ggctcacgga tcggcgcaca ctacagatgg aatgcgaacc agacggggct ggagttcgac    240

cagtggctgg agacgtcgca ggacctgaag aaagccttca actacgggag gctgatctca    300

aggaaatacg acattcaaag ctccacacta ccggccggtc tctatgctct gaacgggacg    360

ctcaacgccg ccaccttcga aggcagtctg tctgaggtgg agagcctgac ctacaacagc    420

ctgatgtccc taacaacgaa cccccaggac aaagtcaaca accagctggt gaccaaagga    480

gtcacagtcc tgaatctacc aacagggttc gacaagccat acgtccgcct agaggacgag    540

acaccccagg gtctccagtc aatgaacggg gccaagatga ggtgcacagc tgcaattgca    600
```

-continued ccacggaggt acgagatcga cctcccatcc caacgcctac cccccgttcc tgcgacagga 660
gccctcacca ctctctacga gggaaacgcc gacatcgtca actcaacaac agtgacggga 720
gacataaact tcagtctggc agaacaaccc gcagtcgaga ccaagttcga cttccagctg 780
gacttcatgg gccttgacaa tgacgtccca gtggtcacag tggtcagctc cgtgctggcc 840
acaaacgaca actacagagg agtctcagcc aagatgaccc agtccatccc gaccgagaac 900
atcaccaagc cgatcaccag ggtcaagctg tcgtacaaga tcaaccaaca gacagcaatc 960
ggcaatgtcg ccaccctggg cacaatgggt ccagcatccg tctccttctc atcggggaac 1020
ggaaacgtcc ccggcgtgct cagaccgatc acactggtgg cctatgagaa gatgacaccg 1080
ctgtccatcc tgaccgtagc tggagtgtcc aactacgagc tgatcccaaa cccagaactc 1140
ctcaagaaca tggtgacacg ctatggcaag tacgaccccg agggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgg 1359

<210> SEQ ID NO 69
<211> LENGTH: 756
<212> TYPE: DNA
<213> ORGANISM: Aquabirnavirus infect. pancreatic necrosis virus

<400> SEQUENCE: 69
gtcgcagctc ctgtactgtc cacgctgttt ccaatggcag caccactcat aggaatggca 60
gaccaattca ttggagatct caccaagagc aacgcagcag gcggaaggta ccactccatg 120
gccgcaggag ggcgctacaa agacgtgctc gagtcctggg caagcggagg gcccgatgga 180
aaattctccc gagccctcaa gaacaggctg gagtccgcca actacgagga agtcgagctt 240
ccacccccct caaaaggagt catcgtccct gtggtgcaca cagtcaagag tgcaccaggc 300
gaggcattcg ggtccctggc aatcataatt ccaggggagt accccgagct tctagatgcc 360
aaccagcagg tcctatccca cttcgcaaac gacaccggga gcgtgtgggg cataggagag 420
gacataccct tcgagggaga caacatgtgc tacactgcac tcccactcaa ggagatcaag 480
agaaacggga acatagtagt cgagaagatc tttgctgggc caatcatggg tccctctgct 540
caactaggac tgtccctact tgtgaacgac atcgaggacg gagttccaag gatggtattc 600
accggcgaaa tcgccgatga cgaggagaca atcataccaa tctgcggagt agacatcaaa 660
gccatcgcag cccatgaaca agggctgcca ctcatcggca accaaccagg agtggacgag 720
gaggtgcgaa acacatccct ggccgcgcac ctgatc 756

<210> SEQ ID NO 70
<211> LENGTH: 645
<212> TYPE: DNA
<213> ORGANISM: Aquabirnavirus infect. pancreatic necrosis virus

<400> SEQUENCE: 70
atcaagtacc tgggagagct gatggcatca aatgcatccg ggatggacga ggaactgcaa 60
cgcctcctga acgccacaat ggcacgggcc aaagaagtcc aggacgccga gatctacaaa 120
cttcttaagc tcatggcatg gaccagaaag aacgacctca ccgaccacat gtacgagtgg 180
tcgaaagagg accccgatgc actaaagttc ggaaagctca tcagcacgcc accaaagcac 240
cctgagaagc ccaaaggacc agaccaacac cacgcccaag aggcgagagc cacccgcata 300
tcactggacg ccgtgagagc cggggcggac ttcgccacgc cggagtgggt cgcgctgaac 360
aactaccgcg gcccatctcc cgggcagttc aagtactacc tgatcaccgg acgagaacca 420
gaaccaggtg acgagtacga ggactacata aaacaaccca tcgtgaaacc gaccgatatg 480
aacaaaatca gacgtctagc caacagtgtg tacggcctcc cacaccagga accagcacca 540
gaggagttct acgatgcagt tgcagctgta ttcgcacaga acggaggcag aggtcccgac 600
caggaccaaa tgcaagacct cagggagcta gcaagacaga tgaaa 645

<210> SEQ ID NO 71
<211> LENGTH: 2818
<212> TYPE: DNA
<213> ORGANISM: Aquabirnavirus infect. pancreatic necrosis virus

<400> SEQUENCE: 71
atgcaagatg aacacaaaca aggcaaccgc aacttacttg aaatccatta tgcttccaga 60
gactggacca gcaagcatcc cggacgacat aacggagaga cacatcttaa aacaagagac 120
ctcgtcatac aacttagagg tctccgaatc aggaagtggc attcttgttt gtttccctgg 180
ggcaccaggc tcacggatcg gcgcacacta cagatggaat gcgaaccaga cggggctgga 240
gttcgaccag tggctggaga cgtcgcagga cctgaagaaa gccttcaact acgggaggct 300
gatctcaagg aaatacgaca ttcaaagctc cacactaccg gccggtctct atgctctgaa 360
cgggacgctc aacgccgcca ccttcgaagg cagtctgtct gaggtggaga gcctgaccta 420
caacagcctg atgtccctaa caacgaaccc ccaggacaaa gtcaacaacc agctggtgac 480
caaaggagtc acagtcctga atctaccaac agggttcgac aagccatacg tccgcctaga 540
ggacgagaca ccccagggtc tccagtcaat gaacggggcc aagatgaggt gcacagctgc 600
aattgcacca cggaggtacg agatcgacct cccatcccaa cgcctacccc ccgttcctgc 660
gacaggagcc ctcaccactc tctacgaggg aaacgccgac atcgtcaact caacaacagt 720
gacgggagac ataaacttca gtctggcaga acaacccgca gtcgagacca agttcgactt 780
ccagctggac ttcatgggcc ttgacaatga cgtcccagtg gtcacagtgg tcagctccgt 840
gctggccaca aacgacaact acagaggagt ctcagccaag atgacccagt ccatcccgac 900
cgagaacatc accaagccga tcaccagggt caagctgtca tacaagatca accaacagac 960
agcaatcggc aatgtcgcca ccctgggcac aatgggtcca gcatccgtct ccttctcatc 1020
ggggaacgga aacgtccccg gcgtgctcag accaatcaca ctggtggcct atgagaagat 1080
gacaccgctg tccatcctga ccgtagctgg agtgtccaac tacgagctga tcccaaaccc 1140
agaactcctc aagaacatgg tgacacgcta tggcaagtat gaccccgagg gtctcaacta 1200
tgccaagatg atcctgtccc acagggaaga gctggacatc aggacagtgt ggaggacaga 1260
ggagtacaag gagaggacca gagtcttcaa cgaaatcacg gacttctcca gtgacctgcc 1320
cacgtcaaag gcatggggct ggagagacat agtcagagga attcggaaag tcgcagctcc 1380
tgtactgtcc acgctgtttc caatggcagc accactcata ggaatggcag accaattcat 1440
tggagatctc accaagacca acgcagcagg cggaaggtac cactccatgg ccgcaggagg 1500
gcgctacaaa gacgtgctcg agtcctgggc aagcggaggg cccgatggaa aattctcccg 1560
agccctcaag aacaggctgg agtccgccaa ctacgaggaa gtcgagcttc cacccccctc 1620
aaaaggagtc atcgtccctg tggtgcacac agtcaagagt gcaccaggcg aggcattcgg 1680
gtccctggca atcataattc caggggagta ccccgagctt ctagatgcca accagcaggt 1740
cctatcccac ttcgcaaacg acaccgggag cgtgtggggc ataggagagg acatacccttt 1800 cgagggagac aacatgtgct acactgcact cccactcaag gagatcaaga gaaacgggaa 1860
catagtagtc gagaagatct ttgctgggcc aatcatgggt ccctctgctc aactaggact 1920
gtccctactt gtgaacgaca tcgaggacgg agttccaagg atggtattca ccggcgaaat 1980
cgccgatgac gaggagacaa tcataccaat ctgcggagtg gacatcaagg ccatcgcagc 2040
ccatgaacaa gggctgccac tcatcggcaa ccaaccagga gtggacgagg aggtgcgaaa 2100
cacatccctg gccgcgcacc tgatccagac cggaaccctg cccgtacaac gcgcaaaggg 2160
ctccaacaag aggatcaagt acctgggaga gctgatggca tcaaatgcat ccgggatgga 2220
cgaggaactg caacgcctcc tgaacgccac aatggcacgg gccaaagaag tccaggacgc 2280
cgagatctac aaacttctta agctcatggc atggaccaga aagaacgacc tcaccgacca 2340
catgtacgag tggtcgaaag aggaccccga tgcactaaag ttcggaaagc tcatcagcac 2400
gccaccaaag caccctgaga agcccaaagg accagaccaa caccacgccc aagaggcgag 2460
agccacccgc atatcactgg acgccgtgag agccggggcg gacttcgcca cgccggagtg 2520
ggtcgcgctg aacaactacc gcggcccatc tcccgggcag ttcaagtact acctgatcac 2580
cggacgagaa ccagaaccag gtgacgagta cgaggactac ataaaacaac ccatcgtgaa 2640
accgaccgat atgaacaaaa tcagacgtct agccaacagt gtgtacggcc tcccacacca 2700
ggaaccagca ccagaggagt tctacgatgc agttgcagct gtattcgcac agaacggagg 2760
cagaggtccc gaccaggacc aaatgcaaga cctcagggag ctagcaagac agatgaaa 2818

<210> SEQ ID NO 72
<211> LENGTH: 402
<212> TYPE: DNA
<213> ORGANISM: Aquabirnavirus infect. pancreatic necrosis virus

<400> SEQUENCE: 72
atgcaagatg aacacaaaca aggcaaccgc aacttacttg aaatccatta tgcttccaga 60
gactggacca gcaagcatcc cggacgacat aacggagaga cacatcttaa aacaagagac 120
ctcgtcatac aacttagagg tctccgaatc aggaagtggc attcttgttt gtttccctgg 180
ggcaccaggc tcacggatcg gcgcacacta cagatggaat gcgaaccaga cggggctgga 240
gttcgaccag tggctggaga cgtcgcagga cctgaagaaa gccttcaact acgggaggct 300
gatctcaagg aaatacgaca ttcaaagctc cacactaccg gccggtctct atgctctgaa 360
cgggacgctc aacgccgcca ccttcgaagg cagtctgtct ga 402

<210> SEQ ID NO 73
<211> LENGTH: 1369
<212> TYPE: DNA
<213> ORGANISM: Aquabirnavirus infect. pancreatic necrosis virus

<400> SEQUENCE: 73
atgaacacaa acaaggcaac cgcaacttac ttgaaatcca ttatgcttcc agagactgga 60
ccagcaagca tcccggacga cataacggag agacacatct taaaacaaga gacctcgtca 120
tacaacttag aggtctccga atcaggaagt ggcattcttg tttgtttccc tggggcacca 180
ggctcacgga tcggcgcaca ctacagatgg aatgcgaacc agacggggct ggagttcgac 240
cagtggctgg agacgtcgca ggacctgaag aaagccttca actacgggag gctgatctca 300
aggaaatacg acattcaaag ctccacacta ccggccggtc tctatgctct gaacgggacg 360
ctcaacgccg ccaccttcga aggcagtctg tctgaggtgg agagcctgac ctacaacagc 420
ctgatgtccc taacaacgaa cccccaggac aaagtcaaca accagctggt gaccaaagga 480
gtcacagtcc tgaatctacc aacagggttc gacaagccat acgtccgcct agaggacgag 540
acaccccagg gtctccagtc aatgaacggg gccaagatga ggtgcacagc tgcaattgca 600
ccacggaggt acgagatcga cctcccatcc caacgcctac cccccgttcc tgcgacagga 660
gccctcacca ctctctacga gggaaacgcc gacatcgtca actcaacaac agtgacggga 720
gacataaact tcagtctggc agaacaaccc gcagtcgaga ccaagttcga cttccagctg 780
gacttcatgg gccttgacaa tgacgtccca gtggtcacag tggtcagctc cgtgctggcc 840
acaaacgaca actacagagg agtctcagcc aagatgaccc agtccatccc gaccgagaac 900
atcaccaagc cgatcaccag ggtcaagctg tcatacaaga tcaaccaaca gacagcaatc 960
ggcaatgtcg ccaccctggg cacaatgggt ccagcatccg tctccttctc atcggggaac 1020
ggaaacgtcc ccggcgtgct cagaccaatc acactggtgg cctatgagaa gatgacaccg 1080
ctgtccatcc tgaccgtagc tggagtgtcc aactacgagc tgatcccaaa cccagaactc 1140
ctcaagaaca tggtgacacg ctatggcaag tatgaccccg agggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgga aagtcgcag 1369

<210> SEQ ID NO 74
<211> LENGTH: 756
<212> TYPE: DNA
<213> ORGANISM: Aquabirnavirus infect. pancreatic necrosis virus

<400> SEQUENCE: 74
gtcgcagctc ctgtactgtc cacgctgttt ccaatggcag caccactcat aggaatggca 60
gaccaattca ttggagatct caccaagacc aacgcagcag gcggaaggta ccactccatg 120
gccgcaggag ggcgctacaa agacgtgctc gagtcctggg caagcggagg gcccgatgga 180
aaattctccc gagccctcaa gaacaggctg gagtccgcca actacgagga agtcgagctt 240
ccacccccct caaaaggagt catcgtccct gtggtgcaca cagtcaagag tgcaccaggc 300
gaggcattcg ggtccctggc aatcataatt ccaggggagt accccgagct tctagatgcc 360
aaccagcagg tcctatccca cttcgcaaac gacaccggga gcgtgtgggg cataggagag 420
gacataccct tcgagggaga caacatgtgc tacactgcac tcccactcaa ggagatcaag 480
agaaacggga acatagtagt cgagaagatc tttgctgggc caatcatggg tccctctgct 540
caactaggac tgtccctact tgtgaacgac atcgaggacg gagttccaag gatggtattc 600
accggcgaaa tcgccgatga cgaggagaca atcataccaa tctgcggagt ggacatcaag 660
gccatcgcag cccatgaaca agggctgcca ctcatcggca accaaccagg agtggacgag 720
gaggtgcgaa acacatccct ggccgcgcac ctgatc 756

<210> SEQ ID NO 75
<211> LENGTH: 645
<212> TYPE: DNA
<213> ORGANISM: Aquabirnavirus infect. pancreatic necrosis virus

<400> SEQUENCE: 75
atcaagtacc tgggagagct gatggcatca aatgcatccg ggatggacga ggaactgcaa 60
cgcctcctga acgccacaat ggcacgggcc aaagaagtcc aggacgccga gatctacaaa 120
cttcttaagc tcatggcatg gaccagaaag aacgacctca ccgaccacat gtacgagtgg 180
tcgaaagagg accccgatgc actaaagttc ggaaagctca tcagcacgcc accaaagcac 240
cctgagaagc ccaaaggacc agaccaacac cacgcccaag aggcgagagc cacccgcata 300

-continued

```
tcactggacg ccgtgagagc cggggcggac ttcgccacgc cggagtgggt cgcgctgaac    360

aactaccgcg gcccatctcc cgggcagttc aagtactacc tgatcaccgg acgagaacca    420

gaaccaggtg acgagtacga ggactacata aaacaaccca tcgtgaaacc gaccgatatg    480

aacaaaatca gacgtctagc caacagtgtg tacggcctcc cacaccagga accagcacca    540

gaggagttct acgatgcagt tgcagctgta ttcgcacaga acggaggcag aggtcccgac    600

caggaccaaa tgcaagacct cagggagcta gcaagacaga tgaaa                    645
```

<210> SEQ ID NO 76
<211> LENGTH: 2818
<212> TYPE: DNA
<213> ORGANISM: Aquabirnavirus infect. pancreatic necrosis virus

<400> SEQUENCE: 76

```
atgcaagatg aacacaaaca aggcaaccgc aacttacttg aaatccatta tgcttccaga     60

gactggacca gcaagcatcc cggacgacat aacggagaga cacatcttaa aacaagagac    120

ctcgtcatac aacttagagg tctccgaatc aggaagtggc attcttgttt gtttccctgg    180

ggcaccaggc tcacggatcg gcgcacacta cagatggaat gcgaaccaga cggggctgga    240

gttcgaccag tggctggaga cgtcgcagga cctgaagaaa gccttcaact acgggaggct    300

gatctcaagg aaatacgaca ttcaaagctc cacactaccg gccggtctct atgctctgaa    360

cgggacgctc aacgccgcca ccttcgaagg cagtctgtct gaggtggaga gcctgaccta    420

caacagcctg atgtccctaa caacgaaccc ccaggacaaa gtcaacaacc agctggtgac    480

caaaggagtc acagtcctga atctaccaac agggttcgac aagccatacg tccgcctaga    540

ggacgagaca ccccagggtc tccagtcaat gaacggggcc aagatgaggt gcacagctgc    600

aattgcacca cggaggtacg agatcgacct cccatcccaa cgcctacccc ccgttcctgc    660

gacaggaacc ctcaccactc tctacgaggg aaacgccgac atcgtcaact caacaacagt    720

gacgggagac ataaacttca gtctggcaga acaacccgca gtcgagacca agttcgactt    780

ccagctggac ttcatgggcc ttgacaatga cgtcccagtg gtcacagtgg tcagctccgt    840

gctggccaca aacgacaact acagaggagt ctcagccaag atgacccagt ccatcccgac    900

cgagaacatc accaagccga tcaccagggt caagctgtca tacaaggtca accaacagac    960

agcaatcggc aatgtcgcca ccctgggcac aatgggtcca gcatccgtct ccttctcatc   1020

ggggaacgga aacgtccccg gcgtgctcag accaatcaca ctggtggcct atgagaagat   1080

gacaccgctg tccatcctga ccgtagctgg agtgtccaac tacgagctga tcccaaaccc   1140

agaactcctc aagaacatgg tgacacgcta tggcaagtac gaccccgagg gtctcaacta   1200

tgccaagatg atcctgtccc acagggaaga gctggacatc aggacagtgt ggaggacaga   1260

ggagtacaag gagaggacca gagtcttcaa cgaaatcacg gacttctcca gtgacctgcc   1320

cacgtcaaag gcatggggct ggagagacat agtcagagga attcggaaag tcgcagctcc   1380

tgtactgtcc acgctgtttc caatggcagc accactcata ggaatggcag accaattcat   1440

tggagatctc accaagacca acgcagcagg cggaaggtac cactccatgg ccgcaggagg   1500

gcgctacaaa gacgtgctcg agtcctgggc aagcggaggg cccgatggaa aattctcccg   1560

agccctcaag aacaggctgg agtccgccaa ctacgaggaa gtcgagcttc caccccccctc  1620

aaaaggagtc atcgtccctg tggtgcacac agtcaagagt gcaccaggcg aggcattcgg   1680

gtccctggca atcataattc caggggagta ccccgagctt ctagatgcca accagcaggt   1740

cctatcccac ttcgcaaacg acaccgggag cgtgtggggc ataggagagg acatacccctt  1800
```

-continued

```
cgagggagac aacatgtgct acactgcact cccactcaag gagatcaaga gaaacgggaa   1860
catagtagtc gagaagatct ttgctgggcc aatcatgggt ccctctgctc aactaggact   1920
gtccctactt gtgaacgaca tcgaggacgg agttccaagg atggtattca ccggcgaaat   1980
cgccgatgac gaggagacaa tcataccaat ctgcggagta gacatcaaag ccatcgcagc   2040
ccatgaacaa gggctgccac tcatcggcaa ccaaccagga gtggacgagg aggtgcgaaa   2100
cacatccctg gccgcgcacc tgatccagac cggaaccctg cccgtacaac gcgcaaaggg   2160
ctccaacaag aggatcaagt acctgggaga gctgatggca tcaaatgcat ccgggatgga   2220
cgaggaactg caacgcctcc tgaacgccac aatggcacgg gccaaagaag tccaggacgc   2280
cgagatctac aaacttctta agctcatggc atggaccaga aagaacgacc tcaccgacca   2340
catgtacgag tggtcgaaag aggaccccga tgcactaaag ttcggaaagc tcatcagcac   2400
gccaccaaag caccccgaga agcccaaagg accagaccaa caccacgccc aagaggcgag   2460
agccacccgc atatcactgg acgccgtgag agccggggcg gacttcgcca cgccggagtg   2520
ggtcgcgctg aacaactacc gcggcccatc tcccgggcag ttcaagtact acctgatcac   2580
cggacgagaa ccagaaccag gtgacgagta cgaggactac ataaaacaac ccatcgtgaa   2640
accgaccgac atgaacaaaa tcagacgtct agccaacagt gtgtacggcc tcccacacca   2700
ggaaccagca ccagaggagt tctacgatgc agttgcagct gtattcgcac agaacggagg   2760
cagaggtccc gaccaggacc aaatgcaaga cctcagggag ctagcaagac agatgaaa     2818
```

```
<210> SEQ ID NO 77
<211> LENGTH: 402
<212> TYPE: DNA
<213> ORGANISM: Aquabirnavirus infect. pancreatic necrosis virus

<400> SEQUENCE: 77

atgcaagatg aacacaaaca aggcaaccgc aacttacttg aaatccatta tgcttccaga     60
gactggacca gcaagcatcc cggacgacat aacggagaga cacatcttaa aacaagagac    120
ctcgtcatac aacttagagg tctccgaatc aggaagtggc attcttgttt gtttccctgg    180
ggcaccaggc tcacggatcg gcgcacacta cagatggaat gcgaaccaga cggggctgga    240
gttcgaccag tggctggaga cgtcgcagga cctgaagaaa gccttcaact acgggaggct    300
gatctcaagg aaatacgaca ttcaaagctc cacactaccg gccggtctct atgctctgaa    360
cgggacgctc aacgccgcca ccttcgaagg cagtctgtct ga                       402
```

```
<210> SEQ ID NO 78
<211> LENGTH: 1359
<212> TYPE: DNA
<213> ORGANISM: Aquabirnavirus infect. pancreatic necrosis virus

<400> SEQUENCE: 78

atgaacacaa acaaggcaac cgcaacttac ttgaaatcca ttatgcttcc agagactgga     60
ccagcaagca tcccggacga cataacggag agacacatct taaaacaaga gacctcgtca    120
tacaacttag aggtctccga atcaggaagt ggcattcttg tttgtttccc tggggcacca    180
ggctcacgga tcggcgcaca ctacagatgg aatgcgaacc agacggggct ggagttcgac    240
cagtggctgg agacgtcgca ggacctgaag aaagccttca actacgggag gctgatctca    300
aggaaatacg acattcaaag ctccacacta ccggccggtc tctatgctct gaacgggacg    360
ctcaacgccg ccaccttcga aggcagtctg tctgaggtgg agagcctgac ctacaacagc    420
ctgatgtccc taacaacgaa cccccaggac aaagtcaaca accagctggt gaccaaagga    480
```

-continued

```
gtcacagtcc tgaatctacc aacagggttc gacaagccat acgtccgcct agaggacgag    540

acaccccagg gtctccagtc aatgaacggg gccaagatga ggtgcacagc tgcaattgca    600

ccacggaggt acgagatcga cctcccatcc caacgcctac cccccgttcc tgcgacagga    660

accctcacca ctctctacga gggaaacgcc gacatcgtca actcaacaac agtgacggga    720

gacataaact tcagtctggc agaacaaccc gcagtcgaga ccaagttcga cttccagctg    780

gacttcatgg gccttgacaa tgacgtccca gtggtcacag tggtcagctc cgtgctggcc    840

acaaacgaca actacagagg agtctcagcc aagatgaccc agtccatccc gaccgagaac    900

atcaccaagc cgatcaccag ggtcaagctg tcatacaagg tcaaccaaca gacagcaatc    960

ggcaatgtcg ccaccctggg cacaatgggt ccagcatccg tctccttctc atcggggaac   1020

ggaaacgtcc ccggcgtgct cagaccaatc acactggtgg cctatgagaa gatgacaccg   1080

ctgtccatcc tgaccgtagc tggagtgtcc aactacgagc tgatcccaaa cccagaactc   1140

ctcaagaaca tggtgacacg ctatggcaag tacgaccccg agggtctcaa ctatgccaag   1200

atgatcctgt cccacaggga agagctggac atcaggacag tgtggaggac agaggagtac   1260

aaggagagga ccagagtctt caacgaaatc acggacttct ccagtgacct gcccacgtca   1320

aaggcatggg gctggagaga catagtcaga ggaattcgg                           1359
```

<210> SEQ ID NO 79
<211> LENGTH: 756
<212> TYPE: DNA
<213> ORGANISM: Aquabirnavirus infect. pancreatic necrosis virus

<400> SEQUENCE: 79

```
gtcgcagctc ctgtactgtc cacgctgttt ccaatggcag caccactcat aggaatggca     60

gaccaattca ttggagatct caccaagacc aacgcagcag gcggaaggta ccactccatg    120

gccgcaggag ggcgctacaa agacgtgctc gagtcctggg caagcggagg gcccgatgga    180

aaattctccc gagccctcaa gaacaggctg gagtccgcca actacgagga agtcgagctt    240

ccaccccccct caaaaggagt catcgtccct gtggtgcaca cagtcaagag tgcaccaggc    300

gaggcattcg ggtccctggc aatcataatt ccaggggagt accccgagct tctagatgcc    360

aaccagcagg tcctatccca cttcgcaaac gacaccggga gcgtgtgggg cataggagag    420

gacataccct tcgagggaga caacatgtgc tacactgcac tcccactcaa ggagatcaag    480

agaaacggga acatagtagt cgagaagatc tttgctgggc caatcatggg tccctctgct    540

caactaggac tgtccctact tgtgaacgac atcgaggacg gagttccaag gatggtattc    600

accggcgaaa tcgccgatga cgaggagaca atcataccaa tctgcggagt agacatcaaa    660

gccatcgcag cccatgaaca agggctgcca ctcatcggca accaaccagg agtggacgag    720

gaggtgcgaa acacatccct ggccgcgcac ctgatc                              756
```

<210> SEQ ID NO 80
<211> LENGTH: 645
<212> TYPE: DNA
<213> ORGANISM: Aquabirnavirus infect. pancreatic necrosis virus

<400> SEQUENCE: 80

```
atcaagtacc tgggagagct gatggcatca aatgcatccg ggatggacga ggaactgcaa     60

cgcctcctga acgccacaat ggcacgggcc aaagaagtcc aggacgccga gatctacaaa    120

cttcttaagc tcatggcatg gaccagaaag aacgacctca ccgaccacat gtacgagtgg    180

tcgaaagagg accccgatgc actaaagttc ggaaagctca tcagcacgcc accaaagcac    240
```

-continued

```
cccgagaagc ccaaaggacc agaccaacac cacgcccaag aggcgagagc cacccgcata    300

tcactggacg ccgtgagagc cggggcggac ttcgccacgc cggagtgggt cgcgctgaac    360

aactaccgcg gcccatctcc cggcagttc aagtactacc tgatcaccgg acgagaacca    420

gaaccaggtg acgagtacga ggactacata aaacaaccca tcgtgaaacc gaccgacatg    480

aacaaaatca gacgtctagc caacagtgtg tacggcctcc cacaccagga accagcacca    540

gaggagttct acgatgcagt tgcagctgta ttcgcacaga acggaggcag aggtcccgac    600

caggaccaaa tgcaagacct cagggagcta gcaagacaga tgaaa                    645
```

<210> SEQ ID NO 81
<211> LENGTH: 2818
<212> TYPE: DNA
<213> ORGANISM: Aquabirnavirus infect. pancreatic necrosis virus

<400> SEQUENCE: 81

```
atgcaagatg aacacaaaca aggcaaccgc aacttacttg aaatccatta tgcttccaga     60

gactggacca gcaagcatcc cggacgacat aacggagaga cacatcttaa aacaagagac    120

ctcgtcatat aacttagagg tctccgaatc aggaagtggc attcttgttt gtttccctgg    180

ggcaccaggc tcacggatcg gcgcacacta cagatggaac gcgaaccaga cggggctgga    240

gttcgaccag tggctggaga cgtcgcagga cctgaagaaa gccttcaact acgggaggct    300

gatctcaagg aaatacgaca ttcaaagctc cacactaccg gccggtctct atgctctgaa    360

cgggacgctc aacgccgcca ccttcgaagg cagtctgtct gaggtggaga gcctgaccta    420

caacagcctg atgtccctaa caacgaaccc ccaggacaaa gtcaacaacc agctggtgac    480

caaaggagtc acagtcctga atctaccaac agggttcgac aagccatacg tccgcctaga    540

ggacgagaca ccccagggtc tccagtcaat gaacggggcc aagatgaggt gcacagctgc    600

aattgcacca cggaggtacg agatcgacct cccatcccaa cgcctacccc ccgttcctgc    660

gacaggaacc ctcaccactc tctacgaggg aaacgccgac atcgtcaact caacaacagt    720

gacgggagac ataaacttca gtctggcaga acaacccgca gtcgagacca agttcgactt    780

ccagctggac ttcatgggcc ttgacaatga cgtcccagtg gtcacagtgg tcagctccgt    840

gctggctaca aacgacaact acagaggagt ctcagccaag atgacccagt ccatcccgac    900

cgagaacatc accaagccga tcaccagggt caagctgtca tacaaggtca accaacagac    960

agcaatcggc aatgtcgcca ccctgggcac aatgggtcca gcatccgtct ccttctcatc   1020

ggggaacgga aacgtccccg gcgtgctcag accaatcaca ctggtggcct atgagaagat   1080

gacaccgctg tccatcctga ccgtagctgg agtgtccaac tacgagctga tcccaaaccc   1140

agaactcctc aagaacatgg tgacacgcta tggcaagtat gaccccgagg gtctcaacta   1200

tgccaagatg atcctgtccc acagggaaga gctggacatc aggacagtgt ggaggacaga   1260

ggagtacaag gagaggacca gagtcttcaa cgaaatcacg gacttctcca gtgacctgcc   1320

cacgtcaaag gcatggggct ggagagacat agtcagagga attcggaaag tcgcagctcc   1380

tgtactgtcc acgctgtttc caatggcagc accactcata ggaatggcag accaattcat   1440

tggagatctc accaagacca acgcagcagg cggaaggtac cactccatgg ccgcaggagg   1500

gcgctacaaa gacgtgctcg agtcctgggc aagcggaggg cccgatggaa aattctcccg   1560

agccctcaag aacaggctgg agtccgccaa ctacgaggaa gtcgagcttc caccccccctc   1620

aaaaggagtc atcgtccctg tggtgcacac agtcaagagt gcaccaggcg aggcattcgg   1680

gtccctggca atcataattc caggggagta ccccgagctt ctagatgcca accagcaggt   1740
```

-continued

```
cctatcccac ttcgcaaacg acaccgggag cgtgtggggc ataggagagg acataccctt   1800

cgagggagac aacatgtgct acactgcact cccactcaag gagatcaaga gaaacgggaa   1860

catagtagtc gagaagatct ttgctgggcc aatcatgggt ccctctgctc aactaggact   1920

gtccctactt gtgaacgaca tcgaggacgg agttccaagg atggtattca ccggcgaaat   1980

cgccgatgac gaggagacaa tcataccaat ctgcggagta gacatcaaag ccatcgcagc   2040

ccatgaacaa gggctgccac tcatcggcaa ccaaccagga gtggacgagg aggtgcgaaa   2100

cacatccctg gccgcgcacc tgatccagac cggaaccctg cccgtacaac gcgcaaaggg   2160

ctccaacaag aggatcaagt acctgggaga gctgatggca tcaaatgcat ccgggatgga   2220

cgaggaactg caacgcctcc tgaacgccac aatggcacgg gccaaagaag tccaggacgc   2280

cgagatctac aaacttctta agctcatggc atggaccaga aagaacgacc tcaccgacca   2340

catgtacgag tggtcgaaag aggaccccga tgcactaaag ttcggaaagc tcatcagcac   2400

gccaccaaag caccctgaga agcccaaagg accagaccaa caccacgccc aagaggcgag   2460

agccacccgc atatcactgg acgccgtgag agccggggcg gacttcgcca cgccggagtg   2520

ggtcgcgctg aacaactacc gcggcccatc tcccgggcag ttcaagtact acctgatcac   2580

cggacgagaa ccagaaccag gtgacgagta cgaggactac ataaaacaac ccatcgtgaa   2640

accgaccgat atgaacaaaa tcagacgtct agccaacagt gtgtacggcc tcccacacca   2700

ggaaccagca ccagaggagt tctacgatgc agttgcagct gtattcgcac agaacggagg   2760

cagaggtccc gaccaggacc aaatgcaaga cctcagggag ctagcaagac agatgaaa     2818
```

<210> SEQ ID NO 82
<211> LENGTH: 402
<212> TYPE: DNA
<213> ORGANISM: Aquabirnavirus infect. pancreatic necrosis virus

<400> SEQUENCE: 82

```
atgcaagatg aacacaaaca aggcaaccgc aacttacttg aaatccatta tgcttccaga     60

gactggacca gcaagcatcc cggacgacat aacggagaga cacatcttaa aacaagagac    120

ctcgtcatat aacttagagg tctccgaatc aggaagtggc attcttgttt gtttccctgg    180

ggcaccaggc tcacggatcg gcgcacacta cagatggaac gcgaaccaga cggggctgga    240

gttcgaccag tggctggaga cgtcgcagga cctgaagaaa gccttcaact acgggaggct    300

gatctcaagg aaatacgaca ttcaaagctc cacactaccg gccggtctct atgctctgaa    360

cgggacgctc aacgccgcca ccttcgaagg cagtctgtct ga                       402
```

<210> SEQ ID NO 83
<211> LENGTH: 1359
<212> TYPE: DNA
<213> ORGANISM: Aquabirnavirus infect. pancreatic necrosis virus

<400> SEQUENCE: 83

```
atgaacacaa acaaggcaac cgcaacttac ttgaaatcca ttatgcttcc agagactgga     60

ccagcaagca tcccggacga cataacggag agacacatct taaaacaaga gacctcgtca    120

tataacttag aggtctccga atcaggaagt ggcattcttg tttgtttccc tggggcacca    180

ggctcacgga tcggcgcaca ctacagatgg aacgcgaacc agacggggct ggagttcgac    240

cagtggctgg agacgtcgca ggacctgaag aaagccttca actacgggag gctgatctca    300

aggaaatacg acattcaaag ctccacacta ccggccggtc tctatgctct gaacgggacg    360

ctcaacgccg ccaccttcga aggcagtctg tctgaggtgg agagcctgac ctacaacagc    420
```

-continued

```
ctgatgtccc taacaacgaa cccccaggac aaagtcaaca accagctggt gaccaaagga    480

gtcacagtcc tgaatctacc aacagggttc gacaagccat acgtccgcct agaggacgag    540

acaccccagg gtctccagtc aatgaacggg gccaagatga ggtgcacagc tgcaattgca    600

ccacggaggt acgagatcga cctcccatcc caacgcctac cccccgttcc tgcgacagga    660

accctcacca ctctctacga gggaaacgcc gacatcgtca actcaacaac agtgacggga    720

gacataaact tcagtctggc agaacaaccc gcagtcgaga ccaagttcga cttccagctg    780

gacttcatgg gccttgacaa tgacgtccca gtggtcacag tggtcagctc cgtgctggct    840

acaaacgaca actacagagg agtctcagcc aagatgaccc agtccatccc gaccgagaac    900

atcaccaagc cgatcaccag ggtcaagctg tcatacaagg tcaaccaaca gacagcaatc    960

ggcaatgtcg ccaccctggg cacaatgggt ccagcatccg tctccttctc atcggggaac   1020

ggaaacgtcc ccggcgtgct cagaccaatc acactggtgg cctatgagaa gatgacaccg   1080

ctgtccatcc tgaccgtagc tggagtgtcc aactacgagc tgatcccaaa cccagaactc   1140

ctcaagaaca tggtgacacg ctatggcaag tatgaccccg agggtctcaa ctatgccaag   1200

atgatcctgt cccacaggga agagctggac atcaggacag tgtggaggac agaggagtac   1260

aaggagagga ccagagtctt caacgaaatc acggacttct ccagtgacct gcccacgtca   1320

aaggcatggg gctggagaga catagtcaga ggaattcgg                          1359
```

```
<210> SEQ ID NO 84
<211> LENGTH: 756
<212> TYPE: DNA
<213> ORGANISM: Aquabirnavirus infect. pancreatic necrosis virus

<400> SEQUENCE: 84

gtcgcagctc ctgtactgtc cacgctgttt ccaatggcag caccactcat aggaatggca     60

gaccaattca ttggagatct caccaagacc aacgcagcag gcggaaggta ccactccatg    120

gccgcaggag ggcgctacaa agacgtgctc gagtcctggg caagcggagg gcccgatgga    180

aaattctccc gagccctcaa gaacaggctg gagtccgcca actacgagga agtcgagctt    240

ccaccccccct caaaaggagt catcgtccct gtggtgcaca cagtcaagag tgcaccaggc    300

gaggcattcg ggtccctggc aatcataatt ccaggggagt accccgagct tctagatgcc    360

aaccagcagg tcctatccca cttcgcaaac gacaccggga gcgtgtgggg cataggagag    420

gacataccct tcgagggaga caacatgtgc tacactgcac tcccactcaa ggagatcaag    480

agaaacggga acatagtagt cgagaagatc tttgctgggc caatcatggg tccctctgct    540

caactaggac tgtccctact tgtgaacgac atcgaggacg gagttccaag gatggtattc    600

accggcgaaa tcgccgatga cgaggagaca atcataccaa tctgcggagt agacatcaaa    660

gccatcgcag cccatgaaca agggctgcca ctcatcggca accaaccagg agtggacgag    720

gaggtgcgaa acacatccct ggccgcgcac ctgatc                             756
```

```
<210> SEQ ID NO 85
<211> LENGTH: 645
<212> TYPE: DNA
<213> ORGANISM: Aquabirnavirus infect. pancreatic necrosis virus

<400> SEQUENCE: 85

atcaagtacc tgggagagct gatggcatca aatgcatccg ggatggacga ggaactgcaa     60

cgcctcctga acgccacaat ggcacgggcc aaagaagtcc aggacgccga gatctacaaa    120

cttcttaagc tcatggcatg gaccagaaag aacgacctca ccgaccacat gtacgagtgg    180
```

```
tcgaaagagg accccgatgc actaaagttc ggaaagctca tcagcacgcc accaaagcac    240

cctgagaagc ccaaaggacc agaccaacac cacgcccaag aggcgagagc cacccgcata    300

tcactggacg ccgtgagagc cggggcggac ttcgccacgc cggagtgggt cgcgctgaac    360

aactaccgcg gcccatctcc cgggcagttc aagtactacc tgatcaccgg acgagaacca    420

gaaccaggtg acgagtacga ggactacata aaacaaccca tcgtgaaacc gaccgatatg    480

aacaaaatca gacgtctagc caacagtgtg tacggcctcc cacaccagga accagcacca    540

gaggagttct acgatgcagt tgcagctgta ttcgcacaga acggaggcag aggtcccgac    600

caggaccaaa tgcaagacct cagggagcta gcaagacaga tgaaa                    645
```

<210> SEQ ID NO 86
<211> LENGTH: 2818
<212> TYPE: DNA
<213> ORGANISM: Aquabirnavirus infect. pancreatic necrosis virus

<400> SEQUENCE: 86

```
atgcaagatg aacacaaaca aggcaaccgc aacttacttg aaatccatta tgcttccaga     60

gactggacca gcaagcatcc cggacgacat aacggagaga cacatcttaa aacaagagac    120

ctcgtcatac aacttagagg tctccgaatc aggaagtggc attcttgttt gtttccctgg    180

ggcaccaggc tcacggatcg gcgcacacta cagatggaat gcgaaccaga cggggctgga    240

gttcgaccag tggctggaga cgtcgcagga cctgaagaaa gccttcaact acgggaggct    300

gatctcaagg aaatacgaca ttcaaagctc cacactaccg gccggtctct atgctctgaa    360

cgggacgctc aacgccgcca ccttcgaagg cagtctgtct gaggtggaga gcctgaccta    420

caacagcctg atgtccctaa caacgaaccc ccaggacaaa gtcaacaacc agctggtgac    480

caaaggagtc acagtcctga atctaccaac agggttcgac aagccatacg tccgcctaga    540

ggacgagaca ccccagggtc tccagtcaat gaacggggcc aagatgaggt gcacagctgc    600

aattgcacca cggaggtacg agatcgacct cccatcccaa cgcctacccc ccgtccctgc    660

gacaggagcc ctcaccactc tctacgaggg aaacgccgac atcgtcaact caacaacagt    720

gacgggagat ataaacttca gtctggcaga acaacccgca gtcgagacca agttcgactt    780

ccagctggac ttcatgggcc ttgacaatga cgtcccagtg gtcacagtgg tcagctccgt    840

gctggccaca aacgacaact acagaggagt ctcagccaag atgacccagt ccatcccgac    900

cgagaacatc accaagccga tcaccagggt caagctgtca tacaagatca accaacagac    960

agcaatcggc aatgtcgcca ccctgggcac aatgggtcca gcatccgtct ccttctcatc   1020

ggggaacgga aacgtccccg gcgtgctcag accaatcaca ctggtggcct atgagaagat   1080

gacaccgctg tccatcctga ccgtggctgg agtgtccaac tacgagctga tcccaaaccc   1140

agaactcctc aagaacatgg tgacacgcta tggcaagtat gaccccgagg gtctcaacta   1200

tgccaagatg atcctgtccc acagggaaga gctggacatc aggacagtgt ggaggacaga   1260

ggagtacaag gagaggacca gagtcttcaa cgaaatcacg gacttctcca gtgacctgcc   1320

cacgtcaaag gcatggggct ggagagacat agtcagagga attcggaaag tcgcagctcc   1380

tgtactgtcc acgctgtttc caatggcagc accactcata ggaatggcag accaattcat   1440

tggagatctc accaagacca acgcagcagg cggaaggtac cactccatgg ccgcaggagg   1500

gcgctacaaa gacgtgctcg agtcctgggc aagcggaggg cctgatggaa aattctcccg   1560

agccctcaag aacaggctgg agtccgccaa ctacgaggaa gtcgagcttc cacccccctc   1620

aaaaggagtc atcgtccctg tggtgcacac agtcaagagt gcaccaggcg aggcattcgg   1680
```

-continued

```
gtccctggca atcataattc caggggagta ccccgagctt ctagatgcca accagcaggt   1740

cctatcccac ttcgcaaacg acaccgggag cgtgtggggc ataggagagg acataccctt   1800

cgagggagac aacatgtgct acactgcact cccactcaag gagatcaaga gaaacgggaa   1860

catagtagtc gagaagatct ttgctgggcc aatcatgggt ccctctgctc aactaggact   1920

gtccctactt gtgaacgaca tcgaggacgg agttccaagg atggtattca ccggcgaaat   1980

cgccgatgac gaggagacaa tcataccaat ctgcggagta gacatcaaag ccatcgcagc   2040

ccatgaacaa gggctgccac tcatcggcaa ccaaccagga gtggacgagg aggtgcgaaa   2100

cacatccctg gccgcgcacc tgatccagac cggaaccctg cccgtacaac gcgcaaaggg   2160

ctccaacaag aggatcaagt acctgggaga gctgatggca tcaaatgcat ccgggatgga   2220

cgaggaactg caacgcctcc tgaacgccac aatggcacgg gccaaagaag tccaggacgc   2280

cgagatctac aaacttctta agctcatggc atggaccaga aagaacgacc tcaccgacca   2340

catgtacgag tggtcgaaag aggaccccga tgcactaaag ttcggaaagc tcatcagcac   2400

gccaccaaag caccctgaga agcccaaagg acctgaccaa caccacgccc aagaggcgag   2460

agccacccgc atatcactgg acgccgtgag agccggggcg gacttcgcca cgccggagtg   2520

ggtcgcgctg aacaactacc gcggcccatc tcccgggcag ttcaagtact acctgatcac   2580

cggacgagaa ccagaaccag gtgacgagta cgaggactac ataaaacaac ccatcgtgaa   2640

accgaccgat atgaacaaaa tcagacgtct agccaacagt gtgtacggcc tcccacacca   2700

ggaaccagca ccagaggagt tctacgatgc agttgcagct gtattcgcac agaacggagg   2760

cagaggtccc gaccaggacc aaatgcaaga cctcagggag ctagcaagac agatgaaa     2818
```

<210> SEQ ID NO 87
<211> LENGTH: 402
<212> TYPE: DNA
<213> ORGANISM: Aquabirnavirus infect. pancreatic necrosis virus

<400> SEQUENCE: 87

```
atgcaagatg aacacaaaca aggcaaccgc aacttacttg aaatccatta tgcttccaga     60

gactggacca gcaagcatcc cggacgacat aacggagaga cacatcttaa aacaagagac    120

ctcgtcatac aacttagagg tctccgaatc aggaagtggc attcttgttt gtttccctgg    180

ggcaccaggc tcacggatcg gcgcacacta cagatggaat gcgaaccaga cggggctgga    240

gttcgaccag tggctggaga cgtcgcagga cctgaagaaa gccttcaact acgggaggct    300

gatctcaagg aaatacgaca ttcaaagctc cacactaccg gccggtctct atgctctgaa    360

cgggacgctc aacgccgcca ccttcgaagg cagtctgtct ga                       402
```

<210> SEQ ID NO 88
<211> LENGTH: 1359
<212> TYPE: DNA
<213> ORGANISM: Aquabirnavirus infect. pancreatic necrosis virus

<400> SEQUENCE: 88

```
atgaacacaa acaaggcaac cgcaacttac ttgaaatcca ttatgcttcc agagactgga     60

ccagcaagca tcccggacga cataacggag agacacatct taaaacaaga gacctcgtca    120

tacaacttag aggtctccga atcaggaagt ggcattcttg tttgtttccc tggggcacca    180

ggctcacgga tcggcgcaca ctacagatgg aatgcgaacc agacggggct ggagttcgac    240

cagtggctgg agacgtcgca ggacctgaag aaagccttca actacgggag gctgatctca    300

aggaaatacg acattcaaag ctccacacta ccggccggtc tctatgctct gaacgggacg    360
```

-continued ctcaacgccg ccaccttcga aggcagtctg tctgaggtgg agagcctgac ctacaacagc 420
ctgatgtccc taacaacgaa cccccaggac aaagtcaaca accagctggt gaccaaagga 480
gtcacagtcc tgaatctacc aacagggttc gacaagccat acgtccgcct agaggacgag 540
acaccccagg gtctccagtc aatgaacggg gccaagatga ggtgcacagc tgcaattgca 600
ccacggaggt acgagatcga cctcccatcc caacgcctac cccccgtccc tgcgacagga 660
gccctcacca ctctctacga gggaaacgcc gacatcgtca actcaacaac agtgacggga 720
gatataaact tcagtctggc agaacaaccc gcagtcgaga ccaagttcga cttccagctg 780
gacttcatgg gccttgacaa tgacgtccca gtggtcacag tggtcagctc cgtgctggcc 840
acaaacgaca actacagagg agtctcagcc aagatgaccc agtccatccc gaccgagaac 900
atcaccaagc cgatcaccag ggtcaagctg tcatacaaga tcaaccaaca gacagcaatc 960
ggcaatgtcg ccaccctggg cacaatgggt ccagcatccg tctccttctc atcggggaac 1020
ggaaacgtcc ccggcgtgct cagaccaatc acactggtgg cctatgagaa gatgacaccg 1080
ctgtccatcc tgaccgtggc tggagtgtcc aactacgagc tgatcccaaa cccagaactc 1140
ctcaagaaca tggtgacacg ctatggcaag tatgaccccg agggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgg 1359

<210> SEQ ID NO 89
<211> LENGTH: 756
<212> TYPE: DNA
<213> ORGANISM: Aquabirnavirus infect. pancreatic necrosis virus

<400> SEQUENCE: 89
gtcgcagctc ctgtactgtc cacgctgttt ccaatggcag caccactcat aggaatggca 60
gaccaattca ttggagatct caccaagacc aacgcagcag gcggaaggta ccactccatg 120
gccgcaggag ggcgctacaa agacgtgctc gagtcctggg caagcggagg gcctgatgga 180
aaattctccc gagccctcaa gaacaggctg gagtccgcca actacgagga agtcgagctt 240 ccaccccccct caaaaggagt catcgtccct gtggtgcaca cagtcaagag tgcaccaggc 300
gaggcattcg ggtccctggc aatcataatt ccaggggagt accccgagct tctagatgcc 360
aaccagcagg tcctatccca cttcgcaaac gacaccggga gcgtgtgggg cataggagag 420
gacataccct tcgagggaga caacatgtgc tacactgcac tcccactcaa ggagatcaag 480
agaaacggga acatagtagt cgagaagatc tttgctgggc caatcatggg tccctctgct 540
caactaggac tgtccctact tgtgaacgac atcgaggacg gagttccaag gatggtattc 600
accggcgaaa tcgccgatga cgaggagaca atcataccaa tctgcggagt agacatcaaa 660
gccatcgcag cccatgaaca agggctgcca ctcatcggca accaaccagg agtggacgag 720
gaggtgcgaa acacatccct ggccgcgcac ctgatc 756

<210> SEQ ID NO 90
<211> LENGTH: 645
<212> TYPE: DNA
<213> ORGANISM: Aquabirnavirus infect. pancreatic necrosis virus

<400> SEQUENCE: 90
atcaagtacc tgggagagct gatggcatca aatgcatccg ggatggacga ggaactgcaa 60
cgcctcctga acgccacaat ggcacgggcc aaagaagtcc aggacgccga gatctacaaa 120

-continued

```
cttcttaagc tcatggcatg gaccagaaag aacgacctca ccgaccacat gtacgagtgg    180

tcgaaagagg accccgatgc actaaagttc ggaaagctca tcagcacgcc accaaagcac    240

cctgagaagc ccaaaggacc tgaccaacac cacgcccaag aggcgagagc cacccgcata    300

tcactggacg ccgtgagagc cggggcggac ttcgccacgc cggagtgggt cgcgctgaac    360

aactaccgcg gcccatctcc cggggcagttc aagtactacc tgatcaccgg acgagaacca    420

gaaccaggtg acgagtacga ggactacata aaacaaccca tcgtgaaacc gaccgatatg    480

aacaaaatca gacgtctagc caacagtgtg tacggcctcc cacaccagga accagcacca    540

gaggagttct acgatgcagt tgcagctgta ttcgcacaga acggaggcag aggtcccgac    600

caggaccaaa tgcaagacct cagggagcta gcaagacaga tgaaa                     645
```

<210> SEQ ID NO 91
<211> LENGTH: 2811
<212> TYPE: DNA
<213> ORGANISM: Aquabirnavirus infect. pancreatic necrosis virus

<400> SEQUENCE: 91

```
atgaacacaa acaaggcaac cgcaacttac ctgaaatcca ttatgcttcc agagactgga     60

ccagcaagca tcccggatga cacaacggag agacacatcc taaaacaaga gacctcgtca    120

tacaacctag aggtctccga atcaggaagt ggcattcttg tctgtttccc tggggcacca    180

ggctcacgga tcggtgcaca ctacagatgg aatgcgaacc agacggggct ggagttcgac    240

cagtggctgg agacgtcgca ggacctgaag aaagccttca actacgggag gctgatctca    300

aggaaatacg acatccaaag ctccacacta ccggccggtc tctatgctct gaacgggacg    360

ctcaacgctg ccaccttcga aggcagtctg tctgaggtgg agagcctgac ctacaacagc    420

ctgatgtccc taacaacgaa cccccaggac aaagtcaaca accagctggt gaccaaagga    480

gtcacagtcc tgaatctacc aacagggttc gacaaaccat acgtccgcct agaggacgag    540

acaccccagg gtctccagtc aatgaacggg gccaagatga ggtgcacagc tgcaattgca    600

ccgcggaagt acgagatcga cctcccatcc caacgcctac cccccgttcc tgcgacagga    660

gccctcacca ctctctatga gggaaacgcc gacatcgtca actccacgac agtgacggga    720

gacataaact tcagtctggc agaacaaccc gcaatcgaga ccaagttcga cttccagctg    780

gacttcatgg gccttgacaa cgacgtccca gttgtcacag tggtcagctc cgtgctggcc    840

acaaatgaca actacagagg agtctcagcc aagatgaccc agtccatccc gaccgagaac    900

atcacaaagc cgatcaccag ggtcaagctg tcatacaaga tcaaccagca gacagcaatc    960

ggcaacgtcg ccaccctggg cacaatgggt ccagcatccg tctccttctc atcagggaac   1020

ggaaatgtcc ctggcgtgct cagaccaatc acactggtgg cctatgagaa gatgacaccg   1080

ctgtccatcc tgaccgtagc tggagtgtcc aactacgagc tgatcccaaa cccagaactc   1140

ctcaagaaca tggtgacacg ctatggcaag tatgaccccg aaggtctcaa ctatgccaag   1200

atgatccttt cccacaggga agagctggac atcaggacag tgtggaggac agaggagtac   1260

aaggagagga ccagagtctt caacgaaatc acggacttct ccagtgacct gcccacgtca   1320

aaggcatggg gctggagaga catagtcaga ggaattcgga aagtcgcagc tcctgtactg   1380

tccacgctgt ttccaatggc agcaccactc ataggaatgg cagaccaatt cattggagat   1440

ctcaccaaga ccaacgcagc aggcggaagg taccactcca tggccgcagg agggcgccac   1500

aaagacgtgc ttgagtcctg ggcaagcgga gggcccgacg gaaaattctc ccgagccctc   1560

aagaacaggc tggagtccgc caactacgag gaagtcgagc ttccaccccc ctcaaaagga   1620
```

-continued

```
gtcatcgtcc ctgtggtgca cacagtcaag agtgcaccag gcgaggcatt cgggtccctg   1680

gcaatcataa ttccagggga gtaccccgag cttctagatg ccaaccagca ggtcctatcc   1740

cacttcgcaa acgacaccgg gagcgtgtgg ggcataggag aggacatacc cttcgaggga   1800

gacaacatgt gctacactgc actcccactc aaggagatca aaagaaacgg gaacatagta   1860

gtcgagaaga tctttgctgg accaatcatg ggtccctctg ctcaactagg actgtcccta   1920

cttgtgaacg acatcgagga cggagttcca aggatggtat tcaccggcga aatcgccgat   1980

gacgaggaga caatcatacc aatctgcggt gtagacatca aagccatcgc agcccatgaa   2040

caagggctgc cactcatcgg caaccaacca ggagtggacg aggaggtgcg aaacacatcc   2100

ctggccgcac acctgatcca gaccggaacc ctgcccgtac aacgcgcaaa gggctccaac   2160

aagaggatca agtacctggg agagctgatg gcatcaaatg catccgggat ggacgaggaa   2220

ctgcaacgcc tcctgaacgc cacaatggca cgggccaaag aagtccagga cgccgagatc   2280

tacaaacttc tcaagctcat ggcatggacc agaaagaacg acctcaccga ccacatgtac   2340

gagtggtcaa aagaggaccc caatgcacta aagttcggaa agctcatcag cacgccacca   2400

aagcaccccg agaagcccaa aggaccagac caacaccacg cccaagaggc gagagccacc   2460

cgcatatcac tggacgccgt gagagccggg gcggacttcg ccacaccgga atgggtcgcg   2520

ctgaacaact accgcggccc atctcccggg cagttcaagt actacctgat cactggacga   2580

gaaccagaac caggcgacga gtacgaggac tacataaaac aacccattgt gaaaccgacc   2640

gacatgaaca aaatcagacg tctagccaac agtgtgtacg gcctcccaca ccaggaacca   2700

gcaccagagg agttctacga tgcagttgca gctgtattcg cacagaacgg aggcagaggt   2760

cccgaccagg accaaatgca agacctcagg gagctcgcaa gacagatgaa a            2811
```

```
<210> SEQ ID NO 92
<211> LENGTH: 402
<212> TYPE: DNA
<213> ORGANISM: Aquabirnavirus infect. pancreatic necrosis virus

<400> SEQUENCE: 92

atgcaagatg aacacaaaca aggcaaccgc aacttacctg aaatccatta tgcttccaga     60

gactggacca gcaagcatcc cggatgacac aacggagaga cacatcctaa aacaagagac    120

ctcgtcatac aacctagagg tctccgaatc aggaagtggc attcttgtct gtttccctgg    180

ggcaccaggc tcacggatcg gtgcacacta cagatggaat gcgaaccaga cggggctgga    240

gttcgaccag tggctggaga cgtcgcagga cctgaagaaa gccttcaact acgggaggct    300

gatctcaagg aaatacgaca tccaaagctc cacactaccg gccggtctct atgctctgaa    360

cgggacgctc aacgctgcca ccttcgaagg cagtctgtct ga                       402
```

```
<210> SEQ ID NO 93
<211> LENGTH: 1359
<212> TYPE: DNA
<213> ORGANISM: Aquabirnavirus infect. pancreatic necrosis virus

<400> SEQUENCE: 93

atgaacacaa acaaggcaac cgcaacttac ctgaaatcca ttatgcttcc agagactgga     60

ccagcaagca tcccggatga cacaacggag agacacatcc taaaacaaga gacctcgtca    120

tacaacctag aggtctccga atcaggaagt ggcattcttg tctgtttccc tggggcacca    180

ggctcacgga tcggtgcaca ctacagatgg aatgcgaacc agacggggct ggagttcgac    240

cagtggctgg agacgtcgca ggacctgaag aaagccttca actacgggag gctgatctca    300
```

aggaaatacg acatccaaag ctccacacta ccggccggtc tctatgctct gaacgggacg 360
ctcaacgctg ccaccttcga aggcagtctg tctgaggtgg agagcctgac ctacaacagc 420
ctgatgtccc taacaacgaa cccccaggac aaagtcaaca accagctggt gaccaaagga 480
gtcacagtcc tgaatctacc aacagggttc gacaaaccat acgtccgcct agaggacgag 540
acaccccagg gtctccagtc aatgaacggg gccaagatga ggtgcacagc tgcaattgca 600
ccgcggaagt acgagatcga cctcccatcc caacgcctac cccccgttcc tgcgacagga 660
gccctcacca ctctctatga gggaaacgcc gacatcgtca actccacgac agtgacggga 720
gacataaact tcagtctggc agaacaaccc gcaatcgaga ccaagttcga cttccagctg 780
gacttcatgg gccttgacaa cgacgtccca gttgtcacag tggtcagctc cgtgctggcc 840
acaaatgaca actacagagg agtctcagcc aagatgaccc agtccatccc gaccgagaac 900
atcacaaagc cgatcaccag ggtcaagctg tcatacaaga tcaaccagca gacagcaatc 960
ggcaacgtcg ccaccctggg cacaatgggt ccagcatccg tctccttctc atcagggaac 1020
ggaaatgtcc ctggcgtgct cagaccaatc acactggtgg cctatgagaa gatgacaccg 1080
ctgtccatcc tgaccgtagc tggagtgtcc aactacgagc tgatcccaaa cccagaactc 1140
ctcaagaaca tggtgacacg ctatggcaag tatgaccccg aaggtctcaa ctatgccaag 1200
atgatccttt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgg 1359

<210> SEQ ID NO 94
<211> LENGTH: 756
<212> TYPE: DNA
<213> ORGANISM: Aquabirnavirus infect. pancreatic necrosis virus

<400> SEQUENCE: 94
gtcgcagctc ctgtactgtc cacgctgttt ccaatggcag caccactcat aggaatggca 60
gaccaattca ttggagatct caccaagacc aacgcagcag gcggaaggta ccactccatg 120
gccgcaggag ggcgccacaa agacgtgctt gagtcctggg caagcggagg gcccgacgga 180
aaattctccc gagccctcaa gaacaggctg gagtccgcca actacgagga agtcgagctt 240
ccacccccct caaaaggagt catcgtccct gtggtgcaca cagtcaagag tgcaccaggc 300
gaggcattcg ggtccctggc aatcataatt ccaggggagt accccgagct tctagatgcc 360
aaccagcagg tcctatccca cttcgcaaac gacaccggga gcgtgtgggg cataggagag 420
gacataccct tcgagggaga caacatgtgc tacactgcac tcccactcaa ggagatcaaa 480
agaaacggga acatagtagt cgagaagatc tttgctggac caatcatggg tccctctgct 540
caactaggac tgtccctact tgtgaacgac atcgaggacg gagttccaag gatggtattc 600
accggcgaaa tcgccgatga cgaggagaca atcataccaa tctgcggtgt agacatcaaa 660
gccatcgcag cccatgaaca agggctgcca ctcatcggca accaaccagg agtggacgag 720
gaggtgcgaa acacatccct ggccgcacac ctgatc 756

<210> SEQ ID NO 95
<211> LENGTH: 645
<212> TYPE: DNA
<213> ORGANISM: Aquabirnavirus infect. pancreatic necrosis virus

<400> SEQUENCE: 95
atcaagtacc tgggagagct gatggcatca aatgcatccg ggatggacga ggaactgcaa 60

-continued

```
cgcctcctga acgccacaat ggcacgggcc aaagaagtcc aggacgccga gatctacaaa    120

cttctcaagc tcatggcatg gaccagaaag aacgacctca ccgaccacat gtacgagtgg    180

tcaaaagagg accccaatgc actaaagttc ggaaagctca tcagcacgcc accaaagcac    240

cccgagaagc ccaaaggacc agaccaacac cacgcccaag aggcgagagc cacccgcata    300

tcactggacg ccgtgagagc cggggcggac ttcgccacac cggaatgggt cgcgctgaac    360

aactaccgcg gcccatctcc cgggcagttc aagtactacc tgatcactgg acgagaacca    420

gaaccaggcg acgagtacga ggactacata aaacaaccca ttgtgaaacc gaccgacatg    480

aacaaaatca gacgtctagc caacagtgtg tacggcctcc cacaccagga accagcacca    540

gaggagttct acgatgcagt tgcagctgta ttcgcacaga acggaggcag aggtcccgac    600

caggaccaaa tgcaagacct cagggagctc gcaagacaga tgaaa                    645
```

```
<210> SEQ ID NO 96
<211> LENGTH: 2818
<212> TYPE: DNA
<213> ORGANISM: Aquabirnavirus infect. pancreatic necrosis virus

<400> SEQUENCE: 96

atgcaagatg aacacaaaca aggcaaccgc aacttacttg aaatccatta tgcttccaga     60

gactggacca gcaagcatcc cggacgacat aacggagaga cacatcttaa aacaagagac    120

ctcgtcatac aacttagagg tctccgaatc aggaagtggc attcttgttt gtttccctgg    180

ggcaccaggc tcacggatcg gcgcacacta cagatggaat gcgaaccaga cggggctgga    240

gttcgaccag tggctggaga cgtcgcagga cctgaagaaa gccttcaact acgggaggct    300

gatctcaagg aaatacgaca ttcaaagctc cacactaccg gccggtctct atgctctgaa    360

cgggacgctc aacgccgcca ccttcgaagg cagtctgtct gaggtggaga gcctgaccta    420

caacagcctg atgtccctaa caacgaaccc ccaggacaaa gtcaacaacc agctggtgac    480

caaaggagtc acagtcctga atctaccaac agggttcgac aagccatacg tccgcctaga    540

ggacgagaca ccccagggtc tccagtcaat gaacggggcc aagatgaggt gcacagctgc    600

aattgcacca cggaggtacg agatcgacct cccatcccaa cgcctacccc ccgtccctgc    660

gacaggagcc ctcaccactc tctacgaggg aaacgccgac atcgtcaact caacaacagt    720

gacgggagat ataaacttca gtctggcaga acaacccgca gtcgagacca agttcgactt    780

ccagctggac ttcatgggcc ttgacaatga cgtcccagtg gtcacagtgg tcagctccgt    840

gctggccaca aacgacaact acagaggagt ctcagccaag atgacccagt ccatcccgac    900

cgagaacatc accaagccga tcaccagggt caagctgtca tacaagatca accaacagac    960

agcaatcggc aatgtcgcca ccctgggcac aatgggtcca gcatccgtct ccttctcatc   1020

ggggaacgga aacgtccccg gcgtgctcag accaatcaca ctggtggcct atgagaagat   1080

gacaccgctg tccatcctga ccgtggctgg agtgtccaac tacgagctga tcccaaaccc   1140

agaactcctc aagaacatgg tgacacgcta tggcaagtat gaccccgagg gtctcaacta   1200

tgccaagatg atcctgtccc acagggaaga gctggacatc aggacagtgt ggaggacaga   1260

ggagtacaag gagaggacca gagtcttcaa cgaaatcacg gacttctcca gtgacctgcc   1320

cacgtcaaag gcatggggct ggagagacat agtcagagga attcggaaag tcgcagctcc   1380

tgtactgtcc acgctgtttc caatggcagc accactcata ggaatggcag accaattcat   1440

tggagatctc accaagacca acgcagcagg cggaaggtac cactccatgg ccgcaggagg   1500

gcgctacaaa gacgtgctcg agtcctgggc aagcggaggg cccgacggaa gattctcccg   1560
```

-continued agccctcaaa aaccggctgg agtccgccaa ctacgaggaa gtcgagcttc caccccccctc 1620 aaaaggagtc atcgtccctg tggtgcacac agtcaagagt gcaccaggcg aggcattcgg 1680
gtccctggca atcataattc caggggagta ccccgagctt ctagatgcca accagcaggt 1740
cctatcccac ttcgcaaacg acaccgggag cgtgtggggc ataggagagg acataccctt 1800
cgagggagac aacatgtgct acactgcact cccactcaag gagatcaaaa gaaacgggaa 1860
catagtagtc gagaagatct ttgctggacc aatcatgggt ccctctgctc aactaggact 1920
gtccctactt gtgaacgaca tcgaggacgg agttccaagg atggtattca ccggcgaaat 1980
cgccgatgac gaggagacaa tcataccaat ctgcggtgta gacatcaaag ccatcgcagc 2040
ccatgaacaa gggctgccac tcatcggcaa ccaaccagga gtggacgagg aggtgcgaaa 2100
cacatccctg gccgcacacc tgatccagac cggaaccctg cccgtacaac gcgcaaaggg 2160
ctccaacaag aggatcaagt acctgggaga gctgatggca tcaaatgcat ccgggatgga 2220
cgaggaactg caacgcctcc tgaacgccac aatggcacgg gccaaagaag tccaggacgc 2280
cgagatctac aaacttctta agctcatggc atggaccaga aagaacgacc tcaccgacca 2340
catgtacgag tggtcaaaag aggaccccga tgcactaaag ttcggaaagc tcatcagcac 2400
gccaccaaag caccccgaga agcccaaagg accagaccaa caccatgccc aagaggcgag 2460
agccacccgc atatcactgg acgccgtgag agccggggcg gacttcgcca caccggaatg 2520
ggtcgcgctg aacaactacc gcggcccatc tcccgggcag ttcaagtact acctgatcac 2580
tggacgagaa ccagaaccag gcgacgagta cgaggactac ataaaacaac ccattgtgaa 2640
accgaccgac atgaacaaaa tcagacgtct agccaacagt gtgtacggcc tcccacacca 2700
ggaaccagca ccagaggagt tctacgatgc agttgcagct gtattcgcac agaacggagg 2760
cagaggtccc gaccaggacc aaatgcaaga cctcagggag ctcgcaagac agatgaaa 2818

<210> SEQ ID NO 97
<211> LENGTH: 402
<212> TYPE: DNA
<213> ORGANISM: Aquabirnavirus infect. pancreatic necrosis virus

<400> SEQUENCE: 97
atgcaagatg aacacaaaca aggcaaccgc aacttacttg aaatccatta tgcttccaga 60
gactggacca gcaagcatcc cggacgacat aacggagaga cacatcttaa aacaagagac 120
ctcgtcatac aacttagagg tctccgaatc aggaagtggc attcttgttt gtttccctgg 180
ggcaccaggc tcacggatcg gcgcacacta cagatggaat gcgaaccaga cggggctgga 240
gttcgaccag tggctggaga cgtcgcagga cctgaagaaa gccttcaact acgggaggct 300
gatctcaagg aaatacgaca ttcaaagctc cacactaccg gccggtctct atgctctgaa 360
cgggacgctc aacgccgcca ccttcgaagg cagtctgtct ga 402

<210> SEQ ID NO 98
<211> LENGTH: 1359
<212> TYPE: DNA
<213> ORGANISM: Aquabirnavirus infect. pancreatic necrosis virus

<400> SEQUENCE: 98
atgaacacaa acaaggcaac cgcaacttac ttgaaatcca ttatgcttcc agagactgga 60
ccagcaagca tcccggacga cataacggag agacacatct taaaacaaga gacctcgtca 120
tacaacttag aggtctccga atcaggaagt ggcattcttg tttgtttccc tggggcacca 180
ggctcacgga tcggcgcaca ctacagatgg aatgcgaacc agacggggct ggagttcgac 240

-continued

```
cagtggctgg agacgtcgca ggacctgaag aaagccttca actacgggag gctgatctca    300

aggaaatacg acattcaaag ctccacacta ccggccggtc tctatgctct gaacgggacg    360

ctcaacgccg ccaccttcga aggcagtctg tctgaggtgg agagcctgac ctacaacagc    420

ctgatgtccc taacaacgaa cccccaggac aaagtcaaca accagctggt gaccaaagga    480

gtcacagtcc tgaatctacc aacagggttc gacaagccat acgtccgcct agaggacgag    540

acaccccagg gtctccagtc aatgaacggg gccaagatga ggtgcacagc tgcaattgca    600

ccacggaggt acgagatcga cctcccatcc caacgcctac cccccgtccc tgcgacagga    660

gccctcacca ctctctacga gggaaacgcc gacatcgtca actcaacaac agtgacggga    720

gatataaact tcagtctggc agaacaaccc gcagtcgaga ccaagttcga cttccagctg    780

gacttcatgg gccttgacaa tgacgtccca gtggtcacag tggtcagctc cgtgctggcc    840

acaaacgaca actacagagg agtctcagcc aagatgaccc agtccatccc gaccgagaac    900

atcaccaagc cgatcaccag ggtcaagctg tcatacaaga tcaaccaaca gacagcaatc    960

ggcaatgtcg ccaccctggg cacaatgggt ccagcatccg tctccttctc atcggggaac   1020

ggaaacgtcc ccggcgtgct cagaccaatc acactggtgg cctatgagaa gatgacaccg   1080

ctgtccatcc tgaccgtggc tggagtgtcc aactacgagc tgatcccaaa cccagaactc   1140

ctcaagaaca tggtgacacg ctatggcaag tatgaccccg agggtctcaa ctatgccaag   1200

atgatcctgt cccacaggga agagctggac atcaggacag tgtggaggac agaggagtac   1260

aaggagagga ccagagtctt caacgaaatc acggacttct ccagtgacct gcccacgtca   1320

aaggcatggg gctggagaga catagtcaga ggaattcgg                          1359
```

```
<210> SEQ ID NO 99
<211> LENGTH: 756
<212> TYPE: DNA
<213> ORGANISM: Aquabirnavirus infect. pancreatic necrosis virus

<400> SEQUENCE: 99

gtcgcagctc ctgtactgtc cacgctgttt ccaatggcag caccactcat aggaatggca     60

gaccaattca ttggagatct caccaagacc aacgcagcag gcggaaggta ccactccatg    120

gccgcaggag ggcgctacaa agacgtgctc gagtcctggg caagcggagg gcccgacgga    180

agattctccc gagccctcaa aaaccggctg gagtccgcca actacgagga agtcgagctt    240

ccaccccccct caaaaggagt catcgtccct gtggtgcaca cagtcaagag tgcaccaggc    300

gaggcattcg ggtccctggc aatcataatt ccaggggagt accccgagct tctagatgcc    360

aaccagcagg tcctatccca cttcgcaaac gacaccggga gcgtgtgggg cataggagag    420

gacataccct tcgagggaga caacatgtgc tacactgcac tcccactcaa ggagatcaaa    480

agaaacggga acatagtagt cgagaagatc tttgctggac caatcatggg tccctctgct    540

caactaggac tgtccctact tgtgaacgac atcgaggacg gagttccaag gatggtattc    600

accggcgaaa tcgccgatga cgaggagaca atcataccaa tctgcggtgt agacatcaaa    660

gccatcgcag cccatgaaca agggctgcca ctcatcggca accaaccagg agtggacgag    720

gaggtgcgaa acacatccct ggccgcacac ctgatc                              756
```

```
<210> SEQ ID NO 100
<211> LENGTH: 645
<212> TYPE: DNA
<213> ORGANISM: Aquabirnavirus infect. pancreatic necrosis virus

<400> SEQUENCE: 100
```

-continued

```
atcaagtacc tgggagagct gatggcatca aatgcatccg ggatggacga ggaactgcaa     60

cgcctcctga acgccacaat ggcacgggcc aaagaagtcc aggacgccga gatctacaaa    120

cttcttaagc tcatggcatg gaccagaaag aacgacctca ccgaccacat gtacgagtgg    180

tcaaaagagg accccgatgc actaaagttc ggaaagctca tcagcacgcc accaaagcac    240

cccgagaagc ccaaaggacc agaccaacac catgcccaag aggcgagagc cacccgcata    300

tcactggacg ccgtgagagc cggggcggac ttcgccacac cggaatgggt cgcgctgaac    360

aactaccgcg gcccatctcc cgggcagttc aagtactacc tgatcactgg acgagaacca    420

gaaccaggcg acgagtacga ggactacata aaacaaccca ttgtgaaacc gaccgacatg    480

aacaaaatca gacgtctagc caacagtgtg tacggcctcc cacaccagga accagcacca    540

gaggagttct acgatgcagt tgcagctgta ttcgcacaga acggaggcag aggtcccgac    600

caggaccaaa tgcaagacct cagggagctc gcaagacaga tgaaa                     645
```

<210> SEQ ID NO 101
<211> LENGTH: 1359
<212> TYPE: DNA
<213> ORGANISM: Aquabirnavirus infect. pancreatic necrosis virus

<400> SEQUENCE: 101

```
atgaacacaa acaaggcaac cgcaacttac ttgaaatcca ttatgcttcc agagactgga     60

ccagcaagca tcccggacga cataacggag agacacatct taaaacaaga gacctcgtca    120

tacaacttag aggtctccga atcaggaagt ggcattcttg tttgtttccc tggggcacca    180

ggctcacgga tcggcgcaca ctacagatgg aatgcgaacc agacggggct ggagttcgac    240

cagtggctgg agacgtcgca ggacctgaag aaagccttca actacgggag gctgatctca    300

aggaaatacg acattcaaag ctccacacta ccggccggtc tctatgctct gaacgggacg    360

ctcaacgccg ccaccttcga aggcagtctg tctgaggtgg agagcctgac ctacaacagc    420

ctgatgtccc taacaacgaa cccccaggac aaagtcaaca accagctggt gaccaaagga    480

gtcacagtcc tgaatctacc aacagggttc gacaagccat acgtccgcct agaggacgag    540

acaccccagg gtctccagtc aatgaacggg gccaagatga ggtgcacagc tgcaattgca    600

ccacggaggt acgagatcga cctcccatcc caacgcctac cccccgtccc tgcgacagga    660

gccctcacca ctctctacga gggaaacgcc gacatcgtca actcaacaac agtgacggga    720

gatataaact tcagtctggc agaacaaccc gcagtcgaga ccaagttcga cttccagctg    780

gacttcatgg gccttgacaa tgacgtccca gtggtcacag tggtcagctc cgtgctggcc    840

acaaacgaca actacagagg agtctcagcc aagatgaccc agtccatccc gaccgagaac    900

atcaccaagc cgatcaccag ggtcaagctg tcatacaaga tcaaccaaca gacagcaatc    960

ggcaatgtcg ccaccctggg cacaatgggt ccagcatccg tccccctctc atcggggaac   1020

ggaaacgtcc ccggcgtgct cagaccaatc acactggtgg cctatgagaa gatgacaccg   1080

ctgtccatcc tgaccgtggc tggagtgtcc aactacgagc tgatcccaaa cccagaactc   1140

ctcaagaaca tggtgacacg ctatggcaag tatgaccccg agggtctcaa ctatgccaag   1200

atgatcctgt cccacaggga agagctggac atcaggacag tgtggaggac agaggagtac   1260

aaggagagga ccagagtctt caacgaaatc acggacttct ccagtgacct gcccacgtca   1320

aaggcatggg gctggagaga catagtcaga ggaattcgg                          1359
```

<210> SEQ ID NO 102
<211> LENGTH: 1359
<212> TYPE: DNA

<213> ORGANISM: Aquabirnavirus infect. pancreatic necrosis virus

<400> SEQUENCE: 102
atgaacacaa acaaggcaac cgcaacttac ctgaaatcca ttatgcttcc agagactgga 60
ccagcaagca tcccggacga cataacggag agacacatct taaaacaaga gacctcgtca 120
tacaacttag aggtctccga atcaggaagt ggcattcttg tttgtttccc tggggcacca 180
ggctcacgga tcggtgcaca ctacagatgg aatgcgaacc agacggggct ggagttcgac 240
cagtggctgg agacgtcgca ggacctgaag aaagccttca actacgggag gctgatctca 300
aggaaatatg acatccaaag ctccacacta ccggccggtc tctatgctct gaacgggacg 360
ctcaacgctg ccaccttcga aggcagtctg tctgaggtgg agagcctgac ctacaacagc 420
ctgatgtccc taacaacgaa cccccaggac aaagtcaaca accagctggt gaccaaagga 480
gtcacagtcc tgaatctacc aacagggttc gacaaaccat acgtccgcct agaggacgag 540
acaccccagg gtctccagtc aatgaacggg gccaagatga ggtgcacagc tgcaattgca 600
ccgcggaggt acgagatcga cctcccatcc caacgcctac cccccgttac tgcgacagga 660
gccctcacca ctctctacga gggaaacgcc gacatcgtca actccacgac agtgacggga 720
gacataaact tcagtctgac agaacaaccc gcagtcgaga ccaagttcga cttccagctg 780
gacttcatgg gccttgacaa cgacgtccca gttgtcacag tggtcagctc cgtgctggcc 840
acaaatgaca actacagagg agtctcagcc aagatgaccc agtccatccc gaccgagaac 900
atcacaaagc cgatcaccag ggtcaagctg tcatacaaga tcaaccagca gacagcaatc 960
ggcaacgtcg ccaccctggg cacaatgggt ccagcatccg tctccttctc atcagggaac 1020
ggaaatgtcc ccggcgtgct cagaccaatc acactggtgg cctatgagaa gatgacaccg 1080
ctgtccatcc tgaccgtagc tggagtgtcc aactacgagc tgatcccaaa cccagaactc 1140
ctaaagaaca tggtgacacg ctatggcaag tacgaccccg aaggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgg 1359

<210> SEQ ID NO 103
<211> LENGTH: 2811
<212> TYPE: DNA
<213> ORGANISM: Aquabirnavirus infect. pancreatic necrosis virus

<400> SEQUENCE: 103
atgaacacaa acaaggcaac cgcaacttac ctgaaatcca ttatgcttcc agagactgga 60
ccagcaagca tcccggacga cataacggag agacacatct taaaacaaga gacctcgtca 120
tacaacttag aggtctccga atcaggaagt ggcattcttg tttgtttccc tggggcacca 180
ggctcacgga tcggtgcaca ctacagatgg aatgcgaacc agacggggct ggagttcgac 240
cagtggctgg agacgtcgca ggacctgaag aaagccttca actacgggag gctgatctca 300
aggaaatacg acatccaaag ctccacacta ccggccggtc tctatgctct gaacgggacg 360
ctcaacgctg ccaccttcga aggcagtctg tctgaggtgg agagcctgac ctacaacagc 420
ctgatgtccc taacaacgaa cccccaggac aaagtcaaca accagctggt gaccaaagga 480
gtcacagtcc tgaatctacc aacagggttc gacaaaccat acgtccgcct agaggacgag 540
acaccccagg gtctccagtc aatgaacggg gccaagatga ggtgcacagc tgcaattgca 600
ccgcggaggt acgagatcga cctcccatcc caacgcctac cccccgttac tgcgacagga 660

-continued

```
gccctcacca ctctctacga gggaaacgcc gacatcgtca actccacgac agtgacggga    720

gacataaact tcagtctgac agaacaaccc gcagtcgaga ccaagttcga cttccagctg    780

gacttcatgg gccttgacaa cgacgtccca gttgtcacag tggtcagctc cgtgctggcc    840

acaaatgaca actacagagg agtctcagcc aagatgaccc agtccatccc gaccgagaac    900

atcacaaagc cgatcaccag ggtcaagctg tcatacaaga tcaaccagca gacagcaatc    960

ggcaacgtcg ccaccctggg cacaatgggt ccagcatccg tctccttctc atcagggaac   1020

gggaatgtcc ccggcgtgct cagaccaatc acactggtgg cctatgagaa gatgacaccg   1080

ctgtccatcc tgaccgtagc tggagtgtcc aactacgagc tgatcccaaa cccagaactc   1140

ctaaagaaca tggtaacacg ctatggcaag tacgaccccg aaggtctcaa ctatgccaag   1200

atgatcctgt cccacaggga agagctggac atcaggacag tgtggaggac agaggagtac   1260

aaggagagga ccagagtctt caacgaaatc acggacttct ccagtgacct gcccacgtca   1320

aaggcatggg gctggagaga catagtcaga ggaattcgga aagtcgcagc tcctgtactg   1380

tccacgctgt ttccaatggc agcaccactc ataggaatgg cagaccaatt cattggagat   1440

ctcaccaaga ccaacgcagc aggcggaagg taccactcca tggccgcagg agggcgccac   1500

aaagacgtgc tcgagtcctg ggcaagcgga gggcccgacg gaaaattctc ccgagccctc   1560

aagaacaggc tggagtccgc caactacgag gaagtcgagc ttccaccccc ctcaaaagga   1620

gtcatcgtcc ctgtggtgca cacagtcaag agtgcaccag gcgaggcatt cgggtccctg   1680

gcaatcataa ttccagggga gtaccccgag cttctagatg ccaaccagca ggtcctatcc   1740

cacttcgcaa acgacaccgg gagcgtgtgg ggcataggag aggacatacc cttcgaggga   1800

gacaacatgt gctacactgc actcccactc aaggagatca aaagaaacgg gaacatagta   1860

gtcgagaaga tctttgctgg accaatcatg ggtccctctg ctcaactagg actgtcccta   1920

cttgtgaacg acatcgagga cggagttcca aggatggtat tcaccggcga aatcgccgat   1980

gacgaggaga caatcatacc aatctgcggt gtagacatca aagccatcgc agcccatgaa   2040

caagggctgc cactcatcgg caaccaacca ggagtggacg aggaggtgcg aaacacatcc   2100

ctggccgcac acctgatcca gaccggaacc ctgcccgtac aacgcgcaaa gggctccaac   2160

aagaggatca agtacctggg agagctgatg gcatcaaatg catccgggat ggacgaggaa   2220

ctgcaacgcc tcctgaacgc cacaatggca cgggccaaag aagtccagga cgccgagatc   2280

tacaaacttc tcaagctcat ggcatggacc agaaagaacg acctcaccga ccacatgtac   2340

gagtggtcaa aagaggaccc caatgcacta aagttcggaa agctcatcag cacgccacca   2400

aagcaccccg agaagcccaa aggaccagac caacaccacg cccaagaggc gagagccacc   2460

cgcatatcac tggacgccgt gagagccggg gcggacttcg ccacaccgga atgggtcgcg   2520

ctgaacaact accgcggccc atctcccggg cagttcaagt actacctgat cactggacga   2580

gaaccagaac caggcgacga gtacgaggac tacataaaac aacccattgt gaaaccgacc   2640

gacatgaaca aaatcagacg tctagccaac agtgtgtacg gcctcccaca ccaggaacca   2700

gcaccagagg agttctacga tgcagttgca gctgtattcg cacagaacgg aggcagaggt   2760

cccgaccagg accaaatgca agacctcagg gagctcgcaa gacagatgaa a            2811
```

<210> SEQ ID NO 104
<211> LENGTH: 402
<212> TYPE: DNA
<213> ORGANISM: Aquabirnavirus infect. pancreatic necrosis virus

<400> SEQUENCE: 104

-continued

```
atgcaagatg aacacaaaca aggcaaccgc aacttacctg aaatccatta tgcttccaga     60

gactggacca gcaagcatcc cggacgacat aacggagaga cacatcttaa aacaagagac    120

ctcgtcatac aacttagagg tctccgaatc aggaagtggc attcttgttt gtttccctgg    180

ggcaccaggc tcacggatcg gtgcacacta cagatggaat gcgaaccaga cggggctgga    240

gttcgaccag tggctggaga cgtcgcagga cctgaagaaa gccttcaact acgggaggct    300

gatctcaagg aaatacgaca tccaaagctc cacactaccg gccggtctct atgctctgaa    360

cgggacgctc aacgctgcca ccttcgaagg cagtctgtct ga                       402
```

<210> SEQ ID NO 105
<211> LENGTH: 1359
<212> TYPE: DNA
<213> ORGANISM: Aquabirnavirus infect. pancreatic necrosis virus

<400> SEQUENCE: 105

```
atgaacacaa acaaggcaac cgcaacttac ctgaaatcca ttatgcttcc agagactgga     60

ccagcaagca tcccggacga cataacggag agacacatct taaaacaaga gacctcgtca    120

tacaacttag aggtctccga atcaggaagt ggcattcttg tttgtttccc tggggcacca    180

ggctcacgga tcggtgcaca ctacagatgg aatgcgaacc agacggggct ggagttcgac    240

cagtggctgg agacgtcgca ggacctgaag aaagccttca actacgggag gctgatctca    300

aggaaatacg acatccaaag ctccacacta ccggccggtc tctatgctct gaacgggacg    360

ctcaacgctg ccaccttcga aggcagtctg tctgaggtgg agagcctgac ctacaacagc    420

ctgatgtccc taacaacgaa cccccaggac aaagtcaaca accagctggt gaccaaagga    480

gtcacagtcc tgaatctacc aacagggttc gacaaaccat acgtccgcct agaggacgag    540

acaccccagg gtctccagtc aatgaacggg gccaagatga ggtgcacagc tgcaattgca    600

ccgcggaggt acgagatcga cctcccatcc caacgcctac cccccgttac tgcgacagga    660

gccctcacca ctctctacga gggaaacgcc gacatcgtca actccacgac agtgacggga    720

gacataaact tcagtctgac agaacaaccc gcagtcgaga ccaagttcga cttccagctg    780

gacttcatgg gccttgacaa cgacgtccca gttgtcacag tggtcagctc cgtgctggcc    840

acaaatgaca actacagagg agtctcagcc aagatgaccc agtccatccc gaccgagaac    900

atcacaaagc cgatcaccag ggtcaagctg tcatacaaga tcaaccagca gacagcaatc    960

ggcaacgtcg ccaccctggg cacaatgggt ccagcatccg tctccttctc atcagggaac   1020

gggaatgtcc ccggcgtgct cagaccaatc acactggtgg cctatgagaa gatgacaccg   1080

ctgtccatcc tgaccgtagc tggagtgtcc aactacgagc tgatcccaaa cccagaactc   1140

ctaaagaaca tggtaacacg ctatggcaag tacgaccccg aaggtctcaa ctatgccaag   1200

atgatcctgt cccacaggga agagctggac atcaggacag tgtggaggac agaggagtac   1260

aaggagagga ccagagtctt caacgaaatc acggacttct ccagtgacct gcccacgtca   1320

aaggcatggg gctggagaga catagtcaga ggaattcgg                          1359
```

<210> SEQ ID NO 106
<211> LENGTH: 756
<212> TYPE: DNA
<213> ORGANISM: Aquabirnavirus infect. pancreatic necrosis virus

<400> SEQUENCE: 106

```
gtcgcagctc ctgtactgtc cacgctgttt ccaatggcag caccactcat aggaatggca     60

gaccaattca ttggagatct caccaagacc aacgcagcag gcggaaggta ccactccatg    120
```

```
gccgcaggag ggcgccacaa agacgtgctc gagtcctggg caagcggagg gcccgacgga    180

aaattctccc gagccctcaa gaacaggctg gagtccgcca actacgagga agtcgagctt    240

ccacccccct caaaaggagt catcgtccct gtggtgcaca cagtcaagag tgcaccaggc    300

gaggcattcg ggtccctggc aatcataatt ccaggggagt accccgagct tctagatgcc    360

aaccagcagg tcctatccca cttcgcaaac gacaccggga gcgtgtgggg cataggagag    420

gacataccct tcgagggaga caacatgtgc tacactgcac tcccactcaa ggagatcaaa    480

agaaacggga acatagtagt cgagaagatc tttgctggac caatcatggg tccctctgct    540

caactaggac tgtccctact tgtgaacgac atcgaggacg gagttccaag gatggtattc    600

accggcgaaa tcgccgatga cgaggagaca atcataccaa tctgcggtgt agacatcaaa    660

gccatcgcag cccatgaaca agggctgcca ctcatcggca accaaccagg agtggacgag    720

gaggtgcgaa acacatccct ggccgcacac ctgatc                              756
```

<210> SEQ ID NO 107
<211> LENGTH: 645
<212> TYPE: DNA
<213> ORGANISM: Aquabirnavirus infect. pancreatic necrosis virus

<400> SEQUENCE: 107

```
atcaagtacc tgggagagct gatggcatca aatgcatccg ggatggacga ggaactgcaa     60

cgcctcctga acgccacaat ggcacgggcc aaagaagtcc aggacgccga gatctacaaa    120

cttctcaagc tcatggcatg gaccagaaag aacgacctca ccgaccacat gtacgagtgg    180

tcaaaagagg accccaatgc actaaagttc ggaaagctca tcagcacgcc accaaagcac    240

cccgagaagc ccaaaggacc agaccaacac cacgcccaag aggcgagagc cacccgcata    300

tcactggacg ccgtgagagc cggggcggac ttcgccacac cggaatgggt cgcgctgaac    360

aactaccgcg gcccatctcc cgggcagttc aagtactacc tgatcactgg acgagaacca    420

gaaccaggcg acgagtacga ggactacata aaacaaccca ttgtgaaacc gaccgacatg    480

aacaaaatca gacgtctagc caacagtgtg tacggcctcc cacaccagga accagcacca    540

gaggagttct acgatgcagt tgcagctgta ttcgcacaga acggaggcag aggtcccgac    600

caggaccaaa tgcaagacct cagggagctc gcaagacaga tgaaa                    645
```

<210> SEQ ID NO 108
<211> LENGTH: 2811
<212> TYPE: DNA
<213> ORGANISM: Aquabirnavirus infect. pancreatic necrosis virus

<400> SEQUENCE: 108

```
atgaacacaa acaaggcaac cgcaacttac ctgaaatcca ttatgcttcc agagactgga     60

ccagcaagca tcccggacga cataacggag agacacatct taaaacaaga gacctcgtca    120

tacaacttag aggtctccga atcaggaagt ggcattcttg tttgtttccc tggggcacca    180

ggctcacgga tcggtgcaca ctacagatgg aatgcgaacc agacggggct ggagttcgac    240

cagtggctgg agacgtcgca ggacctgaag aaagccttca actacgggag gctgatctca    300

aggaaatacg acatccaaag ctccacacta ccggccggtc tctatgctct gaacgggacg    360

ctcaacgctg ccaccttcga aggcagtctg tctgaggtgg agagcctgac ctacaacagc    420

ctgatgtccc taacaacgaa cccccaggac aaagtcaaca accagctggt gaccaaagga    480

gtcacagtcc tgaatctacc aacagggttc gacaaaccat acgtccgcct agaggacgag    540

acaccccagg gtctccagtc aatgaacggg gccaagatga ggtgcacagc tgcaattgca    600
```

-continued ccgcggaggt acgagatcga cctcccatcc caacgcctac cccccgttac tgcgacagga 660
gccctcacca ctctctacga gggaaacgcc gacatcgtca actccacgac agtgacggga 720
gacataaact tcagtctgac agaacaaccc gcagtcgaga ccaagttcga cttccagctg 780
gacttcatgg gccttgacaa cgacgtccca gttgtcacag tggtcagctc cgtgctggcc 840
acaaatgaca actacagagg agtctcagcc aagatgaccc agtccatccc gaccgagaac 900
atcacaaagc cgatcaccag ggtcaagctg tcatacaaga tcaaccagca gacagcaatc 960
ggcaacgtcg ccaccctggg cacaatgggt ccagcatccg tctccttctc atcagggaac 1020
gggaatgtcc ccggcgtgct cagaccaatc acactggtgg cctatgagaa gatgacaccg 1080
ctgtccatcc tgaccgtagc tggagtgtcc aactacgagc tgatcccaaa cccagaactc 1140
ctaaagaaca tggtaacacg ctatggcaag tacgaccccg aaggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgga aagtcgcagc tcctgtactg 1380
tccacgctgt ttccaatggc agcaccactc ataggaatgg cagaccaatt cattggagat 1440
ctcaccaaga ccaacgcagc aggcggaagg taccactcca tggccgcagg agggcgccac 1500
aaagacgtgc tcgagtcctg ggcaagcgga gggcccgacg gaaaattctc ccgagccctc 1560
aagaacaggc tggagtccgc caactacgag gaagtcgagc ttccaccccc ctcaaaagga 1620
gtcatcgtcc ctgtggtgca cacagtcaag agtgcaccag gcgaggcatt cgggtccctg 1680
gcaatcataa ttccagggga gtaccccgag cttctagatg ccaaccagca ggtcctatcc 1740
cacttcgcaa acgacaccgg gagcgtgtgg ggcataggag aggacatacc cttcgaggga 1800
gacaacatgt gctacactgc actcccactc aaggagatca aaagaaacgg gaacatagta 1860
gtcgagaaga tctttgctgg accaatcatg ggtccctctg ctcaactagg actgtcccta 1920
cttgtgaacg acatcgagga cggagttcca aggatggtat tcaccggcga aatcgccgat 1980
gacgaggaga caatcatacc aatctgcggt gtagacatca aagccatcgc agcccatgaa 2040
caagggctgc cactcatcgg caaccaacca ggagtggacg aggaggtgcg aaacacatcc 2100
ctggccgcac acctgatcca gaccggaacc ctgcccgtac aacgcgcaaa gggctccaac 2160
aagaggatca agtacctggg agagctgatg gcatcaaatg catccgggat ggacgaggaa 2220
ctgcaacgcc tcctgaacgc cacaatggca cgggcaaaag aagtccagga cgccgagatc 2280
tacaaacttc tcaagctcat ggcatggacc agaaagaacg acctcaccga ccacatgtac 2340
gagtggtcaa aagaggaccc caatgcacta aagttcggaa agctcatcag cacgccacca 2400
aagcaccccg agaagcccaa aggaccagac caacaccacg cccaagaggc gagagccacc 2460
cgcatatcac tggacgccgt gagagccggg gcggacttcg ccacaccgga atgggtcgcg 2520
ctgaacaact accgcggccc atctcccggg cagttcaagt actacctgat cactggacga 2580
gaaccagaac caggcgacga gtacgaggac tacataaaac aacccattgt gaaaccgacc 2640
gacatgaaca aaatcagacg tctagccaac agtgtgtacg gcctcccaca ccaggaacca 2700
gcaccagagg agttctacga tgcagttgca gctgtattcg cacagaacgg aggcagaggt 2760
cccgaccagg accaaatgca agacctcagg gagctcgcaa gacagatgaa a 2811

<210> SEQ ID NO 109
<211> LENGTH: 402
<212> TYPE: DNA
<213> ORGANISM: Aquabirnavirus infect. pancreatic necrosis virus

<400> SEQUENCE: 109
atgcaagatg aacacaaaca aggcaaccgc aacttacctg aaatccatta tgcttccaga 60
gactggacca gcaagcatcc cggacgacat aacggagaga cacatcttaa aacaagagac 120
ctcgtcatac aacttagagg tctccgaatc aggaagtggc attcttgttt gtttccctgg 180
ggcaccaggc tcacggatcg gtgcacacta cagatggaat gcgaaccaga cggggctgga 240
gttcgaccag tggctggaga cgtcgcagga cctgaagaaa gccttcaact acgggaggct 300
gatctcaagg aaatacgaca tccaaagctc cacactaccg gccggtctct atgctctgaa 360
cgggacgctc aacgctgcca ccttcgaagg cagtctgtct ga 402

<210> SEQ ID NO 110
<211> LENGTH: 1359
<212> TYPE: DNA
<213> ORGANISM: Aquabirnavirus infect. pancreatic necrosis virus

<400> SEQUENCE: 110
atgaacacaa acaaggcaac cgcaacttac ctgaaatcca ttatgcttcc agagactgga 60
ccagcaagca tcccggacga cataacggag agacacatct taaaacaaga gacctcgtca 120
tacaacttag aggtctccga atcaggaagt ggcattcttg tttgtttccc tggggcacca 180
ggctcacgga tcggtgcaca ctacagatgg aatgcgaacc agacggggct ggagttcgac 240
cagtggctgg agacgtcgca ggacctgaag aaagccttca actacgggag gctgatctca 300
aggaaatacg acatccaaag ctccacacta ccggccggtc tctatgctct gaacgggacg 360
ctcaacgctg ccaccttcga aggcagtctg tctgaggtgg agagcctgac ctacaacagc 420
ctgatgtccc taacaacgaa cccccaggac aaagtcaaca accagctggt gaccaaagga 480
gtcacagtcc tgaatctacc aacagggttc gacaaaccat acgtccgcct agaggacgag 540
acaccccagg gtctccagtc aatgaacggg gccaagatga ggtgcacagc tgcaattgca 600
ccgcggaggt acgagatcga cctcccatcc caacgcctac cccccgttac tgcgacagga 660
gccctcacca ctctctacga gggaaacgcc gacatcgtca actccacgac agtgacggga 720
gacataaact tcagtctgac agaacaaccc gcagtcgaga ccaagttcga cttccagctg 780
gacttcatgg gccttgacaa cgacgtccca gttgtcacag tggtcagctc cgtgctggcc 840
acaaatgaca actacagagg agtctcagcc aagatgaccc agtccatccc gaccgagaac 900
atcacaaagc cgatcaccag ggtcaagctg tcatacaaga tcaaccagca gacagcaatc 960
ggcaacgtcg ccaccctggg cacaatgggt ccagcatccg tctccttctc atcagggaac 1020
gggaatgtcc ccggcgtgct cagaccaatc acactggtgg cctatgagaa gatgacaccg 1080
ctgtccatcc tgaccgtagc tggagtgtcc aactacgagc tgatcccaaa cccagaactc 1140
ctaaagaaca tggtaacacg ctatggcaag tacgaccccg aaggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgg 1359

<210> SEQ ID NO 111
<211> LENGTH: 756
<212> TYPE: DNA
<213> ORGANISM: Aquabirnavirus infect. pancreatic necrosis virus

<400> SEQUENCE: 111
gtcgcagctc ctgtactgtc cacgctgttt ccaatggcag caccactcat aggaatggca 60
gaccaattca ttggagatct caccaagacc aacgcagcag gcggaaggta ccactccatg 120
gccgcaggag ggcgccacaa agacgtgctc gagtcctggg caagcggagg gcccgacgga 180
aaattctccc gagccctcaa gaacaggctg gagtccgcca actacgagga agtcgagctt 240 ccaccccccct caaaaggagt catcgtccct gtggtgcaca cagtcaagag tgcaccaggc 300
gaggcattcg ggtccctggc aatcataatt ccaggggagt accccgagct tctagatgcc 360
aaccagcagg tcctatccca cttcgcaaac gacaccggga gcgtgtgggg cataggagag 420
gacataccct tcgagggaga caacatgtgc tacactgcac tcccactcaa ggagatcaaa 480
agaaacggga acatagtagt cgagaagatc tttgctggac caatcatggg tccctctgct 540
caactaggac tgtccctact tgtgaacgac atcgaggacg gagttccaag gatggtattc 600
accggcgaaa tcgccgatga cgaggagaca atcataccaa tctgcggtgt agacatcaaa 660
gccatcgcag cccatgaaca agggctgcca ctcatcggca accaaccagg agtggacgag 720
gaggtgcgaa acacatccct ggccgcacac ctgatc 756

<210> SEQ ID NO 112
<211> LENGTH: 645
<212> TYPE: DNA
<213> ORGANISM: Aquabirnavirus infect. pancreatic necrosis virus

<400> SEQUENCE: 112
atcaagtacc tgggagagct gatggcatca aatgcatccg ggatggacga ggaactgcaa 60
cgcctcctga acgccacaat ggcacgggca aaagaagtcc aggacgccga gatctacaaa 120
cttctcaagc tcatggcatg gaccagaaag aacgacctca ccgaccacat gtacgagtgg 180
tcaaaagagg accccaatgc actaaagttc ggaaagctca tcagcacgcc accaaagcac 240
cccgagaagc ccaaaggacc agaccaacac cacgcccaag aggcgagagc cacccgcata 300
tcactggacg ccgtgagagc cggggcggac ttcgccacac cggaatgggt cgcgctgaac 360
aactaccgcg gcccatctcc cgggcagttc aagtactacc tgatcactgg acgagaacca 420
gaaccaggcg acgagtacga ggactacata aaacaaccca ttgtgaaacc gaccgacatg 480
aacaaaatca gacgtctagc caacagtgtg tacggcctcc cacaccagga accagcacca 540
gaggagttct acgatgcagt tgcagctgta ttcgcacaga acggaggcag aggtcccgac 600
caggaccaaa tgcaagacct cagggagctc gcaagacaga tgaaa 645

<210> SEQ ID NO 113
<211> LENGTH: 2811
<212> TYPE: DNA
<213> ORGANISM: Aquabirnavirus infect. pancreatic necrosis virus

<400> SEQUENCE: 113
atgaacacaa acaaggcaac cgcaacttac ctgaaatcca ttatgcttcc agagactgga 60
ccagcaagca tcccggacga cataacggag agacacatcc taaaacaaga gacctcgtca 120
tacaacttag aggtctccga atcaggaagt ggcattcttg tttgtttccc tggggcacca 180
ggctcacgga tcggtgcaca ctacagatgg aatgcgaacc agacggggct ggagttcgac 240
cagtggctgg agacgtcgca ggacctgaag aaagccttca actacgggag gctgatctca 300
aggaaatacg acatccaaag ctccacacta ccggccggtc tctatgctct gaacgggacg 360
ctcaacgctg ccaccttcga aggcagtctg tccgaggtgg agagcctgac ctacaacagc 420
ctgatgtccc taacaacgaa cccccaggac aaagtcaaca accagctggt gaccaaagga 480
gtcacagtcc tgaatctacc aacagggttc gacaaaccat acgtccgcct agaggacgag 540

-continued

```
acaccccagg gtctccagtc aatgaacggg gccaagatga ggtgcacagc tgcaattgca    600

ccgcggaggt acgagatcga cctcccatcc caacgcctac cccccgttac tgcgacagga    660

gccctcacca ctctctacga gggaaacgcc gacatcgtca actccacgac agtgacggga    720

gacataaact tcagtctgac agaacaaccc gcagtcgaga ccaagttcga cttccagctg    780

gacttcatgg gccttgacaa cgacgtccca gttgtcacag tggtcagctc cgtgctggcc    840

acaaatgaca actacagagg agtctcagcc aagatgaccc agtccatccc gaccgagaac    900

atcacaaagc cgatcaccag ggtcaagctg tcatacaagc tcaaccagca gacagcaatc    960

ggcaacgtcg ccaccctggg cacaatgggc ccagcatccg tctccttctc atcagggaac   1020

gggaatgtcc ccggcgtgct cagaccaatc acactggtgg cctatgagaa gatgacaccg   1080

ctgtccatcc tgaccgtagc tggagtgtcc aactacgagc tgatcccaaa cccagaactc   1140

ctaaagaaca tggtaacacg ctatggcaag tacgaccccg aaggtctcaa ctatgccaag   1200

atgatcctgt cccacaggga agagctggac atcaggacag tgtggaggac agaggagtac   1260

aaggagagga ccagagtctt caacgaaatc acggacttct ccagtgacct gcccacgtca   1320

aaagcatggg gctggagaga catagtcaga ggaattcgga aagtcgcagc tcctgtactg   1380

tccacgctgt ttccaatggc agcaccactc ataggaatgg cagaccaatt cattggagat   1440

ctcaccaaga ccaacgcagc aggcggaagg taccactcca tggccgcagg agggcgccac   1500

aaagacgtgc tcgagtcctg ggcaagcgga gggcccgacg gaaaattctc ccgagccctc   1560

aagaacaggc tggagtccgc caactacgag gaagtcgagc ttccaccccc ctcaaaagga   1620

gtcatcgtcc ctgtggtgca cacagtcaag agtgcaccag gcgaggcatt cgggtccctg   1680

gcaatcataa ttccagggga gtaccccgag cttctagatg ccaaccagca ggtcctatcc   1740

cacttcgcaa acgacaccgg gagcgtgtgg ggcataggag aggacatacc cttcgaggga   1800

gacaacatgt gctacactgc actcccactc aaggagatca aaagaaacgg gaacatagta   1860

gtcgagaaga tctttgctgg accaatcatg ggtccctctg ctcaactagg actgtcccta   1920

cttgtgaacg acatcgagga cggagttcca aggatggtat tcaccggcga aatcgccgat   1980

gacgaggaga caatcatacc aatctgcggt gtagacatca aagccatcgc agcccacgaa   2040

caagggctgc cactcatcgg caaccaacca ggagtggacg aggaggtgcg aaacacatcc   2100

ctggccgcac acctgatcca gaccggaacc ctgcccgtac aacgcgcaaa gggctccaac   2160

aagaggatca agtacctggg agagctgatg gcatcaaatg catccgggat ggacgaggaa   2220

ctgcaacgcc tcctgaacgc cacaatggca cgggccaaag aagtccagga cgccgagatc   2280

tacaaacttc tcaagctcat ggcatggacc agaaagaacg acctcaccga ccacatgtac   2340

gagtggtcaa aagaggaccc caatgcacta aagttcggaa agctcatcag cacgccacca   2400

aagcaccccg agaagcccaa aggaccagac caacaccacg cccaagaggc gagagccacc   2460

cgcatatcac tggacgccgt gagagccggg gcggacttcg ccacaccgga atgggtcgcg   2520

ctgaacaact accgcggccc atctcccggg cagttcaagt actacctgat cactggacga   2580

gaaccagaac caggcgacga gtacgaggac tacataaaac aacccattgt gaaaccgacc   2640

gacatgaaca aaatcagacg tctagccaac agtgtgtacg gcctcccaca ccaggaacca   2700

gcaccagagg agttctacga tgcagttgca gctgtattcg cacagaacgg aggcagaggt   2760

cccgaccagg accaaatgca agacctcagg gagctcgcaa gacagatgaa a            2811
```

<210> SEQ ID NO 114
<211> LENGTH: 402
<212> TYPE: DNA

<213> ORGANISM: Aquabirnavirus infect. pancreatic necrosis virus

<400> SEQUENCE: 114
atgcaagatg aacacaaaca aggcaaccgc aacttacctg aaatccatta tgcttccaga 60
gactggacca gcaagcatcc cggacgacat aacggagaga cacatcctaa aacaagagac 120
ctcgtcatac aacttagagg tctccgaatc aggaagtggc attcttgttt gtttccctgg 180
ggcaccaggc tcacggatcg gtgcacacta cagatggaat gcgaaccaga cggggctgga 240
gttcgaccag tggctggaga cgtcgcagga cctgaagaaa gccttcaact acgggaggct 300
gatctcaagg aaatacgaca tccaaagctc cacactaccg gccggtctct atgctctgaa 360
cgggacgctc aacgctgcca ccttcgaagg cagtctgtcc ga 402

<210> SEQ ID NO 115
<211> LENGTH: 1359
<212> TYPE: DNA
<213> ORGANISM: Aquabirnavirus infect. pancreatic necrosis virus

<400> SEQUENCE: 115
atgaacacaa acaaggcaac cgcaacttac ctgaaatcca ttatgcttcc agagactgga 60
ccagcaagca tcccggacga cataacggag agacacatcc taaaacaaga gacctcgtca 120
tacaacttag aggtctccga atcaggaagt ggcattcttg tttgtttccc tggggcacca 180
ggctcacgga tcggtgcaca ctacagatgg aatgcgaacc agacggggct ggagttcgac 240
cagtggctgg agacgtcgca ggacctgaag aaagccttca actacgggag gctgatctca 300
aggaaatacg acatccaaag ctccacacta ccggccggtc tctatgctct gaacgggacg 360
ctcaacgctg ccaccttcga aggcagtctg tccgaggtgg agagcctgac ctacaacagc 420
ctgatgtccc taacaacgaa cccccaggac aaagtcaaca accagctggt gaccaaagga 480
gtcacagtcc tgaatctacc aacagggttc gacaaaccat acgtccgcct agaggacgag 540
acaccccagg gtctccagtc aatgaacggg gccaagatga ggtgcacagc tgcaattgca 600
ccgcggaggt acgagatcga cctcccatcc caacgcctac cccccgttac tgcgacagga 660
gccctcacca ctctctacga gggaaacgcc gacatcgtca actccacgac agtgacggga 720
gacataaact tcagtctgac agaacaaccc gcagtcgaga ccaagttcga cttccagctg 780
gacttcatgg gccttgacaa cgacgtccca gttgtcacag tggtcagctc cgtgctggcc 840
acaaatgaca actacagagg agtctcagcc aagatgaccc agtccatccc gaccgagaac 900
atcacaaagc cgatcaccag ggtcaagctg tcatacaagc tcaaccagca gacagcaatc 960
ggcaacgtcg ccaccctggg cacaatgggc ccagcatccg tctccttctc atcagggaac 1020
gggaatgtcc ccggcgtgct cagaccaatc acactggtgg cctatgagaa gatgacaccg 1080
ctgtccatcc tgaccgtagc tggagtgtcc aactacgagc tgatcccaaa cccagaactc 1140
ctaaagaaca tggtaacacg ctatggcaag tacgaccccg aaggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaagcatggg gctggagaga catagtcaga ggaattcgg 1359

<210> SEQ ID NO 116
<211> LENGTH: 756
<212> TYPE: DNA
<213> ORGANISM: Aquabirnavirus infect. pancreatic necrosis virus

<400> SEQUENCE: 116

```
gtcgcagctc ctgtactgtc cacgctgttt ccaatggcag caccactcat aggaatggca    60

gaccaattca ttggagatct caccaagacc aacgcagcag gcggaaggta ccactccatg   120

gccgcaggag ggcgccacaa agacgtgctc gagtcctggg caagcggagg gcccgacgga   180

aaattctccc gagccctcaa gaacaggctg gagtccgcca actacgagga agtcgagctt   240

ccacccccct caaaaggagt catcgtccct gtggtgcaca cagtcaagag tgcaccaggc   300

gaggcattcg ggtccctggc aatcataatt ccaggggagt accccgagct tctagatgcc   360

aaccagcagg tcctatccca cttcgcaaac gacaccggga gcgtgtgggg cataggagag   420

gacataccct tcgagggaga caacatgtgc tacactgcac tcccactcaa ggagatcaaa   480

agaaacggga acatagtagt cgagaagatc tttgctggac caatcatggg tccctctgct   540

caactaggac tgtccctact tgtgaacgac atcgaggacg gagttccaag gatggtattc   600

accggcgaaa tcgccgatga cgaggagaca atcataccaa tctgcggtgt agacatcaaa   660

gccatcgcag cccacgaaca agggctgcca ctcatcggca accaaccagg agtggacgag   720

gaggtgcgaa acacatccct ggccgcacac ctgatc                             756
```

<210> SEQ ID NO 117
<211> LENGTH: 645
<212> TYPE: DNA
<213> ORGANISM: Aquabirnavirus infect. pancreatic necrosis virus

<400> SEQUENCE: 117

```
atcaagtacc tgggagagct gatggcatca aatgcatccg ggatggacga ggaactgcaa    60

cgcctcctga acgccacaat ggcacgggcc aaagaagtcc aggacgccga gatctacaaa   120

cttctcaagc tcatggcatg gaccagaaag aacgacctca ccgaccacat gtacgagtgg   180

tcaaaagagg accccaatgc actaaagttc ggaaagctca tcagcacgcc accaaagcac   240

cccgagaagc ccaaaggacc agaccaacac cacgcccaag aggcgagagc cacccgcata   300

tcactggacg ccgtgagagc cggggcggac ttcgccacac cggaatgggt cgcgctgaac   360

aactaccgcg gcccatctcc cgggcagttc aagtactacc tgatcactgg acgagaacca   420

gaaccaggcg acgagtacga ggactacata aaacaaccca ttgtgaaacc gaccgacatg   480

aacaaaatca gacgtctagc caacagtgtg tacggcctcc cacaccagga accagcacca   540

gaggagttct acgatgcagt tgcagctgta ttcgcacaga acggaggcag aggtcccgac   600

caggaccaaa tgcaagacct cagggagctc gcaagacaga tgaaa                   645
```

<210> SEQ ID NO 118
<211> LENGTH: 2811
<212> TYPE: DNA
<213> ORGANISM: Aquabirnavirus infect. pancreatic necrosis virus

<400> SEQUENCE: 118

```
atgaacacaa acaaggcaac cgcaacttac ctgaaatcca ttatgcttcc agagactgga    60

ccagcaagca tcccggacga cataacggag agacacatct taaaacaaga gacctcgtca   120

tacaacttag aggtctccga atcaggaagt ggcattcttg tttgtttccc tggggcacca   180

ggctcacgga tcggtgcaca ctacagatgg aatgcgaacc agacggggct ggagttcgac   240

cagtggctgg agacgtctca ggacctgaag aaagccttca actacgggag gctgatctca   300

aggaaatacg acatccaaag ctccacacta ccggccggtc tctatgctct gaacgggacg   360

ctcaacgctg ccaccttcga aggcagtctg tctgaggtgg agagcctgac ctacaacagc   420

ctgatgtccc taacaacgaa cccccaggac aaagtcaaca accagctggt gaccaaagga   480
```

-continued

```
gtcacagtcc tgaatctacc aacagggttc gacaaaccat acgtccgcct agaggacgag    540
acaccccagg gtctccagtc aatgaacggg gccaagatga ggtgcacagc tgcaattgca    600
ccgcggaggt acgagatcga cctcccatcc caacgcctac cccccgttac tgcgacagga    660
gccctcacca ctctctacga gggaaacgcc gacatcgtca actccacgac agtgacggga    720
gacataaact tcagtctgac agaacaaccc gcagtcgaga ccaagttcga cttccagctg    780
gacttcatgg gccttgacaa cgacgtccca gttgtcacag tggtcagctc cgtgctggcc    840
acaaatgaca actacagagg agtctcagcc aagatgaccc agtccatccc gaccgagaac    900
atcacaaagc cgatcaccag ggtcaagctg tcatacaaga tcaaccagca gacagcaatc    960
ggcaacgtcg ccaccctggg cacaatgggt ccagcatccg tctccttctc atcagggaac   1020
gggaatgtcc ccggcgtgct cagaccaatc acactggtgg cctatgagaa gatgacaccg   1080
ctgtccatcc tgaccgtagc tggagtgtcc aactacgagc tgatcccaaa cccagaactc   1140
ctaaagaaca tggtaacacg ctatggcaag tacgaccccg aaggtctcaa ctatgccaag   1200
atgatcctgt cccacaggga agagctggac atcaggacag tgtggaggac agaggagtac   1260
aaggagagga ccagagtctt caacgaaatc acggacttct ccagtgacct gcccacgtca   1320
aaggcatggg gctggagaga catagtcaga ggaattcgga aagtcgcagc tcctgtactg   1380
tccacgctgt ttccaatggc agcaccactc ataggaatgg cagaccaatt cattggagat   1440
ctcaccaaga ccaacgcagc aggcggaagg taccactcca tggccgcagg agggcgctac   1500
aaagacgtgc tcgagtcctg ggcaagcgga gggcccgacg gaaaattctc ccgagccctc   1560
aagaacaggc tggagtccgc caactacgag gaagtcgagc ttccaccccc ctcaaaagga   1620
gtcatcgtcc ctgtggtgca cacagtcaag agtgcaccag gcgaggcatt cgggtccctg   1680
gcaatcataa ttccagggga gtaccccgag cttctagatg ccaaccagca ggtcctatcc   1740
cacttcgcaa acgacaccgg gagcgtgtgg ggcataggag aggatatacc cttcgaggga   1800
gacaacatgt gctacactgc actcccactc aaggagatca aaagaaacgg gaacatagta   1860
gtcgagaaga tctttgctgg accaatcatg ggtccctctg ctcaactagg actgtcccta   1920
cttgtgaacg acatcgagga cggagttcca aggatggtat tcaccggcga aatcgccgat   1980
gacgaggaga caatcatacc aatctgcggt gtagacatca aagccatcgc agcccatgaa   2040
caagggctgc cactcatcgg caaccaacca ggagtggacg aggaggtgcg aaacacatcc   2100
ctggccgcac acctgatcca gaccggaacc ctgcccgttc aacgcgcaaa gggctccaac   2160
aagaggatca agtacctggg agagctgatg gcatcaaatg catccgggat ggacgaggaa   2220
ctgcaacgcc tcctgaacgc cacaatggca cgggccaaag aagtccagga cgccgagatc   2280
tacaaacttc tcaagctcat ggcatggacc agaaagaacg acctcaccga ccacatgtac   2340
gagtggtcaa aagaggaccc caatgcacta aagttcggaa agctcatcag cacgccacca   2400
aagcaccccg agaagcccaa aggaccagac caacaccatg cccaagaggc gagagccacc   2460
cgcatatcac tggacgccgt gagagccggg gcggacttcg ccacaccgga atgggtcgcg   2520
ctgaacaact accgcggccc atctcccggg cagttcaagt accacctgat cactggacga   2580
gaaccagaac caggcgacga gtacgaggac tacataaaac aacccattgt gaaaccgacc   2640
gacatgaaca aaatcagacg tctagccaac agtgtgtacg gcctcccaca ccaggaacca   2700
gcaccagagg agttctacga tgcagttgca gctgtattcg cacagaacgg aggcagaggt   2760
cccgaccagg accaaatgca agacctcagg gagctcgcaa gacagatgaa a            2811
```

<210> SEQ ID NO 119

<211> LENGTH: 402
<212> TYPE: DNA
<213> ORGANISM: Aquabirnavirus infect. pancreatic necrosis virus

<400> SEQUENCE: 119

```
atgcaagatg aacacaaaca aggcaaccgc aacttacctg aaatccatta tgcttccaga     60
gactggacca gcaagcatcc cggacgacat aacggagaga cacatcttaa aacaagagac    120
ctcgtcatac aacttagagg tctccgaatc aggaagtggc attcttgttt gtttccctgg    180
ggcaccaggc tcacggatcg gtgcacacta cagatggaat gcgaaccaga cggggctgga    240
gttcgaccag tggctggaga cgtctcagga cctgaagaaa gccttcaact acgggaggct    300
gatctcaagg aaatacgaca tccaaagctc cacactaccg gccggtctct atgctctgaa    360
cgggacgctc aacgctgcca ccttcgaagg cagtctgtct ga                       402
```

<210> SEQ ID NO 120
<211> LENGTH: 1359
<212> TYPE: DNA
<213> ORGANISM: Aquabirnavirus infect. pancreatic necrosis virus

<400> SEQUENCE: 120

```
atgaacacaa acaaggcaac cgcaacttac ctgaaatcca ttatgcttcc agagactgga     60
ccagcaagca tcccggacga cataacggag agacacatct taaaacaaga gacctcgtca    120
tacaacttag aggtctccga atcaggaagt ggcattcttg tttgtttccc tggggcacca    180
ggctcacgga tcggtgcaca ctacagatgg aatgcgaacc agacggggct ggagttcgac    240
cagtggctgg agacgtctca ggacctgaag aaagccttca actacgggag gctgatctca    300
aggaaatacg acatccaaag ctccacacta ccggccggtc tctatgctct gaacgggacg    360
ctcaacgctg ccaccttcga aggcagtctg tctgaggtgg agagcctgac ctacaacagc    420
ctgatgtccc taacaacgaa cccccaggac aaagtcaaca accagctggt gaccaaagga    480
gtcacagtcc tgaatctacc aacagggttc gacaaaccat acgtccgcct agaggacgag    540
acaccccagg gtctccagtc aatgaacggg gccaagatga ggtgcacagc tgcaattgca    600
ccgcggaggt acgagatcga cctcccatcc caacgcctac cccccgttac tgcgacagga    660
gccctcacca ctctctacga gggaaacgcc gacatcgtca actccacgac agtgacggga    720
gacataaact tcagtctgac agaacaaccc gcagtcgaga ccaagttcga cttccagctg    780
gacttcatgg gccttgacaa cgacgtccca gttgtcacag tggtcagctc cgtgctggcc    840
acaaatgaca actacagagg agtctcagcc aagatgaccc agtccatccc gaccgagaac    900
atcacaaagc cgatcaccag ggtcaagctg tcatacaaga tcaaccagca gacagcaatc    960
ggcaacgtcg ccaccctggg cacaatgggt ccagcatccg tctccttctc atcagggaac   1020
gggaatgtcc ccggcgtgct cagaccaatc acactggtgg cctatgagaa gatgacaccg   1080
ctgtccatcc tgaccgtagc tggagtgtcc aactacgagc tgatcccaaa cccagaactc   1140
ctaaagaaca tggtaacacg ctatggcaag tacgaccccg aaggtctcaa ctatgccaag   1200
atgatcctgt cccacaggga agagctggac atcaggacag tgtggaggac agaggagtac   1260
aaggagagga ccagagtctt caacgaaatc acggacttct ccagtgacct gcccacgtca   1320
aaggcatggg gctggagaga catagtcaga ggaattcgg                          1359
```

<210> SEQ ID NO 121
<211> LENGTH: 756
<212> TYPE: DNA
<213> ORGANISM: Aquabirnavirus infect. pancreatic necrosis virus

<400> SEQUENCE: 121
gtcgcagctc ctgtactgtc cacgctgttt ccaatggcag caccactcat aggaatggca 60
gaccaattca ttggagatct caccaagacc aacgcagcag gcggaaggta ccactccatg 120
gccgcaggag ggcgctacaa agacgtgctc gagtcctggg caagcggagg gcccgacgga 180
aaattctccc gagccctcaa gaacaggctg gagtccgcca actacgagga agtcgagctt 240 ccaccccccct caaaaggagt catcgtccct gtggtgcaca cagtcaagag tgcaccaggc 300
gaggcattcg ggtccctggc aatcataatt ccaggggagt accccgagct tctagatgcc 360
aaccagcagg tcctatccca cttcgcaaac gacaccggga gcgtgtgggg cataggagag 420
gatataccct tcgagggaga caacatgtgc tacactgcac tcccactcaa ggagatcaaa 480
agaaacggga acatagtagt cgagaagatc tttgctggac caatcatggg tccctctgct 540
caactaggac tgtccctact tgtgaacgac atcgaggacg gagttccaag gatggtattc 600
accggcgaaa tcgccgatga cgaggagaca atcataccaa tctgcggtgt agacatcaaa 660
gccatcgcag cccatgaaca agggctgcca ctcatcggca accaaccagg agtggacgag 720
gaggtgcgaa acacatccct ggccgcacac ctgatc 756

<210> SEQ ID NO 122
<211> LENGTH: 645
<212> TYPE: DNA
<213> ORGANISM: Aquabirnavirus infect. pancreatic necrosis virus

<400> SEQUENCE: 122
atcaagtacc tgggagagct gatggcatca aatgcatccg ggatggacga ggaactgcaa 60
cgcctcctga acgccacaat ggcacgggcc aaagaagtcc aggacgccga gatctacaaa 120
cttctcaagc tcatggcatg gaccagaaag aacgacctca ccgaccacat gtacgagtgg 180
tcaaaagagg accccaatgc actaaagttc ggaaagctca tcagcacgcc accaaagcac 240
cccgagaagc ccaaaggacc agaccaacac catgcccaag aggcgagagc cacccgcata 300
tcactggacg ccgtgagagc cggggcggac ttcgccacac cggaatgggt cgcgctgaac 360
aactaccgcg gcccatctcc cgggcagttc aagtaccacc tgatcactgg acgagaacca 420
gaaccaggcg acgagtacga ggactacata aaacaaccca ttgtgaaacc gaccgacatg 480
aacaaaatca gacgtctagc caacagtgtg tacggcctcc cacaccagga accagcacca 540
gaggagttct acgatgcagt tgcagctgta ttcgcacaga acggaggcag aggtcccgac 600
caggaccaaa tgcaagacct cagggagctc gcaagacaga tgaaa 645

<210> SEQ ID NO 123
<211> LENGTH: 2811
<212> TYPE: DNA
<213> ORGANISM: Aquabirnavirus infect. pancreatic necrosis virus

<400> SEQUENCE: 123
atgaacacaa acaaggcaac cgcaacttac ctgaaatcca ttatgcttcc agagactgga 60
ccagcaagca tcccggacga cataacggag agacacatct taaaacaaga gacctcgtca 120
tacaacttag aggtctccga atcaggaagt ggcattcttg tttgtttccc tggggcacca 180
ggctcacgga tcggtgcaca ctacagatgg aatgcgaacc agacggggct ggagttcgac 240
cagtggctgg agacgtcgca ggacctgaag aaagccttca actacgggag gctgatctca 300
aggaaatatg acatccaaag ctccacacta ccggccggtc tctatgctct gaacgggacg 360
ctcaacgctg ccaccttcga aggcagtctg tctgaggtgg agagcctgac ctacaacagc 420

-continued

```
ctgatgtccc taacaacgaa cccccaggac aaagtcaaca accagctggt gaccaaagga    480
gtcacagtcc tgaatctacc aacagggttc gacaaaccat acgtccgcct agaggacgag    540
acaccccagg gtctccagtc aatgaacggg gccaagatga ggtgcacagc tgcaattgca    600
ccgcggaggt acgagatcga cctcccatcc caacgcctac cccccgttac tgcgacagga    660
gccctcacca ctctctacga gggaaacgcc gacatcgtca actccacgac agtgacggga    720
gacataaact tcagtctgac agaacaaccc gcagtcgaga ccaagttcga cttccagctg    780
gacttcatgg gccttgacaa cgacgtccca gttgtcacag tggtcagctc cgtgctggcc    840
acaaatgaca actacagagg agtctcagcc aagatgaccc agtccatccc gaccgagaac    900
atcacaaagc cgatcaccag ggtcaagctg tcatacaaga tcaaccagca gacagcaatc    960
ggcaacgtcg ccaccctggg cacaatgggt ccagcatccg tctccttctc atcagggaac   1020
ggaaatgtcc ccggcgtgct cagaccaatc acactggtgg cctatgagaa gatgacaccg   1080
ctgtccatcc tgaccgtagc tggagtgtcc aactacgagc tgatcccaaa cccagaactc   1140
ctaaagaaca tggtgacacg ctatggcaag tacgaccccg aaggtctcaa ctatgccaag   1200
atgatcctgt cccacaggga agagctggac atcaggacag tgtggaggac agaggagtac   1260
aaggagagga ccagagtctt caacgaaatc acggacttct ccagtgacct gcccacgtca   1320
aaggcatggg gctggagaga catagtcaga ggaattcgga aagtcgcagc tcctgtactg   1380
tccacgctgt ttccaatggc agcaccactc ataggaatgg cagaccaatt cattggagat   1440
ctcaccaaga ccaacgcagc aggcggaagg taccactcca tggccgcagg agggcgctac   1500
aaagacgtgc tcgagtcctg ggcaagcgga gggcccgacg gaaaattctc ccgagccctc   1560
aagaacaggc tggagtccgc caactacgag gaagtcgagc ttccaccccc ctcaaaagga   1620
gtcatcgtcc ctgtggtgca cacagtcaag agtgcaccag gcgaggcatt cgggtccctg   1680
gcaatcataa ttccagggga gtaccccgag cttctagatg ccaaccagca ggtcctatcc   1740
cacttcgcaa acgacaccgg gagcgtgtgg ggcataggag aggacatacc cttcgaggga   1800
gacaacatgt gctacactgc actcccactc aaggagatca aaagaaacgg gaacatagta   1860
gtcgagaaga tctttgctgg accaatcatg ggtccctctg ctcaactagg actgtcccta   1920
ctagtgaacg acatcgagga cggagttcca aggatggtat tcaccggcga aatcgccgat   1980
gacgaggaga caatcatacc aatctgcggt gtagacatca aagccatcgc agcccatgaa   2040
caagggctgc cactcatcgg caaccaacca ggagtggacg aggaggtgcg aaacacatcc   2100
ctggccgcac acctgatcca gaccggaacc ctgcccgtac aacgcgcaaa gggctccaac   2160
aagaggatca agtacctggg agagctgatg gcatcaaatg catccgggat ggacgaggaa   2220
ctgcaacgcc tcctgaacgc cacaatggca cgggccaaag aagtccagga cgccgagatc   2280
tacaaacttc ttaagctcat ggcatggacc agaaagaacg acctcaccga ccacatgtac   2340
gagtggtcaa aagaggaccc cgatgcacta aagttcggaa agctcatcag cacgccacca   2400
aagcaccccg agaagcccaa aggaccagac caacaccatg cccaagaggc gagagccacc   2460
cgcatatcac tggacgccgt gagagccggg gcggacttcg ccacaccgga atgggtcgcg   2520
ctgaacaact accgcggccc atctcccggg cagttcaagt actacctgat cactggacga   2580
gaaccagaac caggcgacga gtacgaggac tacataaaac aacccattgt gaaaccgacc   2640
gacatgaaca aaatcagacg tctagccaac agtgtgtacg gcctcccaca ccaggaacca   2700
gcaccagagg agttctacga tgcagttgca gctgtattcg cacagaacgg aggcagaggt   2760
cccgaccagg accaaatgca agacctcagg gagctcgcaa gacagatgaa a            2811
```

-continued

<210> SEQ ID NO 124
<211> LENGTH: 402
<212> TYPE: DNA
<213> ORGANISM: Aquabirnavirus infect. pancreatic necrosis virus

<400> SEQUENCE: 124
atgcaagatg aacacaaaca aggcaaccgc aacttacctg aaatccatta tgcttccaga 60
gactggacca gcaagcatcc cggacgacat aacggagaga cacatcttaa aacaagagac 120
ctcgtcatac aacttagagg tctccgaatc aggaagtggc attcttgttt gtttccctgg 180
ggcaccaggc tcacggatcg gtgcacacta cagatggaat gcgaaccaga cggggctgga 240
gttcgaccag tggctggaga cgtcgcagga cctgaagaaa gccttcaact acgggaggct 300
gatctcaagg aaatatgaca tccaaagctc cacactaccg gccggtctct atgctctgaa 360
cgggacgctc aacgctgcca ccttcgaagg cagtctgtct ga 402

<210> SEQ ID NO 125
<211> LENGTH: 1359
<212> TYPE: DNA
<213> ORGANISM: Aquabirnavirus infect. pancreatic necrosis virus

<400> SEQUENCE: 125
atgaacacaa acaaggcaac cgcaacttac ctgaaatcca ttatgcttcc agagactgga 60
ccagcaagca tcccggacga cataacggag agacacatct taaaacaaga gacctcgtca 120
tacaacttag aggtctccga atcaggaagt ggcattcttg tttgtttccc tggggcacca 180
ggctcacgga tcggtgcaca ctacagatgg aatgcgaacc agacggggct ggagttcgac 240
cagtggctgg agacgtcgca ggacctgaag aaagccttca actacgggag gctgatctca 300
aggaaatatg acatccaaag ctccacacta ccggccggtc tctatgctct gaacgggacg 360
ctcaacgctg ccaccttcga aggcagtctg tctgaggtgg agagcctgac ctacaacagc 420
ctgatgtccc taacaacgaa cccccaggac aaagtcaaca accagctggt gaccaaagga 480
gtcacagtcc tgaatctacc aacagggttc gacaaaccat acgtccgcct agaggacgag 540
acaccccagg gtctccagtc aatgaacggg gccaagatga ggtgcacagc tgcaattgca 600
ccgcggaggt acgagatcga cctcccatcc caacgcctac cccccgttac tgcgacagga 660
gccctcacca ctctctacga gggaaacgcc gacatcgtca actccacgac agtgacggga 720
gacataaact tcagtctgac agaacaaccc gcagtcgaga ccaagttcga cttccagctg 780
gacttcatgg gccttgacaa cgacgtccca gttgtcacag tggtcagctc cgtgctggcc 840
acaaatgaca actacagagg agtctcagcc aagatgaccc agtccatccc gaccgagaac 900
atcacaaagc cgatcaccag ggtcaagctg tcatacaaga tcaaccagca gacagcaatc 960
ggcaacgtcg ccaccctggg cacaatgggt ccagcatccg tctccttctc atcagggaac 1020
ggaaatgtcc ccggcgtgct cagaccaatc acactggtgg cctatgagaa gatgacaccg 1080
ctgtccatcc tgaccgtagc tggagtgtcc aactacgagc tgatcccaaa cccagaactc 1140
ctaaagaaca tggtgacacg ctatggcaag tacgaccccg aaggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgg 1359

<210> SEQ ID NO 126
<211> LENGTH: 756
<212> TYPE: DNA

<213> ORGANISM: Aquabirnavirus infect. pancreatic necrosis virus

<400> SEQUENCE: 126
gtcgcagctc ctgtactgtc cacgctgttt ccaatggcag caccactcat aggaatggca 60
gaccaattca ttggagatct caccaagacc aacgcagcag gcggaaggta ccactccatg 120
gccgcaggag ggcgctacaa agacgtgctc gagtcctggg caagcggagg gcccgacgga 180
aaattctccc gagccctcaa gaacaggctg gagtccgcca actacgagga agtcgagctt 240 ccaccccccct caaaaggagt catcgtccct gtggtgcaca cagtcaagag tgcaccaggc 300
gaggcattcg ggtccctggc aatcataatt ccaggggagt accccgagct tctagatgcc 360
aaccagcagg tcctatccca cttcgcaaac gacaccggga gcgtgtgggg cataggagag 420
gacataccct tcgagggaga caacatgtgc tacactgcac tcccactcaa ggagatcaaa 480
agaaacggga acatagtagt cgagaagatc tttgctggac caatcatggg tccctctgct 540
caactaggac tgtccctact agtgaacgac atcgaggacg gagttccaag gatggtattc 600
accggcgaaa tcgccgatga cgaggagaca atcataccaa tctgcggtgt agacatcaaa 660
gccatcgcag cccatgaaca agggctgcca ctcatcggca accaaccagg agtggacgag 720
gaggtgcgaa acacatccct ggccgcacac ctgatc 756

<210> SEQ ID NO 127
<211> LENGTH: 645
<212> TYPE: DNA
<213> ORGANISM: Aquabirnavirus infect. pancreatic necrosis virus

<400> SEQUENCE: 127
atcaagtacc tgggagagct gatggcatca aatgcatccg ggatggacga ggaactgcaa 60
cgcctcctga acgccacaat ggcacgggcc aaagaagtcc aggacgccga gatctacaaa 120
cttcttaagc tcatggcatg gaccagaaag aacgacctca ccgaccacat gtacgagtgg 180
tcaaaagagg accccgatgc actaaagttc ggaaagctca tcagcacgcc accaaagcac 240
cccgagaagc ccaaaggacc agaccaacac catgcccaag aggcgagagc cacccgcata 300
tcactggacg ccgtgagagc cggggcggac ttcgccacac cggaatgggt cgcgctgaac 360
aactaccgcg gcccatctcc cgggcagttc aagtactacc tgatcactgg acgagaacca 420
gaaccaggcg acgagtacga ggactacata aaacaaccca ttgtgaaacc gaccgacatg 480
aacaaaatca gacgtctagc caacagtgtg tacggcctcc cacaccagga accagcacca 540
gaggagttct acgatgcagt tgcagctgta ttcgcacaga acggaggcag aggtcccgac 600
caggaccaaa tgcaagacct cagggagctc gcaagacaga tgaaa 645

<210> SEQ ID NO 128
<211> LENGTH: 2811
<212> TYPE: DNA
<213> ORGANISM: Aquabirnavirus infect. pancreatic necrosis virus

<400> SEQUENCE: 128
atgaacacaa acaaggcaac cgcaacttac ctgaaatcca ttatgcttcc agagactgga 60
ccagcaagca tcccggacga cataacggag agacacatct taaaacaaga gacctcgtca 120
tacaacttag aggtctccga atcaggaagt ggcattcttg tttgtttccc tggggcacca 180
ggctcacgga tcggtgcaca ctacagatgg aatgcgaacc agacggggct ggagttcgac 240
cagtggctgg agacgtcgca ggacctgaag aaagccttca actacgggag gctgatctca 300
aggaaatacg acatccaaag ctccacacta ccggccggtc tctatgctct gaacgggacg 360

-continued

```
ctcaacgctg ccacctttga aggcagtctg tctgaggtgg agagcctgac ctacaacagc    420
ctgatgtccc taacaacgaa cccccaggac aaagtcaaca accagctggt gaccaaagga    480
gtcacagtcc tgaatctacc aacagggttc gacaaaccat acgtccgcct agaggacgag    540
acaccccagg gtctccagtc aatgaacggg gccaagatga ggtgcacagc tgcaattgca    600
ccgcggaggt acgagatcga cctcccatcc caacgcctac cccccgttcc tgcgacagga    660
gccctcacca ctctctacga gggaaacgcc gacatcgtca actccacgac agtgacggga    720
gacataaact tcagtctggc agaacaaccc gcagtcgaga ccaagttcga cttccagctg    780
gacttcatgg gccttgacaa cgacgtccca gttgtcacag tggtcagctc cgtgctggcc    840
acaaatgaca actacagagg agtctcagcc aagatgaccc agtccatccc gaccgagaac    900
atcacaaagc cgatcaccag ggtcaagctg tcatacaaga tcaaccagca gacagcaatc    960
ggcaacgtcg ccaccctggg cacaatgggt ccagcatccg tctccttctc atcagggaac   1020
ggaaatgtcc ccggcgtgct cagaccaatc acactggtgg cctatgagaa gatgacaccg   1080
ctgtccatcc tgaccgtagc tggagtgtcc aactacgagc tgatcccaaa cccagaactc   1140
ctcaagaaca tggtgacacg ctatggcaag tacgaccccg aaggtctcaa ctatgccaag   1200
atgatcctgt cccacaggga agagctggac atcaggacag tgtggaggac agaggagtac   1260
aaggagagga ccagagtctt caacgaaatc acggacttct ccagtgacct gcccacgtca   1320
aaggcatggg gctggagaga catagtcaga ggaattcgga aagtcgcagc tcctgtactg   1380
tccacgctgt ttccaatggc agcaccactc ataggaatgg cagaccaatt cattggagat   1440
ctcaccaaga ccaacgcagc aggcggaagg taccactcca tggccgcagg agggcgccac   1500
aaagacgtgc tcgagtcctg ggcaagcgga gggcccgacg gaaaattctc ccgagccctc   1560
aagaacaggc tggagtccgc caactacgag gaagtcgagc ttccaccccc ctcaaaagga   1620
gtcatcgtcc ctgtggtgca cacagtcaag agtgcaccag gcgaggcatt cgggtccctg   1680
gcaatcataa ttccagggga gtaccccgag cttctagatg ccaaccagca ggtcctatcc   1740
cacttcgcaa acgacaccgg gagcgtgtgg ggcataggag aggacatacc cttcgaggga   1800
gacaacatgt gctacactgc actcccactc aaggagatca aaagaaacgg gaacatagta   1860
gtcgagaaga tctttgctgg accaatcatg ggtccctctg ctcaactagg actgtcccta   1920
cttgtgaacg acatcgagga cggagttcca aggatggtat tcaccggcga aatcgccgat   1980
gacgaggaga caatcatacc aatctgcggt gtagacatca aagccatcgc agcccatgaa   2040
caagggctgc cactcatcgg caaccaacca ggagtggacg aggaggtgcg aaacacatcc   2100
ctggccgcac acctgatcca gaccggaacc ctgcccgtac aacgcgcaaa gggctccaac   2160
aagaggatca agtacctggg agagctgatg gcatcaaatg catccgggat ggacgaggaa   2220
ctgcaacgcc tcctgaacgc cacaatggca cgggccaaag aagtccagga cgccgagatc   2280
tacaaacttc ttaagctcat ggcatggacc agaaagaacg acctcaccga ccacatgtac   2340
gagtggtcaa aagaggaccc cgatgcacta aagttcggaa agctcatcag cacgccacca   2400
aagcaccctg agaagcccaa aggaccagac caacaccacg cccaagaggc gagagccacc   2460
cgcatatcac tggacgccgt gagagccggg gcggacttcg ccacaccgga atgggtcgcg   2520
ctgaacaact accgcggccc atctcccggg cagttcaagt actacctgat caccggacga   2580
gaaccagaac caggcgacga gtacgaggac tacataaaac aacccattgt gaaaccgacc   2640
gacatgaaca aaatcagacg tctagccaac agtgtgtacg gcctcccaca ccaggaacca   2700
gcaccagagg agttctatga tgcagttgca gctgtattcg cacagaacgg aggcagaggt   2760
```

-continued cccgaccagg accaaatgca agacctcagg gagctcgcaa gacagatgaa a 2811

<210> SEQ ID NO 129
<211> LENGTH: 402
<212> TYPE: DNA
<213> ORGANISM: Aquabirnavirus infect. pancreatic necrosis virus

<400> SEQUENCE: 129
atgcaagatg aacacaaaca aggcaaccgc aacttacctg aaatccatta tgcttccaga 60
gactggacca gcaagcatcc cggacgacat aacggagaga cacatcttaa aacaagagac 120
ctcgtcatac aacttagagg tctccgaatc aggaagtggc attcttgttt gtttccctgg 180
ggcaccaggc tcacggatcg gtgcacacta cagatggaat gcgaaccaga cggggctgga 240
gttcgaccag tggctggaga cgtcgcagga cctgaagaaa gccttcaact acgggaggct 300
gatctcaagg aaatacgaca tccaaagctc cacactaccg gccggtctct atgctctgaa 360
cgggacgctc aacgctgcca cctttgaagg cagtctgtct ga 402

<210> SEQ ID NO 130
<211> LENGTH: 1359
<212> TYPE: DNA
<213> ORGANISM: Aquabirnavirus infect. pancreatic necrosis virus

<400> SEQUENCE: 130
atgaacacaa acaaggcaac cgcaacttac ctgaaatcca ttatgcttcc agagactgga 60
ccagcaagca tcccggacga cataacggag agacacatct taaaacaaga gacctcgtca 120
tacaacttag aggtctccga atcaggaagt ggcattcttg tttgtttccc tggggcacca 180
ggctcacgga tcggtgcaca ctacagatgg aatgcgaacc agacggggct ggagttcgac 240
cagtggctgg agacgtcgca ggacctgaag aaagccttca actacgggag gctgatctca 300
aggaaatacg acatccaaag ctccacacta ccggccggtc tctatgctct gaacgggacg 360
ctcaacgctg ccacctttga aggcagtctg tctgaggtgg agagcctgac ctacaacagc 420
ctgatgtccc taacaacgaa cccccaggac aaagtcaaca accagctggt gaccaaagga 480
gtcacagtcc tgaatctacc aacagggttc gacaaaccat acgtccgcct agaggacgag 540
acaccccagg gtctccagtc aatgaacggg gccaagatga ggtgcacagc tgcaattgca 600
ccgcggaggt acgagatcga cctcccatcc caacgcctac cccccgttcc tgcgacagga 660
gccctcacca ctctctacga gggaaacgcc gacatcgtca actccacgac agtgacggga 720
gacataaact tcagtctggc agaacaaccc gcagtcgaga ccaagttcga cttccagctg 780
gacttcatgg gccttgacaa cgacgtccca gttgtcacag tggtcagctc cgtgctggcc 840
acaaatgaca actacagagg agtctcagcc aagatgaccc agtccatccc gaccgagaac 900
atcacaaagc cgatcaccag ggtcaagctg tcatacaaga tcaaccagca gacagcaatc 960
ggcaacgtcg ccaccctggg cacaatgggt ccagcatccg tctccttctc atcagggaac 1020
ggaaatgtcc ccggcgtgct cagaccaatc acactggtgg cctatgagaa gatgacaccg 1080
ctgtccatcc tgaccgtagc tggagtgtcc aactacgagc tgatcccaaa cccagaactc 1140
ctcaagaaca tggtgacacg ctatggcaag tacgaccccg aaggtctcaa ctatgccaag 1200
atgatcctgt cccacaggga agagctggac atcaggacag tgtggaggac agaggagtac 1260
aaggagagga ccagagtctt caacgaaatc acggacttct ccagtgacct gcccacgtca 1320
aaggcatggg gctggagaga catagtcaga ggaattcgg 1359

<210> SEQ ID NO 131

-continued

<211> LENGTH: 756
<212> TYPE: DNA
<213> ORGANISM: Aquabirnavirus infect. pancreatic necrosis virus

<400> SEQUENCE: 131
gtcgcagctc ctgtactgtc cacgctgttt ccaatggcag caccactcat aggaatggca 60
gaccaattca ttggagatct caccaagacc aacgcagcag gcggaaggta ccactccatg 120
gccgcaggag ggcgccacaa agacgtgctc gagtcctggg caagcggagg gcccgacgga 180
aaattctccc gagccctcaa gaacaggctg gagtccgcca actacgagga agtcgagctt 240
ccacccccct caaaaggagt catcgtccct gtggtgcaca cagtcaagag tgcaccaggc 300
gaggcattcg ggtccctggc aatcataatt ccaggggagt accccgagct tctagatgcc 360
aaccagcagg tcctatccca cttcgcaaac gacaccggga gcgtgtgggg catagagag 420 gacataccct tcgagggaga caacatgtgc tacactgcac tcccactcaa ggagatcaaa 480
agaaacggga acatagtagt cgagaagatc tttgctggac caatcatggg tccctctgct 540
caactaggac tgtccctact tgtgaacgac atcgaggacg gagttccaag gatggtattc 600
accggcgaaa tcgccgatga cgaggagaca atcataccaa tctgcggtgt agacatcaaa 660
gccatcgcag cccatgaaca agggctgcca ctcatcggca accaaccagg agtggacgag 720
gaggtgcgaa acacatccct ggccgcacac ctgatc 756

<210> SEQ ID NO 132
<211> LENGTH: 645
<212> TYPE: DNA
<213> ORGANISM: Aquabirnavirus infect. pancreatic necrosis virus

<400> SEQUENCE: 132
atcaagtacc tgggagagct gatggcatca aatgcatccg ggatggacga ggaactgcaa 60
cgcctcctga acgccacaat ggcacgggcc aaagaagtcc aggacgccga gatctacaaa 120
cttcttaagc tcatggcatg gaccagaaag aacgacctca ccgaccacat gtacgagtgg 180
tcaaaagagg accccgatgc actaaagttc ggaaagctca tcagcacgcc accaaagcac 240
cctgagaagc ccaaaggacc agaccaacac cacgcccaag aggcgagagc cacccgcata 300
tcactggacg ccgtgagagc cggggcggac ttcgccacac cggaatgggt cgcgctgaac 360
aactaccgcg gcccatctcc cgggcagttc aagtactacc tgatcaccgg acgagaacca 420
gaaccaggcg acgagtacga ggactacata aaacaaccca ttgtgaaacc gaccgacatg 480
aacaaaatca gacgtctagc caacagtgtg tacggcctcc cacaccagga accagcacca 540
gaggagttct atgatgcagt tgcagctgta ttcgcacaga acggaggcag aggtcccgac 600
caggaccaaa tgcaagacct cagggagctc gcaagacaga tgaaa 645

<210> SEQ ID NO 133
<211> LENGTH: 2811
<212> TYPE: DNA
<213> ORGANISM: Aquabirnavirus infect. pancreatic necrosis virus

<400> SEQUENCE: 133
atgaacacaa acaaggcaac cgcaacttac ctgaaatcca ttatgcttcc agagactgga 60
ccagcaagca tcccggacga cataacggag agacacatct taaaacaaga gacctcgtca 120
tacaacttag aggtctccga atcaggaagt ggcattcttg tttgtttccc tggggcacca 180
ggctcacgga tcggtgcaca ctacagatgg aatgcgaacc agacggggct ggagttcgac 240
cagtggctgg agacgtcgca ggacctgaag aaagccttca actacgggag gctgatctca 300

-continued

```
aggaaatatg acatccaaag ctccacacta ccggccggtc tctatgctct gaacgggacg    360
ctcaacgctg ccaccttcga aggcagtctg tctgaggtgg agagcctgac ctacaacagc    420
ctgatgtccc taacaacgaa cccccaggac aaagtcaaca accagctggt gaccaaagga    480
gtcacagtcc tgaatctacc aacagggttc gacaaaccat acgtccgcct agaggacgag    540
acaccccagg gtctccagtc aatgaacggg gccaagatga ggtgcacagc tgcaattgca    600
ccgcggaggt acgagatcga cctcccatcc caacgcctac cccccgttac tgcgacagga    660
gccctcacca ctctctacga gggaaacgcc gacatcgtca actccacgac agtgacggga    720
gacataaact tcagtctgac agaacaaccc gcagtcgaga ccaagttcga cttccagctg    780
gacttcatgg gccttgacaa cgacgtccca gttgtcacag tggtcagctc cgtgctggcc    840
acaaatgaca actacagagg agtctcagcc aagatgaccc agtccatccc gaccgagaac    900
atcacaaagc cgatcaccag ggtcaagctg tcatacaaga tcaaccagca gacagcaatc    960
ggcaacgtcg ccaccctagg cacaatgggt ccggcatccg tctccttctc atcagggaac   1020
ggaaatgtcc ccggcgtgct cagaccaatc acactggtgg cctatgagaa gatgacaccg   1080
ctgtccatcc tgaccgtagc tggagtgtcc aactacgagc tgatcccaaa cccagaactc   1140
ctaaagaaca tggtgacacg ctatggcaag tacgaccccg aaggtctcaa ctatgccaag   1200
atgatcctgt cccacaggga agagctggac atcaggacag tgtggaggac agaggagtac   1260
aaggagagga ccagagtctt caacgaaatc acggacttct ccagtgacct gcccacgtca   1320
aaggcatggg gctggagaga catagtcaga ggaattcgga aagtcgcagc tcctgtactg   1380
tccacgctgt ttccaatggc agcaccactc ataggaatgg cagaccaatt cattggagat   1440
ctcaccaaga ccaacgcagc aggcggaagg taccactcca tggccgcagg agggcgctac   1500
aaagacgtgc tcgagtcctg ggcaagcgga gggcccgacg gaagattctc ccgagccctc   1560
aaaaacaggc tggagtccgc caactacgag gaagtcgagc ttccaccccc ctcaaaagga   1620
gtcatcgtcc ctgtggtgca cacagtcaag agtgcaccag gcgaggcatt cgggtccctg   1680
gcaatcataa ttccagggga gtaccccgag cttctagatg ccaaccagca ggtcctatcc   1740
cacttcgcaa acgacaccgg gagcgtgtgg ggcataggag aggacatacc cttcgaggga   1800
gacaacatgt gctacactgc actcccactc aaggagatca aaagaaacgg gaacatagta   1860
gtcgagaaga tctttgctgg accaatcatg ggtccctctg ctcaactagg actgtcccta   1920
cttgtgaacg acatcgagga cggagttcca aggatggtat tcaccggcga aatcgccgat   1980
gacgaggaga caatcatacc aatctgcggt gtagacatca aagccatcgc agcccatgaa   2040
caagggctgc cactcatcgg caaccaacca ggagtggacg aggaggtgcg aaacacatcc   2100
ctggccgcac acctgatcca gaccggaacc ctgcccgtac aacgcgcaaa gggctccaac   2160
aagaggatca agtacctggg agagctgatg gcatcaaatg catccgggat ggacgaggaa   2220
ctgcaacgcc tcctgaacgc cacaatggca cgggccaaag aagtccagga cgccgagatc   2280
tacaaacttc ttaagctcat ggcatggacc agaaagaacg acctcaccga ccacatgtac   2340
gagtggtcaa aagaggaccc cgatgcacta aagttcggaa agctcatcag cacgccacca   2400
aagcaccccg agaagcccaa aggaccagac caacaccatg cccaagaggc gagagccacc   2460
cgcatatcac tggacgccgt gagagccggg gcggacttcg ccacaccgga atgggtcgcg   2520
ctgaacaact accgcggccc atctcccggg cagttcaagt actacctgat cactggacga   2580
gaaccagaac caggcgacga gtacgaggac tacataaaac aacccattgt gaaaccgacc   2640
gacatgaaca aaatcagacg tctagccaac agtgtgtacg gcctcccaca ccaggaacca   2700
```

-continued

```
gcaccagagg agttctacga tgcagttgca gctgtattcg cacagaacgg aggcagaggt   2760

cccgaccagg accaaatgca agacctcagg gagctcgcaa gacagatgaa a            2811


<210> SEQ ID NO 134
<211> LENGTH: 402
<212> TYPE: DNA
<213> ORGANISM: Aquabirnavirus infect. pancreatic necrosis virus

<400> SEQUENCE: 134

atgcaagatg aacacaaaca aggcaaccgc aacttacctg aaatccatta tgcttccaga     60

gactggacca gcaagcatcc cggacgacat aacggagaga cacatcttaa aacaagagac    120

ctcgtcatac aacttagagg tctccgaatc aggaagtggc attcttgttt gtttccctgg    180

ggcaccaggc tcacggatcg gtgcacacta cagatggaat gcgaaccaga cggggctgga    240

gttcgaccag tggctggaga cgtcgcagga cctgaagaaa gccttcaact acgggaggct    300

gatctcaagg aaatatgaca tccaaagctc cacactaccg gccggtctct atgctctgaa    360

cgggacgctc aacgctgcca ccttcgaagg cagtctgtct ga                       402


<210> SEQ ID NO 135
<211> LENGTH: 1359
<212> TYPE: DNA
<213> ORGANISM: Aquabirnavirus infect. pancreatic necrosis virus

<400> SEQUENCE: 135

atgaacacaa acaaggcaac cgcaacttac ctgaaatcca ttatgcttcc agagactgga     60

ccagcaagca tcccggacga cataacggag agacacatct taaaacaaga gacctcgtca    120

tacaacttag aggtctccga atcaggaagt ggcattcttg tttgtttccc tggggcacca    180

ggctcacgga tcggtgcaca ctacagatgg aatgcgaacc agacggggct ggagttcgac    240

cagtggctgg agacgtcgca ggacctgaag aaagccttca actacgggag gctgatctca    300

aggaaatatg acatccaaag ctccacacta ccggccggtc tctatgctct gaacgggacg    360

ctcaacgctg ccaccttcga aggcagtctg tctgaggtgg agagcctgac ctacaacagc    420

ctgatgtccc taacaacgaa cccccaggac aaagtcaaca accagctggt gaccaaagga    480

gtcacagtcc tgaatctacc aacagggttc gacaaaccat acgtccgcct agaggacgag    540

acaccccagg gtctccagtc aatgaacggg gccaagatga ggtgcacagc tgcaattgca    600

ccgcggaggt acgagatcga cctcccatcc caacgcctac cccccgttac tgcgacagga    660

gccctcacca ctctctacga gggaaacgcc gacatcgtca actccacgac agtgacggga    720

gacataaact tcagtctgac agaacaaccc gcagtcgaga ccaagttcga cttccagctg    780

gacttcatgg gccttgacaa cgacgtccca gttgtcacag tggtcagctc cgtgctggcc    840

acaaatgaca actacagagg agtctcagcc aagatgaccc agtccatccc gaccgagaac    900

atcacaaagc cgatcaccag ggtcaagctg tcatacaaga tcaaccagca gacagcaatc    960

ggcaacgtcg ccaccctagg cacaatgggt ccggcatccg tctccttctc atcagggaac   1020

ggaaatgtcc ccggcgtgct cagaccaatc acactggtgg cctatgagaa gatgacaccg   1080

ctgtccatcc tgaccgtagc tggagtgtcc aactacgagc tgatcccaaa cccagaactc   1140

ctaaagaaca tggtgacacg ctatggcaag tacgaccccg aaggtctcaa ctatgccaag   1200

atgatcctgt cccacaggga agagctggac atcaggacag tgtggaggac agaggagtac   1260

aaggagagga ccagagtctt caacgaaatc acggacttct ccagtgacct gcccacgtca   1320

aaggcatggg gctggagaga catagtcaga ggaattcgg                          1359
```

<210> SEQ ID NO 136
<211> LENGTH: 402
<212> TYPE: DNA
<213> ORGANISM: Aquabirnavirus infect. pancreatic necrosis virus

<400> SEQUENCE: 136
atgcaagatg aacacaaaca aggcaaccgc aacttacctg aaatccatta tgcttccaga 60
gactggacca gcaagcatcc cggacgacat aacggagaga cacatcttaa aacaagagac 120
ctcgtcatac aacttagagg tctccgaatc aggaagtggc attcttgttt gtttccctgg 180
ggcaccaggc tcacggatcg gtgcacacta cagatggaat gcgaaccaga cggggctgga 240
gttcgaccag tggctggaga cgtcgcagga cctgaagaaa gccttcaact acgggaggct 300
gatctcaagg aaatatgaca tccaaagctc cacactaccg gccggtctct atgctctgaa 360
cgggacgctc aacgctgcca ccttcgaagg cagtctgtct ga 402

<210> SEQ ID NO 137
<211> LENGTH: 645
<212> TYPE: DNA
<213> ORGANISM: Aquabirnavirus infect. pancreatic necrosis virus

<400> SEQUENCE: 137
atcaagtacc tgggagagct gatggcatca aatgcatccg ggatggacga ggaactgcaa 60
cgcctcctga acgccacaat ggcacgggcc aaagaagtcc aggacgccga gatctacaaa 120
cttcttaagc tcatggcatg gaccagaaag aacgacctca ccgaccacat gtacgagtgg 180
tcaaaagagg accccgatgc actaaagttc ggaaagctca tcagcacgcc accaaagcac 240
cccgagaagc ccaaaggacc agaccaacac catgcccaag aggcgagagc cacccgcata 300
tcactggacg ccgtgagagc cggggcggac ttcgccacac cggaatgggt cgcgctgaac 360
aactaccgcg gcccatctcc cgggcagttc aagtactacc tgatcactgg acgagaacca 420
gaaccaggcg acgagtacga ggactacata aaacaaccca ttgtgaaacc gaccgacatg 480
aacaaaatca gacgtctagc caacagtgtg tacggcctcc cacaccagga accagcacca 540
gaggagttct acgatgcagt tgcagctgta ttcgcacaga acggaggcag aggtcccgac 600
caggaccaaa tgcaagacct cagggagctc gcaagacaga tgaaa 645

<210> SEQ ID NO 138
<211> LENGTH: 2811
<212> TYPE: DNA
<213> ORGANISM: Aquabirnavirus infect. pancreatic necrosis virus

<400> SEQUENCE: 138
atgaacacaa acaaggcaac cgcaacttac ctgaaatcca ttatgcttcc agagactgga 60
ccagcaagca tcccggatga cacaacggag agacacatcc taaaacaaga gacctcgtca 120
tacaacctag aggtctccga atcaggaagt ggcattcttg tctgtttccc tggggcacca 180
ggctcacgga tcggtgcaca ctacagatgg aatgcgaacc agacggggct ggagttcgac 240
cagtggctgg agacgtcgca ggacctgaag aaagccttca actacgggag gctgatctca 300
aggaaatacg acatccaaag ctccacacta ccggccggtc tctatgctct gaacgggacg 360
ctcaacgctg ccaccttcga aggcagtctg tctgaggtgg agagcctgac ctacaacagc 420
ctgatgtccc taacaacgaa cccccaggac aaagtcaaca accagctggt gaccaaagga 480
gtcacagtcc tgaatctacc aacagggttc gacaaaccat acgtccgcct agaggacgag 540
acaccccagg gtctccagtc aatgaacggg gccaagatga ggtgcacagc tgcaattgca 600

-continued

```
ccgcggaggt acgagatcga cctcccatcc caacgcctac cccccgttcc tgcgacagga    660
gccctcacca ctctctatga gggaaacgcc gacatcgtca actccacgac agtgacggga    720
gacataaact tcagtctggc agaacaaccc gcaatcgaga ccaagttcga cttccagctg    780
gacttcatgg gccttgacaa cgacgtccca gttgtcacag tggtcagctc cgtgctggcc    840
acaaatgaca actacagagg agtctcagcc aagatgaccc agtccatccc gaccgagaac    900
atcacaaagc cgatcaccag ggtcaagctg tcatacaaga tcaaccagca gacagcaatc    960
ggcaacgtcg ccaccctggg cacaatgggt ccagcatccg tctccttctc atcagggaac   1020
ggaaatgtcc ctggcgtgct cagaccaatc acactggtgg cctatgagaa gatgacaccg   1080
ctgtccatcc tgaccgtagc tggagtgtcc aactacgagc tgatcccaaa cccagaactc   1140
ctcaagaaca tggtgacacg ctatggcaag tatgaccccg aaggtctcaa ctatgccaag   1200
atgatccttt cccacaggga agagctggac atcaggacag tgtggaggac agaggagtac   1260
aaggagagga ccagagtctt caacgaaatc acggacttct ccagtgacct gcccacgtca   1320
aaggcatggg gctggagaga catagtcaga ggaattcgga aagtcgcagc tcctgtactg   1380
tccacgctgt ttccaatggc agcaccactc ataggaatgg cagaccaatt cattggagat   1440
ctcaccaaga ccaacgcagc aggcggaagg taccactcca tggccgcagg agggcgccac   1500
aaagacgtgc tcgagtcctg ggcaagcgga gggcccgacg gaaaattctc ccgagccctc   1560
aagaacaggc tggagtccgc caactacgag gaagtcgagc ttccaccccc ctcaaaagga   1620
gtcatcgtcc ctgtggtgca cacagtcaag agtgcaccag gcgaggcatt cgggtccctg   1680
gcaatcataa ttccagggga gtaccccgag cttctagatg ccaaccagca ggtcctatcc   1740
cacttcgcaa acgacaccgg gagcgtgtgg ggcataggag aggacatacc cttcgaggga   1800
gacaacatgt gctacactgc actcccactc aaggagatca aaagaaacgg gaacatagta   1860
gtcgagaaga tctttgctgg accaatcatg ggtccctctg ctcaactagg actgtcccta   1920
cttgtgaacg acatcgagga cggagttcca aggatggtat tcaccggcga aatcgccgat   1980
gacgaggaga caatcatacc aatctgcggt gtagacatca aagccatcgc agcccatgaa   2040
caagggctgc cactcatcgg caaccaacca ggagtggacg aggaggtgcg aaacacatcc   2100
ctggccgcac acctgatcca gaccggaacc ctgcccgtac aacgcgcaaa gggctccaac   2160
aagaggatca agtacctggg agagctgatg gcatcaaatg catccgggat ggacgaggaa   2220
ctgcaacgcc tcctgaacgc cacaatggca cgggccaaag aagtccagga cgccgagatc   2280
tacaaacttc ttaggctcat ggcatggacc agaaagaacg acctcaccga ccacatgtac   2340
gagtggtcaa aagaggaccc cgatgcacta aagttcggaa agctcatcag cacgccacca   2400
aagcaccctg agaagcccaa aggaccagac caacaccacg cccaagaggc gagagccacc   2460
cgcatatcac tggacgccgt gagagccggg gcggacttcg ccacaccaga atgggtcgcg   2520
ctgaacaact accgcggccc atctcccggg cagttcaagt actacctgat cactggacga   2580
gaaccagaac caggcgacga gtacgaggac tacataaaac aacccattgt gaaaccgacc   2640
gacatgaaca aaatcagacg tctagccaac agtgtgtacg gcctcccaca ccaggaacca   2700
gcaccagagg agttctacga tgcagttgca gctgtattcg cacagaacgg aggcagaggt   2760
cccgaccagg accaaatgca agacctcagg gagctcgcaa gacagatgaa a            2811
```

<210> SEQ ID NO 139
<211> LENGTH: 402
<212> TYPE: DNA
<213> ORGANISM: Aquabirnavirus infect. pancreatic necrosis virus

<400> SEQUENCE: 139

```
atgcaagatg aacacaaaca aggcaaccgc aacttacctg aaatccatta tgcttccaga      60
gactggacca gcaagcatcc cggatgacac aacggagaga cacatcctaa aacaagagac     120
ctcgtcatac aacctagagg tctccgaatc aggaagtggc attcttgtct gtttccctgg     180
ggcaccaggc tcacggatcg gtgcacacta cagatggaat gcgaaccaga cggggctgga     240
gttcgaccag tggctggaga cgtcgcagga cctgaagaaa gccttcaact acgggaggct     300
gatctcaagg aaatacgaca tccaaagctc cacactaccg gccggtctct atgctctgaa     360
cgggacgctc aacgctgcca ccttcgaagg cagtctgtct ga                        402
```

<210> SEQ ID NO 140
<211> LENGTH: 1359
<212> TYPE: DNA
<213> ORGANISM: Aquabirnavirus infect. pancreatic necrosis virus

<400> SEQUENCE: 140

```
atgaacacaa acaaggcaac cgcaacttac ctgaaatcca ttatgcttcc agagactgga      60
ccagcaagca tcccggatga cacaacggag agacacatcc taaaacaaga gacctcgtca     120
tacaacctag aggtctccga atcaggaagt ggcattcttg tctgtttccc tggggcacca     180
ggctcacgga tcggtgcaca ctacagatgg aatgcgaacc agacggggct ggagttcgac     240
cagtggctgg agacgtcgca ggacctgaag aaagccttca actacgggag gctgatctca     300
aggaaatacg acatccaaag ctccacacta ccggccggtc tctatgctct gaacgggacg     360
ctcaacgctg ccaccttcga aggcagtctg tctgaggtgg agagcctgac ctacaacagc     420
ctgatgtccc taacaacgaa cccccaggac aaagtcaaca accagctggt gaccaaagga     480
gtcacagtcc tgaatctacc aacagggttc gacaaaccat acgtccgcct agaggacgag     540
acaccccagg gtctccagtc aatgaacggg gccaagatga ggtgcacagc tgcaattgca     600
ccgcggaggt acgagatcga cctcccatcc caacgcctac cccccgttcc tgcgacagga     660
gccctcacca ctctctatga gggaaacgcc gacatcgtca actccacgac agtgacggga     720
gacataaact tcagtctggc agaacaaccc gcaatcgaga ccaagttcga cttccagctg     780
gacttcatgg gccttgacaa cgacgtccca gttgtcacag tggtcagctc cgtgctggcc     840
acaaatgaca actacagagg agtctcagcc aagatgaccc agtccatccc gaccgagaac     900
atcacaaagc cgatcaccag ggtcaagctg tcatacaaga tcaaccagca gacagcaatc     960
ggcaacgtcg ccaccctggg cacaatgggt ccagcatccg tctccttctc atcagggaac    1020
ggaaatgtcc ctggcgtgct cagaccaatc acactggtgg cctatgagaa gatgacaccg    1080
ctgtccatcc tgaccgtagc tggagtgtcc aactacgagc tgatcccaaa cccagaactc    1140
ctcaagaaca tggtgacacg ctatggcaag tatgaccccg aaggtctcaa ctatgccaag    1200
atgatccttt cccacaggga agagctggac atcaggacag tgtggaggac agaggagtac    1260
aaggagagga ccagagtctt caacgaaatc acggacttct ccagtgacct gcccacgtca    1320
aaggcatggg gctggagaga catagtcaga ggaattcgg                           1359
```

<210> SEQ ID NO 141
<211> LENGTH: 756
<212> TYPE: DNA
<213> ORGANISM: Aquabirnavirus infect. pancreatic necrosis virus

<400> SEQUENCE: 141

```
gtcgcagctc ctgtactgtc cacgctgttt ccaatggcag caccactcat aggaatggca      60
```

-continued

```
gaccaattca ttggagatct caccaagacc aacgcagcag gcggaaggta ccactccatg    120

gccgcaggag ggcgccacaa agacgtgctc gagtcctggg caagcggagg gcccgacgga    180

aaattctccc gagccctcaa gaacaggctg gagtccgcca actacgagga agtcgagctt    240

ccacccccct caaaaggagt catcgtccct gtggtgcaca cagtcaagag tgcaccaggc    300

gaggcattcg ggtccctggc aatcataatt ccaggggagt accccgagct tctagatgcc    360

aaccagcagg tcctatccca cttcgcaaac gacaccggga gcgtgtgggg cataggagag    420

gacataccct tcgagggaga caacatgtgc tacactgcac tcccactcaa ggagatcaaa    480

agaaacggga acatagtagt cgagaagatc tttgctggac caatcatggg tccctctgct    540

caactaggac tgtccctact tgtgaacgac atcgaggacg gagttccaag gatggtattc    600

accggcgaaa tcgccgatga cgaggagaca atcataccaa tctgcggtgt agacatcaaa    660

gccatcgcag cccatgaaca agggctgcca ctcatcggca accaaccagg agtggacgag    720

gaggtgcgaa acacatccct ggccgcacac ctgatc                              756
```

<210> SEQ ID NO 142
<211> LENGTH: 645
<212> TYPE: DNA
<213> ORGANISM: Aquabirnavirus infect. pancreatic necrosis virus

<400> SEQUENCE: 142

```
atcaagtacc tgggagagct gatggcatca aatgcatccg ggatggacga ggaactgcaa     60

cgcctcctga acgccacaat ggcacgggcc aaagaagtcc aggacgccga gatctacaaa    120

cttcttaggc tcatggcatg gaccagaaag aacgacctca ccgaccacat gtacgagtgg    180

tcaaaagagg accccgatgc actaaagttc ggaaagctca tcagcacgcc accaaagcac    240

cctgagaagc ccaaaggacc agaccaacac cacgcccaag aggcgagagc cacccgcata    300

tcactggacg ccgtgagagc cggggcggac ttcgccacac cagaatgggt cgcgctgaac    360

aactaccgcg gcccatctcc cgggcagttc aagtactacc tgatcactgg acgagaacca    420

gaaccaggcg acgagtacga ggactacata aaacaaccca ttgtgaaacc gaccgacatg    480

aacaaaatca gacgtctagc caacagtgtg tacggcctcc cacaccagga accagcacca    540

gaggagttct acgatgcagt tgcagctgta ttcgcacaga acggaggcag aggtcccgac    600

caggaccaaa tgcaagacct cagggagctc gcaagacaga tgaaa                    645
```

<210> SEQ ID NO 143
<211> LENGTH: 159
<212> TYPE: DNA
<213> ORGANISM: Artificial Sequence
<220> FEATURE:
<223> OTHER INFORMATION: Recombinant nucleic acid sequence - Glycine-measles-glycine-tetanus (GMGT) cassette

<400> SEQUENCE: 143

```
ggtggtggcg gcggtggtgg cggcggtggc ctgtctgaaa tcaaaggtgt tatcgttcac     60

cgtctggaag gtgttggtgg cggtggtggt ggcggtggtg gcggcgtgga tgatgcgctg    120

atcaacagca ccaaaattta cagctacttc ccgagcgtg                           159
```

<210> SEQ ID NO 144
<211> LENGTH: 53
<212> TYPE: PRT
<213> ORGANISM: Artificial Sequence
<220> FEATURE:
<223> OTHER INFORMATION: Recombinant amino acid sequence - Glycine-measles-glycine-tetanus (GMGT)

<400> SEQUENCE: 144

```
Gly Gly Gly Gly Gly Gly Gly Gly Gly Gly Leu Ser Glu Ile Lys Gly
 1               5                  10                  15

Val Ile Val His Arg Leu Glu Gly Val Gly Gly Gly Gly Gly Gly Gly
            20                  25                  30

Gly Gly Gly Val Asp Asp Ala Leu Ile Asn Ser Thr Lys Ile Tyr Ser
        35                  40                  45

Tyr Phe Pro Ser Val
    50
```

<210> SEQ ID NO 145
<211> LENGTH: 771
<212> TYPE: DNA
<213> ORGANISM: Aquabirnavirus infect. pancreatic necrosis virus

<400> SEQUENCE: 145

```
atgaacacaa acaaggcaac cgcaacttac ttgaaatcca ttatgcttcc agagactgga      60

ccagcaagca tcccggacga cataacggag agacacatct taaaacaaga gacctcgtca     120

tacaacttag aggtctccga atcaggaagt ggcattcttg tttgtttccc tggggcacca     180

ggctcacgga tcggtgcaca ctacagatgg aatgcgaacc agacggggct ggagttcgac     240

cagtggctgg agacgtcgca ggacctgaag aaagccttca actacgggag gctgatctca     300

aggagatacg acatccaaag ctccacacta ccggccggtc tctatgctct gaacgggacg     360

ctcaacgctg ccaccttcga aggcagtctg tctgaggtgg agaacctgac ctacaacagc     420

ctgatgtccc taacaacgaa cccccaggac aaagtcagca accagctggt gaccaaagga     480

gtcacagtcc tgaatctacc aacagggttc gacaaaccat acgtccgcct agaggacgag     540

acaccccagg gtctccagtc aatgaacggg gccaagatga ggtgcacagc tgcaactgca     600

ccgctgaggt acgagatcga cctcccatcc caacgcctac cccccgttcc tgcgacagga     660

accctcacca ctctctacga gggaaacgcc gacatcgtca actccacaac agtgacggga     720

gacataaact tcagtctggc agaacaaccc gcaaacgaga ccaggttcga c              771
```

<210> SEQ ID NO 146
<211> LENGTH: 257
<212> TYPE: PRT
<213> ORGANISM: Aquabirnavirus infect. pancreatic necrosis virus

<400> SEQUENCE: 146

```
Met Asn Thr Asn Lys Ala Thr Ala Thr Tyr Leu Lys Ser Ile Met Leu
 1               5                  10                  15

Pro Glu Thr Gly Pro Ala Ser Ile Pro Asp Asp Ile Thr Glu Arg His
            20                  25                  30

Ile Leu Lys Gln Glu Thr Ser Ser Tyr Asn Leu Glu Val Ser Glu Ser
        35                  40                  45

Gly Ser Gly Ile Leu Val Cys Phe Pro Gly Ala Pro Gly Ser Arg Ile
    50                  55                  60

Gly Ala His Tyr Arg Trp Asn Ala Asn Gln Thr Gly Leu Glu Phe Asp
65                  70                  75                  80

Gln Trp Leu Glu Thr Ser Gln Asp Leu Lys Lys Ala Phe Asn Tyr Gly
                85                  90                  95

Arg Leu Ile Ser Arg Arg Tyr Asp Ile Gln Ser Ser Thr Leu Pro Ala
            100                 105                 110

Gly Leu Tyr Ala Leu Asn Gly Thr Leu Asn Ala Ala Thr Phe Glu Gly
        115                 120                 125
```

-continued

Ser Leu Ser Glu Val Glu Asn Leu Thr Tyr Asn Ser Leu Met Ser Leu
    130                 135                 140

Thr Thr Asn Pro Gln Asp Lys Val Ser Asn Gln Leu Val Thr Lys Gly
145                 150                 155                 160

Val Thr Val Leu Asn Leu Pro Thr Gly Phe Asp Lys Pro Tyr Val Arg
                165                 170                 175

Leu Glu Asp Glu Thr Pro Gln Gly Leu Gln Ser Met Asn Gly Ala Lys
            180                 185                 190

Met Arg Cys Thr Ala Ala Thr Ala Pro Leu Arg Tyr Glu Ile Asp Leu
        195                 200                 205

Pro Ser Gln Arg Leu Pro Pro Val Pro Ala Thr Gly Thr Leu Thr Thr
    210                 215                 220

Leu Tyr Glu Gly Asn Ala Asp Ile Val Asn Ser Thr Thr Val Thr Gly
225                 230                 235                 240

Asp Ile Asn Phe Ser Leu Ala Glu Gln Pro Ala Asn Glu Thr Arg Phe
                245                 250                 255

Asp

<210> SEQ ID NO 147
<211> LENGTH: 936
<212> TYPE: DNA
<213> ORGANISM: Artificial Sequence
<220> FEATURE:
<223> OTHER INFORMATION: Recombinant nucleic acid sequence - IPNV VP2
      plus Glycine-measles-glycine-tetanus (GMGT)

<400> SEQUENCE: 147
atgaacacaa acaaggcaac cgcaacttac ttgaaatcca ttatgcttcc agagactgga      60
ccagcaagca tcccggacga cataacggag agacacatct taaaacaaga gacctcgtca     120
tacaacttag aggtctccga atcaggaagt ggcattcttg tttgtttccc tggggcacca     180
ggctcacgga tcggtgcaca ctacagatgg aatgcgaacc agacggggct ggagttcgac     240
cagtggctgg agacgtcgca ggacctgaag aaagccttca actacgggag gctgatctca     300
aggagatacg acatccaaag ctccacacta ccggccggtc tctatgctct gaacgggacg     360
ctcaacgctg ccaccttcga aggcagtctg tctgaggtgg agaacctgac ctacaacagc     420
ctgatgtccc taacaacgaa cccccaggac aaagtcagca accagctggt gaccaaagga     480
gtcacagtcc tgaatctacc aacagggttc gacaaaccat acgtccgcct agaggacgag     540
acaccccagg gtctccagtc aatgaacggg gccaagatga ggtgcacagc tgcaactgca     600
ccgctgaggt acgagatcga cctcccatcc caacgcctac cccccgttcc tgcgacagga     660
accctcacca ctctctacga gggaaacgcc gacatcgtca actccacaac agtgacggga     720
gacataaact tcagtctggc agaacaaccc gcaaacgaga ccaggttcga ccatatgggt     780
ggtggcggcg gtggtggcgg cggtggcctg tctgaaatca aaggtgttat cgttcaccgt     840
ctggaaggtg ttggtggcgg tggtggtggc ggtggtggcg gcgtggatga tgcgctgatc     900
aacagcacca aaatttacag ctacttcccg agcgtg                               936

<210> SEQ ID NO 148
<211> LENGTH: 312
<212> TYPE: PRT
<213> ORGANISM: Artificial Sequence
<220> FEATURE:
<223> OTHER INFORMATION: Recombinant amino acid sequence - IPNV VP2
      plus Glycine-measles-glycine-tetanus (GMGT)

<400> SEQUENCE: 148

-continued

```
Met Asn Thr Asn Lys Ala Thr Ala Thr Tyr Leu Lys Ser Ile Met Leu
 1               5                  10                  15

Pro Glu Thr Gly Pro Ala Ser Ile Pro Asp Asp Ile Thr Glu Arg His
            20                  25                  30

Ile Leu Lys Gln Glu Thr Ser Ser Tyr Asn Leu Glu Val Ser Glu Ser
        35                  40                  45

Gly Ser Gly Ile Leu Val Cys Phe Pro Gly Ala Pro Gly Ser Arg Ile
    50                  55                  60

Gly Ala His Tyr Arg Trp Asn Ala Asn Gln Thr Gly Leu Glu Phe Asp
65                  70                  75                  80

Gln Trp Leu Glu Thr Ser Gln Asp Leu Lys Lys Ala Phe Asn Tyr Gly
                85                  90                  95

Arg Leu Ile Ser Arg Arg Tyr Asp Ile Gln Ser Ser Thr Leu Pro Ala
            100                 105                 110

Gly Leu Tyr Ala Leu Asn Gly Thr Leu Asn Ala Ala Thr Phe Glu Gly
        115                 120                 125

Ser Leu Ser Glu Val Glu Asn Leu Thr Tyr Asn Ser Leu Met Ser Leu
    130                 135                 140

Thr Thr Asn Pro Gln Asp Lys Val Ser Asn Gln Leu Val Thr Lys Gly
145                 150                 155                 160

Val Thr Val Leu Asn Leu Pro Thr Gly Phe Asp Lys Pro Tyr Val Arg
                165                 170                 175

Leu Glu Asp Glu Thr Pro Gln Gly Leu Gln Ser Met Asn Gly Ala Lys
            180                 185                 190

Met Arg Cys Thr Ala Ala Thr Ala Pro Leu Arg Tyr Glu Ile Asp Leu
        195                 200                 205

Pro Ser Gln Arg Leu Pro Pro Val Pro Ala Thr Gly Thr Leu Thr Thr
    210                 215                 220

Leu Tyr Glu Gly Asn Ala Asp Ile Val Asn Ser Thr Thr Val Thr Gly
225                 230                 235                 240

Asp Ile Asn Phe Ser Leu Ala Glu Gln Pro Ala Asn Glu Thr Arg Phe
                245                 250                 255

Asp His Met Gly Gly Gly Gly Gly Gly Gly Gly Gly Leu Ser Glu
            260                 265                 270

Ile Lys Gly Val Ile Val His Arg Leu Glu Gly Val Gly Gly Gly Gly
        275                 280                 285

Gly Gly Gly Gly Gly Gly Val Asp Asp Ala Leu Ile Asn Ser Thr Lys
    290                 295                 300

Ile Tyr Ser Tyr Phe Pro Ser Val
305                 310
```

<210> SEQ ID NO 149
<211> LENGTH: 1407
<212> TYPE: DNA
<213> ORGANISM: Artificial Sequence
<220> FEATURE:
<223> OTHER INFORMATION: Recombinant nucleic acid sequence - IPNV VP2
(truncated) + OmpA +
Glycine-measles-glycine-tetanus (GMGT)

<400> SEQUENCE: 149

```
atgaacacaa acaaggcaac cgcaacttac ttgaaatcca ttatgcttcc agagactgga      60

ccagcaagca tcccggacga cataacggag agacacatct taaaacaaga gacctcgtca     120

tacaacttag aggtctccga atcaggaagt ggcattcttg tttgtttccc tggggcacca     180

ggctcacgga tcggtgcaca ctacagatgg aatgcgaacc agacggggct ggagttcgac     240
```

```
cagtggctgg agacgtcgca ggacctgaag aaagccttca actacgggag gctgatctca    300

aggagatacg acatccaaag ctccacacta ccggccggtc tctatgctct gaacgggacg    360

ctcaacgctg ccaccttcga aggcagtctg tctgaggtgg agaacctgac ctacaacagc    420

ctgatgtccc taacaacgaa cccccaggac aaagtcagca accagctggt gaccaaagga    480

gtcacagtcc tgaatctacc aacagggttc gacaaaccat acgtccgcct agaggacgag    540

acaccccagg gtctccagtc aatgaacggg gccaagatga ggtgcacagc tgcaactgca    600

ccgctgaggt acgagatcga cctcccatcc caacgcctac cccccgttcc tgcgacagga    660

accctcacca ctctctacga gggaaacgcc gacatcgtca actccacaac agtgacggga    720

gacataaact tcagtctggc agaacaaccc gcaaacgaga ccaggttcga ccatatgggt    780

gctgctcact tcaacggtct gaacaagatc gaaggcgtga aaaatggtga agaaaacgct    840

gcggcggcca acgccttcgt aggttacaac ttcaacgaga acttcggttc cgaactgggc    900

tacctgtaca ctggccgtgg taacaccgat ggcaaccgtt acgagaacca gggcgctacc    960

ttgtccggta tcgctcgtct gccgctgggg ggcgacttct ctgccttcgc tgaaggtggc   1020

gcctactggg ctcacaccga tggcatgggc accagtgata ccaaagtatc cccgctggcc   1080

ggcctgggcg tgacctacca ggtaaacgac gcgctggatc tgcaagctcg ctaccgctac   1140

atgtgggacg tggctgatct gcacgccgac aacgtacgct acaagtccaa ccagagcgtt   1200

gcgaccctgg aagccgtata ccacccgttc cgctcttcct accatatggg tggtggcggc   1260

ggtggtggcg gcggtggcct gtctgaaatc aaaggtgtta tcgttcaccg tctggaaggt   1320

gttggtggcg gtggtggtgg cggtggtggc ggcgtggatg atgcgctgat caacagcacc   1380

aaaatttaca gctacttccc gagcgtg                                       1407
```

```
<210> SEQ ID NO 150
<211> LENGTH: 469
<212> TYPE: PRT
<213> ORGANISM: Artificial Sequence
<220> FEATURE:
<223> OTHER INFORMATION: Recombinant amino acid sequence - IPNV VP2
      (truncated)   + OmpA +
      Glycine-measles-glycine-tetanus (GMGT)

<400> SEQUENCE: 150

Met Asn Thr Asn Lys Ala Thr Ala Thr Tyr Leu Lys Ser Ile Met Leu
 1               5                  10                  15

Pro Glu Thr Gly Pro Ala Ser Ile Pro Asp Asp Ile Thr Glu Arg His
            20                  25                  30

Ile Leu Lys Gln Glu Thr Ser Ser Tyr Asn Leu Glu Val Ser Glu Ser
        35                  40                  45

Gly Ser Gly Ile Leu Val Cys Phe Pro Gly Ala Pro Gly Ser Arg Ile
    50                  55                  60

Gly Ala His Tyr Arg Trp Asn Ala Asn Gln Thr Gly Leu Glu Phe Asp
65                  70                  75                  80

Gln Trp Leu Glu Thr Ser Gln Asp Leu Lys Lys Ala Phe Asn Tyr Gly
                85                  90                  95

Arg Leu Ile Ser Arg Arg Tyr Asp Ile Gln Ser Ser Thr Leu Pro Ala
            100                 105                 110

Gly Leu Tyr Ala Leu Asn Gly Thr Leu Asn Ala Ala Thr Phe Glu Gly
        115                 120                 125

Ser Leu Ser Glu Val Glu Asn Leu Thr Tyr Asn Ser Leu Met Ser Leu
    130                 135                 140

Thr Thr Asn Pro Gln Asp Lys Val Ser Asn Gln Leu Val Thr Lys Gly
```

-continued

```
145                 150                 155                 160

Val Thr Val Leu Asn Leu Pro Thr Gly Phe Asp Lys Pro Tyr Val Arg
                165                 170                 175

Leu Glu Asp Glu Thr Pro Gln Gly Leu Gln Ser Met Asn Gly Ala Lys
            180                 185                 190

Met Arg Cys Thr Ala Ala Thr Ala Pro Leu Arg Tyr Glu Ile Asp Leu
        195                 200                 205

Pro Ser Gln Arg Leu Pro Pro Val Pro Ala Thr Gly Thr Leu Thr Thr
    210                 215                 220

Leu Tyr Glu Gly Asn Ala Asp Ile Val Asn Ser Thr Thr Val Thr Gly
225                 230                 235                 240

Asp Ile Asn Phe Ser Leu Ala Glu Gln Pro Ala Asn Glu Thr Arg Phe
                245                 250                 255

Asp His Met Gly Ala Ala His Phe Asn Gly Leu Asn Lys Ile Glu Gly
            260                 265                 270

Val Lys Asn Gly Glu Glu Asn Ala Ala Ala Ala Asn Ala Phe Val Gly
        275                 280                 285

Tyr Asn Phe Asn Glu Asn Phe Gly Ser Glu Leu Gly Tyr Leu Tyr Thr
    290                 295                 300

Gly Arg Gly Asn Thr Asp Gly Asn Arg Tyr Glu Asn Gln Gly Ala Thr
305                 310                 315                 320

Leu Ser Gly Ile Ala Arg Leu Pro Leu Gly Gly Asp Phe Ser Ala Phe
                325                 330                 335

Ala Glu Gly Gly Ala Tyr Trp Ala His Thr Asp Gly Met Gly Thr Ser
            340                 345                 350

Asp Thr Lys Val Ser Pro Leu Ala Gly Leu Gly Val Thr Tyr Gln Val
        355                 360                 365

Asn Asp Ala Leu Asp Leu Gln Ala Arg Tyr Arg Tyr Met Trp Asp Val
    370                 375                 380

Ala Asp Leu His Ala Asp Asn Val Arg Tyr Lys Ser Asn Gln Ser Val
385                 390                 395                 400

Ala Thr Leu Glu Ala Val Tyr His Pro Phe Arg Ser Ser Tyr His Met
                405                 410                 415

Gly Gly Gly Gly Gly Gly Gly Gly Gly Gly Leu Ser Glu Ile Lys Gly
            420                 425                 430

Val Ile Val His Arg Leu Glu Gly Val Gly Gly Gly Gly Gly Gly Gly
        435                 440                 445

Gly Gly Gly Val Asp Asp Ala Leu Ile Asn Ser Thr Lys Ile Tyr Ser
    450                 455                 460

Tyr Phe Pro Ser Val
465
```

<210> SEQ ID NO 151
<211> LENGTH: 1422
<212> TYPE: DNA
<213> ORGANISM: Artificial Sequence
<220> FEATURE:
<223> OTHER INFORMATION: Recombinant nucleic acid sequence - IPNV VP2 (truncated) + OmpA + Glycine-measles-glycine-tetanus (GMGT) + measles and tetanus epitopes, without polyGly linker

<400> SEQUENCE: 151

```
atgaacacaa acaaggcaac cgcaacttac ttgaaatcca ttatgcttcc agagactgga      60

ccagcaagca tcccggacga cataacggag agacacatct taaaacaaga gacctcgtca     120

tacaacttag aggtctccga atcaggaagt ggcattcttg tttgtttccc tggggcacca     180
```

-continued

```
ggctcacgga tcggtgcaca ctacagatgg aatgcgaacc agacggggct ggagttcgac    240

cagtggctgg agacgtcgca ggacctgaag aaagccttca actacgggag gctgatctca    300

aggagatacg acatccaaag ctccacacta ccggccggtc tctatgctct gaacgggacg    360

ctcaacgctg ccaccttcga aggcagtctg tctgaggtgg agaacctgac ctacaacagc    420

ctgatgtccc taacaacgaa cccccaggac aaagtcagca accagctggt gaccaaagga    480

gtcacagtcc tgaatctacc aacagggttc gacaaaccat acgtccgcct agaggacgag    540

acaccccagg gtctccagtc aatgaacggg gccaagatga ggtgcacagc tgcaactgca    600

ccgctgaggt acgagatcga cctcccatcc caacgcctac cccccgttcc tgcgacagga    660

accctcacca ctctctacga gggaaacgcc gacatcgtca actccacaac agtgacggga    720

gacataaact tcagtctggc agaacaaccc gcaaacgaga ccaggttcga cgaggcctcc    780

agatccgctc gagccctgtc ggagatcaag ggcgtcatcg tccaccgcct ggagggcgtc    840

gcctccagat ccgctcgaca gtacatcaag gccaactcga agttcatcgg catcaccgag    900

ctgattatgg gtgctgctca cttcaacggt ctgaacaaga tcgaaggcgt gaaaaatggt    960

gaagaaaacg ctgcggcggc caacgccttc gtaggttaca acttcaacga gaacttcggt   1020

tccgaactgg gctacctgta cactggccgt ggtaacaccg atggcaaccg ttacgagaac   1080

cagggcgcta ccttgtccgg tatcgctcgt ctgccgctgg ggggcgactt ctctgccttc   1140

gctgaaggtg gcgcctactg ggctcacacc gatggcatgg gcaccagtga taccaaagta   1200

tccccgctgg ccggcctggg cgtgacctac caggtaaacg acgcgctgga tctgcaagct   1260

cgctaccgct acatgtggga cgtggctgat ctgcacgccg acaacgtacg ctacaagtcc   1320

aaccagagcg ttgcgaccct ggaagccgta taccacccgt tccgctcttc ctacattaat   1380

aagcttatcg ataccgtcga cgaattctgc ggttcccccc gg                      1422
```

<210> SEQ ID NO 152
<211> LENGTH: 474
<212> TYPE: PRT
<213> ORGANISM: Artificial Sequence
<220> FEATURE:
<223> OTHER INFORMATION: Recombinant amino acid sequence - IPNV VP2 (truncated) + OmpA + Glycine-measles-glycine-tetanus (GMGT) + measles and tetanus epitopes, without polyGly linker

<400> SEQUENCE: 152

```
Met Asn Thr Asn Lys Ala Thr Ala Thr Tyr Leu Lys Ser Ile Met Leu
 1               5                  10                  15

Pro Glu Thr Gly Pro Ala Ser Ile Pro Asp Asp Ile Thr Glu Arg His
            20                  25                  30

Ile Leu Lys Gln Glu Thr Ser Ser Tyr Asn Leu Glu Val Ser Glu Ser
        35                  40                  45

Gly Ser Gly Ile Leu Val Cys Phe Pro Gly Ala Pro Gly Ser Arg Ile
    50                  55                  60

Gly Ala His Tyr Arg Trp Asn Ala Asn Gln Thr Gly Leu Glu Phe Asp
65                  70                  75                  80

Gln Trp Leu Glu Thr Ser Gln Asp Leu Lys Lys Ala Phe Asn Tyr Gly
                85                  90                  95

Arg Leu Ile Ser Arg Arg Tyr Asp Ile Gln Ser Ser Thr Leu Pro Ala
            100                 105                 110

Gly Leu Tyr Ala Leu Asn Gly Thr Leu Asn Ala Ala Thr Phe Glu Gly
        115                 120                 125
```

```
Ser Leu Ser Glu Val Glu Asn Leu Thr Tyr Asn Ser Leu Met Ser Leu
    130                 135                 140

Thr Thr Asn Pro Gln Asp Lys Val Ser Asn Gln Leu Val Thr Lys Gly
145                 150                 155                 160

Val Thr Val Leu Asn Leu Pro Thr Gly Phe Asp Lys Pro Tyr Val Arg
                165                 170                 175

Leu Glu Asp Glu Thr Pro Gln Gly Leu Gln Ser Met Asn Gly Ala Lys
            180                 185                 190

Met Arg Cys Thr Ala Ala Thr Ala Pro Leu Arg Tyr Glu Ile Asp Leu
        195                 200                 205

Pro Ser Gln Arg Leu Pro Pro Val Pro Ala Thr Gly Thr Leu Thr Thr
    210                 215                 220

Leu Tyr Glu Gly Asn Ala Asp Ile Val Asn Ser Thr Thr Val Thr Gly
225                 230                 235                 240

Asp Ile Asn Phe Ser Leu Ala Glu Gln Pro Ala Asn Glu Thr Arg Phe
                245                 250                 255

Asp Glu Ala Ser Arg Ser Ala Arg Ala Leu Ser Glu Ile Lys Gly Val
            260                 265                 270

Ile Val His Arg Leu Glu Gly Val Ala Ser Arg Ser Ala Arg Gln Tyr
        275                 280                 285

Ile Lys Ala Asn Ser Lys Phe Ile Gly Ile Thr Glu Leu Ile Met Gly
    290                 295                 300

Ala Ala His Phe Asn Gly Leu Asn Lys Ile Glu Gly Val Lys Asn Gly
305                 310                 315                 320

Glu Glu Asn Ala Ala Ala Ala Asn Ala Phe Val Gly Tyr Asn Phe Asn
                325                 330                 335

Glu Asn Phe Gly Ser Glu Leu Gly Tyr Leu Tyr Thr Gly Arg Gly Asn
            340                 345                 350

Thr Asp Gly Asn Arg Tyr Glu Asn Gln Gly Ala Thr Leu Ser Gly Ile
        355                 360                 365

Ala Arg Leu Pro Leu Gly Gly Asp Phe Ser Ala Phe Ala Glu Gly Gly
    370                 375                 380

Ala Tyr Trp Ala His Thr Asp Gly Met Gly Thr Ser Asp Thr Lys Val
385                 390                 395                 400

Ser Pro Leu Ala Gly Leu Gly Val Thr Tyr Gln Val Asn Asp Ala Leu
                405                 410                 415

Asp Leu Gln Ala Arg Tyr Arg Tyr Met Trp Asp Val Ala Asp Leu His
            420                 425                 430

Ala Asp Asn Val Arg Tyr Lys Ser Asn Gln Ser Val Ala Thr Leu Glu
        435                 440                 445

Ala Val Tyr His Pro Phe Arg Ser Ser Tyr Ile Asn Lys Leu Ile Asp
    450                 455                 460

Thr Val Asp Glu Phe Cys Gly Ser Pro Arg
465                 470
```

<210> SEQ ID NO 153
<211> LENGTH: 810
<212> TYPE: DNA
<213> ORGANISM: Avibirnavirus infectious bursal disease virus

<400> SEQUENCE: 153

```
atggctcatc accatcacca tcacggatcc attgaaggtc gtaccaacct gagcgatcag      60

acccagcaga ttgtcccgtt cattcgtagc ctgctgatgc cgacaactgg ccctgcttca     120

attccggacg ataccctgga aaaacatact ctgcgttccg aaacctcaac ctataattta     180
```

-continued

```
accgtgggcg atacgggtag tggccttatt gtattctttc cgggctttcc tggcagcatt    240

gtgggcgccc actataccct gcaatccaac ggcaattaca aatttgatca gatgctgctg    300

acggcacaaa atctgccggc atcttacaac tactgtcgtt tggtgtctcg tagcctgact    360

gtgcgctctt ctaccctgcc gggtggcgtt tatgctctga atggtacgat caacgccgtc    420

acctttcagg gtagcctttc tgaactgacc gacgtgtctt acaacgggtt gatgtcagcg    480

acggccaaca tcaacgacaa aatcggcaac gtgctggtcg gcgagggcgt taccgttctg    540

agtttgccga cttcatacga cttgggttat gtgcgtcttg gtgatcccat tccggccatt    600

ggtcttgatc cgaaaatggt ggccacctgt gacagcagcg atcgtccgcg cgtttacacg    660

attaccgccg ccgataacta tcaatttagc tcacagtacc agacgggtgg tgtgactatc    720

actctgttca gcgcaaacat cgatgccatc acttcattgt cagttggggg ggaactggta    780

ttcaaaacct cggtgcagtc gctggtcttg                                     810
```

<210> SEQ ID NO 154
<211> LENGTH: 257
<212> TYPE: PRT
<213> ORGANISM: Avibirnavirus infectious bursal disease virus

<400> SEQUENCE: 154

```
Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asn Tyr Gln Phe Ser Ser Gln Tyr Gln Thr Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                245                 250                 255

Leu
```

<210> SEQ ID NO 155
<211> LENGTH: 852
<212> TYPE: DNA
<213> ORGANISM: Artificial Sequence
<220> FEATURE:
<223> OTHER INFORMATION: Recombinant nucleic acid sequence - IBV VP2 + measles T cell epitope

<400> SEQUENCE: 155
atggctcatc accatcacca tcacattgaa ggtcgtacca acctgagcga tcagacccag 60
cagattgtcc cgttcattcg tagcctgctg atgccgacaa ctggccctgc ttcaattccg 120
gacgataccc tggaaaaaca tactctgcgt tccgaaacct caacctataa tttaaccgtg 180
ggcgatacgg gtagtggcct tattgtattc tttccgggct ttcctggcag cattgtgggc 240
gcccactata ccctgcaatc caacggcaat tacaaatttg atcagatgct gctgacggca 300
caaaatctgc cggcatctta caactactgt cgtttggtgt ctcgtagcct gactgtgcgc 360
tcttctaccc tgccgggtgg cgtttatgct ctgaatggta cgatcaacgc cgtcaccttt 420
cagggtagcc tttctgaact gaccgacgtg tcttacaacg ggttgatgtc agcgacggcc 480
aacatcaacg acaaaatcgg caacgtgctg gtcggcgagg gcgttaccgt tctgagtttg 540
ccgacttcat acgacttggg ttatgtgcgt cttggtgatc ccattccggc cattggtctt 600
gatccgaaaa tggtggccac ctgtgacagc agcgatcgtc cgcgcgttta cacgattacc 660
gccgccgata actatcaatt tagctcacag taccagacgg gtggtgtgac tatcactctg 720
ttcagcgcaa acatcgatgc catcacttca ttgtcagttg gggggaact ggtattcaaa 780 acctcggtgc agtcgctggt cttgctgtct gaaatcaaag gtgttatcgt tcaccgtctg 840
gaaggtgttt aa 852

<210> SEQ ID NO 156
<211> LENGTH: 272
<212> TYPE: PRT
<213> ORGANISM: Artificial Sequence
<220> FEATURE:
<223> OTHER INFORMATION: Recombinant amino acid sequence - IBV VP2 + measles T cell epitope

<400> SEQUENCE: 156

Met Thr Asn Leu Ser Asp Gln Thr Gln Gln Ile Val Pro Phe Ile Arg
1 5 10 15

Ser Leu Leu Met Pro Thr Thr Gly Pro Ala Ser Ile Pro Asp Asp Thr
20 25 30

Leu Glu Lys His Thr Leu Arg Ser Glu Thr Ser Thr Tyr Asn Leu Thr
35 40 45

Val Gly Asp Thr Gly Ser Gly Leu Ile Val Phe Phe Pro Gly Phe Pro
50 55 60

Gly Ser Ile Val Gly Ala His Tyr Thr Leu Gln Ser Asn Gly Asn Tyr
65 70 75 80

Lys Phe Asp Gln Met Leu Leu Thr Ala Gln Asn Leu Pro Ala Ser Tyr
85 90 95

Asn Tyr Cys Arg Leu Val Ser Arg Ser Leu Thr Val Arg Ser Ser Thr
100 105 110

Leu Pro Gly Gly Val Tyr Ala Leu Asn Gly Thr Ile Asn Ala Val Thr
115 120 125

Phe Gln Gly Ser Leu Ser Glu Leu Thr Asp Val Ser Tyr Asn Gly Leu
130 135 140

Met Ser Ala Thr Ala Asn Ile Asn Asp Lys Ile Gly Asn Val Leu Val

```
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asn Tyr Gln Phe Ser Ser Gln Tyr Gln Thr Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                245                 250                 255

Leu Leu Ser Glu Ile Lys Gly Val Ile Val His Arg Leu Glu Gly Val
            260                 265                 270


<210> SEQ ID NO 157
<211> LENGTH: 867
<212> TYPE: DNA
<213> ORGANISM: Artificial Sequence
<220> FEATURE:
<223> OTHER INFORMATION: Recombinant nucleic acid sequence - IBV VP2 +
      tetanus T cell epitope

<400> SEQUENCE: 157

atggctcatc accatcacca tcacggatcc attgaaggtc gtaccaacct gagcgatcag     60

acccagcaga ttgtcccgtt cattcgtagc ctgctgatgc cgacaactgg ccctgcttca    120

attccggacg ataccctgga aaaacatact ctgcgttccg aaacctcaac ctataattta    180

accgtgggcg atacgggtag tggccttatt gtattctttc cgggctttcc tggcagcatt    240

gtgggcgccc actataccct gcaatccaac ggcaattaca aatttgatca gatgctgctg    300

acggcacaaa atctgccggc atcttacaac tactgtcgtt tggtgtctcg tagcctgact    360

gtgcgctctt ctaccctgcc gggtggcgtt tatgctctga atggtacgat caacgccgtc    420

acctttcagg gtagcctttc tgaactgacc gacgtgtctt acaacgggtt gatgtcagcg    480

acggccaaca tcaacgacaa aatcggcaac gtgctggtcg gcgagggcgt taccgttctg    540

agtttgccga cttcatacga cttgggttat gtgcgtcttg gtgatcccat tccggccatt    600

ggtcttgatc cgaaaatggt ggccacctgt gacagcagcg atcgtccgcg cgtttacacg    660

attaccgccg ccgataacta tcaatttagc tcacagtacc agacgggtgg tgtgactatc    720

actctgttca gcgcaaacat cgatgccatc acttcattgt cagttggggg ggaactggta    780

ttcaaaacct cggtgcagtc gctggtcttg gtggatgatg cgctgatcaa cagcaccaaa    840

atttacagct acttcccgag cgtgtaa                                        867


<210> SEQ ID NO 158
<211> LENGTH: 275
<212> TYPE: PRT
<213> ORGANISM: Artificial Sequence
<220> FEATURE:
<223> OTHER INFORMATION: Recombinant amino acid sequence - IBV VP2 +
      tetanus T cell epitope

<400> SEQUENCE: 158

Met Thr Asn Leu Ser Asp Gln Thr Gln Gln Ile Val Pro Phe Ile Arg
 1               5                  10                  15

Ser Leu Leu Met Pro Thr Thr Gly Pro Ala Ser Ile Pro Asp Asp Thr
            20                  25                  30
```

```
Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asn Tyr Gln Phe Ser Ser Gln Tyr Gln Thr Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                245                 250                 255

Leu Val Asp Asp Ala Leu Ile Asn Ser Thr Lys Ile Tyr Ser Tyr Phe
            260                 265                 270

Pro Ser Val
        275
```

<210> SEQ ID NO 159
<211> LENGTH: 975
<212> TYPE: DNA
<213> ORGANISM: Artificial Sequence
<220> FEATURE:
<223> OTHER INFORMATION: Recombinant nucleic acid sequence - IBV VP2 + measles T cell epitope, tetanus T cell epitope, and GMGT

<400> SEQUENCE: 159

```
atggctcatc accatcacca tcacggatcc attgaaggtc gtaccaacct gagcgatcag      60

acccagcaga ttgtcccgtt cattcgtagc ctgctgatgc cgacaactgg ccctgcttca     120

attccggacg ataccctgga aaaacatact ctgcgttccg aaacctcaac ctataattta     180

accgtgggcg atacgggtag tggccttatt gtattctttc cgggctttcc tggcagcatt     240

gtgggcgccc actataccct gcaatccaac ggcaattaca aatttgatca gatgctgctg     300

acggcacaaa atctgccggc atcttacaac tactgtcgtt tggtgtctcg tagcctgact     360

gtgcgctctt ctaccctgcc gggtggcgtt tatgctctga atggtacgat caacgccgtc     420

acctttcagg gtagcctttc tgaactgacc gacgtgtctt acaacgggtt gatgtcagcg     480

acggccaaca tcaacgacaa aatcggcaac gtgctggtcg gcgagggcgt taccgttctg     540

agtttgccga cttcatacga cttgggttat gtgcgtcttg gtgatcccat tccggccatt     600
```

```
ggtcttgatc cgaaaatggt ggccacctgt gacagcagcg atcgtccgcg cgtttacacg    660

attaccgccg ccgataacta tcaatttagc tcacagtacc agacgggtgg tgtgactatc    720

actctgttca gcgcaaacat cgatgccatc acttcattgt cagttggggg ggaactggta    780

ttcaaaacct cggtgcagtc gctggtcttg gaattcggtg gtggcggcgg tggtggcggc    840

ggtggcctgt ctgaaatcaa aggtgttatc gttcaccgtc tggaaggtgt tggtggcggt    900

ggtggtggcg gtggtggcgg cgtggatgat gcgctgatca acagcaccaa aatttacagc    960

tacttcccga gcgtg                                                     975


<210> SEQ ID NO 160
<211> LENGTH: 312
<212> TYPE: PRT
<213> ORGANISM: Artificial Sequence
<220> FEATURE:
<223> OTHER INFORMATION: Recombinant amino acid sequence - IBV VP2 +
      measles T cell epitope, tetanus T cell epitope,
      and GMGT

<400> SEQUENCE: 160

Met Thr Asn Leu Ser Asp Gln Thr Gln Gln Ile Val Pro Phe Ile Arg
 1               5                  10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asn Tyr Gln Phe Ser Ser Gln Tyr Gln Thr Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                245                 250                 255

Leu Glu Phe Gly Gly Gly Gly Gly Gly Gly Gly Gly Gly Leu Ser Glu
            260                 265                 270

Ile Lys Gly Val Ile Val His Arg Leu Glu Gly Val Gly Gly Gly Gly
        275                 280                 285
```

```
Gly Gly Gly Gly Gly Gly Val Asp Asp Ala Leu Ile Asn Ser Thr Lys
    290                 295                 300

Ile Tyr Ser Tyr Phe Pro Ser Val
305                 310


<210> SEQ ID NO 161
<211> LENGTH: 372
<212> TYPE: DNA
<213> ORGANISM: Clostridium perfringens

<400> SEQUENCE: 161

aaagattcca gcgctaataa aaacgtgaac gagctggttg cgtacatcac cacgggcggt      60

gaaaagtatg cgggcacgga cgactatatg tatttcggta ttaaaaccaa agatggtcag     120

acccaggagt ggaccatgga taacccgggt aacgatttta tgaccggttc ccaggacacg     180

tacaccttca aactgaagga taaaaatctg aagatcgatg acattcaaaa catgtggatt     240

cgcaaatcca aatacactga gttcggtgat gattacaaac ctgccaacat caaagtgatt     300

gcaaacggca atgtggttct gaataaagat attaatgagt ggatttctgg caactccact     360

tataacatca aa                                                         372


<210> SEQ ID NO 162
<211> LENGTH: 124
<212> TYPE: PRT
<213> ORGANISM: Clostridium perfringens

<400> SEQUENCE: 162

Lys Asp Ser Ser Ala Asn Lys Asn Val Asn Glu Leu Val Ala Tyr Ile
 1               5                  10                  15

Thr Thr Gly Gly Glu Lys Tyr Ala Gly Thr Asp Asp Tyr Met Tyr Phe
            20                  25                  30

Gly Ile Lys Thr Lys Asp Gly Gln Thr Gln Glu Trp Thr Met Asp Asn
        35                  40                  45

Pro Gly Asn Asp Phe Met Thr Gly Ser Gln Asp Thr Tyr Thr Phe Lys
    50                  55                  60

Leu Lys Asp Lys Asn Leu Lys Ile Asp Asp Ile Gln Asn Met Trp Ile
65                  70                  75                  80

Arg Lys Ser Lys Tyr Thr Glu Phe Gly Asp Asp Tyr Lys Pro Ala Asn
                85                  90                  95

Ile Lys Val Ile Ala Asn Gly Asn Val Val Leu Asn Lys Asp Ile Asn
            100                 105                 110

Glu Trp Ile Ser Gly Asn Ser Thr Tyr Asn Ile Lys
        115                 120


<210> SEQ ID NO 163
<211> LENGTH: 423
<212> TYPE: DNA
<213> ORGANISM: Artificial Sequence
<220> FEATURE:
<223> OTHER INFORMATION: Recombinant nucleic acid sequence - Clostridium
      perfringens ToxA plus measles T cell epitope

<400> SEQUENCE: 163

aaagattcca gcgctaataa aaacgtgaac gagctggttg cgtacatcac cacgggcggt      60

gaaaagtatg cgggcacgga cgactatatg tatttcggta ttaaaaccaa agatggtcag     120

acccaggagt ggaccatgga taacccgggt aacgatttta tgaccggttc ccaggacacg     180

tacaccttca aactgaagga taaaaatctg aagatcgatg acattcaaaa catgtggatt     240
```

cgcaaatcca aatacactga gttcggtgat gattacaaac ctgccaacat caaagtgatt 300
gcaaacggca atgtggttct gaataaagat attaatgagt ggatttctgg caactccact 360
tataacatca aagaattcct gtctgaaatc aaaggtgtta tcgttcaccg tctggaaggt 420
gtt 423

<210> SEQ ID NO 164
<211> LENGTH: 141
<212> TYPE: PRT
<213> ORGANISM: Artificial Sequence
<220> FEATURE:
<223> OTHER INFORMATION: Recombinant amino acid sequence - Clostridium perfringens ToxA plus measles T cell epitope

<400> SEQUENCE: 164

Lys Asp Ser Ser Ala Asn Lys Asn Val Asn Glu Leu Val Ala Tyr Ile
1 5 10 15

Thr Thr Gly Gly Glu Lys Tyr Ala Gly Thr Asp Asp Tyr Met Tyr Phe
20 25 30

Gly Ile Lys Thr Lys Asp Gly Gln Thr Gln Glu Trp Thr Met Asp Asn
35 40 45

Pro Gly Asn Asp Phe Met Thr Gly Ser Gln Asp Thr Tyr Thr Phe Lys
50 55 60

Leu Lys Asp Lys Asn Leu Lys Ile Asp Asp Ile Gln Asn Met Trp Ile
65 70 75 80

Arg Lys Ser Lys Tyr Thr Glu Phe Gly Asp Asp Tyr Lys Pro Ala Asn
85 90 95

Ile Lys Val Ile Ala Asn Gly Asn Val Val Leu Asn Lys Asp Ile Asn
100 105 110

Glu Trp Ile Ser Gly Asn Ser Thr Tyr Asn Ile Lys Glu Phe Leu Ser
115 120 125

Glu Ile Lys Gly Val Ile Val His Arg Leu Glu Gly Val
130 135 140

<210> SEQ ID NO 165
<211> LENGTH: 494
<212> TYPE: DNA
<213> ORGANISM: Artificial Sequence
<220> FEATURE:
<223> OTHER INFORMATION: Recombinant nucleic acid sequence - Clostridium perfringens ToxA plus 2 copies of measles T cell epitope

<400> SEQUENCE: 165
aaagattcca gcgctaataa aaacgtgaac gagctggttg cgtacatcac cacgggcggt 60
gaaaagtatg cgggcacgga cgactatatg tatttcggta ttaaaaccaa agatggtcag 120
acccaggagt ggaccatgga taacccgggt aacgatttta tgaccggttc ccaggacacg 180
tacaccttca aactgaagga taaaaatctg aagatcgatg acattcaaaa catgtggatt 240
cgcaaatcca aatacactga gttcggtgat gattacaaac ctgccaacat caaagtgatt 300
gcaaacggca atgtggttct gaataaagat attaatgagt ggatttctgg caactccact 360
tataacatca aagaactgtc tgaaatcaaa ggtgttatcg ttcaccgtct ggaaggtgtt 420
ggtggtggtg gcggcggcgg tggcggcggt ctgtctgaaa tcaaaggtgt tatcgttcac 480
cgtctggaag gtgt 494

<210> SEQ ID NO 166
<211> LENGTH: 165
<212> TYPE: PRT

<213> ORGANISM: Artificial Sequence
<220> FEATURE:
<223> OTHER INFORMATION: Recombinant amino acid sequence - Clostridium perfringens ToxA plus 2 copies of measles T cell epitope

<400> SEQUENCE: 166

```
Lys Asp Ser Ser Ala Asn Lys Asn Val Asn Glu Leu Val Ala Tyr Ile
 1               5                  10                  15

Thr Thr Gly Gly Glu Lys Tyr Ala Gly Thr Asp Asp Tyr Met Tyr Phe
            20                  25                  30

Gly Ile Lys Thr Lys Asp Gly Gln Thr Gln Glu Trp Thr Met Asp Asn
        35                  40                  45

Pro Gly Asn Asp Phe Met Thr Gly Ser Gln Asp Thr Tyr Thr Phe Lys
    50                  55                  60

Leu Lys Asp Lys Asn Leu Lys Ile Asp Asp Ile Gln Asn Met Trp Ile
65                  70                  75                  80

Arg Lys Ser Lys Tyr Thr Glu Phe Gly Asp Asp Tyr Lys Pro Ala Asn
                85                  90                  95

Ile Lys Val Ile Ala Asn Gly Asn Val Val Leu Asn Lys Asp Ile Asn
            100                 105                 110

Glu Trp Ile Ser Gly Asn Ser Thr Tyr Asn Ile Lys Glu Leu Ser Glu
        115                 120                 125

Ile Lys Gly Val Ile Val His Arg Leu Glu Gly Val Gly Gly Gly Gly
    130                 135                 140

Gly Gly Gly Gly Gly Gly Leu Ser Glu Ile Lys Gly Val Ile Val His
145                 150                 155                 160

Arg Leu Glu Gly Val
                165
```

<210> SEQ ID NO 167
<211> LENGTH: 570
<212> TYPE: DNA
<213> ORGANISM: Artificial Sequence
<220> FEATURE:
<223> OTHER INFORMATION: Recombinant nucleic acid sequence - Clostridium perfringens ToxA plus 3 copies of measles T cell epitope

<400> SEQUENCE: 167

```
aaagattcca gcgctaataa aaacgtgaac gagctggttg cgtacatcac cacgggcggt     60

gaaaagtatg cgggcacgga cgactatatg tatttcggta ttaaaaccaa agatggtcag    120

acccaggagt ggaccatgga taacccgggt aacgatttta tgaccggttc ccaggacacg    180

tacaccttca aactgaagga taaaaatctg aagatcgatg acattcaaaa catgtggatt    240

cgcaaatcca aatacactga gttcggtgat gattacaaac ctgccaacat caaagtgatt    300

gcaaacggca atgtggttct gaataaagat attaatgagt ggatttctgg caactccact    360

tataacatca aagaactgtc tgaaatcaaa ggtgttatcg ttcaccgtct ggaaggtgtt    420

ggtggcggtg gcggtggtgg tggcggcggc ctgtctgaaa tcaaaggtgt tatcgttcac    480

cgtctggaag gtgttggtgg cggcggtggc ggtggcggcg gtggcctgtc tgaaatcaaa    540

ggtgttatcg ttcaccgtct ggaaggtgtt                                     570
```

<210> SEQ ID NO 168
<211> LENGTH: 190
<212> TYPE: PRT
<213> ORGANISM: Artificial Sequence
<220> FEATURE:
<223> OTHER INFORMATION: Recombinant amino acid sequence - Clostridium perfringens ToxA plus 3 copies of measles T cell epitope

<400> SEQUENCE: 168

```
Lys Asp Ser Ser Ala Asn Lys Asn Val Asn Glu Leu Val Ala Tyr Ile
 1               5                  10                  15

Thr Thr Gly Gly Glu Lys Tyr Ala Gly Thr Asp Asp Tyr Met Tyr Phe
            20                  25                  30

Gly Ile Lys Thr Lys Asp Gly Gln Thr Gln Glu Trp Thr Met Asp Asn
        35                  40                  45

Pro Gly Asn Asp Phe Met Thr Gly Ser Gln Asp Thr Tyr Thr Phe Lys
    50                  55                  60

Leu Lys Asp Lys Asn Leu Lys Ile Asp Asp Ile Gln Asn Met Trp Ile
65                  70                  75                  80

Arg Lys Ser Lys Tyr Thr Glu Phe Gly Asp Asp Tyr Lys Pro Ala Asn
                85                  90                  95

Ile Lys Val Ile Ala Asn Gly Asn Val Val Leu Asn Lys Asp Ile Asn
            100                 105                 110

Glu Trp Ile Ser Gly Asn Ser Thr Tyr Asn Ile Lys Glu Leu Ser Glu
        115                 120                 125

Ile Lys Gly Val Ile Val His Arg Leu Glu Gly Val Gly Gly Gly Gly
    130                 135                 140

Gly Gly Gly Gly Gly Gly Leu Ser Glu Ile Lys Gly Val Ile Val His
145                 150                 155                 160

Arg Leu Glu Gly Val Gly Gly Gly Gly Gly Gly Gly Gly Gly Gly Leu
                165                 170                 175

Ser Glu Ile Lys Gly Val Ile Val His Arg Leu Glu Gly Val
            180                 185                 190
```

<210> SEQ ID NO 169
<211> LENGTH: 432
<212> TYPE: DNA
<213> ORGANISM: Artificial Sequence
<220> FEATURE:
<223> OTHER INFORMATION: Recombinant nucleic acid sequence - Clostridium perfringens ToxA plus 1 copy of tetanus epitope

<400> SEQUENCE: 169

```
aaagattcca gcgctaataa aaacgtgaac gagctggttg cgtacatcac cacgggcggt      60

gaaaagtatg cgggcacgga cgactatatg tatttcggta ttaaaaccaa agatggtcag     120

acccaggagt ggaccatgga taacccgggt aacgatttta tgaccggttc ccaggacacg     180

tacaccttca aactgaagga taaaaatctg aagatcgatg acattcaaaa catgtggatt     240

cgcaaatcca aatacactga gttcggtgat gattacaaac ctgccaacat caaagtgatt     300

gcaaacggca atgtggttct gaataaagat attaatgagt ggatttctgg caactccact     360

tataacatca aagaattcgt ggatgatgcg ctgatcaaca gcaccaaaat ttacagctac     420

ttcccgagcg tg                                                         432
```

<210> SEQ ID NO 170
<211> LENGTH: 144
<212> TYPE: PRT
<213> ORGANISM: Artificial Sequence
<220> FEATURE:
<223> OTHER INFORMATION: Recombinant amino acid sequence - Clostridium perfringens ToxA plus 1 copy of tetanus epitope

<400> SEQUENCE: 170

```
Lys Asp Ser Ser Ala Asn Lys Asn Val Asn Glu Leu Val Ala Tyr Ile
```

```
 1               5                   10                  15

Thr Thr Gly Gly Glu Lys Tyr Ala Gly Thr Asp Asp Tyr Met Tyr Phe
            20                  25                  30

Gly Ile Lys Thr Lys Asp Gly Gln Thr Gln Glu Trp Thr Met Asp Asn
        35                  40                  45

Pro Gly Asn Asp Phe Met Thr Gly Ser Gln Asp Thr Tyr Thr Phe Lys
    50                  55                  60

Leu Lys Asp Lys Asn Leu Lys Ile Asp Asp Ile Gln Asn Met Trp Ile
65                  70                  75                  80

Arg Lys Ser Lys Tyr Thr Glu Phe Gly Asp Asp Tyr Lys Pro Ala Asn
                85                  90                  95

Ile Lys Val Ile Ala Asn Gly Asn Val Val Leu Asn Lys Asp Ile Asn
            100                 105                 110

Glu Trp Ile Ser Gly Asn Ser Thr Tyr Asn Ile Lys Glu Phe Val Asp
        115                 120                 125

Asp Ala Leu Ile Asn Ser Thr Lys Ile Tyr Ser Tyr Phe Pro Ser Val
    130                 135                 140
```

<210> SEQ ID NO 171
<211> LENGTH: 510
<212> TYPE: DNA
<213> ORGANISM: Artificial Sequence
<220> FEATURE:
<223> OTHER INFORMATION: Recombinant nucleic acid sequence - Clostridium perfringens ToxA + 2 copies of tetanus epitope

<400> SEQUENCE: 171

```
aaagattcca gcgctaataa aaacgtgaac gagctggttg cgtacatcac cacgggcggt     60

gaaaagtatg cgggcacgga cgactatatg tatttcggta ttaaaaccaa agatggtcag    120

acccaggagt ggaccatgga taacccgggt aacgatttta tgaccggttc ccaggacacg    180

tacaccttca aactgaagga taaaaatctg aagatcgatg acattcaaaa catgtggatt    240

cgcaaatcca aatacactga gttcggtgat gattacaaac ctgccaacat caaagtgatt    300

gcaaacggca atgtggttct gaataaagat attaatgagt ggatttctgg caactccact    360

tataacatca aagaagtgga tgatgcgctg atcaacagca ccaaaattta cagctacttc    420

ccgagcgtgg gtggtggtgg tggtggtggt ggtggtgtgg atgatgcgct gatcaacagc    480

accaaaattt acagctactt cccgagcgtg                                     510
```

<210> SEQ ID NO 172
<211> LENGTH: 170
<212> TYPE: PRT
<213> ORGANISM: Artificial Sequence
<220> FEATURE:
<223> OTHER INFORMATION: Recombinant amino acid sequence - Clostridium perfringens ToxA + 2 copies of tetanus epitope

<400> SEQUENCE: 172

```
Lys Asp Ser Ser Ala Asn Lys Asn Val Asn Glu Leu Val Ala Tyr Ile
 1               5                   10                  15

Thr Thr Gly Gly Glu Lys Tyr Ala Gly Thr Asp Asp Tyr Met Tyr Phe
            20                  25                  30

Gly Ile Lys Thr Lys Asp Gly Gln Thr Gln Glu Trp Thr Met Asp Asn
        35                  40                  45

Pro Gly Asn Asp Phe Met Thr Gly Ser Gln Asp Thr Tyr Thr Phe Lys
    50                  55                  60

Leu Lys Asp Lys Asn Leu Lys Ile Asp Asp Ile Gln Asn Met Trp Ile
65                  70                  75                  80
```

```
Arg Lys Ser Lys Tyr Thr Glu Phe Gly Asp Asp Tyr Lys Pro Ala Asn
                85                  90                  95

Ile Lys Val Ile Ala Asn Gly Asn Val Val Leu Asn Lys Asp Ile Asn
            100                 105                 110

Glu Trp Ile Ser Gly Asn Ser Thr Tyr Asn Ile Lys Glu Val Asp Asp
        115                 120                 125

Ala Leu Ile Asn Ser Thr Lys Ile Tyr Ser Tyr Phe Pro Ser Val Gly
    130                 135                 140

Gly Gly Gly Gly Gly Gly Gly Gly Val Asp Asp Ala Leu Ile Asn Ser
145                 150                 155                 160

Thr Lys Ile Tyr Ser Tyr Phe Pro Ser Val
                165                 170


<210> SEQ ID NO 173
<211> LENGTH: 537
<212> TYPE: DNA
<213> ORGANISM: Artificial Sequence
<220> FEATURE:
<223> OTHER INFORMATION: Recombinant nucleic acid sequence - Clostridium
      perfringens ToxA + 1 copy of measles epitope + 1
      copy of tetanus epitope

<400> SEQUENCE: 173

aaagattcca gcgctaataa aaacgtgaac gagctggttg cgtacatcac cacgggcggt      60

gaaaagtatg cgggcacgga cgactatatg tatttcggta ttaaaaccaa agatggtcag     120

acccaggagt ggaccatgga taacccgggt aacgatttta tgaccggttc ccaggacacg     180

tacaccttca aactgaagga taaaaatctg aagatcgatg acattcaaaa catgtggatt     240

cgcaaatcca aatacactga gttcggtgat gattacaaac ctgccaacat caaagtgatt     300

gcaaacggca atgtggttct gaataaagat attaatgagt ggatttctgg caactccact     360

tataacatca aagaattcgg tggtggcggc ggtggtggcg gcggtggcct gtctgaaatc     420

aaaggtgtta tcgttcaccg tctggaaggt gttggtggcg gtggtggtgg cggtggtggc     480

ggcgtggatg atgcgctgat caacagcacc aaaatttaca gctacttccc gagcgtg        537


<210> SEQ ID NO 174
<211> LENGTH: 179
<212> TYPE: PRT
<213> ORGANISM: Artificial Sequence
<220> FEATURE:
<223> OTHER INFORMATION: Recombinant Amino Acid Sequence - Clostridium
      perfringens ToxA + 1 copy of measles epitope + 1
      copy of tetanus epitope

<400> SEQUENCE: 174

Lys Asp Ser Ser Ala Asn Lys Asn Val Asn Glu Leu Val Ala Tyr Ile
 1               5                  10                  15

Thr Thr Gly Gly Glu Lys Tyr Ala Gly Thr Asp Asp Tyr Met Tyr Phe
            20                  25                  30

Gly Ile Lys Thr Lys Asp Gly Gln Thr Gln Glu Trp Thr Met Asp Asn
        35                  40                  45

Pro Gly Asn Asp Phe Met Thr Gly Ser Gln Asp Thr Tyr Thr Phe Lys
    50                  55                  60

Leu Lys Asp Lys Asn Leu Lys Ile Asp Asp Ile Gln Asn Met Trp Ile
65                  70                  75                  80

Arg Lys Ser Lys Tyr Thr Glu Phe Gly Asp Asp Tyr Lys Pro Ala Asn
                85                  90                  95

Ile Lys Val Ile Ala Asn Gly Asn Val Val Leu Asn Lys Asp Ile Asn
```

-continued

```
            100                 105                 110

Glu Trp Ile Ser Gly Asn Ser Thr Tyr Asn Ile Lys Glu Phe Gly Gly
        115                 120                 125

Gly Gly Gly Gly Gly Gly Gly Gly Leu Ser Glu Ile Lys Gly Val Ile
    130                 135                 140

Val His Arg Leu Glu Gly Val Gly Gly Gly Gly Gly Gly Gly Gly Gly
145                 150                 155                 160

Gly Val Asp Asp Ala Leu Ile Asn Ser Thr Lys Ile Tyr Ser Tyr Phe
                165                 170                 175

Pro Ser Val


<210> SEQ ID NO 175
<211> LENGTH: 603
<212> TYPE: DNA
<213> ORGANISM: Eimeria tenella

<400> SEQUENCE: 175

atgcccattc aggcgtctga gctgttctcc atgaacatat gcaacctcct tgaggatctt      60

ggtggtggca gcaacttccg catcaacatg gacgacgaag tcatcagagg attggtcgca     120

gtctaccaag gtcgcaacgt gtggcagcca tcgcagccca ctcctgtttc caggacacct     180

ccgcgcggcc agatgccgcc cccgtctgca cctggtgcac cagctcctga gaagcctggt     240

gcctttgctc aagcacttgc ttcggatgca ttcttcgcaa tgtgtcttgt tgttgctgcc     300

gctgttgtcg ggctccttgg cattgtcctt gaccctgtgg agctcaagca tttgactctc     360

ctcggcttgt ctctcatcgt cggctactac tgcgtgtggg ccgttacgcc ttcgcttcac     420

acaccattga tgtctgtgac gaatgccctt tcgggagtca ttgtcatcgg ctgcatgctc     480

gagtacggaa ccgccatgat atccggattc actcttctcg cactcattgg aaccttcttg     540

gcttccgtca acgttgctgg tggattcttc gtaactcacc gcatgctgaa gatgtttcag     600

ata                                                                   603


<210> SEQ ID NO 176
<211> LENGTH: 468
<212> TYPE: PRT
<213> ORGANISM: Eimeria acervulina

<400> SEQUENCE: 176

Met Arg Ser Leu Leu Val Val Ala Gly Leu Ala Gly Cys Ser Ser Phe
 1               5                  10                  15

Ala Pro Thr Asp Ala Arg His Arg Phe Leu Ser Glu Thr Leu Glu Glu
            20                  25                  30

Pro Glu Asp Val Met Leu Lys Thr Ala Asp Leu His Thr Asn Leu Leu
        35                  40                  45

Arg Glu Pro Pro Met Thr Ile Lys Leu Asp Asn Arg Tyr Lys Phe Thr
    50                  55                  60

Gly Leu Gly Glu Leu Val Ser Gln Leu Ile Asp His His Thr Thr Met
65                  70                  75                  80

Gly Ser Val Gly Ser Ser Gly Thr Met Ala Arg Gln Lys Leu Leu Asn
                85                  90                  95

Tyr His Asn Ser Gln Tyr Phe Gly Glu Ile Lys Ile Gly Thr Pro Gly
            100                 105                 110

Arg Arg Phe Val Val Val Phe Asp Thr Gly Ser Ser Asn Leu Trp Val
        115                 120                 125

Pro Ala Ala Glu Cys Glu Lys Gly Gly Cys Ala Pro His Glu Lys Phe
    130                 135                 140
```

Asp Pro Lys Tyr Ser Ser Thr Phe Ser Pro Ile Arg Ser Leu Thr Gly
145 150 155 160

Asp Pro Ala Val Ala Phe Ile Gln Tyr Gly Thr Gly Ala Cys Val Leu
165 170 175

Arg Met Gly Arg Asp Ile Val Glu Ile Gly Gly Ile Lys Val Pro Asn
180 185 190

Gln Ala Ile Gly Leu Ala Val Glu Glu Ser Thr His Pro Phe Ala Asp
195 200 205

Leu Pro Phe Asp Gly Leu Val Gly Leu Gly Phe Pro Asp Val Ser Gly
210 215 220

Glu Glu Gly Leu Pro Ser Ser Ala Leu Pro Ile Val Asp Gln Met Val
225 230 235 240

Lys Glu Lys Val Leu Asp Arg Asn Val Phe Ser Val Tyr Met Ser Glu
245 250 255

Asp Ile Asn Arg Pro Gly Glu Ile Ser Phe Gly Ala Ala Asp Pro Lys
260 265 270

Tyr Thr Phe Ala Gly His Thr Pro Lys Trp Phe Pro Val Ile Ser Leu
275 280 285

Asp Tyr Trp Glu Ile Gly Leu His Gly Met Lys Ile Asn Gly Lys Ser
290 295 300

Phe Gly Val Cys Glu Lys Arg Gly Cys Arg Ala Ala Val Asp Thr Gly
305 310 315 320

Ser Ser Leu Ile Thr Gly Pro Ser Ser Val Ile Asn Pro Leu Ile Lys
325 330 335

Ala Leu Asn Val Ala Glu Asn Cys Ser Asn Leu Gly Thr Leu Pro Thr
340 345 350

Leu Thr Phe Val Leu Lys Asp Ile Tyr Gly Arg Leu Val Asn Phe Ser
355 360 365

Leu Glu Pro Arg Asp Tyr Val Val Glu Glu Leu Asp Ala Arg Gly Asn
370 375 380

Pro Asn Asn Cys Ala Ala Gly Phe Met Ala Met Asp Val Pro Ala Pro
385 390 395 400

Arg Gly Pro Leu Phe Val Leu Gly Asn Ser Phe Ile Arg Lys Tyr Tyr
405 410 415

Ser Ile Phe Asp Arg Asp His Met Met Val Gly Phe Met Arg Ala Asn
420 425 430

His Glu Gly Ser Gly Pro Leu Ile Lys Gly Tyr Pro Ser Ser Ala Pro
435 440 445

Ser Val Ser Ala Ser Cys Leu Val Ala Ala Ser Ala Ala Ala Phe Ala
450 455 460

Leu Ser Leu Phe
465

<210> SEQ ID NO 177
<211> LENGTH: 1497
<212> TYPE: DNA
<213> ORGANISM: Eimeria acervulina

<400> SEQUENCE: 177
ggcttccctt aaattactga gcccacgaac agccaggtac aatgcgttcc cttctggtcg 60
tggccggcct agctggctgc agttctttcg ctccaaccga tgcaagacat cggtttctga 120
gtgaaacgtt ggaagaaccg gaagatgtaa tgctgaagac ggcagatctt cacacaaatc 180
ttttacgcga accccccatg acgatcaagc tagacaacag atacaagttc actggccttg 240

-continued

```
gcgagctggt ttcacagctg atcgaccatc acaccacaat gggaagcgtt ggttcctctg    300
gaacgatggc ccggcaaaag ctgctcaatt accacaacag ccagtatttt ggcgaaataa    360
agatcggaac tcccggcaga agattcgtag ttgtttttga cactggttcc tcaaatctgt    420
gggttcctgc agcggaatgc gagaaaggag gatgcgcccc ccatgagaaa ttcgacccaa    480
agtattctag cacattttct cccatacggt cgctgactgg agacccagca gtcgcattca    540
ttcaatacgg aactggagca tgcgttcttc gaatgggtcg cgacatcgtg gagatcggcg    600
gcatcaaagt gcccaaccag gcaatcggcc tggcagtcga agaatcaact catccattcg    660
ctgacctgcc tttcgacggg ctggtcggct tgggattccc ggatgtgtct ggggaagagg    720
gacttccatc aagcgcactt cccattgttg accaaatggt taaggagaaa gttctggatc    780
gaaatgtgtt ctccgtctat atgagcgaag acatcaaccg ccccggagag atttcgtttg    840
gagcagcgga cccgaaatat actttcgctg ggcacacacc taagtggttc cccgtcatct    900
ctctagacta ctgggaaatt ggcctacatg gaatgaaaat aaacggaaaa tcctttggcg    960
tatgtgaaaa acgcggatgc cgcgcagccg tggacactgg atccagtttg ataacgggac   1020
catcatctgt catcaatccc ctcatcaaag cactcaacgt tgctgagaat tgctccaatc   1080
ttggaaccct gccaactctc acatttgtcc taaaagacat atatggaagg cttgtaaact   1140
tcagcctcga acccagggac tatgtagtgg aagagcttga tgcgagagga aaccctaaca   1200
actgcgcagc tggattcatg gctatggacg tgccagcacc tcgaggcccc ctgttcgtgc   1260
tcggaaattc cttcatcagg aaatactaca gtattttcga ccgcgatcac atgatggttg   1320
gattcatgcg ggcaaaccac gaaggctccg gaccgctcat caaggggtat ccatcatctg   1380
cgccatcggt gtcagcgtcg tgccttgttg cagccagcgc tgctgcattc gcgctatccc   1440
tcttttaaac gtattccgaa cagtctgcat gtgtgaagtt gcgatgagtg ccatcga      1497
```

<210> SEQ ID NO 178
<211> LENGTH: 351
<212> TYPE: DNA
<213> ORGANISM: Eimeria sp.

<400> SEQUENCE: 178

```
atggtcagta agaaacctgc taaaagtgct aaaccggcta gcgggaaagg gaaagggaaa     60
gggaaaaaac gccgcgcaga aacgtatagc agttatattt ttaaagtgct gaaacaggtg    120
catccggaga cgggcattag caaaaaaagt atgatgatta tgacgtcttt gatcggcgac    180
acctttgaca agatcgcgag tgaggcaggt aaactgtgca agtataacaa gaaggacaca    240
ctgagtagtc gtgaaattca gacagcggtt cgtctggtgc tgccgggcga gctggcgaaa    300
catgcggtca gtgaaggcac gaaagcagtt acgaaatata cgggcaaatg a             351
```

<210> SEQ ID NO 179
<211> LENGTH: 16
<212> TYPE: PRT
<213> ORGANISM: Coronavirus avian infectious bronchitis virus

<400> SEQUENCE: 179

```
Cys Gln Tyr Asn Thr Gly Asn Phe Ser Asp Gly Phe Tyr Pro Phe Thr
 1               5                  10                  15
```

<210> SEQ ID NO 180
<211> LENGTH: 16
<212> TYPE: DNA
<213> ORGANISM: Artificial Sequence
<220> FEATURE:
<223> OTHER INFORMATION: Ribosome binding site -continued

```
<400> SEQUENCE: 180

cacacaggaa acagct                                                  16


<210> SEQ ID NO 181
<211> LENGTH: 16
<212> TYPE: DNA
<213> ORGANISM: Artificial Sequence
<220> FEATURE:
<223> OTHER INFORMATION: Ribosome binding site

<400> SEQUENCE: 181

caagaggagt atatct                                                  16
```